(12) United States Patent
Pyeon et al.

(10) Patent No.: US 9,790,553 B2
(45) Date of Patent: Oct. 17, 2017

(54) BIOMARKERS FOR HUMAN PAPILLOMA VIRUS-ASSOCIATED CANCERS

(75) Inventors: Dohun Pyeon, Centennial, CO (US); Paul F. Lambert, Madison, WI (US); Michael A. Newton, Madison, WI (US); Paul G. Ahlquist, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 13/194,624

(22) Filed: Jul. 29, 2011

(65) Prior Publication Data
US 2011/0301059 A1 Dec. 8, 2011

Related U.S. Application Data

(62) Division of application No. 12/220,465, filed on Jul. 24, 2008, now Pat. No. 8,012,678.

(60) Provisional application No. 60/961,774, filed on Jul. 24, 2007.

(51) Int. Cl.
*C12Q 1/68* (2006.01)
*C12Q 1/70* (2006.01)

(52) U.S. Cl.
CPC ........... *C12Q 1/6886* (2013.01); *C12Q 1/708* (2013.01); *C12Q 2600/112* (2013.01); *C12Q 2600/136* (2013.01)

(58) Field of Classification Search
None
See application file for complete search history.

(56) References Cited

U.S. PATENT DOCUMENTS

| 6,235,470 B1 | 5/2001 | Sidransky |
| 6,803,189 B2 | 10/2004 | Keesee et al. |
| 7,125,663 B2 | 10/2006 | Schlegel et al. |
| 2003/0215895 A1* | 11/2003 | Wennerberg et al. ........ 435/7.23 |

OTHER PUBLICATIONS

Nalam et al, Bio Repr 77:167c-168, 2007 (abstract only).*
Pyeon et al, Cancer Res. 67:4605-4619, May 2007, IDS item #12, filed Aug. 19, 2011.*
Martinez et al, EJC 43:415-432, online pub Oct. 31, 2006.*
Slebos et al, Clin Can Res, 12:701-709, online pub Feb. 2006.*
Smith et al , J Nat Can Ins, 96:449-455, 2004.*
Kawano et al Am J of Otol 26:308-313, 2005.*
Ono et al Gene 226:95-102, 1999.*
Affymetrix Catalog, Data Sheet: GeneChip Human Genome Arrays, Jul. 2002.
Baak, et al., Predictive Testing of Early CIN Behaviour by Molecular Biomarkers, Cellular Oncology, 2005, 27:277-280.
Baak, et al., Dynamic Behavioural Interpretation of Cervical Intraepithelial Neoplasia with Molecular Biomarkers, J. Clin. Pathol., 2006, 59:1017-1028.
Chung, et al., Molecular Classification of Head and Neck Squamous Cell Carcinomas Using Patterns of Gene Expression Cancer Cell, 2004, 5:489-500.
Cromer, et al., Identification of Genes Associated with Tumorigenesis and Metastatic Potential of Hypopharyngeal Cancer by Microarray Analysis, Oncogene, 2004, 23:2484-2498.
Ginos, et al., Identification of a Gene Expression Signature Associated with Recurrent Disease in Squamous Cell Carcinoma of the Head and Neck, Cancer Research, 2004, 64:55-63.
Hunter, et al., Opinion—Profiling Early Head and Neck Cancer, Nature Reviews/Cancer, 2005, 5:127-135.
Martin, et al., Molecular Profiling of Cervical Neoplasia, Expert. Rev. Mol. Dian., 2006, 6(2):217-229.
Mukherjee, et al., MCM Immunocytochemistry as a First Line Cervical Screening Test in Developing Countries: A Prospective Cohort Study in a Regional Cancer Centre in India, British Journal of Cancer, 2007, 96:1107-1111.
Nalam, et al., Testicular Cell Adhesion Molecule 1 (TCAM1): An Important Mediator of Germ Cell—Sertoli Cell Interactions?, Biology of Reproduction, 2007, 77:167-c-168, Abstract Only.
Pyeon, et al., Fundamental Differences in Cell-Cycle Deregulation in Human Papillomavirus-Positive and -Negative Head/Neck and Cervical Cancers, 23rd International Papillomavirus Conference & Clinical Workshop, Prague, Czech Republic, Sep. 1-7, 2006.
Pyeon, et al., Fundamental Differences in Cell Cycle Deregulation in Human Papillomavirus-Positive and Human Papillomavirus-Negative Head/Neck and Cervical Cancers, Cancer Research, 2007, 67(10):4605-4619.
Simpson, et al., Cancer/Testis Antigens, Gametogenesis and Cancer, Nature Reviews/Cancer, 2005, 5:615-625.
Slebos, et al., Gene Expression Differences Associated with Human Papillomavirus Status in Head and Neck Squamous Cell Carcinoma, Clinical Cancer Research, 2006, 12(3):701-709.

(Continued)

Primary Examiner — Lei Yao
(74) Attorney, Agent, or Firm — Quarles & Brady LLP

(57) ABSTRACT

Cervical cancer cells and HPV$^+$ head and neck cancer cells express three testis-specific genes not normally expressed in somatic cells: testicular cell adhesion molecule 1 (TCAM1), synaptonemal complex protein 2 (SYCP2) and stromal antigen 3 (STAG3). Among the three markers, TCAM1 and SYCP2 are early detection markers. Various methods for identifying a human or non-human animal as a candidate for further examination for cervical cancer, preneoplastic lesion for cervical cancer, head and neck cancer, or preneoplastic lesion for head and neck cancer are disclosed. Methods of detecting said cancers and preneoplastic lesions, methods of screening for drugs for treating said cancers and preneoplastic lesions, methods for monitoring the effectiveness of a treatment for said cancers, and methods of treating said cancers are also disclosed. Further disclosed are kits that can be used to practice the above methods.

5 Claims, 15 Drawing Sheets
(10 of 15 Drawing Sheet(s) Filed in Color)

(56) References Cited

OTHER PUBLICATIONS

PCT International Search Report, Application No. PCT/US2008/071081, Dec. 30, 2008.
Vogel, C., et al. Sequence signatures and mRNA concentration can explain two-thirds of protein abundance variation in a human cell line, 2010, Molecular Systems Biology 6; Article No. 400; pp. 1-9.

* cited by examiner

BIOMARKERS FOR HUMAN PAPILLOMA VIRUS-ASSOCIATED CANCERS

CROSS-REFERENCE TO RELATED APPLICATION

This application is a divisional application of U.S. application Ser. No. 12/220,465 filed on Jul. 24, 2008, which issued as U.S. Pat. No. 8,012,678 on Sep. 6, 2011, which claims the benefit of U.S. Provisional Patent Application No. 60/961,774 filed Jul. 24, 2007. Both applications are incorporated herein by reference as if set forth in its entirety.

STATEMENT REGARDING FEDERALLY SPONSORED RESEARCH OR DEVELOPMENT

This invention was made with government support under CA097944, CA022443 and CA064364 awarded by the National Institutes of Health. The government has certain rights in the invention.

BACKGROUND OF THE INVENTION

Cervical cancer is the second most common malignancy in women worldwide and is a major cause of morbidity and mortality. Human papillomaviruses (HPV) are DNA viruses that infect and replicate in cutaneous and mucosal epithelia. High-risk mucosotropic HPV genotypes, including HPV16, HPV18 and HPV31, are associated with nearly all cervical cancers.

Head and neck cancer, which arises in mucosal epithelia lining various cavities in the head and neck region, such as the oral cavity and throat, is the sixth most common cancer in the United States with a survival rate of about 50%. 20-30% of head and neck cancers are associated with HPV; whereas the rest are linked to other risk factors, such as tobacco and alcohol.

The art, however, needs methods for predicting and diagnosing HPV, as well as diseases associated with HPV.

BRIEF SUMMARY

Cervical cancer (CC) cells and HPV$^+$ head and neck cancer (HNC) cells express three testis-specific genes not normally expressed in somatic cells: testicular cell adhesion molecule 1 (TCAM1), synaptonemal complex protein 2 (SYCP2) and stromal antigen 3 (STAG3). Among the three markers, TCAM1 and SYCP2 are early detection markers. Various methods for identifying a human or non-human animal as a candidate for further examination for CC, preneoplastic lesion for CC, HNC and preneoplastic lesion for HNC are disclosed. Methods of detecting CC and preneoplastic lesions thereof, methods of detecting HNC and preneoplastic lesions thereof, methods of screening for drugs for treating said cancers and preneoplastic lesions, methods for monitoring the effectiveness of a treatment for said cancers, and methods of treating said cancers are also disclosed. Further disclosed are kits that can be used to practice the above methods.

These and other features, objects and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing executed in color. Copies of this patent or patent application publication with color drawings will be provided by the Office upon request and payment of the necessary fee.

Figure 1:
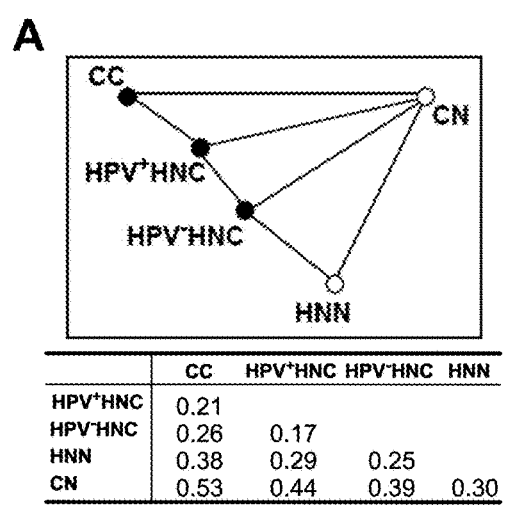
FIG. 1: Global gene expression analysis showed similarities and differences among HPV$^+$ HNC, HPV HNC and CC. (A) Multidimensional scaling measurements between all indicated pairs of tumor and normal classes of the distances between class-averaged log 2 expression levels over all 54,675 Affymetrix probe sets. The relative distances between each class are approximated in the two-dimensional projection at the left and tabulated at below. (B) Pairwise comparisons of expression alterations from normal for three cancers are shown as scatter plots of average log 2 fold change from normal. Pearson correlations (R) measure global concordance in expression alterations between cancer pairs. Genes are highlighted that show differential expression between HPV$^+$ HNC and HPV HNC; tracking into the HPV$^+$ HNC vs. HPV$^+$ CC comparison, these genes are predominantly equivalently expressed between these HPV$^+$ cancers. Dotted lines show median expression changes of red and blue genes, and red and blue arrows indicate the median shifted from HPV$^+$ HNC/HPV HNC comparison to HPV$^+$ HNC/CC comparison. (C) Differential expression analysis revealed genes significantly altered between the respective tissue classes. The results of three pairwise comparisons are summarized in the Venn diagram and tabulated fully in Table 3 (HPV$^+$ vs. HPV−), Supplementary Table S5 (Tumor vs. Normal) and Supplementary Table S6 (HNC vs. CC).
Figure 1:
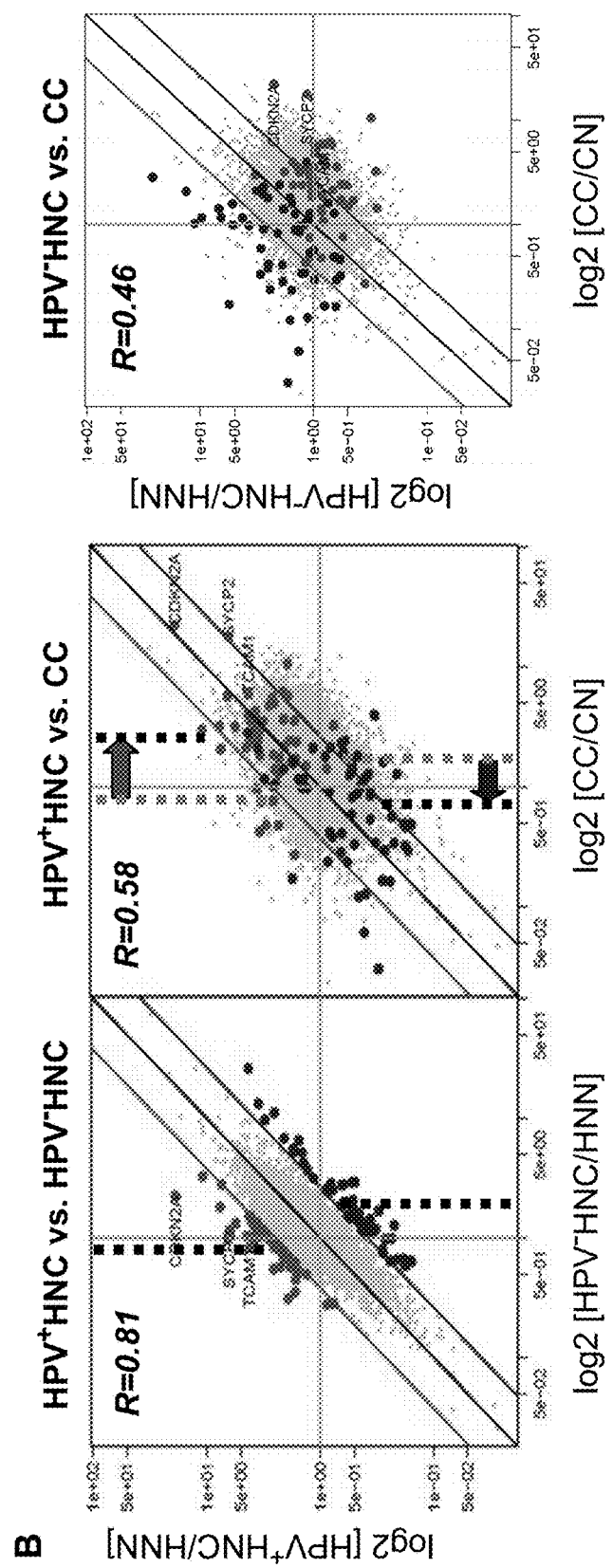
Figure 1:
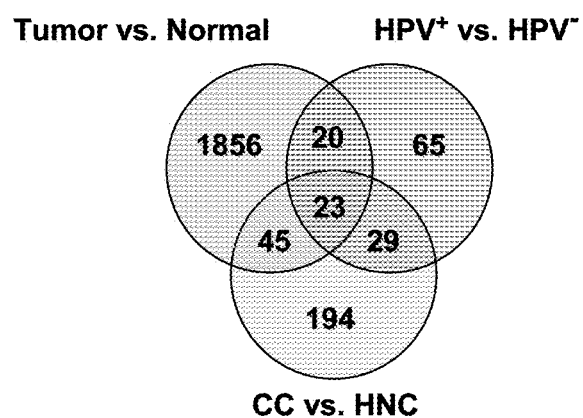

While the present invention is susceptible to various modifications and alternative forms, exemplary embodiments thereof are shown by way of example in the drawings and are described herein in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DESCRIPTION OF EXEMPLARY EMBODIMENTS

The present invention is based, in part, on the inventors' observation that human primary tumors of CC cells and HPV$^+$ HNC cells expressed three testis-specific genes not normally expressed in somatic cells. These three testis-specific genes were TCAM1, SYCP2 and STAG3. TCAM1 was also upregulated in preneoplastic lesions of cervical cells. Consistent with this finding, which suggests that TCAM1 upregulation is an early event in cancer development, TCAM1 expression was upregulated in early passages of NIKS (a spontaneously immortalized human keratinocyte cell line; see, 54) following HPV infection. A similar observation was made for SYCP2. Therefore, TCAM1 and SYCP2 can be detection markers not only for CC and HNC, but also for the corresponding preneoplastic lesions.

While not intending to be bound to any particular theory, the inventors believe that patients may develop an immune response to these three testis-specific antigens when they are overexpressed in preneoplastic and cancerous tissues; therefore, detecting or measuring the level of an antibody to one of these antigens in a body fluid, such as blood, provides a useful detection tool for CCs and HNCs as well as the corresponding preneoplastic lesions. In addition, TCAM1 resembles intracellular adhesion molecules in amino acid sequence and is expected to be located on cell surface. Accordingly, TCAM1 can be digested at a cell surface, and the extracellular domain part can be released into circulation. Cells containing TCAM1 also can be exfoliated and released into circulation. Either way, a body fluid can be used for detecting the upregulation of TCAM1 in cancer or preneoplastic cells.

The three testis-specific antigens are well known in the art. For example, the amino acid sequences for TCAM1 from mouse and rat can be found at NCBI GenBank Accession numbers CAM23792 (SEQ ID NO:1) and BAA75217 (SEQ ID NO:2), respectively; whereas the cDNA sequence for TCAM1 from human, mouse and rat can be found at NCBI GenBank Accession numbers NR_002947 (SEQ ID NO:3), NM_029467 (SEQ ID NO:4) and NM_021673 (SEQ ID NO:5), respectively.

Likewise, the amino acid sequences for SYCP2 from human, mouse, rat, pig, frog and chimpanzee can be found at NCBI GenBank Accession numbers CAM28338 (SEQ ID NO:6), NP_796165 (SEQ ID NO:7), NP_570091 (SEQ ID NO:8), CAN13245 (SEQ ID NO:9), NP_001072339 (SEQ ID NO:10) and XP_001141311 (SEQ ID NO:11), respectively; whereas the cDNA sequence for SYCP2 from human, mouse, rat, pig, frog and chimpanzee can be found at NCBI GenBank Accession numbers NM_014258 (SEQ ID NO:12), NM_177191 (SEQ ID NO:13), NM_130735 (SEQ ID NO:14), CR956363 (SEQ ID NO:15), NM_001078871 (SEQ ID NO:16) and XM_514753 (SEQ ID NO:17), respectively.

Furthermore, the amino acid sequences for STAG3 from human, mouse, rat, chimpanzee and duck-billed platypus can be found at NCBI GenBank Accession numbers CAB59367 (SEQ ID NO:18), NP_058660 (SEQ ID NO:19), NP_446182 (SEQ ID NO:20), XP_519253 (SEQ ID NO:21) and XP_001516109 (SEQ ID NO:22), respectively; whereas the cDNA sequence for STAG3 from human, mouse, rat, chimpanzee and duck-billed platypus can be found at NCBI GenBank Accession numbers NM_001025202 (SEQ ID NO:23), NM_016964 (SEQ ID NO:24), NM_053730 (SEQ ID NO:25), XM_519253 (SEQ ID NO:26) and XM_001516059 (SEQ ID NO:27), respectively.

As used herein, "cervical cancer" (CC) refers to carcinoma of the uterine cervix (e.g., carcinoma in situ, invasive carcinoma and metastatic carcinoma). CC is preceded with a well-recognized preoplastic lesion, cervical intraepithelial neoplasia (CIN) or squamous intraepithelial lesions (SIL) in the case of squamous cell carcinoma, and cervical glandular epithelial neoplasia in the case of adenocarcinoma.

As used herein, "head and neck cancer" (HNC) refers to cancer that arises in mucosal epithelia in the head or neck region, such as cancers in the nasal cavity, sinuses (e.g., paranasal sinuses), lip, mouth (e.g., oral cavity), salivary gland, throat (e.g., nasopharynx, oropharynx and hypopharynx), larynx, thyroid and parathyroid. One example of HNC is squamous cell carcinoma.

Although the examples below used samples from subjects with CC and HNC, the inventors contemplate that the methods can be used with any HPV-associated cancer including, but not limited to, anal cancer, CC, HNC, penile cancer, vaginal cancer and vulvar cancer.

In a first aspect, the present invention is summarized as a method for identifying a human or non-human animal as a candidate for further examination for CC. The method includes the steps of obtaining a tissue sample from a region of the cervix of the human or non-human animal, measuring the expression of TCAM1, SYCP2 or STAG3 at the mRNA or protein level in the cells of the tissue sample, and comparing the expression level to a normal standard, wherein a higher than normal expression indicates that the human or non-human animal is a candidate for further examination for CC.

In one embodiment of the first aspect, the tissue sample can be a cervical smear such as a Papanicolaou (Pap) smear. In another embodiment of the first aspect, the tissue sample can be a fluid collected by vaginal rinsing.

In a second aspect, the present invention is summarized as a method for detecting CC in a human or non-human animal. The method includes the steps of obtaining a tissue sample from a region of the cervix of the human or non-human animal, measuring the expression of TCAM1, SYCP2 and/or STAG3 at the protein or mRNA level in the cells of the tissue sample, and comparing the expression level to a normal standard wherein a higher than normal expression indicates CC.

In one embodiment of the second aspect, the tissue sample can be a cervical smear such as a Pap smear or biopsy sample from the cervix. In another embodiment of the second aspect, the tissue sample can be a fluid collected by vaginal rinsing. Optionally, the method also includes the step of observing CC in the human or non-human animal, e.g., by standard pathological evaluation of a biopsy tissue specimen from the cervix (e.g., histopathological analysis). Known techniques such as radiographic imaging studies may be employed to evaluate for the presence of metastatic lesions.

In a third aspect, the present invention is summarized as a method for detecting preneoplastic lesion of the cervix in a human or non-human animal. The method includes the steps of obtaining a tissue sample from a region of the cervix of the human or non-human animal, measuring the expression of TCAM1 or SYCP2 at the protein and/or mRNA level in the cells of the tissue sample, and comparing the expression level to a normal standard wherein a higher than normal expression indicates a preneoplastic lesion in the cervix.

In one embodiment of the third aspect, the tissue sample can be a cervical smear, such as a Pap smear or a biopsy sample from the cervix. In another embodiment of the third aspect, the tissue sample can be a fluid collected by vaginal rinsing. Optionally, the method also includes the step of observing a preneoplastic lesion of the cervix in the human or non-human animal, e.g., by standard pathological evaluation of a biopsy tissue specimen from the cervix (e.g., histopathological analysis).

In a fourth aspect, the present invention is summarized as a method for identifying a human or non-human animal as a candidate for further examination for HNC. The method includes the steps of obtaining a tissue sample from a head or neck region of the human or non-human animal, measuring the expression of TCAM1 at the protein level, SYCP2 at the protein level, or STAG3 at the protein or mRNA level in the cells of the tissue sample, and comparing the expression level to a normal standard wherein a higher than normal expression indicates that the human or non-human animal is a candidate for further examination for HNC.

In one embodiment of the fourth aspect, the tissue sample can be a saliva specimen, preferably containing exfoliated epithelial cells, or mouth rinse, preferably containing exfoliated epithelial cells. In obtaining a mouth rinse sample, it is preferred that both the mouth and throat are rinsed. In another embodiment of the fourth aspect, the tissue sample can be a mouth swab sample.

In a fifth aspect, the present is summarized as a method for detecting HNC in a human or non-human animal. The method includes the steps of obtaining a tissue sample from a head or neck region of the human or non-human animal, measuring the expression of TCAM1 at the protein level, SYCP2 at the protein level, or STAG3 at the protein or mRNA level in the cells of the tissue sample, and comparing the expression level to a normal standard wherein a higher than normal expression indicates head and neck cancer.

In one embodiment of the fifth aspect, the tissue sample can be obtained from a head or neck region at least part of which is suspected of being cancerous or having preneoplastic development. In another embodiment of the fifth aspect, the tissue sample can be a saliva specimen, preferably containing exfoliated epithelial cells, or mouth rinse, preferably containing exfoliated epithelial cells. In obtaining a mouth rinse sample, it is preferred that both the mouth and throat are rinsed. In yet another embodiment of the fifth aspect, the tissue sample can be a mouth swab sample. Optionally, the method includes the step of observing HNC in the human or non-human animal, e.g., by standard pathological evaluation of a biopsy tissue specimen from the head and neck region (e.g., histopathological analysis). Known techniques such as radiographic imaging studies may be employed to evaluate for the presence of metastatic lesions.

In a sixth aspect, the present invention is summarized as a method for detecting preneoplastic lesion for HNC in a human or non-human animal. The method includes the steps of obtaining a tissue sample from a head or neck region of the human or non-human animal, measuring the expression of TCAM1 or SYCP2 at the protein or mRNA level in the cells of the tissue sample, and comparing the expression level to a normal standard wherein a higher than normal expression indicates a preneoplastic lesion in the head and neck region.

In one embodiment of the sixth aspect, the tissue sample can be obtained from a head or neck region at least part of which is suspected of being cancerous or having preneoplastic development. In another embodiment of the sixth aspect, the tissue sample can be a saliva specimen, preferably containing exfoliated epithelial cells, or mouth rinse, preferably containing exfoliated epithelial cells. In obtaining a mouth rinse sample, it is preferred that both the mouth and throat are rinsed. In yet another embodiment of the sixth aspect, the tissue sample can be a mouth swab sample. Optionally, the method includes the step of observing a preneoplastic lesion in the head and neck region of the human or non-human animal, e.g., by standard pathological evaluation of a biopsy tissue specimen from the head and neck region (e.g., histopathological analysis).

In a seventh aspect, the present invention is summarized as a method for identifying a human or non-human animal as a candidate for further examination for CC, preneoplastic lesion for CC, HNC, preneoplastic lesion for HNC or HPV infection. The method includes the steps of determining the level of TCAM1 in a body fluid from the human or non-human animal, comparing the level to a normal standard, and identifying the human or non-human animal as a candidate for further examination for CC, preneoplastic lesion for CC, HNC, preneoplastic lesion for HNC or HPV infection when the level exceeds the normal standard.

In one embodiment of the seventh aspect, the body fluid can be blood, plasma, serum, lymph, ascitic fluid, a gynecological fluid, urine, a fluid collected by vaginal rinsing, a saliva specimen or a fluid collected by mouth rinsing.

In an eighth aspect, the present invention is summarized as a method for identifying a human or non-human animal as a candidate for further examination for CC, preneoplastic lesion for CC, HNC, preneoplastic lesion for HNC or HPV infection. The method includes the steps of determining the level of TCAM1 antibodies in a body fluid from the human or non-human animal, comparing the level to a normal standard, and identifying the human or non-human animal as a candidate for further examination for CC, preneoplastic lesion for CC, HNC, preneoplastic lesion for HNC or HPV infection when the level exceeds the normal standard.

In one embodiment of the eighth aspect, the body fluid can be blood, plasma, serum, lymph, ascitic fluid, a gynecological fluid, urine, a fluid collected by vaginal rinsing, a saliva specimen or a fluid collected by mouth rinsing.

In a ninth aspect, the present invention is summarized as a method for detecting HPV infection in a human or non-human animal. The method includes the steps of obtaining a tissue sample from the human or non-human animal, measuring the expression of TCAM1 and SYCP2 at the protein or mRNA level in the cells of the tissue sample, and comparing the expression level to a normal standard wherein a higher than normal expression indicates HPV infection.

A normal standard employed in any of the above methods can be readily established by one of ordinary skill in the art. For example, the expression level in HPV⁻ cells of the same human or non-human animal, preferably in the same type of cells from the same tissue during an HPV⁻ or cancer/preneoplastic lesion-free period, can be used as a normal standard. As another example, the expression level in HPV⁻ cells of a different human or non-human animal, preferably in the same type of cells from the same tissue during a HPV⁻ or cancer/preneoplastic lesion-free period, can be used as a normal standard. Given that testis-specific antigens are typically not expressed in somatic cells, any significant expression detected would represent a higher than normal expression. Similarly, TCAM1 protein level or TCAM1 antibody level in a body fluid from HPV⁻ or cancer/preneoplastic lesion-free individuals can likewise be used as a normal standard.

Any tissue sample used in the methods of the present invention can be subjected to a variety of well-known, post-collection preparative and storage techniques (e.g., nucleic acid and/or protein extraction, fixation, storage, freezing, ultrafiltration, concentration, centrifugation, etc.) prior to being used for detecting or measuring the expression of a marker provided herein.

When the mouth, throat or cervix area is rinsed to collect a tissue sample for detecting TCAM1, a suitable protease, such as trypsin, chymotrypsin or arginine carboxylase, that can cleave and release the entire or a substantial part of the extracellular domain of TCAM1 can be included in the rinsing fluid.

In a tenth aspect, the present invention is summarized as a method for identifying an agent as a candidate for treating CC or HNC. The method includes the steps of exposing CC cells or HNC cells expressing TCAM1, SYCP2 or STAG3 to a test agent, measuring the expression level of the marker, and comparing the expression level to that of control cells not exposed to the test agent, wherein a lower than control expression indicates that the agent is a candidate for treating CC or HNC. The cancer cells used can be either established cancer cell lines or cancer cells from one or more patients.

In an eleventh aspect, the present invention is summarized as a method for determining the effectiveness of a treatment for CC or HNC. The method includes the steps of measuring the expression of TCAM1, SYCP2 or STAG3 in a first sample from a CC or HNC patient prior to providing at least a portion of the treatment to the patient, measuring the expression of the marker in a second sample from the patient after said portion of the treatment is provided to the patient, and comparing the expression levels of the first sample and second sample, wherein a lower expression level in the second sample indicates that the treatment is effective.

In a twelfth aspect, the present invention is summarized as a method for treating or preventing CC, a preneoplastic lesion of CC, HNC, or a preneoplastic lesion of HNC in a human or non-human animal. The method includes the step of administering to the human or non-human animal having CC or HNC an active agent in an amount effective to treat CC or HNC, wherein the active agent contains a therapeutic agent (e.g., a chemotherapeutic agent) for CC, HNC or preneoplastic lesions thereof and a binding agent that can bind to TCAM1 (e.g., a ligand or antibody of TCAM1). The therapeutic agent and the binding agent are linked together. The therapeutic agent can be linked to the binding agent either covalently, through a linker or a chemical bond, or noncovalently, through ionic, van der Waals, electrostatic or hydrogen bonds. The therapeutic agent is typically a cytotoxic agent that can cause the death of a target cell. Similarly, an active agent can also contain a therapeutic agent and a targeting nucleic acid that can hybridize to a portion of the mRNA of TCAM1, SYCP2 or STAG3, wherein the therapeutic agent and the targeting nucleic acid are linked together.

As used herein, "antibody" includes an immunoglobulin molecule immunologically reactive with a particular antigen, and includes both polyclonal and monoclonal antibodies. The term also includes genetically engineered forms such as chimeric antibodies (e.g., humanized murine antibodies) and heteroconjugate antibodies (e.g., bispecific antibodies). For example, the term includes bivalent or bispecific molecules, diabodies, triabodies and tetrabodies. Bivalent and bispecific molecules are described in, e.g., Kostelny et al., J Immunol 148:1547 (1992); Pack & Pluckthun, Biochemistry 31:1579 (1992); Zhu et al., Protein Sci. 6:781 (1997); Hu et al., Cancer Res. 56:3055 (1996); Adams et al., Cancer Res. 53:4026 (1993); and McCartney et al., Protein Eng. 8:301 (1995). The term "antibody" also includes antigen binding forms of antibodies, including fragments with antigen-binding capability (e.g., Fab', F(ab')$_2$, Fab, Fv and rIgG). The term also refers to recombinant single chain Fv fragments (scFv). Preferably, antibodies employed to practice the present invention bind to its target protein with an affinity (association constant) of equal to or greater than $10^7$ M$^{-1}$.

In a thirteenth aspect, the present invention is summarized as a kit for detecting the expression of TCAM1, SYCP2 or STAG3. The kit includes at least one of (i) an agent such as an antibody or a ligand that specifically binds to TCAM1, SYCP2 or STAG3 and (ii) a nucleic acid (e.g., a primer for PCR amplification or a probe for detection) that hybridizes to a polynucleotide containing a nucleotide sequence of TCAM1, SYCP2 or STAG3 cDNA or complements thereof. The kit also includes at least one control sample having a known amount of (i) a polypeptide containing an amino acid sequence of TCAM1, SYCP2 or STAG3 or (ii) a polynucleotide containing a nucleotide sequence of TCAM1, SYCP2 or STAG3 cDNA or complements thereof.

Examples of control samples include CC cells, preneoplastic cervical cells, normal cervical cells, HNC cells, preneoplastic head and neck cells, normal head and neck cells, an extract of any of the foregoing cells, a body fluid sample of a human or non-human animal having CC or HNC cancer, and a body fluid sample of a normal human or non-human animal.

In one embodiment of the thirteenth aspect, the control sample can be an isolated polypeptide containing an amino acid sequence of TCAM1, SYCP2 or STAG3. In another embodiment of the thirteenth aspect, the control sample can be an isolated nucleic acid containing a nucleotide sequence of TCAM1, SYCP2 or STAG3 cDNA or complements thereof.

Expression of a marker provided herein may be assessed by any of a wide variety of well-known methods for detecting the expression of a gene at the protein or mRNA level. Non-limiting examples of such methods include immunological methods for detection of a target protein, protein purification methods, protein function or activity assays, nucleic acid hybridization methods, nucleic acid reverse transcription methods and nucleic acid amplification methods.

Preferably, expression of a marker can be assessed at the protein level using an antibody (e.g., a radio-labeled, chromophore-labeled, fluorophore-labeled or enzyme-labeled antibody) or an antibody derivative (e.g., an antibody conjugated with a substrate or with the protein or ligand of a protein-ligand pair (e.g., biotin-streptavidin)) that binds specifically to the marker protein or fragment thereof. For example, enzyme linked immunosorbent assays (ELISAs), Western blot analysis and in situ hybridizations can be employed for this purpose.

Alternatively, expression of a marker can be assessed at the mRNA level by preparing and detecting/measuring mRNA/cDNA from cells. For example, RT-PCR (e.g., quantitative RT-PCR), Southern blot analysis, Northern blot analysis, and in situ hybridizations can be used for this purpose. It is well within the capability of one of ordinary skill in the art to design primers and probes for assessing the expression of a marker at the mRNA level.

As for any cell surface protein, the expression of TCAM1 can be analyzed either qualitatively or quantitatively by flow cytometry. In addition, in vivo medical imaging can be used to detect or quantify the expression of TCAM1. For example, a suitable contrast agent can be linked to a TCAM1 binding agent (e.g., a TCAM1 ligand or antibody) and administered to an individual. Cells that express TCAM1 can be imaged as the contrast agent is retained by these cells due to the binding of the antibody to TCAM1 on the surface of the cells. Similarly, a suitable contrast agent can be linked to a targeting nucleic acid that can hybridize to TCAM1 mRNA and administered to an individual. Cells that express TCAM1 will retain the contrast agent as the targeting nucleic acid hybridizes to TCAM1 mRNA in these cells. As a result, cells that express TCAM1 can be imaged. Any suitable medical imaging techniques can be used. Examples of such techniques include ultrasound, computerized tomography (CT), magnetic resonance imaging (MRI) and nuclear medicine techniques such as gamma ray detection by a gamma ray detector (e.g., a gamma scintillation camera or a 3-dimensional imaging camera), positron emission tomography (PET) and single photon emission computed tomography (SPECT). One of ordinary skill in the art can readily link a contrast agent to a TCAM1 binding agent or TCAM1 mRNA targeting nucleic acid (e.g., covalently through a linker or a chemical bond). For example, for MRI detection, a superparamagnetic iron oxide nanoparticle (SPION) can be conjugated to a TCAM1 antibody or TCAM1 mRNA targeting nucleic acid for administration and MRI detection. For nuclear medicine detection, radionuclide-labeled TCAM1 antibody or radionuclide-labeled TCAM1 mRNA targeting nucleic acid can be administered and radiation emission from the nucleotide can be measured and an image thereof can be obtained. WO 2006/023888 describes linking a medical imaging contrast agent to a nucleic acid probe for imaging gene expression in various tissues by, e.g., MRI. WO 2006/023888 is herein incorporated by reference as if set forth in its entirety.

By way of example, but not limitation, examples of the present invention are described below.

EXAMPLES

Example 1: Differences in Gene Expression in Human Papillomavirus-Positive and -Negative Head/Neck and Cervical Cancers and Gene Expression in Preneoplastic Lesion of Cervical Cancer

APPENDIX I

Appendix I provides supplementary methods figures, and tables and is herein incorporated by reference in its entirety.

Materials and Methods

Tissue Samples:

15 and 27 HNC samples were from the University of Iowa and Harvard School of Public Health, respectively. 5 and 9 FINN samples were from the University of Iowa and the National Disease Research Interchange (NDRI), respectively (Supplementary Table S1). CC and normal cervical samples were from the Gynecologic Oncology Group. Patient information is presented in Table 1A and Supplementary Table S1. All tissue samples were fresh frozen in liquid nitrogen and collected with patients' consent under approval of the Institutional Review Boards from all participating institutions. Also, all the tumor samples were primary resections collected before the initiation of chemotherapy or radiotherapy. Each sample was processed, and RNA was prepared and labeled as described in Supplementary Methods.

Human and HPV Microarrays:

Human gene expression was profiled using Affymetrix U133 Plus 2.0 Arrays (Affymetrix; Santa Clara, Calif.). For HPV detection and genotyping, 70-mer oligonucleotide probes with a $T_M$ of 80° C. (Supplementary Methods) were designed using Oligowiz 1.0 (16), were purchased from MWG-Biotech (High Point, N.C.) and were spotted in quadruplicate on epoxy glass slides (TeleChem International, Inc.; Sunnyvale, Calif.) with a BioRobotics MicroGrid II (Genomic Solutions; Ann Arbor, Mich.). HPV array hybridization was carefully optimized using RNA from known HPV⁺ and HPV⁻ keratinocyte cell lines (Supplementary Methods). HPV arrays were hybridized with biotin-labeled cRNA, processed as in Supplementary Methods, and scanned using an Agilent DNA Microarray Scanner (Agilent; Palo Alto, Calif.). Images were analyzed using Axon GenePix Pro 5.1 Software (Molecular Devices; Sunnyvale, Calif.). 10 μg of cRNA was used for Affymetrix microarray hybridization and scanning at the University of Wisconsin Biotechnology Gene Expression Center (Madison, Wis.). To obtain statistically significant sample number in each group while minimizing unnecessary sample processing and microarray use, inventors selected HNC samples based in part on HPV status.

Statistical Analysis:

Tools in R (17) and Bioconductor (18) were adapted for statistical analysis. Probe set summary measures were computed by robust multiarray averaging (19) applied to the combined set of 84 microarrays. Average base-2 log expression was used to summarize each probe-set's expression within a tissue class. Multidimensional scaling allowed global (i.e., averaged over the genome) comparisons between classes, and class-restricted nonparametric bootstrap sampling (20) was used to measure the significance of observed differences between global correlations computed on pairs of tumor classes. Permutation testing was used to confirm that each measured correlation was significantly non-zero. The primary analysis of differential gene expression at the probe-set level was done in three pairwise comparisons: Tumor versus Normal, HPV$^+$ vs. HPV$^-$, and HNC vs. CC. Fold changes and t-statistics were used to identify differentially expressed probe sets; the latter were converted to q-values to control false discovery rate (21).

Enrichment of gene ontology (GO) categories for differentially expressed genes was measured using random-set testing methods (22, 23). Briefly, the proportion of significantly altered genes and the average log fold change for all genes in each of 2760 GO categories were compared, respectively, to their distributions on a random set of genes in order to obtain standardized enrichment Z scores. A category was considered significantly enriched for altered genes if both of these Z scores exceeded 4 (nominal p-value $3 \times 10^{-5}$). Calculations used version 1.0 of the R package allez, and the October 2005 build of Bioconductor package hgu133plus2. The same Z score standardization applied to class-averaged expression profiles (above) was used to compute GO profiles for each tissue class. These were correlated between classes to assess the similarity of tissue classes.

Figure 2:
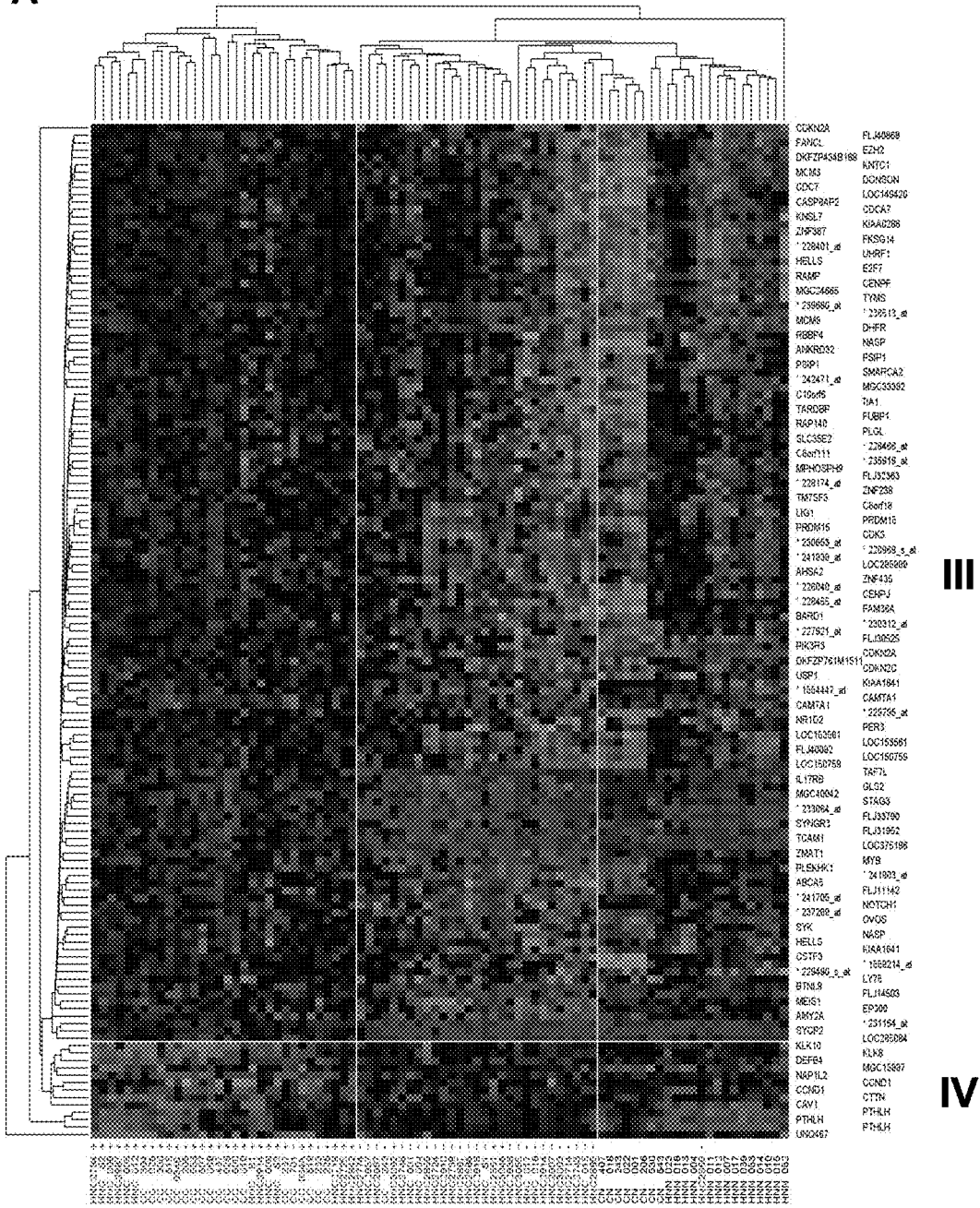
FIG. 2: Gene expression signatures for HPV$^+$ vs. HPV$^−$ cancers and HNC vs. CC cancers. (A) Normalized expression values are shown for all 84 samples and 137 probe sets that were significantly differentially expressed between the HPV$^+$ cancers and the HPV cancers. As shown in the key at the bottom right, colors indicate high (red) and low (green) expression, corresponding to a +7.5 to −8.2 log 2 scale of fold change relative to each gene's average across all 84 microarrays. These genes were ordered by hierarchical clustering based on similarities in their expression changes across the samples (see, dendogram at left). Gene sets III and IV showed significantly up- or downregulated probe sets, respectively. HPV$^+$ cancer samples are indicated as red text and HPV cancer samples are indicated as blue text on the bottom of a heat map. X axis is patient sample; Y axis is the probe sets, which are listed in order below in Table 2A. (B) Like (A), but using 291 probe sets that were significantly differentially expressed between CC and HNC. Again, X axis is patient sample; Y axis is the probe sets, which are listed in order below in Table 2B. Gene sets V and VII showed significantly upregulated probe sets in CC vs. HNC, while gene set VI showed significantly downregulated probe sets. CC samples are indicated as red text, and HNC samples are indicated as blue text on the bottom of the heat map. * indicates probe set ID that does not have annotated gene name. HPV status is shown as + and − on each sample ID.
Figure 2:
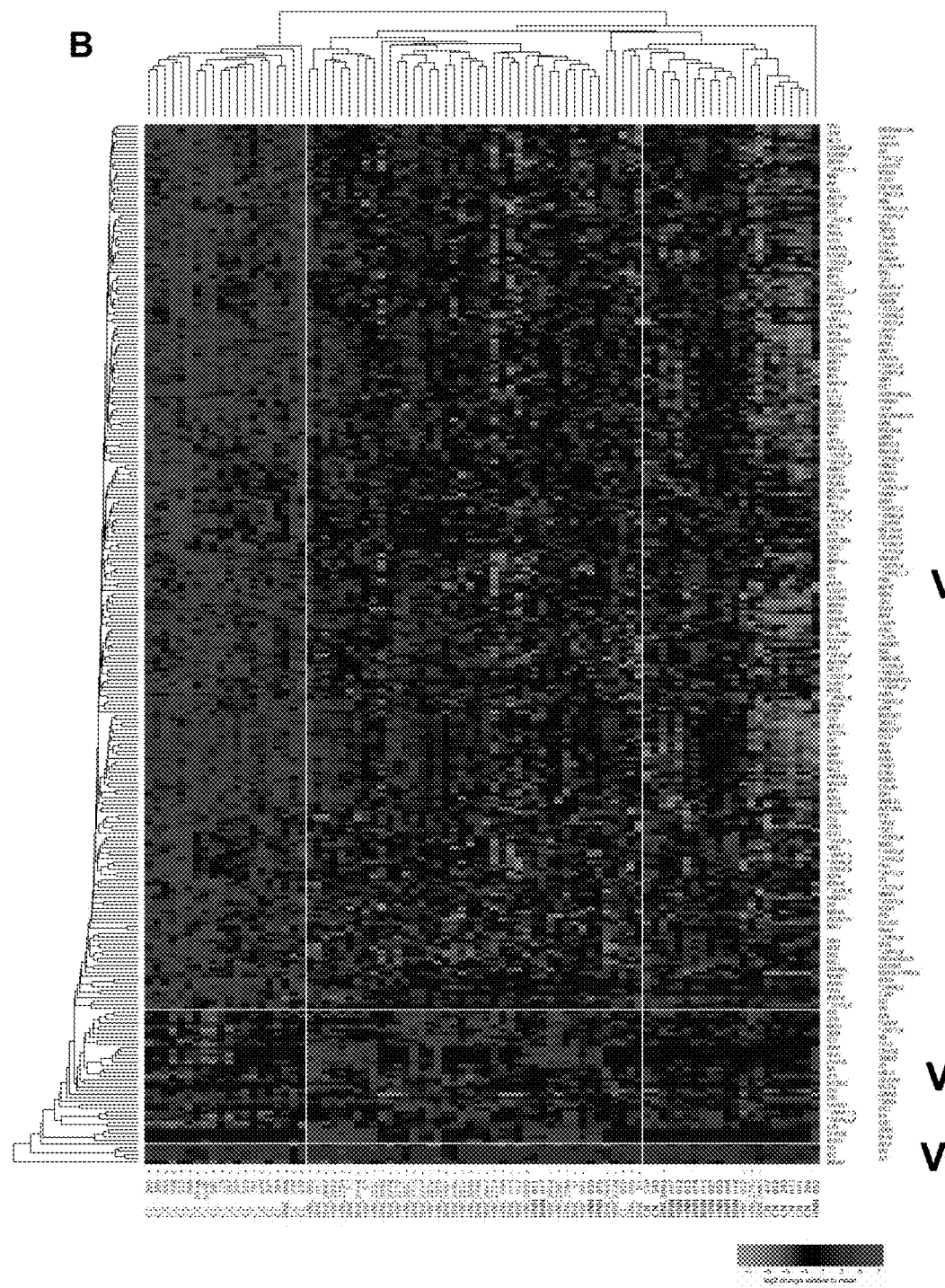

The inventors developed a parametric testing strategy (20) to evaluate the significance of apparent profile-defined tumor subgroups of the HPV$^+$ HNC tumors (Supplementary FIG. S4A-C). Specifically, a multivariate normal distribution was fit to data from the 16 HPV$^+$ HNC arrays using n=100 genes most differentially expressed between HPV$^+$ cancers and HPV$^-$ cancers (FIG. 2A). The rationale was that such a unimodal Gaussian distribution represents a baseline null hypothesis of no actual subgrouping from which the significance of apparent subgroups could be gauged. Because the sample covariance matrix was rank deficient, inventors an empirical Bayes estimate of covariance (24) and repeatedly ($10^4$ times) sampled multivariate random n-vectors from a centered normal population with this covariance matrix. Using each bootstrap sample we divided the 16 tumors according to the subgrouping derived at the penultimate merge of a hierarchical cluster analysis. Each split was scored by the average of the squared t-statistics between the two subgroups, which is large if the subgroups are relatively well separated. The average squared t statistic on the subgroups identified by hierarchical clustering of the actual data was compared to the distribution of such scores derived, as above, on the null hypothesis that the profiles emerge from a single, multivariate normal, population, and a p-value was computed. To assess sensitivity, the inventors repeated the calculations at a range of gene set sizes n.

Tissue culture, quantitative reverse transcriptase-PCR, Western blot analysis and immunohistochemistry were performed as described in Supplementary Methods.

Results

Tissue Samples, Microarray Profiling, and HPV Status:

Eighty four samples including 42 HNC, 14 head and neck normals (HNN), 20 CC and 8 cervical normals (CN) were cryosectioned, and selected sections were stained with hematoxylin and eosin, verified free of autolysis and freezing artifacts, and analyzed histopathologically. Relevant patient information is summarized in Table 1A. All tumor samples were collected prior to chemo- or radiotherapy. For all normal tissues and tumors with less than 90% cancer cells (61/84), laser microdissection was performed to capture normal epithelial or tumor cells, respectively. Complementary RNA (cRNA) was prepared and hybridized to Affymetrix U133 Plus 2.0 microarrays containing oligonucleotide probes for all known expressed human mRNAs. Normalization was performed as described in Experimental Procedures. Resulting microarray data were deposited to the NCBI Gene Expression Omnibus database under general accession number GSE6791.

HPV status and genotype were determined by hybridization to custom-made 70-mer oligonucleotide microarrays containing probes for all 37 known mucosotropic HPV genotypes plus positive and negative control probes. These microarrays were sufficiently sensitive to detect HPV in cell lines harboring a few extrachromosomal copies or a single integrated copy of HPV DNA. No normal tissue showed any significant HPV signal but, consistent with prior findings (3), 16 of 42 HNCs harbored HPV (13 HPV16, two HPV33, and one HPV18; Table 1B). About half of CC were HPV16-positive, with lesser numbers carrying HPV genotypes 18, 31, 33, 35, 58 or 66 (Table 1B). Three of 20 CCs hybridized well to control cell mRNA probes but showed no detectable HPV signal. PCR with consensus HPV L1 primers MY09-MY11 (25) confirmed absence of detectable HPV DNA in these samples.

Since these samples shared some expression patterns with HPV$^+$ CC and HNCs (see, below), they may contain HPV, possibly with sequence variations inhibiting detection by these sequence-specific methods (26). However, varying the HPV status assigned to these three CCs had only minimal effects on the gene expression signature differentiating HPV$^+$ and HPV$^-$ cancers. Comparisons of HPV$^+$ and HPV$^-$ cancers with these samples included as HPV$^-$ CC, as HPV$^+$ CC, or excluded all revealed HPV$-$ specific expression signatures dominated by a robust common core of nearly 140 genes. The analysis below reports HPV$^+$ and HPV$^-$ cancer comparisons based on the original HPV$^-$ assignment of these CCs, since this yielded the best-conserved core expression signature (137 genes), while the alternate assumptions each added some additional genes whose differential expression levels were not as well conserved across the analyses.

Gene Expression Relationships Among HPV$^+$ and HPV$^-$ HNCs and CCs:

Global pairwise comparisons of complete mRNA expression profiles between all tumor and normal sample classes were performed by multidimensional scaling (27). This analysis (FIG. 1A) measures for each pair of tumor and normal classes the distances between class-averaged log 2 expression levels over all 54,675 Affymetrix probe sets. Not surprisingly, the most closely related classes were HPV$^+$ HNC and HPV$^-$ HNC (average distance=0.17). Notably, next closest were the two HPV$^+$ cancers, HPV$^+$ HNC and HPV+ CC, whose distance of 0.21 was closer than either to its corresponding normal (0.29, 0.53).

The global effect of virus-specific and tissue-specific factors is further illustrated in FIG. 1B, which compares for paired tumor classes the log 2 average expression levels, relative to corresponding normals, of all probe sets. The indicated Pearson correlation coefficients confirm that the highest correlation is between HPV+ HNC and HPV− HNC (R=0.81). The substantial correlation between HPV+ HNCs and HPV CCs (R=0.58), well above HPV+ CCs and HPV− HNCs (R=0.46), again implies a substantial role for virus-dependent, tissue-independent factors in gene expression changes. HPV+ HNC vs. HPV+ CC correlation exceeds the HPV− HNC vs. HPV+ CC correlation in over 90% of bootstrap sampled data sets, and all correlations were significant by permutation analysis. Thus, both HPV status and tissue type contribute to the relatedness and distinction of HPV+ HNCs, HPV− HNCs and HPV+ CCs.

To offset variation in probe set-level measurements, the inventors performed similar correlation analyses on fold changes averaged over Gene Ontology (GO) gene classes rather than individual probe-sets, reinforcing the findings above (Supplementary FIG. S3A).

While HPV+ HNC and HPV− HNC exhibited generally high positive correlation in gene expression changes from normal, many genes had altered expression between these two classes. FIG. 1B highlights 47 genes selectively upregulated (red points) and 45 genes selectively downregulated (blue points) by >2.6 fold in HPV+ HNC relative to HPV− HNC (see also, Supplementary Table S3A and S3B). Notably, for genes that were highly upregulated in HPV+ HNC relative to HPV− HNC, parallel comparison of expression levels between HPV+ HNC and CC shifted their distribution in the plot dramatically rightward, revealing substantial correlated expression in these two HPV+ cancers (red arrow and points in FIG. 1B, middle panel).

Conversely, genes that were significantly downregulated in HPV+ HNC relative to HPV− HNC showed a substantial but opposite leftward shift into greater correlation in a comparison plot of expression levels between HPV+ HNC and CC (blue arrow and points in FIG. 1B, middle panel). Thus, the tumor-specific expression changes in these genes correlated much more strongly with the presence of HPV than the tissue site.

To further analyze gene expression changes based on tumor/normal, HPV+/HPV−, and HNC/CC differences, the inventors identified for each comparison differentially expressed genes with fold change >2 and t-test q-value <0.001. By these criteria, as shown in FIG. 1C, 1701 and 243 genes were up- and downregulated, respectively, in tumors relative to normals, while 124 and 13 genes were up- and downregulated in HPV+ relative to HPV− cancers, and 256 and 35 genes were up- and downregulated in CC relative to HNC.

More specifically, in tumor/normal comparisons (Supplementary FIG. 53B and Table S5), HPV+ HNC, HPV− HNC and CC all were upregulated relative to normals for a gene set I including keratins (KRT8, 17, 18), caveolin (CAV2), interferon α-inducible protein 6-16 (G1P3), matrix metallopeptidase 12 (MMP12), collagens (COL4A1, COL4A2) and phospholipid scramblase 1 (PLSCR1), and downregulated for another set II including other keratins (KRT4, 13, 15), programmed cell death 4 (PDCD4), protein tyrosine kinase 6 (PTK6), epithelial membrane protein 1 (EMP1), extracellular matrix protein 1 (ECM1), interleukin 1 receptor (IL1R2) and transglutaminase 3 (TGM3).

Relative to HPV− HNC (FIG. 2A, Table 2A), HPV+ HNC and CC showed significantly increased expression of gene set III, including PC4/SFRS1-interacting protein 1 (PSIP1), V-myb (MYB), synaptogyrin 3 (SYNGR3), SWI/SNF-related, matrix-associated, actin-dependent regulator of chromatin (SMARCA2), SYCP2, p16 (CDKN2A), lymphoid-specific helicase (HELLS) and TCAM1, while expression was decreased for gene set IV, including parathyroid hormone-like hormone (PTHLH), cortactin (CTTN), kallikreins (KLK8, 10), cyclin D1 (CCND1), caveolin 1 (CAV1) and defensin β4 (DEFB4). At the GO category level (Supplementary Table S4A), HPV+ cancers were upregulated relative to HPV− cancers for annotations related to DNA replication and cell cycle, and downregulated in genes involved in epidermal development and hormone activity.

In comparison between CC and HNC (FIG. 2B, Supplementary Table S6), CCs showed significantly upregulated expression of gene sets V and VII, including estrogen receptor 1 (ESR1), keratin 19 (KRT19), X (inactive)-specific transcript (XIST) and zinc finger protein 367 (ZNF367), while HNC showed increased expression of gene set VI (FIG. 2B, Supplementary Table S6), including dermatopontin (DPT), desmocollin 1 (DSC1), melanoma antigen A12 (MAGEA12) and chromosome Y open reading frame 15B (CYorf15B).

A Distinct Subgroup in HPV− Cancers:

Hierarchical clustering of differentially expressed genes between HPV+ and HPV− cancers revealed two subgroups of HPV+ cancers (Supplementary FIGS. S4A and S4B). These subgroups (α and β) were not correlated with any identified sample characteristics including anatomical site, age, or clinical stage (Supplementary Table S1A0) and were robustly preserved when the grouping was repeated using different agglomeration methods for clustering and varying numbers of differentially expressed genes.

The smaller subgroup, α showed high up-regulation of a set of B lymphocyte/lymphoma-related genes including baculoviral IAP repeat 3 (BIRC3), butyrophilin-like 9 (BTNL9), DKFZ P56400823, homeobox C6 (HOXC6), and B-cell CLL/lymphoma 11A (BCL11A) (Supplementary FIG. S4C, Supplementary Table S7). B cell-related gene expression by this tumor subgroup was not due to tumor-infiltrating B cells, since there was no correlation between this subgroup and expression of CD19, CD20, and immunoglobulins, which are expressed in B cells throughout most or all circulating stages (28).

Subgroup α also was upregulated relative to other HPV+ cancers for genes expressed by endothelial cells, including vascular cell adhesion molecule 1 (VCAM1) and zinc finger protein 62 (ZNF62) and downregulated for genes, including several small proline-rich proteins (SPRR1A and SPRR2A), keratins (KRT6B and KRT 16), and gap junction proteins (GJB2 and GJB6) (Supplementary FIG. S4C; Supplementary Table S7). Expression of synaptopodin (SYNPO2), an important regulator of cell migration (29), was increased >20-fold in this subgroup relative to other HPV+ cancers, suggesting potentially increased invasiveness.

Due to variations among microarray platforms and methods, reproducibility of expression profiling has been one of the biggest challenges in microarray studies of cancer (30). Chung et al. (5) recently reported dividing 60 HNCs into four subgroups by gene expression patterns. However, clustering of the inventors' samples based on the genes reported as differentially-expressed signatures of these four subgroups revealed little significant correlation. Possible causes for this lack of correlation include use of whole samples in the prior study vs. selectively microdissected samples here, differences in the microarray platforms used, or limitations in sample group sizes in these studies. Supplementary FIG. S5A shows the best association of our HNC samples into four groups based on the prior signature gene sets. Though weak, the B lymphocyte/lymphoma-related subset a identified, showed the most similarity for Chung et al.'s subgroup 2, in that most genes in Chung et al.'s set E were downregulated and, for two of the 6 relevant tumors (HNC005, HNC012), some genes in set F were upregulated, primarily including mesenchymal markers associated with poorer clinical outcomes (5, 31): syndecan, vimentin, and some collagens.

Figure 3:
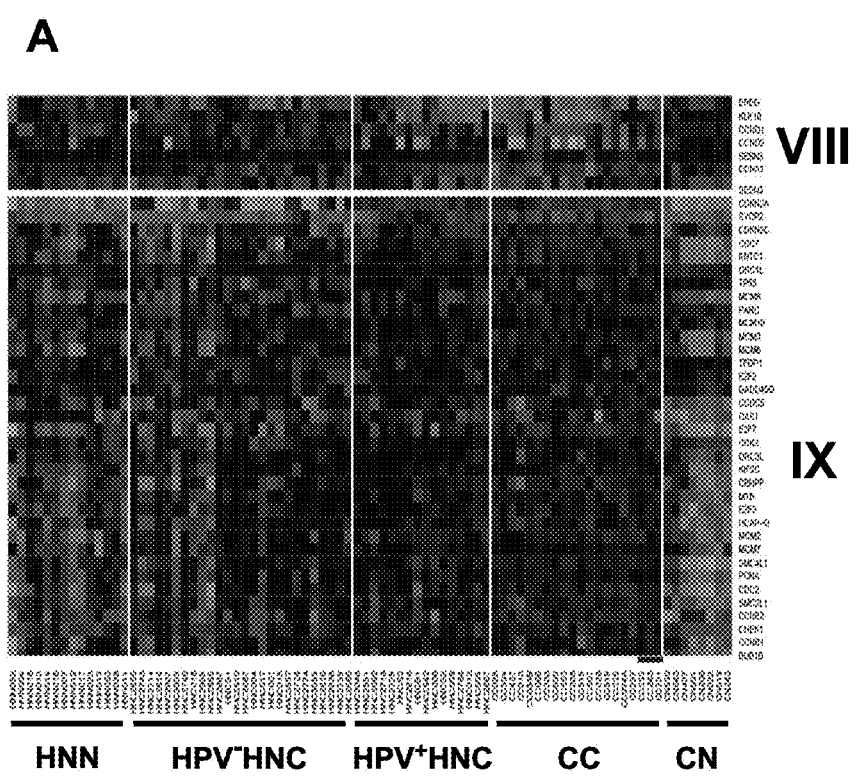
FIG. 3: Cell cycle-related genes were upregulated in HPV$^+$ cancers. X axis is patient sample; y axis is probe sets, which are listed in order below in Table 3A. Highly upregulated genes in HPV$^+$ cancers were analyzed by gene ontology grouping (A). Cell cycle-related genes were selected and plotted on a heat map. HPV$^−$ CCs are indicated with blue bars. Up- and downregulated genes were indicated in cell cycle pathway provided by the KEGG database (B). The red and blue boxes indicate upregulated genes in HPV$^+$ and HPV$^-$ cancers compared to corresponding normal tissue, respectively. A part of the cell cycle-related genes was analyzed using qRT-PCR (C). Fold changes of the gene expression in near-diploid immortalized keratinocytes (NIKS) relative to gene expression in NIKS-16 are shown. Data are represented as mean+/−standard deviation.
Figure 3:
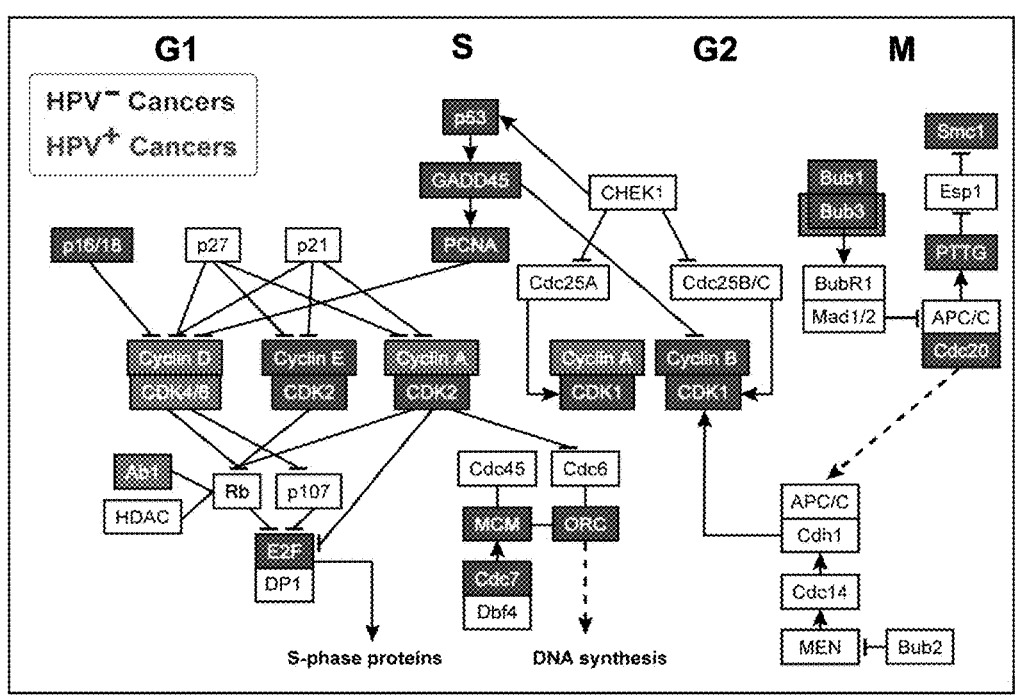
Figure 3:
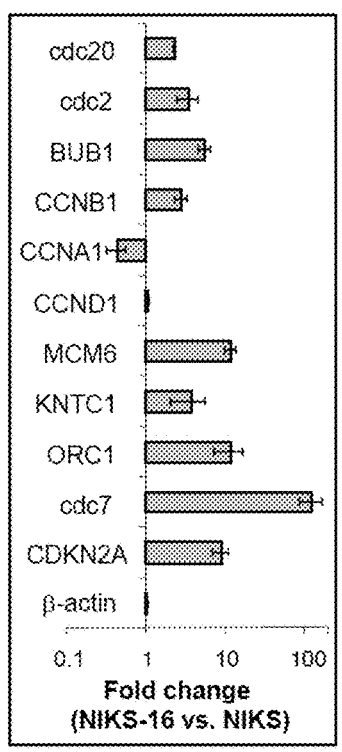

HP$^+$ and HPV$^-$ Cancers are Activated in Different Components of the Cell Cycle Pathway:

E7 oncoproteins of high risk HPVs induce DNA replication and mitosis by multiple mechanisms including interacting with pRb, HDACs and other factors to activate cell cycle-regulated transcription factors such as E2F (32-34). However, the extent of resulting gene expression changes, the full contributions of other HPV genes and additional genetic changes to oncogenesis, and the relation of these effects to those in HPV$^-$ HNC have not been determined. To test for differential expression in HPV$^+$ versus HPV$^-$ cancers, we examined cell cycle-related genes based on GO classification. A significant subset of cell cycle-regulated genes was differentially expressed in HPV$^+$ HNC and CC relative to HPV$^-$HNC (FIG. 3A, Table 2B). As shown in FIG. 3B, HPV$^-$ HNCs upregulated, relative to HPV$^+$ cancers, a small set of cell cycle-specific genes including cyclin D1/D2 (CCND1 and CCND2) (G1-associated) and cyclin A1 (CCNA1) (FIGS. 3A, set VIII, and 3B).

By contrast, HPV$^+$ cancers upregulated, relative to HPV$^-$ HNC, a much larger set of cell cycle-specific genes such as cyclin E2 (CCNE2; G1-associated), cyclin B1 (CCNB1; G2-associated), and multiple MCMs (FIGS. 3A, set IX, and 3B). Among these, many genes that enhance DNA replication and cell mitosis including proliferating cell nuclear antigen (PCNA), E2Fs, cdc2, cdc7 and MCMs were significantly upregulated in HPV$^+$ HNC and CC relative to HPV$^-$HNC, implying that the HPV$^+$ cancers were more active in cell division.

Figure 4:
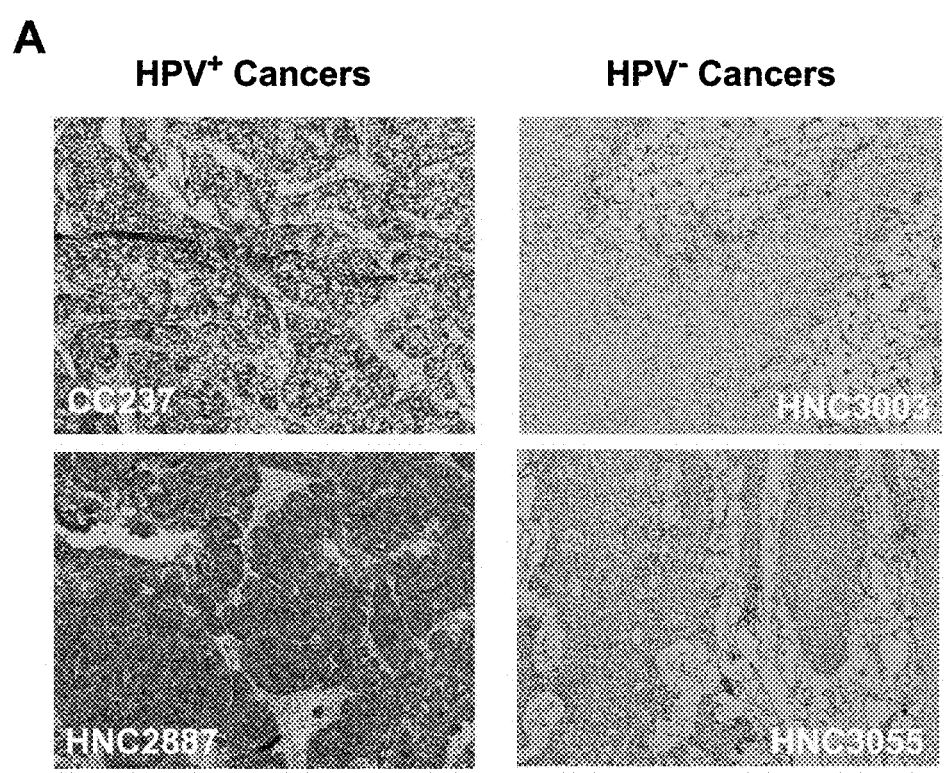
FIG. 4: Proliferating cell nuclear antigen (PCNA) protein expression was upregulated in HPV$^+$ cancers. Using anti-human PCNA antibody, immunohistochemistry (IHC) was performed with sections of 11 HPV$^+$ and 10 HPV$^-$ cancers. IHC images were analyzed and quantified as described previously (53; see, Supplementary Methods). Representative IHC images (A) and calculated density of all samples (B) are shown. Red bars indicate the mean values of each class. Tissue was also briefly counter-stained with hematoxylin.
Figure 4:
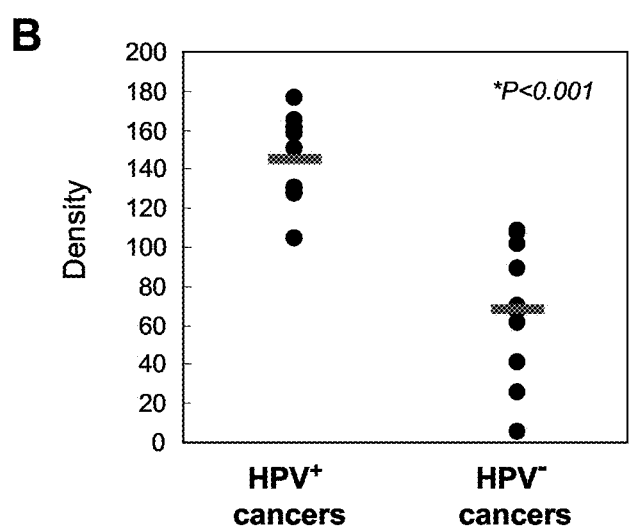

A subset of these genes were analyzed by quantitative reverse transcriptase-polymerase chain reaction (qRT-PCR) with total RNA extracted from naturally immortalized human keratinocyte lines NIKS-16 and NIKS, which have and lack an extrachromosomal HPV16 genome, respectively (35). In keeping with the microarray results, p16, cdc7, origin recognition complex 1 (ORC1), kinetochore-associated protein (KNTC1), MCM6, cyclin B1 (CCNB1), BUB1, cdc2 and cdc20 were highly upregulated by HPV16, while cyclin A1 (CCNA1) was downregulated (FIG. 3C). Since the NIKS-16 cells were only 5 to 6 passages after stable HPV16 transfection, these results indicate that HPV deregulates a subset of cell cycle-related genes soon after being acquired by cells. To eliminate possible effects of the prior spontaneous immortalization of NIKS cells, the inventors measured gene expression levels in normal (i.e., early passage) cervical epithelial cells transduced with HPV16 E6 and/or E7 oncogenes. The results confirmed NIKS data, showing an upregulation of CCNB1, cdc2, ORC1 and p16 by HPV16 E6 and E7 expression (Supplementary FIG. S6). Moreover, immunohistochemistry showed that tumor cells in HPV$^+$ cancers expressed significantly (p<0.001) higher levels of PCNA protein than HPV$^-$ tumor cells (FIG. 4). In addition, PCNA protein levels were highly correlated with cell cycle-related gene expression levels (Supplementary Table S9). Together, these results indicate that HPV acts in HPV$^+$ HNCs and CCs to deregulate the cell cycle pathway in shared ways that are markedly distinct from HPV$^-$HNCs.

Figure 5:
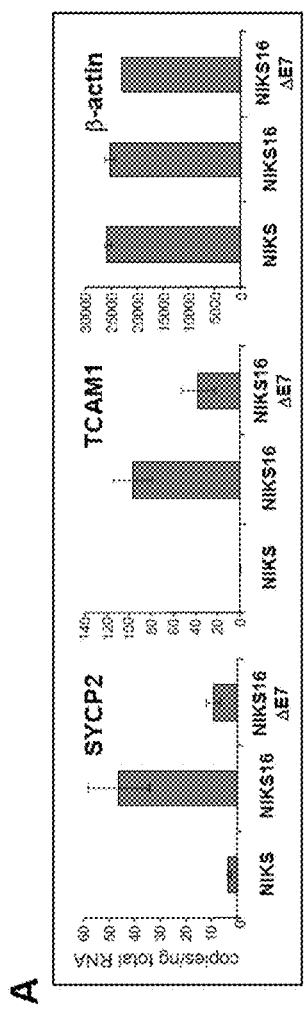
FIG. 5: Testis-specific genes SYCP2 and TCAM1 were induced by HPV16. Real time qRT-PCR was performed with total RNA extracted from NIKS cells with and without HPV16 (A). Also, total RNA from NIKS-16 cells without HPV16 E7 protein expression was used to show that testis-specific gene induction was partially by E7 protein. SYCP2 induction in HPV$^+$ cell lines was confirmed with Western blot analysis using anti-human SYCP2 antibody (B). Real time qRT-PCR was performed with total RNA extracted from primary cervical keratinocytes with either or both HPV16 E6 and E7 delivered by recombinant retrovirus. Retrovirus without HPV16 gene was used as mock control (C). STAG3 mRNA expression in various cell lines was quantified using qRT-PCR, and relative fold change to NIKS cells were plotted (D). Data are represented as mean+/−standard deviation.
Figure 5:
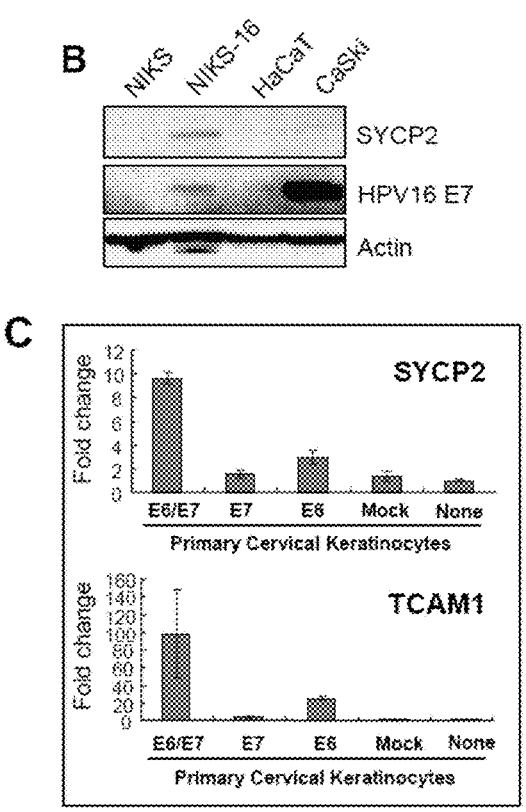
Figure 5:
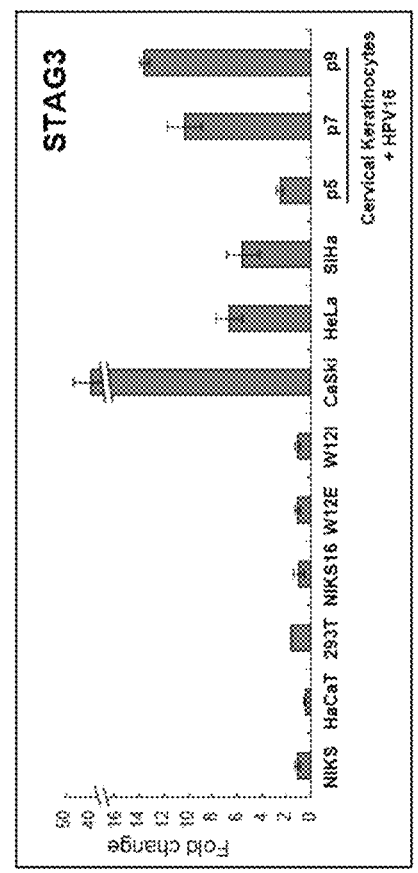

Upregulation of Novel Testis Antigens in HPV$^+$ Cancers:

Genes highly upregulated in HPV$^+$ cancers relative to HPV$^-$ HNC included two testis-specific genes not normally expressed in somatic cells—SYCP2 and TCAM1 (FIG. 2A and Table 2A). qRT-PCR showed that SYCP2 and TCAM1 expression increased >15 and >100,000 fold, respectively, in HPV16$^+$ NIKS-16 relative to HPV16$^-$ NIKS cells (FIG. 5A). SYCP2 also was detected at the protein level in NIKS-16 but not NIKS cells (FIG. 5B). Comparative studies with NIKS16ΔE7 cells (FIG. 5A) and in primary cervical keratinocytes with or without HPV16 E6 and/or E7 expression (FIG. 5C), showed that SYCP2 and TCAM1 expression are synergistically upregulated by E6 and E7.

A third testis-specific gene upregulated in HPV$^+$ HNC and CC relative to HPV$^-$HNC was STAG3 (Table 2A). Unlike SYCP2 and TCAM1, STAG3 mRNA was not upregulated in early passage NIKS-16 relative to NIKS cells nor in early passage HPV$^+$ W12 cells (FIG. 5D). However, in three HPV$^+$ cervical carcinoma cell lines (i.e., CaSki, HeLa and SiHa), STAG3 expression was increased ~6-40-fold over NIKS. Additionally, the inventors observed a passage-dependent, increased expression of STAG3 in cervical epithelial cells harboring HPV16 (cervical keratinocytes +HPV16; FIG. 5D). These data suggest that STAG3 induction was not an immediate effect of the virus, but rather a delayed response.

SYCP2 and TCAM1 were induced by HPV16 in human neonatal keratinocytes and cervical keratinocytes within a few cell passages, and this induction was dependent on E6 and E7 (FIGS. 5A and 5C). TCAM1(52) in particular could be a useful biomarker and therapeutic target as it is expressed on the cell surface and thus is directly accessible.

Figure 6:
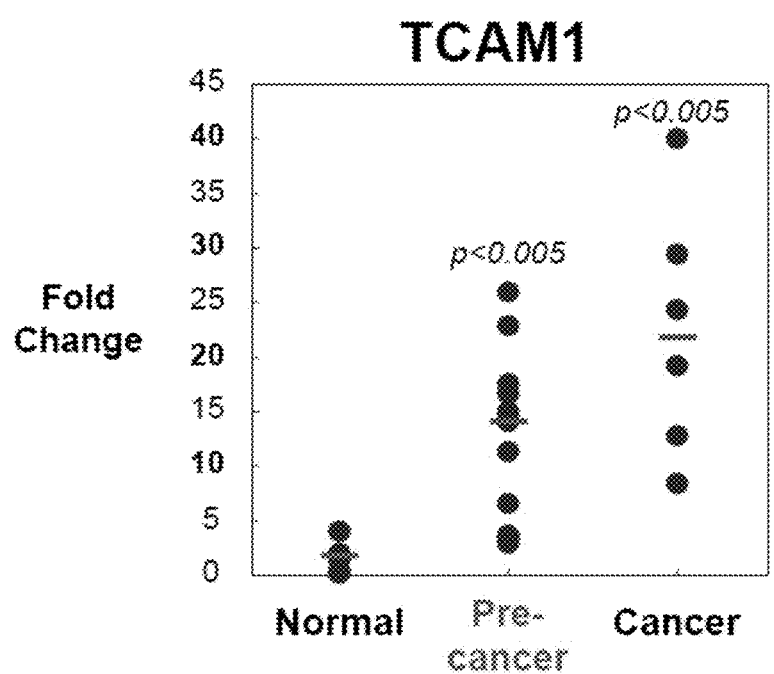
FIG. 6: TCAM1 expression was significantly induced in preneoplastic lesions of cervix (CIN).

TCAM1 Expression in Preneoplastic Lesion of Cervical Cancer:

TCAM1 expression in HPV+ preneoplastic lesions of cervix (CIN stages 1-3) was studied, and the inventors found that TCAM1 expression was induced significantly in preneoplastic lesions of cervix (see, pre-cancer in FIG. 6).

TABLE 1A

Patient information.

| Head and Neck Cancers | | |
|---|---|---|
| Cases and Controls | N = 54/56 [A] | % |
| Case | 40 | 74.1 |
| Control | 14 | 25.9 |
| Age (mean = 59.9, ±15.2) | | |
| ≤55 years | 19 | 35.2 |
| >55 years | 35 | 64.8 |
| Gender | | |
| Female | 20 | 37.0 |
| Male | 34 | 63.0 |
| Tumor Site | | |
| Oral Cavity | 32 | 59.3 |
| Oropharynx | 22 | 40.7 |
| Normal Controls Only | N = 14 | % |
| Age (mean = 58.0, ±23.6) | | |
| ≤55 years | 6 | 42.9 |
| >55 years | 8 | 57.1 |

TABLE 1A

Patient information.

| Gender | | |
|---|---|---|
| Female | 9 | 64.3 |
| Male | 5 | 35.7 |
| Tumor Site | | |
| Oral Cavity | 9 | 64.3 |
| Oropharynx | 5 | 35.7 |

| Cases Only | N = 40/42 [A] | % |
|---|---|---|
| Age (mean = 60.0, ±11.3) | | |
| ≤55 years | 13 | 32.5 |
| >55 years | 27 | 67.5 |
| Gender | | |
| Female | 11 | 27.5 |
| Male | 29 | 72.5 |
| Tumor Site | | |
| Oral Cavity | 23 | 57.5 |
| Oropharynx | 17 | 42.5 |
| Stage | | |
| I/II | 6 | 15.0 |
| III | 8 | 20.0 |
| IV | 10 | 25.0 |
| Unknown | 16 | 40.0 |
| Grade | | |
| Poorly/undifferentiated | 12 | 30.0 |
| Well/moderately diff'd | 28 | 70.0 |

Cervical Cancers

| Cases and Controls | N = 28 | % |
|---|---|---|
| Case | 20 | 71.4 |
| Control | 8 | 28.5 |
| Age (mean = 43.9, ±10.4) | | |
| ≤45 years | 18 | 64.3 |
| >45 years | 10 | 35.7 |

| Normal Controls Only | N = 8 | % |
|---|---|---|
| Age (mean = 58.0, ±23.6) | | |
| ≤45 years | 3 | 37.5 |
| >45 years | 5 | 62.5 |

| Cases Only | N = 20 | % |
|---|---|---|
| Age (mean = 42.5, ±10.6) | | |
| ≤45 years | 7 | 35.0 |
| >45 years | 13 | 67.0 |
| Stage | | |
| IB | 16 | 80.0 |
| II/III | 3 | 15.0 |
| IV | 1 | 5.0 |
| Grade | | |
| Poorly/undifferentiated | 12 | 60.0 |
| Well/moderately diff'd | 8 | 40.0 |

[A] Two patients have missing data.

TABLE 1B

HPV status in tumor samples.

| | Head and Neck | | Cervix | |
|---|---|---|---|---|
| Diagnosis | Cancer | Normal | Cancer | Normal |
| Total | 42 | 14 | 20 | 8 |
| HPV negative | 26 | 14 | 3 | 8 |
| HPV positive | 16 | — | 17 | — |
| HPV16 | 13 | — | 8 | — |
| HPV18 | 1 | — | 3 | — |
| HPV31 | — | — | 1 | — |
| HPV33 | 2 | — | 1 | — |
| HPV35 | — | — | 2 | — |
| HPV58 | — | — | 1 | — |
| HPV66 | — | — | 1 | — |

TABLE 2A

Differentially expressed genes in HPV$^+$ cancers vs. HPV$^-$ cancers.

| Probeset ID* | Gene title | Gene symbol | t-statistic | Overlaps† |
|---|---|---|---|---|
| 207039_at | cyclin-dependent kinase inhibitor 2A (melanoma, p16, inhibits CDK4) | CDKN2A | 6.73 | T/N, CC/HNC |
| 228286_at | hypothetical protein FLJ40869 | FLJ40869 | 5.45 | CC/HNC |
| 218397_at | Fanconi anemia, complementation group L | FANCL | 5.63 | CC/HNC |
| 203358_s_at | enhancer of zeste homolog 2 (*Drosophila*) | EZH2 | 6.41 | CC/HNC |
| 218783_at | DKFZP434B168 protein | DKFZP434B168 | 6.00 | CC/HNC |
| 206316_s_at | kinetochore associated 1 | KNTC1 | 6.26 | T/N, CC/HNC |
| 201555_at | MCM3 minichromosome maintenance deficient 3 (*S. cerevisiae*) | MCM3 | 5.88 | T/N, CC/HNC |
| 221677_s_at | downstream neighbor of SON | DONSON | 6.08 | T/N, CC/HNC |
| 204510_at | CDC7 cell division cycle 7 (*S. cerevisiae*) | CDC7 | 6.42 | T/N, CC/HNC |
| 227255_at | casein kinase | LOC149420 | 5.59 | CC/HNC |
| 222201_s_at | CASP8 associated protein 2 | CASP8AP2 | 5.09 | T/N, CC/HNC |
| 224428_s_at | cell division cycle associated 7 | CDCA7 | 4.36 | CC/HNC |
| 219306_at | kinesin-like 7 | KNSL7 | 5.45 | CC/HNC |
| 212621_at | KIAA0286 protein | KIAA0286 | 4.60 | T/N |
| 229551_x_at | zinc finger protein 367 | ZNF367 | 6.29 | T/N, CC/HNC |
| 222848_at | leucine zipper protein FKSG14 | FKSG14 | 4.37 | T/N, CC/HNC |
| 228401_at | — | — | 4.49 | T/N, CC/HNC |
| 225655_at | ubiquitin-like, containing PHD and RING finger domains, 1 | UHRF1 | 4.69 | T/N, CC/HNC |
| 227350_at | Helicase, lymphoid-specific | HELLS | 5.13 | T/N, CC/HNC |
| 228033_at | E2F transcription factor 7 | E2F7 | 4.36 | T/N, CC/HNC |
| 218585_s_at | RA-regulated nuclear matrix-associated protein | RAMP | 4.99 | T/N, CC/HNC |
| 209172_s_at | centromere protein F, 350/400 ka (mitosin) | CENPF | 4.51 | T/N, CC/HNC |
| 226456_at | hypothetical protein MGC24665 | MGC24665 | 6.23 | T/N |
| 202589_at | thymidylate synthetase | TYMS | 5.51 | T/N |

TABLE 2A-continued

Differentially expressed genes in HPV+ cancers vs. HPV− cancers.

| Probeset ID* | Gene title | Gene symbol | t-statistic | Overlaps† |
|---|---|---|---|---|
| 239680_at | — | — | 5.19 | CC/HNC |
| 236513_at | — | — | 4.85 | CC/HNC |
| 224320_s_at | MCM8 minichromosome maintenance deficient 8 | MCM8 | 5.73 | T/N |
| 202532_s_at | dihydrofolate reductase | DHFR | 5.24 | None |
| 210371_s_at | retinoblastoma binding protein 4 | RBBP4 | 4.73 | T/N, CC/HNC |
| 201970_s_at | nuclear autoantigenic sperm protein (histone-binding) | NASP | 6.42 | T/N, CC/HNC |
| 223542_at | ankyrin repeat domain 32 | ANKRD32 | 4.40 | T/N, CC/HNC |
| 209337_at | PC4 and SFRS1 interacting protein 1 | PSIP1 | 6.01 | CC/HNC |
| 205961_s_at | PC4 and SFRS1 interacting protein 1 | PSIP1 | 5.59 | CC/HNC |
| 206542_s_at | SWI/SNF related, matrix associated, actin-dep chromatin regulator | SMARCA2 | 4.88 | None |
| 242471_at | — | — | 4.97 | None |
| 229442_at | hypothetical protein MGC33382 | MGC33382 | 4.45 | T/N, CC/HNC |
| 203482_s_at | chromosome 10 open reading frame 6 | C10orf6 | 6.24 | CC/HNC |
| 201448_at | TIA1 cytotoxic granule-associated RNA binding protein | TIA1 | 5.60 | None |
| 221264_s_at | TAR DNA binding protein | TARDBP | 5.57 | None |
| 214093_s_at | Far upstream element (FUSE) binding protein 1 | FUBP1 | 4.78 | None |
| 209285_s_at | retinoblastoma-associated protein 140 | RAP140 | 5.56 | None |
| 230120_s_at | plasminogen-like | PLGL | 5.39 | None |
| 217122_s_at | solute carrier family 35, member E2 | SLC35E2 | 7.47 | None |
| 228466_at | Clone IMAGE: 111714 mRNA sequence | — | 5.59 | None |
| 212179_at | chromosome 6 open reading frame 111 | C6orf111 | 5.31 | None |
| 235919_at | — | — | 5.10 | None |
| 215731_s_at | M-phase phosphoprotein 9 | MPHOSPH9 | 4.64 | None |
| 229886_at | FLJ32363 protein | FLJ32363 | 5.87 | None |
| 228174_at | — | — | 6.44 | None |
| 212774_at | zinc finger protein 238 | ZNF238 | 4.65 | None |
| 226478_at | Transmembrane 7 superfamily member 3 | TM7SF3 | 4.64 | None |
| 42361_g_at | chromosome 6 open reading frame 18 | C6orf18 | 5.76 | CC/HNC |
| 202726_at | ligase I, DNA, ATP-dependent | LIG1 | 6.26 | None |
| 231931_at | PR domain containing 15 | PRDM15 | 7.15 | CC/HNC |
| 230777_s_at | PR domain containing 15 | PRDM15 | 6.54 | CC/HNC |
| 229468_at | cyclin-dependent kinase 3 | CDK3 | 5.45 | None |
| 230653_at | — | — | 5.15 | None |
| 220969_s_at | — | — | 4.93 | CC/HNC |
| 241838_at | — | — | 4.90 | None |
| 235231_at | hypothetical protein LOC285989 | LOC285989 | 4.47 | None |
| 212980_at | AHA1, activator of heat shock 90 kDa protein ATPase homolog 2 | AHSA2 | 4.47 | None |
| 219676_at | zinc finger protein 435 | ZNF435 | 5.16 | None |
| 226040_at | Hypothetical protein LOC283585 | — | 4.43 | None |
| 223513_at | centromere protein J | CENPJ | 5.41 | T/N, CC/HNC |
| 228455_at | CDNA FLJ43677 fis, clone SYNOV4009295 | — | 5.28 | CC/HNC |
| 225786_at | Family with sequence similarity 36, member A | FAM36A | 4.56 | CC/HNC |
| 205345_at | BRCA1 associated RING domain 1 | BARD1 | 5.04 | CC/HNC |
| 227921_at | — | — | 4.97 | None |
| 230312_at | — | — | 4.35 | None |
| 225841_at | hypothetical protein FLJ30525 | FLJ30525 | 6.64 | T/N |
| 202743_at | phosphoinositide-3-kinase, regulatory subunit 3 (p55, gamma) | PIK3R3 | 5.96 | None |
| 209644_x_at | cyclin-dependent kinase inhibitor 2A (melanoma, p16, inhibits CDK4) | CDKN2A | 6.39 | T/N |
| 225355_at | hypothetical protein DKFZP761M1511 | DKFZP761M1511 | 5.05 | None |
| 204159_at | cyclin-dependent kinase inhibitor 2C (p18, inhibits CDK4) | CDKN2C | 5.83 | None |
| 202412_s_at | ubiquitin specific protease 1 | USP1 | 5.55 | T/N |
| 243539_at | KIAA1841 protein | KIAA1841 | 4.86 | None |
| 1554447_at | CDNA clone MGC: 32876 IMAGE: 4734912, complete cds | — | 4.53 | CC/HNC |
| 213268_at | calmodulin binding transcription activator 1 | CAMTA1 | 5.53 | None |
| 1555370_a_at | calmodulin binding transcription activator 1 | CAMTA1 | 4.80 | None |
| 229795_at | — | — | 4.27 | T/N |
| 225768_at | nuclear receptor subfamily 1, group D, member 2 | NR1D2 | 4.51 | CC/HNC |
| 221045_s_at | period homolog 3 (*Drosophila*) | PER3 | 6.43 | CC/HNC |
| 232889_at | hypothetical protein LOC153561 | LOC153561 | 4.97 | None |
| 213089_at | hypothetical protein LOC153561 | LOC153561 | 4.58 | None |
| 213605_s_at | FLJ40092 protein | FLJ40092 | 5.95 | None |
| 221973_at | Hypothetical protein LOC150759 | LOC150759 | 5.14 | T/N, CC/HNC |
| 213703_at | hypothetical protein LOC150759 | LOC150759 | 5.46 | None |
| 220325_at | TAF7-like RNA polymerase II, TATA box binding protein-assoc factor | TAF7L | 5.11 | None |
| 219255_x_at | interleukin 17 receptor B | IL17RB | 5.67 | None |
| 205531_s_at | glutaminase 2 (liver, mitochondrial) | GLS2 | 4.44 | None |
| 230011_at | similar to mouse meiosis defective 1 gene | MGC40042 | 5.34 | None |
| 219753_at | stromal antigen 3 | STAG3 | 6.09 | None |
| 233064_at | Hypothetical gene supported by AL365406; BC034005 | — | 7.85 | None |
| 1553611_s_at | hypothetical protein FLJ33790 | FLJ33790 | 5.15 | None |
| 205691_at | synaptogyrin 3 | SYNGR3 | 4.84 | T/N |
| 1558217_at | hypothetical protein FLJ31952 | FLJ31952 | 4.64 | None |
| 233320_at | testicular cell adhesion molecule 1 | TCAM1 | 7.07 | T/N, CC/HNC |
| 1556244_s_at | hypothetical protein LOC375196 | LOC375196 | 7.56 | None |
| 226344_at | Zinc finger, matrin type 1 | ZMAT1 | 5.47 | None |
| 204798_at | v-myb myeloblastosis viral oncogene homolog (avian) | MYB | 5.12 | None |

TABLE 2A-continued

Differentially expressed genes in HPV+ cancers vs. HPV− cancers.

| Probeset ID* | Gene title | Gene symbol | t-statistic | Overlaps† |
|---|---|---|---|---|
| 230469_at | pleckstrin homology domain containing, family K member 1 | PLEKHK1 | 6.22 | None |
| 241903_at | — | — | 5.20 | CC/HNC |
| 213353_at | ATP-binding cassette, sub-family A (ABC1), member 5 | ABCA5 | 4.35 | CC/HNC |
| 221103_s_at | hypothetical protein FLJ11142 | FLJ11142 | 5.67 | None |
| 241705_at | — | — | 4.63 | None |
| 218902_at | Notch homolog 1, translocation-associated (*Drosophila*) | NOTCH1 | 5.57 | None |
| 237269_at | — | — | 4.92 | CC/HNC |
| 228245_s_at | ovostatin | OVOS | 4.30 | T/N |
| 244023_at | Spleen tyrosine kinase | SYK | 4.98 | None |
| 242918_at | Nuclear autoantigenic sperm protein (histone-binding) | NASP | 4.60 | None |
| 242890_at | Helicase, lymphoid-specific | HELLS | 4.45 | T/N |
| 220940_at | KIAA1641 | KIAA1641 | 4.22 | None |
| 229666_s_at | cleavage stimulation factor, 3' pre-RNA, subunit 3, 77 kDa | CSTF3 | 4.44 | None |
| 1559214_at | — | — | 4.52 | T/N |
| 229490_s_at | — | — | 4.32 | T/N |
| 205668_at | lymphocyte antigen 75 | LY75 | 4.26 | None |
| 228434_at | Butyrophilin-like 9 | BTNL9 | 4.87 | None |
| 228262_at | hypothetical protein FLJ14503 | FLJ14503 | 5.40 | None |
| 204069_at | Meis1, myeloid ecotropic viral integration site 1 homolog (mouse) | MEIS1 | 4.97 | T/N, CC/HNC |
| 1562921_at | E1A binding protein p300 | EP300 | 4.28 | CC/HNC |
| 208498_s_at | amylase, alpha 2A; pancreatic | AMY2A | 5.32 | None |
| 231164_at | Hypothetical gene supported by AK095200; BC042853 | — | 6.91 | T/N |
| 206546_at | synaptonemal complex protein 2 | SYCP2 | 7.49 | T/N, CC/HNC |
| 1557570_a_at | hypothetical protein LOC285084 | LOC285084 | 5.88 | T/N |
| 209792_s_at | kallikrein 10 | KLK10 | −4.32 | None |
| 206125_s_at | kallikrein 8 (neuropsin/ovasin) | KLK8 | −5.68 | CC/HNC |
| 207356_at | defensin, beta 4 | DEFB4 | −4.28 | CC/HNC |
| 226448_at | hypothetical gene supported by BC009447 | MGC15887 | −4.40 | T/N |
| 219368_at | nucleosome assembly protein 1-like 2 | NAP1L2 | −5.63 | None |
| 208712_at | cyclin D1 (PRAD1: parathyroid adenomatosis 1) | CCND1 | −4.50 | None |
| 208711_s_at | cyclin D1 (PRAD1: parathyroid adenomatosis 1) | CCND1 | −5.27 | None |
| 214073_at | cortactin | CTTN | −5.10 | None |
| 203065_s_at | caveolin 1, caveolae protein, 22 kDa | CAV1 | −4.58 | T/N |
| 210355_at | parathyroid hormone-like hormone | PTHLH | −4.45 | T/N |
| 1556773_at | Parathyroid hormone-like hormone | PTHLH | −4.43 | T/N |
| 211756_at | parathyroid hormone-like hormone | PTHLH | −4.46 | T/N |
| 230835_at | KIPV467 | UNQ467 | −4.37 | CC/HNC |

*In order as shown in FIG. 2A.
†Probe sets differentially expressed in other comparisons are indicated as T/N (tumor vs. normal) and CC/HNC (CC vs. HNC). Please see FIG. 1C.

TABLE 2B

Differentially expressed genes in cancers vs. normals.

| Probeset ID* | Gene title | Gene symbol | t-statistic |
|---|---|---|---|
| 212990_at | Synaptojanin 1 | SYNJ1 | 5.238 |
| 227375_at | Hypothetical protein DKFZp566D1346 | DKFZP566D1346 | 5.318 |
| 212061_at | U2-associated SR140 protein | SR140 | 5.115 |
| 225216_at | Chromosome X open reading frame 39 | CXorf39 | 4.849 |
| 227471_at | HECT domain and ankyrin repeat containing, E3 ubiquitin protein ligase 1 | HACE1 | 5.366 |
| 213387_at | KIAA1240 protein | KIAA1240 | 6.097 |
| 226894_at | — | — | 6.056 |
| 209187_at | Down-regulator of transcription 1, TBP-binding (negative cofactor 2) | DR1 | 5.601 |
| 233898_s_at | FGFR1 oncogene partner 2 | FGFR1OP2 | 4.697 |
| 229173_at | — | — | 5.926 |
| 225539_at | Zinc finger protein 295 | ZNF295 | 6.652 |
| 214820_at | Chromosome 21 open reading frame 107 | C21orf107 | 5.467 |
| 230427_s_at | — | — | 6.054 |
| 204727_at | WD repeat and HMG-box DNA binding protein 1 | WDHD1 | 6.172 |
| 203689_s_at | Fragile X mental retardation 1 | FMR1 | 5.614 |
| 212836_at | Polymerase (DNA-directed), delta 3, accessory subunit | POLD3 | 5.813 |
| 203347_s_at | Likely ortholog of mouse metal response element binding transcription factor 2 | M96 | 5.724 |
| 234995_at | Hypothetical protein AY099107 | LOC152185 | 6.488 |
| 202293_at | Stromal antigen 1 | STAG1 | 7.607 |
| 229027_at | — | — | 6.052 |
| 228334_x_at | KIAA1712 | KIAA1712 | 5.785 |
| 204634_at | NIMA (never in mitosis gene a)-related kinase 4 | NEK4 | 6.113 |
| 219171_s_at | Zinc finger protein 236 | ZNF236 | 4.82 |
| 234997_x_at | — | — | 4.747 |
| 226115_at | ELYS transcription factor-like protein TMBS62 | ELYS | 5.106 |
| 202294_at | — | — | 8.547 |
| 229022_at | — | — | 6.763 |

TABLE 2B-continued

Differentially expressed genes in cancers vs. normals.

| Probeset ID* | Gene title | Gene symbol | t-statistic |
| --- | --- | --- | --- |
| 204835_at | Polymerase (DNA directed), alpha | POLA | 6.672 |
| 203401_at | Phosphoribosyl pyrophosphate synthetase 2 | PRPS2 | 6.139 |
| 225021_at | Zinc finger protein 532 | ZNF532 | 5.759 |
| 220617_s_at | Zinc finger protein 532 | ZNF532 | 6.463 |
| 203482_at | Chromosome 10 open reading frame 6 | C10orf6 | 6.155 |
| 226730_s_at | Ubiquitin specific protease 37 | USP37 | 6.055 |
| 218515_at | Chromosome 21 open reading frame 66 | C21orf66 | 5.504 |
| 212943_at | KIAA0528 gene product | KIAA0528 | 5.973 |
| 218397_at | Fanconi anemia, complementation group L | FANCL | 6.272 |
| 225017_at | Hypothetical protein FLJ12892 | FLJ12892 | 5.375 |
| 228286_at | Hypothetical protein FLJ40869 | FLJ40869 | 5.694 |
| 229303_at | — | — | 5.471 |
| 232362_at | Sarcoma antigen NY-SAR-41 | NY-SAR-41 | 5.009 |
| 225318_at | DDHD domain containing 2 | DDHD2 | 4.732 |
| 214306_at | Optic atrophy 1 (autosomal dominant) | OPA1 | 5.141 |
| 222629_at | REV1-like (yeast) | REV1L | 6.239 |
| 224974_at | Likely ortholog of mouse Sds3 | SDS3 | 6.108 |
| 213140_s_at | Synovial sarcoma translocation gene on chromosome 18-like 1 | SS18L1 | 5.802 |
| 208798_x_at | Golgin-67 | GOLGIN-67 | 5.185 |
| 210425_x_at | — | — | 5.537 |
| 227199_at | Chromosome 21 open reading frame 106 | C21orf106 | 6.379 |
| 236910_at | Mitochondrial ribosomal protein L39 | MRPL39 | 6.352 |
| 228940_at | NADH dehydrogenase (ubiquinone) 1 beta subcomplex, 4, 15 kDa | NDUFB4 | 5.908 |
| 230516_at | Chromosome 7 open reading frame 30 | C7orf30 | 5.057 |
| 243332_at | — | — | 5.676 |
| 225595_at | MRNA; cDNA DKFZp566P1124 (from clone DKFZp566P1124) | — | 4.672 |
| 225594_at | MRNA; cDNA DKFZp566P1124 (from clone DKFZp566P1124) | — | 5.378 |
| 218793_s_at | Sex comb on midleg-like 1 (Drosophila) | SCML1 | 5.387 |
| 239577_at | — | — | 4.466 |
| 222201_s_at | CASP8 associated protein 2 | CASP8AP2 | 5.367 |
| 218979_at | Chromosome 9 open reading frame 76 | C9orf76 | 5.468 |
| 218757_s_at | UPF3 regulator of nonsense transcripts homolog B (yeast) | UPF3B | 7.293 |
| 202633_at | Topoisomerase (DNA) II binding protein 1 | TOPBP1 | 7.354 |
| 227255_at | Casein kinase | LOC149420 | 4.722 |
| 201555_at | MCM3 minichromosome maintenance deficient 3 (S. cerevisiae) | MCM3 | 7.992 |
| 239413_at | KIAA0912 protein | Cep152 | 7.158 |
| 206316_s_at | Kinetochore associated 1 | KNTC1 | 7.584 |
| 228859_at | Prematurely terminated mRNA decay factor-like | LOC91431 | 6.037 |
| 221677_s_at | Downstream neighbor of SON | DONSON | 8.188 |
| 225655_at | Ubiquitin-like, containing PHD and RING finger domains, 1 | UHRF1 | 8.055 |
| 228401_at | — | — | 7.279 |
| 219306_at | Kinesin-like 7 | KNSL7 | 6.072 |
| 235609_at | — | — | 6.233 |
| 203209_at | Replication factor C (activator 1) 5, 36.5 kDa | RFC5 | 5.279 |
| 203432_at | Thymopoietin | TMPO | 4.836 |
| 206102_at | KIAA0186 gene product | KIAA0186 | 5.766 |
| 204510_at | CDC7 cell division cycle 7 (S. cerevisiae) | CDC7 | 7.611 |
| 203358_s_at | Enhancer of zeste homolog 2 (Drosophila) | EZH2 | 6.571 |
| 218783_at | DKFZP434B168 protein | DKFZP434B168 | 5.005 |
| 224428_s_at | Cell division cycle associated 7 | CDCA7 | 4.567 |
| 214804_at | FSH primary response (LRPR1 homolog, rat) 1 | FSHPRH1 | 5.661 |
| 203744_at | High-mobility group box 3 | HMGB3 | 6.469 |
| 212060_at | U2-associated SR140 protein | SR140 | 5.261 |
| 218304_s_at | Oxysterol binding protein-like 11 | OSBPL11 | 5.936 |
| 228386_s_at | Hypothetical protein DKFZp564B1023 | DKFZP564B1023 | 5.527 |
| 215009_s_at | SEC31-like 1 (S. cerevisiae) | SEC31L1 | 5.184 |
| 226350_at | Choroideremia-like (Rab escort protein 2) | CHML | 6.435 |
| 1565951_s_at | Choroideremia-like (Rab escort protein 2) | CHML | 5.487 |
| 242923_at | Hypothetical protein MGC15634 | MGC15634 | 4.925 |
| 205296_at | Retinoblastoma-like 1 (p107) | RBL1 | 4.687 |
| 203276_at | Lamin B1 | LMNB1 | 5.178 |
| 238756_at | Growth arrest-specific 2 like 3 | GAS2L3 | 4.914 |
| 228577_x_at | KIAA1229 protein | KIAA1229 | 5.562 |
| 231909_x_at | KIAA1229 protein | KIAA1229 | 5.05 |
| 226164_x_at | KIAA1238 protein | KIAA1238 | 4.309 |
| 228397_at | — | — | 4.259 |
| 239680_at | — | — | 6.372 |
| 236513_at | — | — | 5.773 |
| 231931_at | PR domain containing 15 | PRDM15 | 6.115 |
| 230777_s_at | PR domain containing 15 | PRDM15 | 5.542 |
| 208174_x_at | U2(RNU2) small nuclear RNA auxiliary factor 1-like 2 | U2AF1L2 | 5.364 |
| 213876_x_at | U2(RNU2) small nuclear RNA auxiliary factor 1-like 2 | U2AF1L2 | 5.517 |
| 42361_g_at | Chromosome 6 open reading frame 18 | C6orf18 | 4.599 |
| 64408_s_at | Calmodulin-like 4 | CALML4 | 4.377 |
| 220969_s_at | — | — | 4.24 |
| 230209_at | Hypothetical protein MGC11349 | MGC11349 | 4.501 |

TABLE 2B-continued

Differentially expressed genes in cancers vs. normals.

| Probeset ID* | Gene title | Gene symbol | t-statistic |
|---|---|---|---|
| 203262_s_at | Family with sequence similarity 50, member A | FAM50A | 6.106 |
| 213947_s_at | Nucleoporin 210 | NUP210 | 5.367 |
| 230395_at | DORA reverse strand protein 1 | DREV1 | 4.248 |
| 1562497_at | MKL/myocardin-like 2 | MKL2 | 5.24 |
| 223797_at | — | — | 4.519 |
| 244625_at | — | — | 4.668 |
| 235646_at | — | — | 5.002 |
| 242737_at | — | — | 6.262 |
| 219280_at | Chromosome 21 open reading frame 107 | C21orf107 | 7.491 |
| 222343_at | BCL2-like 11 (apoptosis facilitator) | BCL2L11 | 6.325 |
| 230534_at | Hypothetical protein MGC15634 | MGC15634 | 5.384 |
| 238699_s_at | Calcium/calmodulin-dependent serine protein kinase (MAGUK family) | CASK | 4.742 |
| 232370_at | Hypothetical protein LOC254057 | LOC254057 | 4.482 |
| 204143_s_at | rTS beta protein | HSRTSBETA | 4.634 |
| 237246_at | — | — | 4.651 |
| 215623_x_at | SMC4 structural maintenance of chromosomes 4-like 1 (yeast) | SMC4L1 | 5.25 |
| 241954_at | — | — | 4.48 |
| 204224_s_at | GTP cyclohydrolase 1 (dopa-responsive dystonia) | GCH1 | 4.677 |
| 222603_at | KIAA1815 | KIAA1815 | 5.974 |
| 223275_at | HMT1 hnRNP methyltransferase-like 6 (*S. cerevisiae*) | HRMT1L6 | 4.656 |
| 228778_at | — | — | 6.636 |
| 203991_s_at | Ubiquitously transcribed tetratricopeptide repeat, X chromosome | UTX | 6.092 |
| 214678_x_at | — | — | 5.425 |
| 203992_s_at | Ubiquitously transcribed tetratricopeptide repeat, X chromosome | UTX | 6.441 |
| 204061_at | Protein kinase, X-linked | PRKX | 4.969 |
| 229305_at | MLF1 interacting protein | MLF1IP | 4.709 |
| 218883_s_at | MLF1 interacting protein | MLF1IP | 6.342 |
| 219990_at | FLJ23311 protein | FLJ23311 | 4.99 |
| 210371_s_at | Retinoblastoma binding protein 4 | RBBP4 | 6.888 |
| 218733_at | Hypothetical protein FLJ10546 | FLJ10546 | 5.501 |
| 233841_s_at | Likely ortholog of mouse Sds3 | SDS3 | 5.987 |
| 221919_at | Heterogeneous nuclear ribonucleoprotein A1 | HNRPA1 | 5.492 |
| 212515_s_at | DEAD (Asp-Glu-Ala-Asp) box polypeptide 3, X-linked | DDX3X | 4.514 |
| 220553_s_at | PRP39 pre-mRNA processing factor 39 homolog (yeast) | PRPF39 | 4.995 |
| 201970_s_at | Nuclear autoantigenic sperm protein (histone-binding) | NASP | 5.843 |
| 212200_at | KIAA0692 protein | KIAA0692 | 5.66 |
| 215017_s_at | Chromosome 1 open reading frame 39 | C1orf39 | 4.318 |
| 235142_at | Zinc finger and BTB domain containing 8 | ZBTB8 | 4.617 |
| 219157_at | Kelch-like 2, Mayven (*Drosophila*) | KLHL2 | 6.137 |
| 236769_at | Hypothetical protein LOC158402 | LOC158402 | 5.643 |
| 227133_at | Chromosome X open reading frame 39 | CXorf39 | 4.437 |
| 220520_s_at | Hypothetical protein FLJ20130 | FLJ20130 | 5.257 |
| 217936_at | Rho GTPase activating protein 5 | ARHGAP5 | 5.74 |
| 223167_s_at | Ubiquitin specific protease 25 | USP25 | 5.464 |
| 205281_s_at | Phosphatidylinositol glycan, class A (paroxysmal nocturnal hemoglobinuria) | PIGA | 5.451 |
| 226302_at | — | — | 4.823 |
| 213285_at | Transmembrane protein 30B | TMEM30B | 4.978 |
| 228565_at | Mixed lineage kinase 4 | KIAA1804 | 4.999 |
| 227356_at | CDNA: FLJ22198 fis, clone HRC01218 | — | 4.591 |
| 228201_at | ADP-ribosylation factor-like 2-like 1 | ARL2L1 | 4.742 |
| 228812_at | — | — | 4.625 |
| 225227_at | *Homo sapiens*, clone IMAGE: 5299642, mRNA | — | 4.459 |
| 232398_at | Hypothetical protein DKFZp434P055 | DKFZp434P055 | 5.822 |
| 233504_at | Chromosome 9 open reading frame 84 | C9orf84 | 5.832 |
| 1554447_at | CDNA clone MGC: 32876 IMAGE: 4734912, complete cds | — | 5.544 |
| 218966_at | Myosin VC | MYO5C | 6.466 |
| 1556105_at | Par-3 partitioning defective 3 homolog (*C. elegans*) | PARD3 | 7.135 |
| 235635_at | — | — | 4.637 |
| 228455_at | CDNA FLJ43677 fis, clone SYNOV4009295 | — | 5.957 |
| 225786_at | Family with sequence similarity 36, member A | FAM36A | 4.716 |
| 223513_at | Centromere protein J | CENPJ | 4.285 |
| 217894_at | Potassium channel tetramerisation domain containing 3 | KCTD3 | 6.689 |
| 204146_at | RAD51 associated protein 1 | RAD51AP1 | 4.219 |
| 203213_at | Cell division cycle 2, G1 to S and G2 to M | CDC2 | 5.255 |
| 201663_s_at | SMC4 structural maintenance of chromosomes 4-like 1 (yeast) | SMC4L1 | 4.65 |
| 201664_at | SMC4 structural maintenance of chromosomes 4-like 1 (yeast) | SMC4L1 | 6.127 |
| 225834_at | Similar to RIKEN cDNA 2700049P18 gene | MGC57827 | 7.226 |
| 228323_at | AF15q14 protein | AF15Q14 | 5.322 |
| 223381_at | Cell division cycle associated 1 | CDCA1 | 4.969 |
| 228033_at | E2F transcription factor 7 | E2F7 | 6.759 |
| 204641_at | NIMA (never in mitosis gene a)-related kinase 2 | NEK2 | 4.905 |
| 209172_s_at | Centromere protein F, 350/400 ka (mitosin) | CENPF | 4.919 |
| 218585_s_at | RA-regulated nuclear matrix-associated protein | RAMP | 5.95 |
| 222680_s_at | RA-regulated nuclear matrix-associated protein | RAMP | 6.996 |
| 222740_at | ATPase family, AAA domain containing 2 | ATAD2 | 5.314 |
| 222848_at | leucine zipper protein FKSG14 | FKSG14 | 5.878 |

TABLE 2B-continued

Differentially expressed genes in cancers vs. normals.

| Probeset ID* | Gene title | Gene symbol | t-statistic |
|---|---|---|---|
| 229551_x_at | Zinc finger protein 367 | ZNF367 | 8.85 |
| 227350_at | Helicase, lymphoid-specific | HELLS | 6.363 |
| 205034_at | Cyclin E2 | CCNE2 | 7.033 |
| 223542_at | Ankyrin repeat domain 32 | ANKRD32 | 7.339 |
| 216228_s_at | WD repeat and HMG-box DNA binding protein 1 | WDHD1 | 4.689 |
| 226747_at | KIAA1344 | KIAA1344 | 5.709 |
| 228597_at | Chromosome 21 open reading frame 45 | C21orf45 | 5.181 |
| 209337_at | PC4 and SFRS1 interacting protein 1 | PSIP1 | 5.364 |
| 205961_s_at | PC4 and SFRS1 interacting protein 1 | PSIP1 | 4.401 |
| 226925_at | acid phosphatase-like 2 | ACPL2 | 4.686 |
| 202983_at | SWI/SNF related, matrix associated, actin dependent regulator of chromatin, subfamily a, member 3 | SMARCA3 | 4.929 |
| 225768_at | Nuclear receptor subfamily 1, group D, member 2 | NR1D2 | 5.387 |
| 229442_at | Hypothetical protein MGC33382 | MGC33382 | 5.117 |
| 212840_at | KIAA0794 protein | KIAA0794 | 4.926 |
| 201329_s_at | v-ets erythroblastosis virus E26 oncogene homolog 2 (avian) | ETS2 | 6.218 |
| 201328_at | v-ets erythroblastosis virus E26 oncogene homolog 2 (avian) | ETS2 | 4.879 |
| 208078_s_at | SNF1-like kinase \ | SNF1LK | 4.865 |
| 1555411_a_at | Cyclin L1 | CCNL1 | 6.615 |
| 1555827_at | Cyclin L1 | CCNL1 | 5.578 |
| 241495_at | Cyclin L1 | CCNL1 | 4.355 |
| 241903_at | — | — | 5.813 |
| 243030_at | — | — | 5.475 |
| 205345_at | BRCA1 associated RING domain 1 | BARD1 | 4.352 |
| 213353_at | ATP-binding cassette, sub-family A (ABC1), member 5 | ABCA5 | 5.381 |
| 240452_at | — | — | 4.398 |
| 230097_at | — | — | 4.269 |
| 236322_at | — | — | 4.201 |
| 242146_at | — | — | 5.106 |
| 1559156_at | Protein inhibitor of activated STAT, 1 | PIAS1 | 4.832 |
| 235926_at | — | — | 4.262 |
| 244753_at | — | — | 4.129 |
| 232058_at | Actinin, alpha 4 | ACTN4 | 4.419 |
| 203767_s_at | Steroid sulfatase (microsomal), arylsulfatase C, isozyme S | STS | 4.633 |
| 213150_at | Homeo box A10 | HOXA10 | 4.669 |
| 235292_at | LOC441069 | — | 4.149 |
| 226374_at | — | — | 4.552 |
| 204286_s_at | Phorbol-12-myristate-13-acetate-induced protein 1 | PMAIP1 | 4.648 |
| 210540_s_at | UDP-Gal: betaGlcNAc beta 1,4-galactosyltransferase, polypeptide 4 | B4GALT4 | 4.992 |
| 237269_at | — | — | 4.908 |
| 226420_at | Ecotropic viral integration site 1 | EVI1 | 5.871 |
| 218901_at | Phospholipid scramblase 4 | PLSCR4 | 6.1 |
| 235165_at | Par-6 partitioning defective 6 homolog beta (C. elegans) | PARD6B | 4.241 |
| 221045_s_at | Period homolog 3 (Drosophila) | PER3 | 4.957 |
| 221973_at | Hypothetical protein LOC150759 | LOC150759 | 4.445 |
| 238593_at | Hypothetical protein FLJ22531 | FLJ22531 | 4.248 |
| 216248_s_at | Nuclear receptor subfamily 4, group A, member 2 | NR4A2 | 4.868 |
| 204622_x_at | Nuclear receptor subfamily 4, group A, member 2 | NR4A2 | 4.882 |
| 206698_at | Kell blood group precursor (McLeod phenotype) | XK | 4.927 |
| 227492_at | — | — | 6.648 |
| 1562921_at | E1A binding protein p300 | EP300 | 4.238 |
| 235144_at | RAS and EF hand domain containing | RASEF | 6.912 |
| 1553986_at | RAS and EF hand domain containing | RASEF | 4.273 |
| 229842_at | — | — | 4.773 |
| 209692_at | Eyes absent homolog 2 (Drosophila) | EYA2 | 6.153 |
| 219313_at | Hypothetical protein DKFZp434C0328 | DKFZp434C0328 | 5.167 |
| 204069_at | Meis1, myeloid ecotropic viral integration site 1 homolog (mouse) | MEIS1 | 4.556 |
| 214464_at | CDC42 binding protein kinase alpha (DMPK-like) | CDC42BPA | 4.303 |
| 214723_x_at | KIAA1641 | KIAA1641 | 5.208 |
| 200800_s_at | Heat shock 70 kDa protein 1A /// heat shock 70 kDa protein 1B | HSPA1A /// HSPA1B | 5.342 |
| 201169_s_at | Basic helix-loop-helix domain containing, class B, 2 | BHLHB2 | 4.172 |
| 214651_s_at | Homeo box A9 | HOXA9 | 7.526 |
| 209905_at | Homeo box A9 | HOXA9 | 7.791 |
| 228904_at | — | — | 5.333 |
| 206546_at | Synaptonemal complex protein 2 | SYCP2 | 5.824 |
| 233320_at | Testicular cell adhesion molecule 1 | TCAM1 | 4.918 |
| 229400_at | Homeo box D10 | HOXD10 | 5.335 |
| 227671_at | X (inactive)-specific transcript | XIST | 5.623 |
| 231592_at | — | — | 4.565 |
| 224589_at | X (inactive)-specific transcript | XIST | 4.966 |
| 205778_at | Kallikrein 7 (chymotryptic, stratum corneum) | KLK7 | −4.171 |
| 206125_s_at | Kallikrein 8 (neuropsin/ovasin) | KLK8 | −4.858 |
| 206192_at | Corneodesmosin | CDSN | −4.747 |
| 235514_at | Hypothetical protein FLJ25084 | FLJ25084 | −4.359 |
| 223582_at | Monogenic, audiogenic seizure susceptibility 1 homolog (mouse) | MASS1 | −4.856 |

TABLE 2B-continued

Differentially expressed genes in cancers vs. normals.

| Probeset ID* | Gene title | Gene symbol | t-statistic |
|---|---|---|---|
| 239352_at | — | — | −4.807 |
| 207356_at | Defensin, beta 4 | DEFB4 | −4.625 |
| 205054_at | Nebulin | NEB | −6.402 |
| 203562_at | Fasciculation and elongation protein zeta 1 (zygin I) | FEZ1 | −4.482 |
| 221898_at | Lung type-I cell membrane-associated glycoprotein | T1A-2 | −4.543 |
| 228492_at | Ubiquitin specific protease 9, Y-linked (fat facets-like, Drosophila) | USP9Y | −6.254 |
| 223646_s_at | Chromosome Y open reading frame 15B | CYorf15B | −7.48 |
| 204410_at | Eukaryotic translation initiation factor 1A, Y-linked | EIF1AY | −5.799 |
| 206700_s_at | Jumonji, AT rich interactive domain 1D (RBP2-like) | JARID1D | −8.832 |
| 223645_s_at | Chromosome Y open reading frame 15B | CYorf15B | −7.22 |
| 230760_at | Zinc finger protein, Y-linked | ZFY | −6.432 |
| 213068_at | Dermatopontin | DPT | −6.491 |
| 213909_at | Leucine rich repeat containing 15 | LRRC15 | −5.414 |
| 201893_x_at | Decorin | DCN | −4.228 |
| 223475_at | CocoaCrisp | LOC83690 | −4.253 |
| 210467_x_at | Melanoma antigen, family A, 12 | MAGEA12 | −4.686 |
| 232523_at | MEGF10 protein | MEGF10 | −5.346 |
| 206584_at | Lymphocyte antigen 96 | LY96 | −4.524 |
| 236313_at | Cyclin-dependent kinase inhibitor 2B (p15, inhibits CDK4) | CDKN2B | 4.437 |
| 205225_at | Estrogen receptor 1 | ESR1 | 4.321 |
| 207039_at | Cyclin-dependent kinase inhibitor 2A (melanoma, p16, inhibits CDK4) | CDKN2A | 4.922 |
| 232170_at | S100 calcium binding protein A7-like 1 | S100A7L1 | −4.32 |
| 207324_s_at | Desmocollin 1 | DSC1 | −3.977 |
| 224646_x_at | — | — | −4.37 |
| 224997_x_at | H19, imprinted maternally expressed untranslated mRNA | H19 | −4.791 |
| 224348_s_at | — | — | −4.566 |
| 205403_at | Interleukin 1 receptor, type II | IL1R2 | −5.361 |
| 211372_s_at | Interleukin 1 receptor, type II | IL1R2 | −4.172 |
| 205000_at | DEAD (Asp-Glu-Ala-Asp) box polypeptide 3, Y-linked | DDX3Y | −8.052 |
| 214131_at | Chromosome Y open reading frame 15B | CYorf15B | −6.626 |
| 204409_s_at | Eukaryotic translation initiation factor 1A, Y-linked | EIF1AY | −5.951 |
| 201909_at | Ribosomal protein S4, Y-linked 1 | RPS4Y1 | −8.251 |
| 201650_at | Keratin 19 | KRT19 | 4.223 |
| 224588_at | X (inactive)-specific transcript | XIST | 9.351 |
| 224590_at | X (inactive)-specific transcript | XIST | 8.602 |
| 214218_s_at | X (inactive)-specific transcript | XIST | 9.127 |
| 221728_x_at | X (inactive)-specific transcript | XIST | 9.808 |
| 230835_at | KIPV467 | UNQ467 | −4.315 |

*In order as shown in FIG. 2B.

TABLE 3A

Cell cycle genes up- or down-regulated in HPV+ cancers vs. HPV− cancers.

| Probeset ID* | Gene title | Gene symbol | t-statistic |
|---|---|---|---|
| 205767_at | Epiregulin | EREG | −3.47 |
| 209792_s_at | Kallikrein 10 | KLK10 | −4.25 |
| 208711_s_at | Cyclin D1 | CCND1 | −5.43 |
| 208712_at | Cyclin D2 | CCND2 | −4.48 |
| 1553869_at | Sestrin 3 | SESN3 | −3.39 |
| 205899_at | Cyclin A1 | CCNA1 | −4.06 |
| 235683_at | Sestrin 3 | SESN3 | −4.05 |
| 207039_at | Cyclin-dependent kinase inhibitor 2A (melanoma, p16, inhibits CDK4) | CDKN2A | 7.09 |
| 206546_at | Synaptonemal complex protein 2 | SYCP2 | 7.36 |
| 204159_at | Cyclin-dependent kinase inhibitor 2C (p18, inhibits CDK4) | CDKN2C | 5.73 |
| 204510_at | CDC7 cell division cycle 7 | CDC7 | 6.51 |
| 206316_s_at | Kinetochore associated 1 | KNTC1 | 6.28 |
| 205085_at | Origin recognition complex, subunit 1-like | ORC1L | 4.96 |
| 201746_at | Tumor protein p53 | TP53 | 3.57 |
| 224320_s_at | MCM8 minichromosome maintenance deficient 8 | MCM8 | 5.61 |
| 213204_at | p53-associated parkin-like cytoplasmic protein | PARC | 5.90 |
| 222962_s_at | MCM10 minichromosome maintenance deficient 10 | MCM10 | 2.74 |
| 201555_at | MCM3 minichromosome maintenance deficient 3 | MCM3 | 5.95 |
| 201930_at | MCM6 minichromosome maintenance deficient 6 | MCM6 | 5.56 |
| 244550_at | Transcription factor Dp-1 | TFDP1 | 3.00 |
| 228361_at | E2F transcription factor 2 | E2F2 | 4.94 |
| 204121_at | Growth arrest and DNA-damage-inducible, gamma | GADD45G | 2.16 |
| 225297_at | Coiled-coil domain containing 5 (spindle associated) | CCDC5 | 3.42 |
| 204457_s_at | Growth arrest-specific 1 | GAS1 | 2.17 |
| 228033_at | E2F transcription factor 7 | E2F7 | 4.39 |
| 204252_at | Cyclin-dependent kinase 2 | CDK2 | 3.77 |

TABLE 3A-continued

Cell cycle genes up- or down-regulated in HPV+ cancers vs. HPV- cancers.

| Probeset ID* | Gene title | Gene symbol | t-statistic |
|---|---|---|---|
| 210028_s_at | Origin recognition complex, subunit 3-like (yeast) | ORC3L | 4.12 |
| 209408_at | Kinesin family member 2C | KIF2C | 5.52 |
| 209172_s_at | Centromere protein F, 350/400 ka (mitosin) | CENPF | 4.55 |
| 219588_s_at | Leucine zipper protein 5 | LUZP5 | 4.86 |
| 203693_s_at | E2F transcription factor 3 | E2F3 | 4.05 |
| 218663_at | Chromosome condensation protein G | HCAP-G | 3.55 |
| 202107_s_at | MCM2 minichromosome maintenance deficient 2, mitotin | MCM2 | 4.37 |
| 208795_s_at | MCM7 minichromosome maintenance deficient 7 | MCM7 | 4.06 |
| 201664_at | SMC4 structural maintenance of chromosomes 4-like 1 | SMC4L1 | 4.44 |
| 201202_at | Proliferating cell nuclear antigen | PCNA | 5.12 |
| 203213_at | Cell division cycle 2, G1 to S and G2 to M | CDC2 | 3.27 |
| 204240_s_at | SMC2 structural maintenance of chromosomes 2-like 1 | SMC2L1 | 1.73 |
| 205034_at | Cyclin E2 | CCNE2 | 3.59 |
| 205393_s_at | CHK1 checkpoint homolog | CHEK1 | 1.05 |
| 214710_s_at | Cyclin B1 | CCNB1 | 1.20 |
| 203755_at | BUB1 budding uninhibited by benzimidazoles 1 homolog beta | BUB1B | 2.77 |

*In order as shown in FIG. 3A.

Example 2: Confirmation of TCAM1, SYCP2 and STAG3 Expression in Human Papillomavirus-Positive Cancers Materials and Methods The above methods were repeated in a second, but larger, group of subjects. The group consisted of 128 samples collected. 79 were HPV+ and 47 were HPV−. Additional details on the subjects are shown below in Table 3.

TABLE 4

Patient information.

| Cases and Controls | N = 128 | 100% |
|---|---|---|
| Normal Controls Only | N = 16 | 12.5% |
| Cases Only | N = 112 | 87.5% |
| Pathology | | |
| CIN1 | N = 14 | 10.9% |
| CIN2 | N = 21 | 16.4% |
| CIN3 | N = 41 | 32.0% |
| Cancer | N = 28 | 21.9% |
| Metaplasia | N = 7 | 5.5% |
| Adenocarcinoma in situ | N = 1 | 0.8% |

Results

Figure 7:
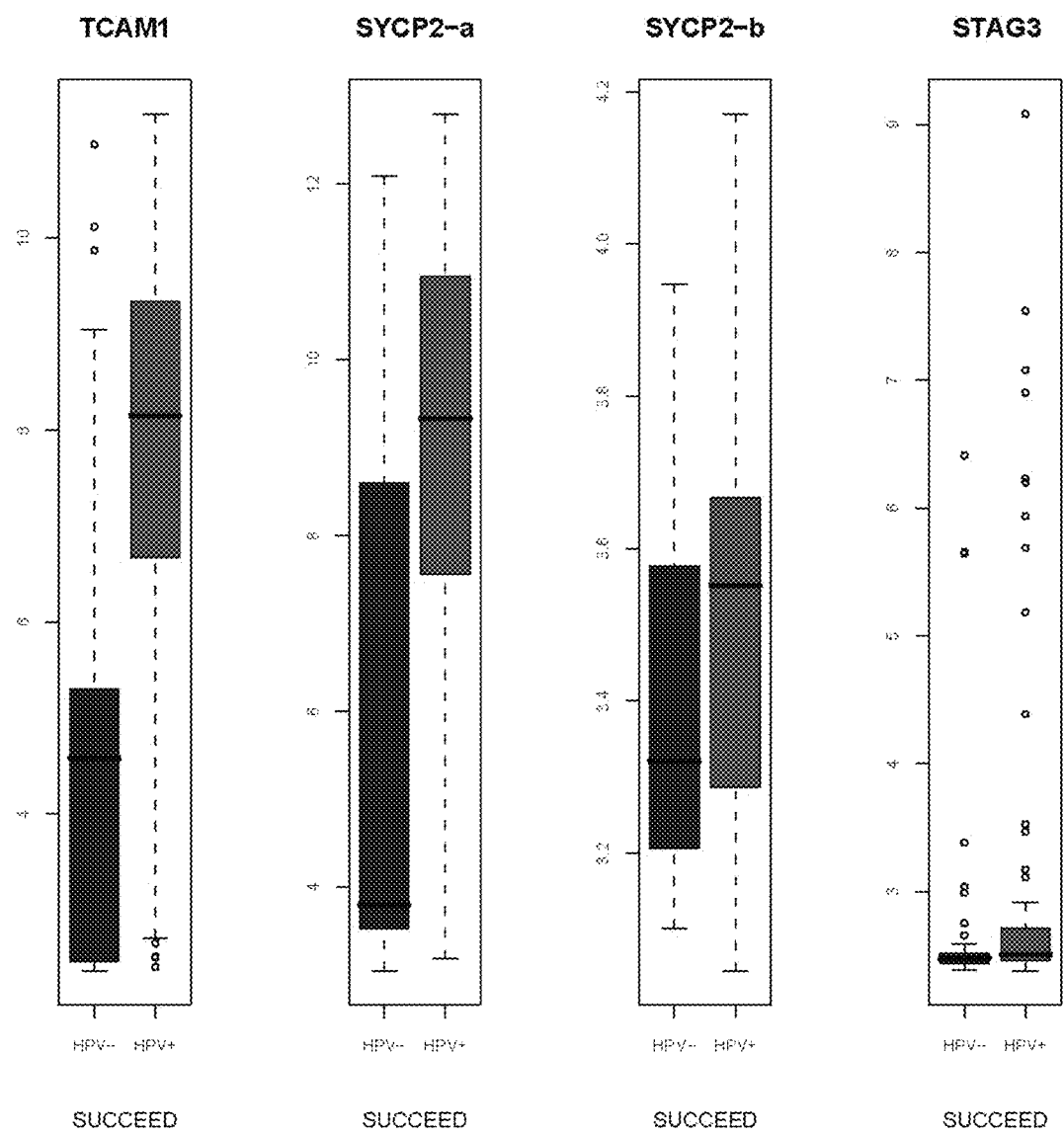
FIG. 7: TCAM1, SYCP2 and STAG2 were all significant induced in HPV+ samples compared to HPV− samples in a second, and larger, study. In the box plots, blue bars indicate HPV+; whereas red bars indicate HPV−; the bars range from 25th to 75th percentiles of each sample. Solid black lines indicate the median. The lines extending from the bars indicate the largest/smallest data point, and circles represent outliers.

As shown in FIG. 7, TCAM1, SYCP2 and STAG3 were significantly upregulated in HPV+ samples, confirming the result shown above in Example 1.

REFERENCES

1. Burd E, "Human papillomavirus and cervical cancer," Clin. Micro. Reviews 16:1-17 (2003).
2. Gillison M & Lowy D, "A causal role for human papillomavirus in head and neck cancer," Lancet 363:1488-1489 (2004).
3. Smith E, et al., "Human papillomavirus in oral exfoliated cells and risk of head and neck cancer," J. Natl. Cancer Inst. 96:449-455 (2004).
4. Hunter K, et al., "Profiling early head and neck cancer," Nat. Rev. Cancer 5:127-135 (2005).
5. Chung C, et al., "Molecular classification of head and neck squamous cell carcinomas using patterns of gene expression," Cancer Cell 5:489-500 (2004).
6. Cromer A, et al., "Identification of genes associated with tumorigenesis and metastatic potential of hypopharyngeal cancer by microarray analysis," Oncogene 23:2484-2498 (2004).
7. Ginos M, et al., "Identification of a gene expression signature associated with recurrent disease in squamous cell carcinoma of the head and neck," Cancer Res. 64:55-63 (2004).
8. Slebos R, et al., "Gene expression differences associated with human papillomavirus status in head and neck squamous cell carcinoma," Clin. Cancer Res. 12:701-709 (2006).
9. Hebner C & Laimins L, "Human papillomaviruses: basic mechanisms of pathogenesis and oncogenicity," Rev. Med. Virol. 16:83-97 (2006).
10. Geng Y, et al., "Regulation of cyclin E transcription by E2Fs and retinoblastoma protein," Oncogene 12:1173-1180 (1996).
11. Ohtani K, et al., "Cell growth-regulated expression of mammalian MCM5 and MCM6 genes mediated by the transcription factor E2F," Oncogene 18:2299-2309 (1999).
12. Thomas M, et al., "The role of the HPV E6 oncoprotein in malignant progression," Papillomavirus Research 115-131 (Campo M, ed.; Norfolk, England; Caister Academic Press; 2006).
13. McCance D, "The biology of the E7 protein of HPV-16," Papillomavirus Research 133-144 (Campo M, ed.; Norfolk, England; Caister Academic Press; 2006).
14. Riley R, et al., "Dissection of human papillomavirus E6 and E7 function in transgenic mouse models of cervical carcinogenesis," Cancer Res. 63:4862-4871 (2003).
15. Hoffmann M, et al., "Human papillomaviruses in head and neck cancer: 8 year-survival-analysis of 73 patients," Cancer Lett. 218:199-206 (2005).
16. Nielsen H, et al., "Design of oligonucleotides for microarrays and perspectives for design of multi-transcriptome arrays," Nucleic Acids Res 31:3491-3496 (2003).
17. Ihaka R & Gentleman R, "A language for data analysis and graphics," J. Comput. Graph. Stat. 5:299-314 (1996).
18. Gentleman R, et al., "Bioconductor: open software development for computational biology and bioinformatics," Genome Biol. 5:R80 (2004).
19. Irizarry R, et al., "Exploration, normalization, and summaries of high density oligonucleotide array probe level data," Biostatistics 4:249-264 (2003).
20. Efron B & Tibshirani R, "An introduction to the bootstrap," (New York; Chapman & Hall; 1993).

21. Storey J & Tibshirani R, "Statistical significance for genomewide studies," Proc. Natl. Acad. Sci. USA 100: 9440-9445 (2003).
22. Sengupta S, et al., "Genome-wide expression profiling reveals EBV-associated inhibition of MHC class I expression in nasopharyngeal carcinoma," Cancer Res. 66:7999-8006 (2006).
23. Newton M, et al., "Random-set methods identify distinct aspects of the enrichment signal in gene-set analysis," Ann. Appl. Stat. 1:185-106 (2007).
24. Ledoit O & Wolf M, "A well-conditioned estimator for large-dimensional covariance matrices," J. Multivariate Analysis 88:365-411 (2004).
25. Nelson J, et al., "A novel and rapid PCR-based method for genotyping human papillomaviruses in clinical samples," J. Clin. Microbiol. 38:688-695 (2000).
26. Walboomers J & Meijer C, "Do HPV-negative cervical carcinomas exist?" J. Pathol. 181:253-254 (1997).
27. Khan J, et al., "Gene expression profiling of alveolar rhabdomyosarcoma with cDNA microarrays," Cancer Res. 58:5009-5013 (1998).
28. Clark E & Lane P, "Regulation of human B-cell activation and adhesion," Annu. Rev. Immunol. 9:97-127 (1991).
29. Asanuma K, et al., "Synaptopodin orchestrates actin organization and cell motility via regulation of RhoA signaling," Nat. Cell. Biol. 8:485-491 (2006).
30. Tinker A, et al., "The challenges of gene expression microarrays for the study of human cancer," Cancer Cell 9:333-339 (2006).
31. Chung C, et al., "Gene expression profiles identify epithelial-to-mesenchymal transition and activation of nuclear factor-{kappa}B signaling as characteristics of a high-risk head and neck squamous cell carcinoma," Cancer Res. 66:8210-8218 (2006).
32. Brake T, et al., "Comparative analysis of cervical cancer in women and in a human papillomavirus-transgenic mouse model: identification of minichromosome maintenance protein 7 as an informative biomarker for human cervical cancer," Cancer Res. 63:8173-8180 (2003).
33. Longworth M, et al., "HPV31 E7 facilitates replication by activating E2F2 transcription through its interaction with HDACs," EMBO J. 24:1821-1830 (2005).
34. Arroyo M, et al., "Association of the human papillomavirus type 16 E7 protein with the S-phase-specific E2F-cyclin A complex," Mol. Cell. Biol. 13:6537-6546 (1993).
35. Flores E, et al., "The human papillomavirus type 16 E7 oncogene is required for the productive stage of the viral life cycle," J. Virol. 74:6622-6631 (2000).
36. Asano M & Wharton R, "E2F mediates developmental and cell cycle regulation of ORC1 in Drosophila," EMBO J. 18:2435-2448 (1999).
37. Yamada M, et al., "A 63-base pair DNA segment containing an Sp1 site but not a canonical E2F site can confer growth-dependent and E2F-mediated transcriptional stimulation of the human ASK gene encoding the regulatory subunit for human Cdc7-related kinase," J. Biol. Chem. 277:27668-27681 (2002).
38. Thacker S, et al., "The contribution of E2F-regulated transcription to Drosophila PCNA gene function," Curr. Biol. 13:53-58 (2003).
39. Furukawa Y, et al., "The role of cellular transcription factor E2F in the regulation of cdc2 mRNA expression and cell cycle control of human hematopoietic cells," J. Biol. Chem. 269:26249-26258 (1994).
40. Skoczylas C, et al., "PP2A-dependent transactivation of the cyclin A promoter by SV40 ST is mediated by a cell cycle-regulated E2F site," Virology 332:596-601 (2005).
41. Strati K, et al., "Identification of biomarkers that distinguish HPV- positive versus HPV- negative head and neck cancers in a mouse model," Proc. Natl. Acad. Sci. USA 103:14152-14157 (2006).
42. Li W, et al., "The expression of key cell cycle markers and presence of human papillomavirus in squamous cell carcinoma of the tonsil," Head Neck 26:1-9 (2004).
43. Khleif S, et al., "Inhibition of cyclin D-CDK4/CDK6 activity is associated with an E2F-mediated induction of cyclin kinase inhibitor activity," Proc. Natl. Acad. Sci. USA 93:4350-5354 (1996).
44. Kraunz K, et al., "Dietary folate is associated with p16(INK4A) methylation in head and neck squamous cell carcinoma," Int. J. Cancer 119:1553-1557 (2006).
45. Bartkova J, et al., "Abnormal patterns of D-type cyclin expression and G1 regulation in human head and neck cancer," Cancer Res. 55:949-956 ( ).
46. Opitz O G, Harada H, Suliman Y, et al. A mouse model of human oral-esophageal cancer. J Clin Invest 2002; 110:761-9.
47. Simpson A J, Caballero O L, Jungbluth A, Chen Y T, Old L J. Cancer/testis antigens, gametogenesis and cancer. Nat Rev Cancer 2005; 5:615-25.
48. Offenberg H H, Schalk J A, Meuwissen R L, et al. SCP2: a major protein component of the axial elements of synaptonemal complexes of the rat. Nucleic Acids Res 1998; 26:2572-9.
49. Prieto I, Suja J A, Pezzi N, et al. Mammalian STAG3 is a cohesin specific to sister chromatid arms in meiosis I. Nat Cell Biol 2001; 3:761-6.
50. Ollinger R, Alsheimer M, Benavente R. Mammalian protein SCP1 forms synaptonemal complex-like structures in the absence of meiotic chromosomes. Mol Biol Cell 2005; 16:212-7.
51. Duensing S, Munger K. Mechanisms of genomic instability in human cancer: insights from studies with human papillomavirus oncoproteins. Int J Cancer 2004; 109:157-62.
52. Ono M, Nomoto K, Nakazato S. Gene structure of rat testicular cell adhesion molecule 1 (TCAM-1), and its physical linkage to genes coding for the growth hormone and BAF60b, a component of SWI/SNF complexes. Gene 1999; 226:95-102.
53. Zhang, D., Pier, T., McNeel, D. G., Wilding, G., and Friedl, A. Effects of a monoclonal anti-alphavbeta3 integrin antibody on blood vessels—a pharmacodynamic study. Invest New Drugs, 2007; 25:49-55.
54. Allen-Hoffmann B L, et al., "Normal growth and differentiation in a spontaneously immortalized near-diploid human keratinocyte cell line, NIKS," J. Invest. Dermatol. 114:444-455 (2000).

Although the invention has been described in connection with specific embodiments, it is understood that the invention is not limited to such specific embodiments but encompasses all such modifications and variations apparent to a skilled artisan that fall within the scope of the appended claims.

We claim:

1. A method for identifying a human or non-human animal as having a preneoplastic lesion for human papillomavirus positive (HPV+) head and neck cancer comprising the steps of:
measuring the expression of a member selected from testicular cell adhesion molecule 1 (TCAM1) and synaptonemal complex protein 2 (SYCP2) protein in cells of a body fluid sample comprising exfoliated epithelial cells, wherein TCAM1 and SYCP2 are co-expressed in the exfoliated epithelial cells, wherein the body fluid sample is selected from the group consisting of a saliva specimen, mouth rinse, throat rinse, mouth swab, and throat swab, and wherein measuring comprises
(i) binding the member to an antibody having specificity for the member, wherein the antibody has specificity for a TCAM1 or SYCP2 polypeptide expressed on exfoliated epithelial cells;
(ii) detecting the binding of the member and the antibody; and
(iii) quantifying an expression level of the member TCAM1 or SYCP2 on the exfoliated epithelial cells by comparing the detected binding level to a normal non-neoplastic control, wherein a higher expression of one member in exfoliated epithelial cells of the body fluid tissue sample relative that of a non-neoplastic control indicates that cells in the body fluid sample are preneoplastic for HPV+ head and neck cancer;
identifying the human or non-human animal as having a preneoplastic lesion for HPV+head and neck cancer in a head or neck region from which the body fluid sample is obtained; and
administering to the identified human or non-human animal having a preneoplastic lesion for HPV+ head and neck cancer a chemotherapeutic agent operably linked to an antibody having specificity for TCAM1.

2. The method of claim 1, wherein the member is TCAM1 and the antibody has specificity to at least a portion of a polypeptide encoded by the nucleotide sequence of SEQ ID NO:3.

3. The method of claim 1, wherein the member is SYCP2 and the antibody has specificity to at least a portion of a polypeptide having the sequence of SEQ ID NO: 6.

4. The method of claim 1, wherein the binding is detected by an immunological protein detection method.

5. A method for detecting a preneoplastic lesion for HPV+ head and neck cancer in a human or non-human animal comprising the steps of:
detecting an expression level of a member in cells of a body fluid sample of a human or non-human animal comprising exfoliated epithelial cells, wherein the body fluid sample is selected from the group consisting of a saliva specimen, mouth rinse, throat rinse, mouth swab, and throat swab, and wherein detecting comprises, in order, the steps of:
(i) binding a member selected from the group consisting of testicular cell adhesion molecule 1 (TCAM1) and synaptonemal complex protein 2 (SYCP2) protein to an antibody having specificity for the member, wherein TCAM1 and SYCP2 are co-expressed in exfoliated epithelial cells, wherein the antibody has specificity for a TCAM1 or SYCP2 polypeptide expressed on the exfoliated epithelial cells of the body fluid sample;
(ii) detecting the binding of the member and the antibody by an immunological protein detection method; and
(iii) quantifying an expression level of the member TCAM1 or SYCP2 on the exfoliated epithelial cells by comparing the detected binding level to a normal non-neoplastic control, wherein a higher expression in exfoliated epithelial cells of the body fluid tissue sample relative that of a non-neoplastic control indicates that cells of the body fluid sample are preneoplastic for HPV+ head and neck cancer in the head or neck region from which the body fluid sample is obtained and the human and non human animal has a preneoplastic lesion for HPV+ head and neck cancer; and
administering to a human or non-human animal having a preneoplastic lesion for HPV+ head and neck cancer a chemotherapeutic agent operably linked to an antibody having specificity for TCAM1.

* * * * *

UNITED STATES PATENT AND TRADEMARK OFFICE
CERTIFICATE OF CORRECTION

Page 1 of 1

PATENT NO. : 9,790,553 B2
APPLICATION NO. : 13/194624
DATED : October 17, 2017
INVENTOR(S) : Dohun Pyeon et al.

It is certified that error appears in the above-identified patent and that said Letters Patent is hereby corrected as shown below:

In the Specification

Column 10, Line 37, "FINN" should be --HNN--.

Column 13, Line 57, "53B" should be --S3B--.

Column 14, Line 32, "S1A0" should be --S1A--.

Column 14, Line 39, "P56400823" should be --P564O0823--.

Column 32, Line 37, "MCMS" should be --MCM5--.

Signed and Sealed this
Twentieth Day of November, 2018

Andrei Iancu
*Director of the United States Patent and Trademark Office*

SEQUENCE LISTING

<160> NUMBER OF SEQ ID NOS: 27

<210> SEQ ID NO 1
<211> LENGTH: 548
<212> TYPE: PRT
<213> ORGANISM: Mus musculus

<400> SEQUENCE: 1

Met Lys Met Leu Leu Gly Val Trp Thr Leu Ala Leu Ile Pro
1               5                   10                  15

Cys Pro Gly Ala Ala Glu Glu Leu Phe Gln Val Ser Val His Pro Asn
                20                  25                  30

Glu Ala Leu Val Glu Phe Gly His Ser Leu Thr Val Asn Cys Ser Thr
                35                  40                  45

Thr Cys Pro Asp Pro Gly Pro Ser Gly Ile Glu Thr Phe Leu Lys Lys
        50                  55                  60

Thr Gln Leu Ser Lys Gly Ser Gln Trp Lys Glu Phe Leu Leu Glu Asp
65                  70                  75                  80

Ile Thr Glu Asp Leu Val Leu Gln Cys Phe Phe Ser Cys Ala Gly Glu
                    85                  90                  95

Gln Lys Asp Thr Val Leu Ala Ile Thr Met Tyr Gln Pro Pro Glu Gln
                100                 105                 110

Val Ile Leu Asp Leu Gln Pro Glu Trp Val Ala Val Asp Glu Ala Phe
                115                 120                 125

Thr Val Thr Cys His Val Pro Ser Val Ala Pro Leu Gln Ser Leu Thr
            130                 135                 140

Leu Thr Leu Leu Gln Gly Asp Gln Glu Leu His Arg Lys Asp Phe Leu
145                 150                 155                 160

Ser Leu Ser Leu Val Ser Gln Arg Ala Glu Val Thr Ala Thr Val Arg
                    165                 170                 175

Ala His Arg Asp Asn Asp Arg Asn Phe Ser Cys Arg Ala Glu Leu
                180                 185                 190

Asp Leu Ser Pro His Gly Gly Gly Leu Phe His Gly Ser Ser Ala Thr
                195                 200                 205

Lys Gln Leu Arg Ile Phe Glu Phe Ser Gln Asn Pro Gln Ile Trp Val
        210                 215                 220

Pro Ser Leu Leu Glu Val Gly Lys Ala Glu Ile Val Ser Cys Glu Val
225                 230                 235                 240

Thr Arg Val Phe Pro Ala Gln Glu Ala Val Phe Arg Met Phe Leu Glu
                    245                 250                 255

Asp Gln Glu Leu Ser Pro Phe Ser Ser Trp Arg Glu Asp Ala Ala Trp
                260                 265                 270

Ala Ser Ala Thr Ile Gln Ala Met Glu Thr Gly Asp Gln Glu Leu Thr
            275                 280                 285

Cys Leu Val Ser Leu Gly Pro Val Glu Gln Lys Thr Arg Lys Pro Val
        290                 295                 300

Tyr Val Tyr Ser Phe Pro Pro Ile Leu Glu Ile Glu Asp Ala Tyr
305                 310                 315                 320

Pro Leu Ala Gly Thr Asp Val Asn Val Thr Cys Ser Gly His Val Leu
                    325                 330                 335

Thr Ser Pro Ser Pro Thr Leu Arg Leu Gln Gly Ser Leu Asn His Ser
                340                 345                 350

Ala Pro Gly Lys Pro Ala Trp Leu Leu Phe Thr Ala Arg Glu Glu Asp
            355                 360                 365

-continued

```
Asp Gly Arg Thr Leu Ser Cys Glu Ala Ser Leu Glu Val Gln Gly Gln
    370                 375                 380

Arg Leu Val Arg Thr Thr Glu Ser Gln Leu His Val Leu Tyr Lys Pro
385                 390                 395                 400

Arg Phe Gln Glu Ser Arg Cys Pro Gly Asn Gln Ile Trp Val Glu Gly
                405                 410                 415

Met His Gln Met Leu Ala Cys Ile Pro Glu Gly Asn Pro Thr Pro Val
                420                 425                 430

Leu Val Cys Val Trp Asn Gly Met Ile Phe Asp Leu Asp Val Pro Gln
            435                 440                 445

Lys Ala Thr Gln Asn His Thr Gly Thr Tyr Cys Cys Thr Ala Thr Asn
450                 455                 460

Pro Leu Gly Ser Val Ser Lys Asp Ile Thr Ile Val Gln Gly Leu
465                 470                 475                 480

Pro Glu Gly Ile Ser Ser Thr Ile Phe Ile Ile Ile Phe Thr
                485                 490                 495

Leu Gly Met Ala Val Ile Thr Val Ala Leu Tyr Leu Asn Tyr Gln Pro
                500                 505                 510

Cys Lys Gly Asn Ser Arg Lys Arg Met His Arg Pro Arg Glu Gln Ser
            515                 520                 525

Lys Gly Glu Glu Ser Gln Phe Ser Asp Ile Arg Ala Glu Glu Cys His
    530                 535                 540

Ala His Leu Cys
545

<210> SEQ ID NO 2
<211> LENGTH: 548
<212> TYPE: PRT
<213> ORGANISM: Rattus norvegicus

<400> SEQUENCE: 2

Met Lys Met Leu Leu Gly Ile Trp Thr Leu Leu Ala Leu Ile Pro
1               5                   10                  15

Cys Pro Gly Thr Thr Glu Val Leu Phe Gln Val Ser Val His Pro Asn
                20                  25                  30

Gln Ala Leu Val Glu Phe Gly His Ser Leu Thr Ile Asn Cys Ser Thr
            35                  40                  45

Thr Cys Pro Asp Pro Gly Pro Ser Gly Ile Glu Thr Phe Leu Lys Lys
    50                  55                  60

Thr Gln Leu Ser Lys Gly Ser Gln Trp Lys Glu Phe Leu Leu Glu Gly
65                  70                  75                  80

Ile Thr Glu Asn Ser Val Leu Gln Cys Phe Phe Ser Cys Ala Gly Val
                85                  90                  95

Gln Lys Asp Thr Ala Leu Asp Ile Thr Met Tyr Gln Pro Pro Glu Gln
            100                 105                 110

Val Ile Leu Asp Leu Gln Pro Glu Trp Val Ala Ile Asp Glu Ala Phe
        115                 120                 125

Thr Val Lys Cys His Val Pro Ser Val Ala Pro Leu Gln Ser Leu Thr
    130                 135                 140

Leu Thr Leu Leu Gln Gly Asp Gln Glu Leu His Arg Lys Asp Phe Leu
145                 150                 155                 160

Ser Leu Ser Leu Val Ser Gln Arg Ala Glu Val Thr Val Asn Val Arg
                165                 170                 175

Ala Gln Arg Glu Asn Asp Arg His Asn Phe Ser Cys Arg Ala Glu Leu
            180                 185                 190
```

Asp Leu Ser Pro His Gly Gly Leu Phe His Gly Ser Ser Ala Thr
            195                 200                 205

Lys Gln Leu Arg Ile Phe Glu Phe Ser Gln Asn Pro Gln Ile Leu Val
210                 215                 220

Pro Ser Leu Leu Glu Val Gly Met Ala Glu Thr Met Ser Cys Glu Val
225                 230                 235                 240

Val Arg Val Phe Pro Ala Gln Glu Ala Val Phe Arg Met Phe Leu Glu
                245                 250                 255

Asp Gln Glu Leu Ser Pro Phe Ser Ser Trp Lys Gly Asp Ala Ala Trp
            260                 265                 270

Ala Ser Ala Thr Ile Gln Ala Met Glu Thr Gly Asp Gln Glu Leu Thr
        275                 280                 285

Cys Leu Val Ser Val Gly Pro Val Gln Lys Ala Arg Lys Pro Val
    290                 295                 300

His Val Tyr Ser Phe Pro Pro Val Leu Glu Ile Glu Asp Ala Tyr
305                 310                 315                 320

Pro Gln Ala Gly Thr Asp Val Asn Val Thr Cys Ser Gly His Val Leu
                325                 330                 335

Thr Ser Pro Ser Pro Thr Leu Arg Leu Gln Gly Ser Leu Asn Leu Ser
            340                 345                 350

Ala Pro Gly Glu Pro Ala Trp Leu Arg Phe Thr Ala Arg Glu Glu Asp
        355                 360                 365

Asp Gly Arg Thr Leu Ser Cys Glu Ala Ser Leu Val Val Gln Gly Gln
    370                 375                 380

Arg Leu Val Lys Thr Thr Lys Ile Gln Leu His Val Leu Tyr Lys Pro
385                 390                 395                 400

Arg Phe Gln Glu Ser Asp Cys Pro Gly Asn Gln Ile Trp Val Glu Gly
                405                 410                 415

Met Asp Gln Met Leu Ala Cys Ile Pro Glu Gly Asn Pro Ile Pro Ala
            420                 425                 430

Leu Val Cys Ile Trp Asn Gly Met Thr Phe Asp Leu Glu Val Pro Gln
        435                 440                 445

Lys Ala Thr Gln Asn His Thr Gly Thr Tyr Ser Cys Thr Ala Thr Asn
    450                 455                 460

Ser Leu Gly Ser Val Ser Lys Asp Ile Ala Val Leu Val Gln Gly Leu
465                 470                 475                 480

His Glu Gly Ile Ser Ser Ser Thr Ile Phe Ile Ile Ile Phe Thr
                485                 490                 495

Leu Gly Met Ala Val Ile Thr Ile Ala Leu Tyr Leu Asn Tyr Gln Pro
            500                 505                 510

Cys Lys Arg Asn Gly Arg Lys Arg Thr His Arg Gln Lys Glu Gln Asn
        515                 520                 525

Lys Gly Gly Glu Arg Gln Phe Ser Asp Ile Gln Ala Glu Glu Cys His
    530                 535                 540

Ala His Leu Cys
545

<210> SEQ ID NO 3
<211> LENGTH: 3291
<212> TYPE: DNA
<213> ORGANISM: Homo sapiens

<400> SEQUENCE: 3
ttttaataga gacggggttt catcatgttg gccaggatgg tcttgatctc ttgaccttgt    60

-continued

```
gatccgcccg cctcggcctc ccaaagtgct gggattacag gcgtgagcca ccgcgcctgg     120
ccgatgtggt tcatatttca ggggtcccgg aagagttgtt tgaggtttct atttggccaa     180
gtcaggccct ggtggagttt ggacagtccc tagtggtcaa ctgcagcact acttgcccag     240
acccaggacc cagtggaatt gagaccttct taaagaaaac tcaggtgggc aaagggcctc     300
agtggaaaga gtttcttctg gaggatgtca cagagaattc catcctgcag tgcttcttct     360
cttgtgcagg gattcaaaag gacacaagcc ttggcatcac tgtgtatcag ccaccagagc     420
aagtgatcct ggagctgcag cctgcctggg tggccgtgga cgaagccttc acagtgaagt     480
gtcatgtacc cagtgtagca cccttggaga gtctcaccct tgcccttctc cagggtaacc     540
aagaactgca tagaaagaac tttacgagct ggctgtggc ctcccaaaga gctgaagtca     600
tcatcagtgt cagagcccaa aaggagaatg acagatgcaa ttcttcctgc catgcagaac     660
tggacttgag tttgcaaggt gggaggctct ttcaaggcag ctcacccatc agaatagtcc     720
ggatctttga attctctcag agtccccaca tctgggtctc ttccctttg gaggctggga     780 tggcggagac tgtgagctgc gaggtggcta gggtgtttcc agccaaagaa gttatgttcc     840
acatgttcct ggaagaccaa gagctgagct ccttcctttc ctgggagggg gacacagcat     900
gggccaatgc taccattcgg accatggagg ctggtgatca ggaactgtct tgctttgcat     960
ctctgggtgc aatggaacag aagacaagaa agctagtgca tagctacaat aagtggcctg    1020
gctcttcctt tttcatacgg gttctctgct gctgaaaaca cagagtaacg ggttggtgat    1080
tcggctgtag acatccctgc tgcccttgc tgggtatgct ctcaagtgaa catgagtctt    1140
catctttctc tggcttccct ccaccaatcc tggagctaaa agaatcatac ccattggcag    1200
ggactgacat taatgtgacc tgctcagggc atgtattaac atcacccagc cctactcttc    1260
ggcttcaggg agccccagac ctccctgctg gggagcctgc ctggcttcta cttactgcca    1320
gggaggaaga tgatggctga aatttctcct gcgaggcctc tttggtggtg cagggtcagc    1380
ggttgatgaa aaccactgtg atccagctcc atatcctatg caagccacag ttagaggaat    1440
ccagttgccc tggcaaacag acctggctgg aagggatgga acacacgctc gcctgcgtcc    1500
caaagggaaa cccagctcca gccttggtgt gtacctggaa tggggtggtc tttgaccttg    1560
aagtgccaca gaaggcaacc tagaaccaca ctggaaccta ccgctacaca gccactaacc    1620
agctgggctc tgtcagcaaa gacattgctg tcattgttca aggactggat gaaggaatca    1680
gctctaccct ctttgtcatt attaccgttg cccttggagt gggtgtcatc accatagcac    1740
tgtatttgag ctatcggccc tgcaaagtgg acaggaggaa attgctctat aggcagaaag    1800
aggaggacaa agaggaggaa agccagtttg ctgttcagga agagaaaagt acaactcata    1860
taattgacag ctatttgatt gaatgagact tctgctactg tggtttccca gggagggaag    1920
aagggataga ggagaaagga agaaacacaa tggcaggctg cattccccctt tgtgtacgtc    1980 tgtcctgtaa aacggtgttt caggccccca tgccccatgt cctgtgtgtc caatatgtcc    2040
acaagctcac ctttctctct ctgtctcttt tttttttttt gagatggagt ctcgctgttg    2100
tcgcctaggc tggagtgcaa tgatgcgatc tcggctcact gcaacttcag cttcccgggt    2160
tcaggtgatt ctcctgcctc agcctccctg gcagctggga ttacaggtgc accacaac    2220 tcctgtctaa ttttttgtatt tttcgtagag atggggtttc accatgttga ccaggctggt    2280
ctcaaactcc tgacctcaag tgatccgccc accttggcct cccaaaatgc tgggattaca    2340
ggtgtgagcc actgcaccca gccacctttc tctttagagc tcactctagt cattaagaat    2400
```

```
ctcagtctca atgtttgatt tgtaagaagg cctcttgctc cttgccaggt gcttcatcag    2460
tccactctta gatacaaaaa aaagatcctg ctgtttcttt atggtttcca ctgccctttt    2520
ctcttaaaca tcatactaaa gtcaggcaca tcttagaaat gcaactcata tttcatggtt    2580
ttctgattac taactgggaa ctaaatttgt agtccaggga caggactttg aagggagtaa    2640
gtatcaaata tggggctagg aatcagagct ctgttcccat ctccactttc ccttgctccc    2700
ctgacctggg cttctggagt gccagctccc agagctgagc ttgttgacat cattaaggat    2760
cagtggcaag cttcaactca gtaaccatct gttgtgggtc ttgggggagt atacagatgg    2820
taagaaattc cactttgggc cagacaagca tcctatctag cccagtgttc tgtctctgaa    2880
gtagaaggta gagttcttcc atgaaattgg cctcataggt taagagctcc aaacatctct    2940
gaattccttt tcatagagtg atcaactgtg agttcgcatt tgtcagtttt ttttttttac    3000
ccatgtgggt gtctaggtta gagttgcaat gtttactctc ccttttcatc aataaggaca    3060
tattttcttc tgtctgtaag caatttcctt gaagcttcaa gaagaatcct cttgtgaaaa    3120
tgttcatatg atttttatgat tctgcttcct tccctgtcct tgggaaagag tatattcacc    3180
ctcagagaag gcgtgaggaa tcaccaaacc agatcttttc tcccaaatca gtcaagaaat    3240
gttcactgga atgttgctat ggtaaaaata aagtggttt tatgatgtcc a              3291

<210> SEQ ID NO 4
<211> LENGTH: 3291
<212> TYPE: DNA
<213> ORGANISM: Mus musculus

<400> SEQUENCE: 4
ttttaataga gacggggttt catcatgttg gccaggatgg tcttgatctc ttgaccttgt      60
gatccgcccg cctcggcctc ccaaagtgct gggattacag gcgtgagcca ccgcgcctgg     120
ccgatgtggt tcatatttca ggggtcccgg aagagttgtt tgaggtttct atttggccaa     180
gtcaggccct ggtggagttt ggacagtccc tagtggtcaa ctgcagcact acttgcccag     240
acccaggacc cagtggaatt gagaccttct taaagaaaac tcaggtgggc aaagggcctc     300
agtggaaaga gttcttctg gaggatgtca cagagaattc catcctgcag tgcttcttct     360
cttgtgcagg gattcaaaag gacacaagcc ttggcatcac tgtgtatcag ccaccagagc     420
aagtgatcct ggagctgcag cctgcctggg tggccgtgga cgaagccttc acagtgaagt     480
gtcatgtacc cagtgtagca cccttggaga gtctcaccct tgcccttctc cagggtaacc     540
aagaactgca tagaaagaac tttacgagct tggctgtggc ctcccaaaga gctgaagtca     600
tcatcagtgt cagagcccaa aaggagaatg acagatgcaa ttcttcctgc catgcagaac     660
tggacttgag tttgcaaggt gggaggctct tcaaggcag ctcacccatc agaatagtcc      720
ggatctttga attctctcag agtccccaca tctgggtctc ttccttttg gaggctggga     780 tggcggagac tgtgagctgc gaggtggcta gggtgtttcc agccaaagaa gttatgttcc     840
acatgttcct ggaagaccaa gagctgagct ccttcctttc ctgggagggg gacacagcat     900
gggccaatgc taccattcgg accatggagg ctggtgatca ggaactgtct tgctttgcat     960
ctctgggtgc aatggaacag aagacaagaa agctagtgca tagctacaat aagtggcctg    1020
gctcttcctt tttcatacgg gttctctgct gctgaaaaca cagagtaacg ggttggtgat    1080
tcggctgtag acatccctgc tgcccttttgc tgggtatgct ctcaagtgaa catgagtctt    1140
catctttctc tggcttccct ccaccaatcc tggagctaaa agaatcatac ccattggcag    1200
ggactgacat taatgtgacc tgctcagggc atgtattaac atcacccagc cctactcttc    1260
```

```
ggcttcaggg agccccagac ctccctgctg gggagcctgc ctggcttcta cttactgcca      1320
gggaggaaga tgatggctga aatttctcct gcgaggcctc tttggtggtg cagggtcagc      1380
ggttgatgaa aaccactgtg atccagctcc atatcctatg caagccacag ttagaggaat      1440
ccagttgccc tggcaaacag acctggctgg aagggatgga acacacgctc gcctgcgtcc      1500
caaagggaaa cccagctcca gccttggtgt gtacctggaa tggggtggtc tttgaccttg      1560
aagtgccaca gaaggcaacc tagaaccaca ctggaaccta ccgctacaca gccactaacc      1620
agctgggctc tgtcagcaaa gacattgctg tcattgttca aggactggat gaaggaatca      1680
gctctaccct ctttgtcatt attaccgttg cccttggagt gggtgtcatc accatagcac      1740
tgtatttgag ctatcggccc tgcaaagtgg acaggaggaa attgctctat aggcagaaag      1800
aggaggacaa agaggaggaa agccagtttg ctgttcagga agagaaaagt acaactcata      1860
taattgacag ctatttgatt gaatgagact tctgctactg tggtttccca gggagggaag      1920
aagggataga ggagaaagga agaaacacaa tggcaggctg cattcccctt tgtgtacgtc      1980
tgtcctgtaa aacggtgttt caggccccca tgccccatgt cctgtgtgtc aatatgtcc      2040 acaagctcac ctttctctct ctgtctcttt tttttttttt gagatggagt ctcgctgttg      2100
tcgcctaggc tggagtgcaa tgatgcgatc tcggctcact gcaacttcag cttcccgggt      2160
tcaggtgatt ctcctgcctc agcctccctg gcagctggga ttacaggtgc accacaac       2220 tcctgtctaa ttttgtatt tttcgtagag atggggtttc accatgttga ccaggctggt      2280
ctcaaactcc tgacctcaag tgatccgccc accttggcct cccaaaatgc tgggattaca      2340
ggtgtgagcc actgcaccca gccacctttc tctttagagc tcactctagt cattaagaat      2400
ctcagtctca atgtttgatt tgtaagaagg cctcttgctc cttgccaggt gcttcatcag      2460
tccactctta gatacaaaaa aaagatcctg ctgtttcttt atggtttcca ctgccctttt      2520
ctcttaaaca tcatactaaa gtcaggcaca tcttagaaat gcaactcata tttcatggtt      2580
ttctgattac taactgggaa ctaaatttgt agtccaggga caggactttg aagggagtaa      2640
gtatcaaata tggggctagg aatcagagct ctgttcccat ctccacttc ccttgctccc       2700 ctgacctggg cttctggagt gccagctccc agagctgagc ttgttgacat cattaaggat      2760
cagtggcaag cttcaactca gtaaccatct gttgtgggtc ttgggggagt atacagatgg      2820
taagaaattc cactttgggc cagacaagca tcctatctag cccagtgttc tgtctctgaa      2880
gtagaaggta gagttcttcc atgaaattgg cctcataggt taagagctcc aaacatctct      2940
gaattccttt tcatagagtg atcaactgtg agttcgcatt tgtcagtttt ttttttttac      3000
ccatgtgggt gtctaggtta gagttgcaat gtttactctc ccttttcatc aataaggaca      3060 tatttcttc tgtctgtaag caatttcctt gaagcttcaa gaagaatcct cttgtgaaaa       3120
tgttcatatg atttatgat tctgcttcct tccctgtcct tgggaaagag tatattcacc       3180
ctcagagaag gcgtgaggaa tcaccaaacc agatctttc tcccaaatca gtcaagaaat       3240
gttcactgga atgttgctat ggtaaaaata aaagtggttt tatgatgtcc a               3291
```

<210> SEQ ID NO 5
<211> LENGTH: 1647
<212> TYPE: DNA
<213> ORGANISM: Rattus norvegicus

<400> SEQUENCE: 5

```
atgaaaatgc ttctgttggg tatctggacg ctgctggcct tgatcccttg tccagggacc        60
```

-continued

```
acagaagtgc tgtttcaggt gtctgttcat ccaaatcagg ccctggtaga gttcggacac      120
tccctaacca tcaactgcag taccacttgc ccagaccccg ggcccagtgg aatcgagacc      180
ttcttaaaga aaacccagct aagcaaaggg tcccagtgga aggagttcct cctggagggc      240
atcacagaga actctgtgct gcaatgcttc ttctcttgtg cggggtgca gaaagacaca       300 gcacttgaca tcaccatgta ccaaccacca gagcaggtga tcctggacct gcagcctgag      360
tgggtggcca ttgatgaagc cttcacagtg aagtgtcacg tgcctagtgt ggcacccctg      420
cagagcctca cccttaccct cctccagggt gaccaagaac tgcacaggaa agacttcctg      480
agtttatctt tggtgtccca aagagctgag gtcaccgtca atgtcagagc ccagcgggag      540
aacgacaggc acaatttctc ctgccgagca gaactggatc tgagcccaca cggtgggggt      600
ttgtttcatg gcagctcagc caccaagcaa ctccggatct ttgaattctc tcagaatccc      660
cagatcttgg tgccttcact gctggaagtt gggatggccg agactatgag ctgtgaggtg      720
gttagggtgt tcccagccca ggaagctgtc ttccgaatgt ttctggaaga ccaggagctg      780
agccctttct cctcctggaa aggagatgca gcatgggcca gtgctaccat tcaggccatg      840
gagaccggtg accaggagct gacctgcctt gtgtctgtgg gtcctgtgga gcagaaagca      900
agaaaaccag tgcatgtcta cagtttccct ccaccagtcc tggagataga agatgcttac      960
ccacaggcag ggacagacgt taatgtgacc tgctcaggtc acgtgctaac atcgcccagc     1020
cctactcttc ggctccaggg atccctaaac ctctctgctc ccggggagcc tgcctggctt     1080
cggtttactg ccagggagga agatgatggc cggactctct cctgtgaggc ctctttggtg     1140
gtgcagggcc agcgactggt caaaaccacc aagatccagc ttcatgtgtt atacaagcca     1200
aggtttcagg aatccgactg ccctggcaac cagatatggg tagaagggat ggatcagatg     1260
cttgcctgca tcccagaggg aaaccccatc ccggctttgg tgtgtatctg gaatgggatg     1320
acctttgacc ttgaggtacc tcagaaggcc acccagaacc acacaggaac ttacagctgc     1380
acagccacca actccctagg ctctgtcagc aaagacatcg ctgtccttgt ccaaggcctg     1440
catgagggaa tcagctcgtc caccatcttc atcatcatca ttttcaccct cggcatggct     1500
gtgatcacca tagcattata tctgaactac cagcccctgca aaagaaacgg taggaaacgg     1560
acgcacaggc agaaagagca gaacaaaggc ggggagagac agttctcgga tatacaagcc     1620
gaggagtgcc acgcgcacct ctgctga                                         1647
```

<210> SEQ ID NO 6
<211> LENGTH: 1023
<212> TYPE: PRT
<213> ORGANISM: Homo sapiens

<400> SEQUENCE: 6

```
Met Pro Ile Arg Pro Asp Leu Gln Gln Leu Glu Lys Cys Ile Asp Asp
1               5                  10                  15

Ala Leu Arg Lys Asn Asp Phe Lys Pro Leu Lys Thr Leu Leu Gln Ile
            20                  25                  30

Asp Ile Cys Glu Asp Val Lys Ile Lys Cys Ser Lys Gln Phe Phe His
        35                  40                  45

Lys Val Asp Asn Leu Ile Cys Arg Glu Leu Asn Lys Glu Asp Ile His
    50                  55                  60

Asn Val Ser Ala Ile Leu Val Ser Val Gly Arg Cys Gly Lys Asn Ile
65                  70                  75                  80

Ser Val Leu Gly Gln Ala Gly Leu Leu Thr Met Ile Lys Gln Gly Leu
                85                  90                  95
```

-continued

Ile Gln Lys Met Val Ala Trp Phe Glu Lys Ser Lys Asp Ile Ile Gln
            100                 105                 110

Ser Gln Gly Asn Ser Lys Asp Glu Ala Val Leu Asn Met Ile Glu Asp
            115                 120                 125

Leu Val Asp Leu Leu Val Ile His Asp Val Ser Asp Glu Gly Lys
130                 135                 140

Lys Gln Val Val Glu Ser Phe Val Pro Arg Ile Cys Ser Leu Val Ile
145                 150                 155                 160

Asp Ser Arg Val Asn Ile Cys Ile Gln Gln Glu Ile Ile Lys Lys Met
                165                 170                 175

Asn Ala Met Leu Asp Lys Met Pro Gln Asp Ala Arg Lys Ile Leu Ser
            180                 185                 190

Asn Gln Glu Met Leu Ile Leu Met Ser Ser Met Gly Glu Arg Ile Leu
            195                 200                 205

Asp Ala Gly Asp Tyr Asp Leu Gln Val Gly Ile Val Glu Ala Leu Cys
            210                 215                 220

Arg Met Thr Thr Glu Lys Gln Arg Gln Glu Leu Ala His Gln Trp Phe
225                 230                 235                 240

Ser Met Asp Phe Ile Ala Lys Ala Phe Lys Arg Ile Lys Asp Ser Glu
            245                 250                 255

Phe Glu Thr Asp Cys Arg Ile Phe Leu Asn Leu Val Asn Gly Met Leu
            260                 265                 270

Gly Asp Lys Arg Arg Val Phe Thr Phe Pro Cys Leu Ser Ala Phe Leu
            275                 280                 285

Asp Lys Tyr Glu Leu Gln Ile Pro Ser Asp Glu Lys Leu Glu Glu Phe
            290                 295                 300

Trp Ile Asp Phe Asn Leu Gly Ser Gln Thr Leu Ser Phe Tyr Ile Ala
305                 310                 315                 320

Gly Asp Asn Asp Asp His Gln Trp Glu Ala Val Thr Val Pro Glu Glu
                325                 330                 335

Lys Val Gln Ile Tyr Ser Ile Glu Val Arg Glu Ser Lys Lys Leu Leu
            340                 345                 350

Thr Ile Ile Leu Lys Asn Thr Val Lys Ile Ser Lys Arg Glu Gly Lys
            355                 360                 365

Glu Leu Leu Leu Tyr Phe Asp Ala Ser Leu Glu Ile Thr Asn Val Thr
            370                 375                 380

Gln Lys Ile Phe Gly Ala Thr Lys His Arg Glu Ser Ile Arg Lys Gln
385                 390                 395                 400

Gly Ile Ser Val Ala Lys Thr Ser Leu His Ile Leu Phe Asp Ala Ser
                405                 410                 415

Gly Ser Gln Ile Leu Val Pro Gly Ser Gln Ile Ser Pro Val Gly Glu
            420                 425                 430

Glu Leu Val Ser Leu Lys Glu Lys Ser Lys Ser Pro Lys Glu Phe Ala
            435                 440                 445

Lys Pro Ser Lys Tyr Ile Lys Asn Ser Asp Lys Gly Asn Arg Asn Asn
            450                 455                 460

Ser Gln Leu Glu Lys Thr Thr Pro Ser Lys Arg Lys Met Ser Glu Ala
465                 470                 475                 480

Ser Met Ile Val Ser Gly Ala Asp Arg Tyr Thr Met Arg Ser Pro Val
                485                 490                 495

Leu Phe Ser Asn Thr Ser Ile Pro Pro Arg Arg Arg Ile Lys Pro
            500                 505                 510

-continued

Pro Leu Gln Met Thr Ser Ser Ala Glu Lys Pro Ser Val Ser Gln Thr
            515                 520                 525

Ser Glu Asn Arg Val Asp Asn Ala Ala Ser Leu Lys Ser Arg Ser Ser
    530                 535                 540

Glu Gly Arg His Arg Arg Asp Asn Ile Asp Lys His Ile Lys Thr Ala
545                 550                 555                 560

Lys Cys Val Glu Asn Thr Glu Asn Lys Asn Val Glu Phe Pro Asn Gln
                565                 570                 575

Asn Phe Ser Glu Leu Gln Asp Val Ile Pro Asp Ser Gln Ala Ala Glu
            580                 585                 590

Lys Arg Asp His Thr Ile Leu Pro Gly Val Leu Asp Asn Ile Cys Gly
        595                 600                 605

Asn Lys Ile His Ser Lys Trp Ala Cys Trp Thr Pro Val Thr Asn Ile
    610                 615                 620

Glu Leu Cys Asn Asn Gln Arg Ala Ser Thr Ser Ser Gly Asp Thr Leu
625                 630                 635                 640

Asn Gln Asp Ile Val Ile Asn Lys Lys Leu Thr Lys Gln Lys Ser Ser
                645                 650                 655

Ser Ser Ile Ser Asp His Asn Ser Glu Gly Thr Gly Lys Val Lys Tyr
            660                 665                 670

Lys Lys Glu Gln Thr Asp His Ile Lys Ile Asp Lys Ala Glu Val Glu
        675                 680                 685

Val Cys Lys Lys His Asn Gln Gln Asn His Pro Lys Tyr Ser Gly
    690                 695                 700

Gln Lys Asn Thr Glu Asn Ala Lys Gln Ser Asp Trp Pro Val Glu Ser
705                 710                 715                 720

Glu Thr Thr Phe Lys Ser Val Leu Leu Asn Lys Thr Ile Glu Glu Ser
                725                 730                 735

Leu Ile Tyr Arg Lys Lys Tyr Ile Leu Ser Lys Asp Val Asn Thr Ala
            740                 745                 750

Thr Cys Asp Lys Asn Pro Ser Ala Ser Lys Asn Val Gln Ser His Arg
        755                 760                 765

Lys Ala Glu Lys Glu Leu Thr Ser Glu Leu Asn Ser Trp Asp Ser Lys
    770                 775                 780

Gln Lys Lys Met Arg Glu Lys Ser Lys Gly Lys Glu Phe Thr Asn Val
785                 790                 795                 800

Ala Glu Ser Leu Ile Ser Gln Ile Asn Lys Arg Tyr Lys Thr Lys Asp
                805                 810                 815

Asp Ile Lys Ser Thr Arg Lys Leu Lys Glu Ser Leu Ile Asn Ser Gly
            820                 825                 830

Phe Ser Asn Lys Pro Val Val Gln Leu Ser Lys Glu Lys Val Gln Lys
        835                 840                 845

Lys Ser Tyr Arg Lys Leu Lys Thr Thr Phe Val Asn Val Thr Ser Glu
    850                 855                 860

Cys Pro Val Asn Asp Val Tyr Asn Phe Asn Leu Asn Gly Ala Asp Asp
865                 870                 875                 880

Pro Ile Ile Lys Leu Gly Ile Gln Glu Phe Gln Ala Thr Ala Lys Glu
                885                 890                 895

Ala Cys Ala Asp Arg Ser Ile Arg Leu Val Gly Pro Arg Asn His Asp
            900                 905                 910

Glu Leu Lys Ser Ser Val Lys Thr Lys Asp Lys Lys Ile Ile Thr Asn
        915                 920                 925

His Gln Lys Lys Asn Leu Phe Ser Asp Thr Glu Thr Glu Tyr Arg Cys

```
                930               935              940
Asp Asp Ser Lys Thr Asp Ile Ser Trp Leu Arg Glu Pro Lys Ser Lys
945                 950              955              960

Pro Gln Leu Ile Asp Tyr Ser Arg Asn Lys Asn Val Lys Asn His Lys
                965              970              975

Ser Gly Lys Ser Arg Ser Ser Leu Glu Lys Gly Gln Pro Ser Ser Lys
                980              985              990

Met Thr Pro Ser Lys Asn Ile Thr Lys Lys Met Asp Lys Thr Ile Pro
                995              1000             1005

Glu Gly Arg Ile Arg Leu Pro Arg Lys Ala Thr Lys   Thr Lys Lys
                1010             1015             1020

<210> SEQ ID NO 7
<211> LENGTH: 1500
<212> TYPE: PRT
<213> ORGANISM: Mus musculus

<400> SEQUENCE: 7

Met Pro Val Arg Pro Asp Leu Gln Gln Leu Glu Lys Cys Ile Asp Asp
1               5                   10                  15

Ala Leu Arg Lys Asn Asp Phe Lys Pro Leu Ala Leu Leu Gln Ile
            20                  25                  30

Asp Ile Cys Glu Asp Val Lys Ile Lys Cys Ser Lys Gln Phe Leu Arg
            35                  40                  45

Lys Leu Asp Asp Leu Ile Cys Arg Glu Leu Asn Lys Lys Asp Ile Gln
        50                  55                  60

Thr Val Ser Ser Ile Leu Ile Ser Ile Gly Arg Cys Ser Lys Asn Ile
65                  70                  75                  80

Phe Ile Leu Gly Gln Ala Gly Leu Gln Thr Met Ile Lys Gln Gly Leu
                85                  90                  95

Val Gln Lys Met Val Ser Trp Phe Glu Asn Ser Lys Glu Ile Ile Leu
            100                 105                 110

Asn Gln Gln Gln Ser Lys Asp Glu Ala Val Met Asn Met Ile Glu Asp
        115                 120                 125

Leu Phe Asp Leu Leu Met Val Ile Tyr Asp Ile Ser Asp Glu Gly Lys
    130                 135                 140

Asn Gln Val Leu Glu Ser Phe Ile Pro Gln Ile Cys Ala Leu Val Ile
145                 150                 155                 160

Asp Ser Arg Val Asn Phe Cys Ile Gln Gln Glu Ala Leu Lys Lys Met
                165                 170                 175

Asn Leu Met Leu Asp Arg Ile Pro Gln Asp Ala Asn Lys Ile Leu Ser
            180                 185                 190

Asn Gln Glu Met Leu Thr Leu Met Ser Asn Met Gly Glu Arg Ile Leu
        195                 200                 205

Asp Val Gly Asp Tyr Glu Leu Gln Val Gly Ile Val Glu Ala Leu Cys
    210                 215                 220

Arg Met Thr Thr Glu Lys Arg Arg Gln Glu Leu Ala Tyr Glu Trp Phe
225                 230                 235                 240

Ser Met Asp Phe Ile Ala Asn Ala Phe Lys Glu Ile Lys Asp Cys Glu
                245                 250                 255

Phe Glu Thr Asp Cys Arg Ile Phe Leu Asn Leu Val Asn Gly Ile Leu
            260                 265                 270

Gly Asp Lys Arg Arg Val Tyr Thr Phe Pro Cys Leu Ser Ala Phe Leu
        275                 280                 285
```

```
Gly Lys Tyr Glu Leu Gln Ile Pro Ser Asp Glu Lys Leu Glu Glu Phe
290                 295                 300

Trp Ile Asp Phe Asn Leu Gly Ser His Thr Leu Ser Phe Tyr Ile Ala
305                 310                 315                 320

Gly Asp Glu Glu Asp His Gln Trp Glu Ala Val Thr Val Pro Glu Glu
            325                 330                 335

Lys Val Gln Met Tyr Asn Ile Glu Val Arg Glu Ser Lys Lys Leu Leu
                340                 345                 350

Thr Leu Thr Leu Lys Asn Ile Val Lys Ile Ser Lys Lys Glu Gly Lys
            355                 360                 365

Glu Leu Leu Phe Tyr Phe Asp Glu Ser Leu Glu Ile Thr Asn Val Thr
370                 375                 380

Lys Lys Val Phe Gly Gly Asn Lys Tyr Lys Glu Phe Thr Arg Lys Gln
385                 390                 395                 400

Gly Ile Ser Val Ala Lys Thr Ser Ile His Val Leu Phe Asp Ala Ser
                405                 410                 415

Gly Ser Gln Ile Leu Val Pro Glu Ser Gln Pro Ser Pro Val Lys Glu
            420                 425                 430

Asn Leu Ile His Leu Lys Glu Lys Ser Asp Ile Gln Lys Lys Leu Val
                435                 440                 445

Asn Pro Leu Glu Leu Gly Asn Ser Ser Ser Gln Asp Glu Ile Thr Thr
450                 455                 460

Pro Ser Arg Lys Lys Met Ser Glu Ala Ser Met Ile Val Pro Asp Thr
465                 470                 475                 480

Asp Arg Tyr Thr Val Arg Ser Pro Ile Leu Leu Ile Asn Thr Ser Thr
                485                 490                 495

Pro Arg Arg Ser Arg Glu Pro Leu Gln Ala Ile Asn Ser Val Glu Lys
            500                 505                 510

Ala Val Ser Lys Thr Ser Glu Ser Gly Met Asp Tyr Ala Ala Ser Pro
                515                 520                 525

Lys Ser Arg Gln Ser Asp Gly Arg Lys Arg Trp Asn Asn Arg Ala Asn
530                 535                 540

His Asn Lys Thr Thr Ala Val Ile Gln Asn Lys Gln Tyr Glu Asp Asn
545                 550                 555                 560

Glu Ser Pro Asp Gln Asn Phe Asn Glu Ile Glu Asp Thr Leu Ser Asn
                565                 570                 575

Val Ser Ser Ala Val Gly Lys Val Asp Lys Pro Val Leu Pro Gly Val
            580                 585                 590

Leu Asp Ile Ser Lys Asn Thr Thr His Ser Arg Trp Ala Cys Trp Thr
595                 600                 605

Pro Val Thr Thr Ile Lys Leu Cys Asn Asn Gln Arg Ser Arg Ala Leu
610                 615                 620

Pro Gly Asp Thr Cys Thr Gln Asp Thr Gly Val Asn Lys Lys Cys Thr
625                 630                 635                 640

Lys Gln Lys Ser Val Ser Asp Asp Ser Glu Glu Thr Gln Lys Gly
                645                 650                 655

Lys Tyr Ser Lys Asp Val Ile Lys Cys Asn Lys Ser Asp Glu Ala Glu
            660                 665                 670

Phe Cys Glu Arg Asn Ile Gln Glu Gln Asn His Pro Lys Tyr Ser Gln
                675                 680                 685

Lys Lys Asn Thr Ala Asn Ala Lys Lys Ser Asp Trp His Ile Glu Ser
690                 695                 700

Glu Thr Thr Tyr Lys Ser Val Leu Leu Asn Lys Thr Thr Glu Glu Ser
```

-continued

```
              705                 710                 715                 720
Leu Ile Tyr Lys Lys Thr Cys Val Leu Ser Lys Asp Val Asn Thr Thr
                    725                 730                 735
Ile Cys Asp Lys Ser Pro Ser Arg Lys Ser Lys Arg Asn His Thr Lys
                    740                 745                 750
Ser Arg Lys Glu Leu Met Ser Glu Leu Thr Ser Cys Glu Leu Glu Glu
                    755                 760                 765
Ile Pro Val Arg Glu Asn Ser Lys Gly Lys Arg Phe Thr Gly Ala Ser
                    770                 775                 780
Glu Ser Leu Ile Asn Gln Ile Ser Arg Arg Tyr Asn Pro Ser Asp Ser
785                 790                 795                 800
Met Met Ser Thr Arg Lys Leu Lys Glu Pro Gln Asp Gly Ser Gly Phe
                    805                 810                 815
Ser Lys Lys Pro Asp Leu Gln Phe Asn Lys Val Gln Arg Lys Ser Tyr
                    820                 825                 830
Arg Lys Leu Lys Ala Thr Val Val Asn Val Thr Ser Glu Cys Pro Leu
                    835                 840                 845
Asp Asp Val Tyr Asn Phe Ser Leu Asn Gly Ala Asp Glu Pro Val Ile
850                 855                 860
Lys Leu Gly Ile Gln Glu Phe Gln Ala Thr Thr Arg Glu Ala Ser Met
865                 870                 875                 880
Asp Asn Ser Leu Lys Leu Val Lys Asn His Asp Glu His Asp Pro Phe
                    885                 890                 895
Leu Lys Thr Lys Asp Lys Arg Met Leu Ser Tyr Glu Lys Lys Thr Leu
                    900                 905                 910
Leu Ser Asp Thr Glu Thr Glu Cys Gly Cys Asp Asp Ser Lys Thr Asp
                    915                 920                 925
Ile Ser Trp Leu Lys Glu Pro Lys Thr Lys Arg Leu Met Asp Tyr Ser
                    930                 935                 940
Arg Asn Lys Asn Thr Thr Lys Tyr Lys Ser Arg Lys Ser Arg Ser Ser
945                 950                 955                 960
Met Glu Lys Gly Gln Pro Arg Pro Thr Met Val Leu Asn Lys Asn Ser
                    965                 970                 975
Met Lys Asn Asp Tyr Glu Val Val Val Asp Gly Arg Thr Arg Leu Pro
                    980                 985                 990
Arg Arg Ala Thr Lys Thr Lys Lys Asn Tyr Lys Asp Leu Ser Thr Ser
                    995                 1000                1005
Glu Ser Glu Ser Glu Ser Glu Lys Glu Cys Ser Tyr Leu Phe Lys
                    1010                1015                1020
Asp Lys Leu Pro Thr Lys Glu Glu Thr Ile His Ser Arg Ala Gln
                    1025                1030                1035
Thr Lys Lys Leu Pro Glu Lys Gln Gln Lys Val Phe Asn Ser Glu
                    1040                1045                1050
Ala Leu Lys Gly Gln Pro Ser Glu Glu Gln Lys Asn Ser Ser Arg
                    1055                1060                1065
Leu Arg Glu Gly Arg Glu Asp Ser Leu Cys Leu Ser Ser Ala Ser
                    1070                1075                1080
Val Ser Arg Ser Ser Ser Val Glu Val Met Arg Cys Thr Glu
                    1085                1090                1095
Lys Ile Thr Glu Arg Asp Phe Thr Gln Asp Tyr Asp Tyr Ile Thr
                    1100                1105                1110
Lys Ser Leu Ser Pro Tyr Pro Lys Ala Pro Ser Pro Glu Phe Leu
                    1115                1120                1125
```

```
Asn Gly Asn Asn Ser Val Val Gly Arg Gly Gln Ser Pro Arg Ile
    1130                1135                1140

Ser Glu Thr Ser Ala Met Cys Val Arg Lys Ser Tyr Ser Pro Ala
    1145                1150                1155

Ser Gly Pro Pro Phe Ser Pro Arg His Thr Pro Thr Lys Asn Asn
    1160                1165                1170

Ser Val Val Asn Met Lys Lys Ala Asn Ser Val Ile Asn Asn Gln
    1175                1180                1185

Arg Thr Gln His Cys Asn Ser Tyr Ser Asp Val Ser Ser Asn Ser
    1190                1195                1200

Ser Glu Lys Leu Tyr Met Glu Pro Glu Ser Pro Glu Ser Cys Asp
    1205                1210                1215

Asn His Met Gln Asn Lys Arg Glu Gly Asn His Ala Ala Ser Pro
    1220                1225                1230

Leu Ser Leu Ser Ser Glu Lys Ile Glu Lys Met Trp Phe Asp Met
    1235                1240                1245

Pro Ser Glu Asn Thr His Val Ser Gly Pro Ser Gln Arg Gly Ser
    1250                1255                1260

Lys Arg Arg Met Tyr Leu Glu Asp Asp Glu Leu Ser Asn Ser Asn
    1265                1270                1275

Glu Ala Glu Val Glu Glu Ala Glu Glu Arg Glu His Leu Leu Ser
    1280                1285                1290

Lys Lys Arg Cys Gln Trp Glu Asn Ser Asp Gln His Thr Phe Lys
    1295                1300                1305

Thr Ser Leu Ser Thr Pro Asp Phe Ser Val Pro Lys Asp Trp Gln
    1310                1315                1320

Gln Glu Leu Gln Gly Ala Gly Met Phe Tyr Asp Asn Ile Ser Ser
    1325                1330                1335

Asp Tyr Lys Arg Lys Thr Asp Ser Gln His Lys Ile Met Asp Asp
    1340                1345                1350

Phe Thr Thr Lys Thr Leu Lys Leu Thr Gln Gln His Leu Met Ala
    1355                1360                1365

Met Thr Ser Gln Ala Gln Gly Arg Arg Asp Glu Asn Val Glu Lys
    1370                1375                1380

Phe Gln Val Thr Leu Leu Asp Glu Leu Glu Lys Val Glu Lys Asp
    1385                1390                1395

Ser Gln Thr Leu Arg Asp Leu Glu Lys Glu Leu Val Asp Ile Glu
    1400                1405                1410

Glu Lys Leu Val Gln Lys Met Arg Ala Tyr His Arg Cys Glu Arg
    1415                1420                1425

Glu Arg Phe Arg Val Leu Lys Thr Ser Leu Asp Lys Ser Phe Leu
    1430                1435                1440

Val Tyr Asn Ser Val Tyr Glu Glu Ser Val Phe Thr Ser Glu Met
    1445                1450                1455

Cys Leu Met Lys Ala Asn Met Lys Met Leu Gln Asp Lys Leu Leu
    1460                1465                1470

Lys Glu Met His Glu Glu Val Leu Asn Ile Arg Arg Gly Leu
    1475                1480                1485

Gln Ser Leu Phe Lys Ala His Glu Gly Asn Asp Ala
    1490                1495                1500
```

<210> SEQ ID NO 8
<211> LENGTH: 1505

<212> TYPE: PRT
<213> ORGANISM: Rattus norvegicus

<400> SEQUENCE: 8

```
Met Pro Val Arg Pro Asp Pro Gln Gln Leu Glu Lys Cys Ile Asp Asp
1               5                   10                  15

Ala Leu Arg Lys Asn Asp Phe Lys Pro Leu Val Thr Leu Leu Gln Ile
            20                  25                  30

Asp Ile Cys Glu Asp Val Lys Ile Lys Cys Ser Lys Gln Phe Leu Arg
        35                  40                  45

Lys Leu Asp Asp Leu Ile Cys Arg Glu Leu His Lys Lys Asp Ile Gln
50                  55                  60

Thr Ile Ser Asn Ile Leu Ile Ser Ile Gly Arg Cys Ser Lys Asn Ile
65                  70                  75                  80

Phe Ile Leu Gly Gln Thr Gly Leu Gln Thr Met Ile Lys Gln Gly Leu
                85                  90                  95

Val Gln Lys Met Val Ser Trp Phe Glu Asn Ser Lys Glu Ile Ile Leu
            100                 105                 110

Ser Gln Arg Gln Ser Lys Asp Glu Ala Val Met Asn Met Ile Glu Asp
        115                 120                 125

Leu Phe Asp Leu Leu Met Val Val Tyr Asp Val Asn Asp Glu Gly Lys
130                 135                 140

Asn Gln Val Leu Glu Ser Phe Ile Pro His Ile Cys Ala Leu Val Ile
145                 150                 155                 160

Asp Ser Arg Val Asn Phe Cys Ile Gln Gln Glu Ala Leu Lys Lys Met
                165                 170                 175

Asn Leu Met Leu Asp Arg Ile Pro Gln Asp Ala Asn Lys Ile Leu Cys
            180                 185                 190

Asn Gln Glu Ile Leu Thr Leu Met Ser Asn Met Gly Arg Ile Leu
        195                 200                 205

Asp Val Gly Asp Tyr Glu Leu Gln Val Gly Ile Val Glu Ala Leu Cys
210                 215                 220

Arg Met Thr Thr Glu Lys Arg Arg Gln Glu Leu Ala Tyr Glu Trp Phe
225                 230                 235                 240

Ser Met Asp Phe Ile Ala Asn Ala Phe Lys Lys Ile Lys Asp Cys Glu
                245                 250                 255

Phe Glu Thr Asp Cys Arg Ile Phe Leu Asn Leu Val Asn Gly Met Leu
            260                 265                 270

Gly Asp Arg Arg Arg Val Phe Thr Phe Pro Cys Leu Ser Ala Phe Leu
        275                 280                 285

Gly Lys Tyr Glu Leu Gln Ile Pro Ser Asp Gly Lys Leu Glu Glu Phe
290                 295                 300

Trp Ile Asp Phe Asn Leu Gly Ser His Thr Leu Ser Phe Tyr Ile Ala
305                 310                 315                 320

Gly Asp Asp Asp His Gln Trp Glu Ala Val Thr Val Pro Glu Glu
                325                 330                 335

Lys Val Asp Met Tyr Asn Ile Glu Val Arg Glu Ser Lys Lys Leu Leu
            340                 345                 350

Thr Leu Thr Leu Lys Asn Ile Val Lys Ile Ser Lys Glu Gly Lys
        355                 360                 365

Glu Leu Leu Leu Tyr Phe Asp Ala Ala Leu Glu Ile Thr Asn Val Thr
370                 375                 380

Lys Lys Leu Phe Gly Gly Asn Lys Tyr Lys Glu Phe Thr Arg Lys Gln
385                 390                 395                 400
```

```
Asp Ile Ser Val Ala Lys Thr Ser Ile His Val Leu Phe Asp Ala Ser
            405                 410                 415

Gly Ser Gln Ile Leu Val Pro Glu Ser Gln Pro Ser Pro Val Lys Glu
        420                 425                 430

Asn Leu Ile His Leu Lys Glu Lys Ser Asn Leu Gln Lys Lys Leu Thr
            435                 440                 445

Asn Pro Leu Glu Pro Asp Asn Ser Ser Ser Gln Arg Asp Arg Lys Asn
450                 455                 460

Ser Gln Asp Glu Ile Thr Thr Pro Ser Arg Lys Lys Met Ser Glu Ala
465                 470                 475                 480

Ser Met Ile Val Pro Asp Thr Asp Arg Tyr Thr Val Arg Ser Pro Ile
                485                 490                 495

Leu Leu Ile Asn Thr Ser Thr Pro Arg Arg Ser Arg Ala Pro Leu Gln
            500                 505                 510

Ala Ile His Ser Ala Glu Lys Ala Val Ser Lys Thr Ser Glu Ser Gly
        515                 520                 525

Val Asp Tyr Ala Val Ser Leu Lys Ser Arg Gln Ser Asp Gly Arg Asn
    530                 535                 540

Arg Gly Asn Asn Arg Ala Asn His Asn Lys Thr Ala Thr Val Gln Asn
545                 550                 555                 560

Lys Gly His Glu His His Glu Ser Pro Asp Gln Thr Phe Asn Glu Ile
                565                 570                 575

Glu Glu Thr Leu Ser Asp Ala Tyr Ala Val Glu Lys Val Asp Lys Pro
            580                 585                 590

Val Leu Pro Gly Val Leu Asp Ile Ser Lys Asn Lys Ala His Ser Arg
        595                 600                 605

Trp Ala Cys Trp Thr Pro Val Thr Thr Ile Lys Leu Cys Asn Asn Gln
    610                 615                 620

Arg Ser Cys Ala Leu Pro Gly Asp Thr Phe Thr Gln Asp Thr Gly Val
625                 630                 635                 640

Asn Lys Lys Cys Thr Lys Gln Lys Ser Val Ser Asp Asp Asp Ser Glu
                645                 650                 655

Glu Thr Gln Arg Val Lys Tyr Ser Lys Asp Val Ile Lys Cys Asn Lys
            660                 665                 670

Ser Glu Glu Ala Glu Val Cys Glu Arg Asn Ile Gln Glu Gln Asn His
        675                 680                 685

Pro Lys Tyr Ser Gln Lys Lys Asn Thr Ala Asn Ala Lys Lys Asn Asp
    690                 695                 700

Trp His Ile Glu Ser Glu Thr Thr Tyr Lys Ser Val Leu Leu Asn Lys
705                 710                 715                 720

Thr Thr Glu Glu Ser Leu Ile Tyr Lys Lys Thr Cys Val Leu Ser Lys
                725                 730                 735

Asp Val Asn Thr Thr Ile Cys Asp Lys Ser Pro Ser Arg Lys Ser Met
            740                 745                 750

Arg Ser His Thr Lys Ser Arg Lys Glu Leu Met Ser Glu Val Thr Ser
        755                 760                 765

Cys Glu Leu Asp Glu Ile Pro Val Arg Glu Asn Ser Lys Gly Lys Arg
    770                 775                 780

Phe Thr Gly Thr Ala Glu Ser Leu Ile Asn Leu Ile Asn Lys Arg Tyr
785                 790                 795                 800

Asn Ser Ser Asp Asp Met Ile Ser Thr Arg Lys Leu Lys Glu Pro Arg
                805                 810                 815
```

-continued

```
Asp Gly Ser Gly Phe Ser Lys Pro Glu Leu Gln Phe Asn Lys Val
            820                 825                 830
Gln Arg Lys Ser Tyr Arg Lys Leu Lys Thr Val Val Asn Val Thr Ser
            835                 840                 845
Glu Cys Pro Leu Asn Asp Val Tyr Asn Phe Ser Leu Asn Gly Ala Asp
            850                 855                 860
Glu Pro Val Ile Lys Leu Gly Ile Gln Glu Phe Gln Ala Thr Thr Arg
865                 870                 875                 880
Glu Ala Ser Met Asp Asn Ser Ile Lys Leu Val Asp Val Arg Asn Arg
                    885                 890                 895
Asp Glu Arg Asp Leu Ser Leu Lys Thr Lys Asp Glu Arg Ile Leu Ser
            900                 905                 910
His Glu Arg Lys Thr Leu Phe Ser Asp Thr Glu Thr Glu Cys Gly Trp
            915                 920                 925
Asp Asp Ser Lys Thr Asp Ile Ser Trp Leu Arg Lys Pro Lys Ser Lys
            930                 935                 940
Arg Leu Met Asp Tyr Ser Arg Asn Lys Asn Thr Lys Lys Cys Lys Ser
945                 950                 955                 960
Ile Lys Ser Arg Ser Ser Thr Glu Lys Gly Gln Pro Arg Ser Thr Val
            965                 970                 975
Val Leu Ser Lys Asn Ile Ala Lys Asn Asp Tyr Glu Val Ile Val Asp
            980                 985                 990
Gly Arg Thr Arg Leu Pro Arg Arg Ala Thr Lys Thr Lys Lys Asn Tyr
            995                 1000                1005
Lys Asp Leu Ser Thr Ser Gly Ser Glu Ser Glu Ser Glu Lys Glu
        1010                1015                1020
Ile Ser Tyr Leu Phe Lys Asp Lys Leu Pro Thr Lys Glu Glu Thr
        1025                1030                1035
Val His Ser Ser Ala Gln Thr Lys Lys Leu Pro Lys Lys Gln Gln
        1040                1045                1050
Lys Val Phe Asn Thr Glu Ala Leu Lys Gly Gln Pro Ser Glu Glu
        1055                1060                1065
Gln Lys Asn Ser Ser Thr Leu Arg Asn Gly Arg Glu Asp Ser Leu
        1070                1075                1080
Tyr Leu Ser Ser Ala Ser Val Ser Gly Ser Ser Ser Val Glu
        1085                1090                1095
Val Met Arg Cys Thr Glu Lys Ile Thr Glu Arg Asp Phe Thr Gln
        1100                1105                1110
Asp Tyr Asp Tyr Ile Thr Lys Ser Leu Ser Pro Tyr Pro Lys Ala
        1115                1120                1125
Ala Ser Pro Glu Phe Leu Asn Arg Ser Asn Arg Val Val Gly His
        1130                1135                1140
Gly Lys Ser Pro Arg Ile Ser Glu Thr Ser Ala Val Cys Val Arg
        1145                1150                1155
Lys Ser Cys Ser Pro Ala Ser Gly Leu Pro Phe Ser Pro Arg His
        1160                1165                1170
Thr Thr Lys Asn Asn Ser Val Met Asn Ile Lys Asn Thr Asn Ser
        1175                1180                1185
Val Ile Asn Asn Gln Arg Thr Gln His Cys Asn Ser Tyr Ser Asp
        1190                1195                1200
Val Ser Ser Asn Ser Ser Glu Lys Leu Tyr Met Glu Pro Glu Ser
        1205                1210                1215
Pro Asp Ser Cys Glu Asn His Val Gln Ser Lys Arg Glu Glu Asn
```

His Ala Ala Ser Pro Phe Ser Leu Ser Ser Glu Lys Ile Glu Lys
        1235                1240                1245

Ile Trp Phe Asp Met Pro Asn Asp Thr His Val Ser Gly Pro
    1250                1255                1260

Ser Gln Arg Gly Ser Lys Arg Arg Met Tyr Leu Glu Asp Glu
    1265                1270                1275

Leu Ser Asn Pro Ser Glu Ala Glu Val Gln Glu Ala Glu Arg
    1280                1285                1290

Glu His Leu Val Ser Lys Lys Leu Cys Gln Arg Glu His Phe Asp
    1295                1300                1305

Gln His Thr Ser Glu Thr Ser Leu Ser Thr Pro Glu Phe Ser Val
    1310                1315                1320

Pro Lys Asp Trp Gln Gln Glu Leu Gln Gly Ala Gly Met Phe Tyr
    1325                1330                1335

Asp Asn Ile Asn Ser Asp Tyr Lys Arg Lys Thr Asp Thr Gln His
    1340                1345                1350

Lys Ile Met Asp Asp Phe Thr Thr Lys Thr Leu Lys Leu Thr Gln
    1355                1360                1365

Gln His Leu Leu Ala Met Ala Cys Gln Ala Arg Gly His Arg Asp
    1370                1375                1380

Glu Asn Ile Asp Lys Phe Gln Val Thr Leu Leu Asp Glu Leu Glu
    1385                1390                1395

Lys Val Glu Lys Asp Ser Gln Thr Leu Arg Asp Leu Glu Lys Glu
    1400                1405                1410

Phe Val Asp Ile Glu Glu Lys Ile Val His Lys Met Arg Ala Phe
    1415                1420                1425

His Gln Ser Glu Arg Glu Arg Phe Arg Ala Leu Lys Thr Ser Leu
    1430                1435                1440

Asp Lys Ser Leu Leu Val Tyr Asn Ser Val Tyr Glu Glu Asn Val
    1445                1450                1455

Leu Thr Ser Glu Met Cys Leu Met Lys Ala Asn Met Lys Met Leu
    1460                1465                1470

Gln Asp Lys Leu Leu Lys Glu Met His Glu Glu Leu Leu Asn
    1475                1480                1485

Ile Arg Arg Gly Leu Glu Ser Leu Phe Lys Asp His Glu Gly Asn
    1490                1495                1500

Asn Ala
    1505

<210> SEQ ID NO 9
<211> LENGTH: 1079
<212> TYPE: PRT
<213> ORGANISM: Sus scrofa

<400> SEQUENCE: 9

Val Ala Trp Phe Glu Lys Ser Lys Glu Ile Ile Leu Ser Gln Gly Ser
1               5                   10                  15

Ser Lys Asp Glu Ala Val Ile Asn Met Ile Glu Asp Phe Phe Asp Leu
            20                  25                  30

Leu Met Val Ile His Asp Ile Asp Asp Glu Gly Lys Arg Gln Val Val
        35                  40                  45

Glu Ser Phe Ile Pro Arg Ile Cys Ala Leu Val Ile Asp Ser Arg Val
    50                  55                  60

```
Asn Ile Cys Val Gln Gln Glu Thr Leu Lys Lys Met Asn Ala Met Leu
 65                  70                  75                  80

Asp Lys Met Pro Gln Asp Ala Arg Lys Ile Leu Phe Asn Gln Glu Met
                 85                  90                  95

Leu Ile Leu Met Ser Ser Met Gly Glu Arg Ile Leu Asp Ala Gly Asp
            100                 105                 110

Tyr Asp Leu Gln Val Gly Ile Val Glu Ala Leu Cys Arg Met Thr Thr
        115                 120                 125

Glu Lys Gln Arg Gln Glu Leu Ala Cys Gln Trp Phe Ser Met Asp Phe
    130                 135                 140

Val Ala Asn Ala Phe Lys Gly Ile Lys Asp Ser Glu Phe Glu Thr Asp
145                 150                 155                 160

Cys Arg Met Phe Leu Asn Leu Val Asn Gly Ile Leu Gly Asp Lys Arg
                165                 170                 175

Arg Val Phe Thr Phe Pro Cys Leu Ser Ala Phe Leu Asp Lys Tyr Glu
            180                 185                 190

Leu Gln Ile Pro Ser Asp Glu Lys Leu Glu Asp Phe Trp Ile Asp Phe
        195                 200                 205

Asn Leu Gly Ser Gln Thr Leu Ser Phe Tyr Ile Ala Gly Asp Asn Asp
    210                 215                 220

Asp His Gln Trp Glu Ala Val Thr Val Pro Glu Glu Lys Val Gln Ile
225                 230                 235                 240

Tyr Ser Ile Glu Val Arg Asp Ser Lys Lys Leu Leu Thr Ile Ile Leu
                245                 250                 255

Lys Asp Thr Val Lys Ile Ser Lys Arg Lys Gly Lys Glu Leu Leu Leu
            260                 265                 270

Tyr Phe Asp Ala Ser Leu Glu Ile Thr Asn Val Thr Gln Lys Ile Phe
        275                 280                 285

Gly Ala Asn Lys Tyr Arg Glu Phe Ser Arg Lys Gln Gly Ile Ser Val
    290                 295                 300

Ala Lys Thr Ser Val His Ile Leu Phe Asp Ala Ser Gly Ser Gln Ile
305                 310                 315                 320

Leu Val Pro Glu Ser Gln Ile Ser Pro Val Glu Glu Leu Ser Thr Leu
                325                 330                 335

Lys Glu Lys Ala Asn Pro Gln Glu Glu Phe Val Lys Pro Pro Lys His
            340                 345                 350

Ile Lys Asn Ser Asn Lys Gly Asp Arg Lys His Gly Gln Pro Glu Ile
        355                 360                 365

Ile Thr Pro Ser Lys Arg Lys Met Ser Glu Ala Ser Met Ile Val Pro
    370                 375                 380

Gly Ala Glu Arg Tyr Thr Val Arg Ser Pro Ile Leu Leu Ile Asn Thr
385                 390                 395                 400

Ser Thr Pro Gln Arg Gly Arg Ile Lys Pro Pro Leu Gln Met Thr Ser
                405                 410                 415

Ser Met Glu Lys Pro Gly Phe Ser Lys Thr Ser Glu Asn Gly Val Asp
            420                 425                 430

Asn Ala Val Ser Leu Lys Ser Arg Pro Cys Glu Glu Arg Asn Arg Glu
        435                 440                 445

Asp Asn Thr Asp Lys His Ile Lys Thr Lys Val Ile Glu Lys Ala Glu
    450                 455                 460

Asn Lys Asp Ile Glu Tyr Pro Asn Gln Asn Phe Asn Glu Leu Gln Glu
465                 470                 475                 480

Ile Val Pro Asp Ser Gln Ala Val Gly Lys Ile Asp Lys Pro Val Leu
```

```
                485                 490                 495
Pro Gly Ile Leu Asp Asn Ile Cys Gly Asn Lys Met His Ser Lys Trp
            500                 505                 510
Ala Cys Trp Thr Pro Val Thr Asn Ile Lys Leu Cys Asn Asn Leu Arg
            515                 520                 525
Ala Ser Ser Ser Ser Glu Asp Thr Phe Asn Gln Asp Ile Ile Ile Asn
            530                 535                 540
Lys Asn Leu Thr Lys Lys Lys Ser Ser Ser Met Ser Asp Asp Asn
545                 550                 555                 560
Ser Glu Glu Thr Ser Lys Val Gln Tyr Gly Lys Glu Leu Met Gln His
            565                 570                 575
Asn Lys Ile Asp Lys Ala Glu Ala Ala Cys Lys Arg Asn Lys Gln
            580                 585                 590
Gln Gln Leu Asp His Ser Lys His Ser Glu Glu Lys Asn Thr Glu Asn
            595                 600                 605
Thr Lys Gln Asn Asp Trp Arg Ile Glu Ser Glu Thr Thr Phe Lys Ser
            610                 615                 620
Val Leu Leu Asn Lys Thr Val Glu Glu Ser Val Ile Tyr Arg Lys Lys
625                 630                 635                 640
Tyr Thr Leu Ser Lys Asp Val Asn Thr Ala Ile Cys Asp Lys Ser Pro
            645                 650                 655
Ser Pro Arg Lys Asn Thr Lys Ser His Arg Lys Ser Gly Lys Arg Leu
            660                 665                 670
Thr Ser Glu Leu Asn Ser Trp Asp Leu Lys Gln Lys Glu Met Arg Glu
            675                 680                 685
Lys Ser Lys Gly Lys Gly Phe Asn Asp Ala Ala Glu Ser Leu Ile Ser
            690                 695                 700
Gln Ile Asn Lys Arg Tyr Lys Pro Lys Asp Gly Thr Lys Ser Thr Arg
705                 710                 715                 720
Lys Leu Lys Glu Ser Leu Ile Asp Ser Gly Phe Ser Asn Lys Ser Asp
            725                 730                 735
Leu Gln Leu Arg Lys Glu Lys Val Gln Lys Ser Tyr Arg Gln Leu
            740                 745                 750
Lys Thr Thr Phe Val Asn Val Thr Ser Glu Cys Pro Leu Asn Asp Val
            755                 760                 765
Tyr Asn Phe Asn Leu Ser Gly Ala Asp Glu Pro Val Ile Lys Leu Gly
            770                 775                 780
Ile Gln Glu Phe Gln Ala Thr Ala Arg Glu Ala Cys Val Asp Ser Thr
785                 790                 795                 800
Ile Thr Leu Val Gly Leu Arg Asn His Asp Glu Leu Glu Thr Ser Leu
            805                 810                 815
Lys Thr Lys Asp Lys Arg Thr Val Thr Asn His Lys Lys Thr Leu
            820                 825                 830
Phe Ser Asp Thr Asp Thr Glu Tyr Lys Cys Asp Asp Ser Lys Thr Asp
            835                 840                 845
Ile Ser Trp Leu Arg Glu Ser Lys Ser Lys Pro Gln Leu Ile Gly Tyr
            850                 855                 860
Ser Arg Asn Lys Asn Val Lys Lys His Lys Ser Gly Lys Ser Arg Ser
865                 870                 875                 880
Ser Leu Glu Arg Glu Gln Pro Arg Ser Lys Met Thr Pro Asp Lys Asn
            885                 890                 895
Ile Thr Lys Lys Val Asp Glu Thr Val Pro Asp Gly Arg Ile Arg Leu
            900                 905                 910
```

```
Pro Arg Arg Ala Ala Lys Thr Lys Asn Tyr Lys Asp Leu Ser Asn
        915                 920                 925

Ser Glu Ser Glu Ser Glu Gln Glu Phe Ser His Ser Phe Lys Glu Lys
    930                 935                 940

Leu Leu Ile Lys Glu Asn Ile His Ser Arg Ser Lys Thr Met Lys Pro
945                 950                 955                 960

Pro Lys Lys Gln Asn Ser Phe Ser Ser Glu Met Gln Lys Asp Ile Ser
                965                 970                 975

Lys Glu Trp Lys Asn Ser Ser Leu Leu Lys Asp Thr Ile Arg Asp Asn
            980                 985                 990

Ser Leu Asp Lys Ser Pro Val Ser Leu Ser Gly Ser Pro Ser Ser Ile
    995                 1000                1005

Glu Val Met Arg Cys Thr Glu Lys Thr Thr Glu Arg Asp Phe Thr
    1010                1015                1020

Gln Asp Phe Asp Tyr Val Thr Lys Ser Leu Ser Pro Tyr Pro Lys
    1025                1030                1035

Thr Ser Ser Pro Glu Ser Leu Asn Ser Gly Val Glu Ser Pro Ile
    1040                1045                1050

Asn Ser Pro Asn Asn Ser Glu Lys Asn Leu Leu Cys Gly Gly Glu
    1055                1060                1065

Ser Cys Ser Pro Ile Pro Gln Ser Gly Phe Leu
    1070                1075

<210> SEQ ID NO 10
<211> LENGTH: 919
<212> TYPE: PRT
<213> ORGANISM: Xenopus tropicalis

<400> SEQUENCE: 10

Met His Pro Lys Gln Glu Ser Lys Leu Glu Ala Asn Ile Asp His Gly
1               5                   10                  15

Leu Arg Thr Lys Gly His Asp Leu Arg Pro Leu Lys Ser Phe Leu Leu
            20                  25                  30

Thr Glu Ser Cys Ala Gly Thr Ser Ile Lys Cys Ser Lys Phe Leu Leu
        35                  40                  45

Gly Lys Leu Asp Lys Leu Ile Cys Met Glu Leu Asp Gln Arg Glu Val
    50                  55                  60

Lys Asn Ala Leu Leu Val Leu Asn Val Ile Leu Lys Phe Ala Ser Cys
65                  70                  75                  80

Met Thr Leu Asn Asn Glu Glu Trp Leu Thr Ala Ser Ile Lys Gln Gly
                85                  90                  95

Leu Val Gln Lys Met Ile Ile Trp Leu Glu Lys Ser Thr Tyr Phe Leu
            100                 105                 110

Ala Tyr Ser Glu Lys Gln Lys Asn Glu Thr Val Leu Asn Phe Ala Glu
        115                 120                 125

Asp Phe Phe Asp Ile Val Met Leu Val His Asp His Ser Ser Glu Gly
    130                 135                 140

Lys Met Gln Ile Leu Glu His Phe Leu Val Arg Ala Cys Ser Leu Val
145                 150                 155                 160

Ser Asn Ala Ala Thr Asn Ile Phe Val Lys Gln Glu Val Val Arg Arg
                165                 170                 175

Leu Asn Leu Met Leu Asn Thr Met Pro Leu Val Ala Arg Lys Lys Ile
            180                 185                 190

Leu Ser Thr Glu Glu Met Thr Ser Ala Met Ala Ser Met Ala Lys Arg
```

```
            195                 200                 205
Ile Leu Asp Ala Gly Asp Phe Asp Leu Gln Val Ala Ile Thr Glu Ala
210                 215                 220

Leu Cys Arg Met Thr Ser Glu Ala Gln Arg Glu Leu Thr Ser Gln Trp
225                 230                 235                 240

Phe Pro Met Glu Phe Ile Ala Glu Ala Phe Lys Arg Ile Lys Asp Ser
                    245                 250                 255

Glu Phe Glu Thr Asp Cys Arg Lys Phe Leu Asn Leu Ile Asn Gly Ile
                260                 265                 270

Leu Gly Gly Lys Lys Ser Val Val Thr Leu Pro Cys Leu Ser Ala Tyr
            275                 280                 285

Leu Asp Asn His Lys Phe Gln Met Pro Cys Asp Glu Lys Leu Glu Glu
290                 295                 300

Phe Trp Ile Asp Phe Asn Thr Gly Thr Gln Ser Ile Ser Phe Tyr Ile
305                 310                 315                 320

Ser Ala Gly Ala Ala Glu Glu His Gln Trp Asp Thr Val Cys Val Lys
                    325                 330                 335

Asp Ser Asp Val Ile Val Tyr Ser Ile Ala Glu Val Asp Asn Asn Lys
                340                 345                 350

Leu Leu Thr Val Asp Leu Lys Ala Pro Ile Ala Ala Gly Gln Tyr Glu
            355                 360                 365

Gly Lys Gln Ile Arg Ile Tyr Phe Ser Cys Pro Leu Asp Ile Leu Ser
370                 375                 380

Ala Ala Gln Arg Val Phe Ala Ala Gln Lys Asn Lys Asp Phe Ile Lys
385                 390                 395                 400

Lys Gln Thr Ala Ser Asp Ala Glu Thr Thr Val Arg Val Ile Phe Glu
                    405                 410                 415

Glu Cys Arg Ser Gln Ile Leu Leu Ser Glu Ser Gln Gly Ser Asn Ser
                420                 425                 430

Ser Val Lys Pro Val Ala Glu Pro Asp Val Lys Asp Phe Ala Gly Lys
            435                 440                 445

Asn Gln Pro Pro Ser Ala Ala Ser Ser Leu Lys Gln Thr Thr Cys Asn
450                 455                 460

His Glu His Asn Thr Asn Ser Leu Met Pro Thr Thr Pro Val Lys Val
465                 470                 475                 480

Lys Met Ser Glu Ser Ser Met Val Gly Ser Gly Leu Lys Ile Thr Asn
                    485                 490                 495

Ile Ala Thr Asn Asn Pro Ala Ser Arg Arg Ile Arg Thr Lys Pro Pro
                500                 505                 510

Leu Glu Met Val Arg Pro Ala Glu Arg Asn Thr Val Pro Pro Asn Lys
            515                 520                 525

Ser Arg Gly Gly Ser Pro Cys Ser Asp Arg Thr Pro Gln Leu Pro Lys
530                 535                 540

His Lys Ser Ser Thr Asp Ala Ala Cys Thr Phe Gln Tyr Val Asn Lys
545                 550                 555                 560

Ala Pro Lys Asp Glu Leu Asn Glu Ile Val Pro Asp Thr Gln Tyr Cys
                    565                 570                 575

Ala Thr Lys Asp Ser Ser Leu Leu Pro Gly Leu Thr Lys Arg Ser Val
                580                 585                 590

Asn Gln His Glu Arg Asn Arg Lys Gln Glu Asn Ser Gly Gly Phe Gly
            595                 600                 605

Asn Lys Ile Ser Val Ser Ser Val Cys Ile Ala Asn Gln Gly Lys Ile
610                 615                 620
```

```
Ser Ser His Leu Val Lys Gln His Ser Asn Glu Ile Ser Thr Thr Pro
625                 630                 635                 640

Thr Lys Glu Met Ser Ala Arg Ser Ser Glu Ser Ser Ile Gln Lys His
            645                 650                 655

Cys Glu Lys His Leu Lys Glu Lys Pro Lys Glu Leu Ile Gln Ala Thr
                660                 665                 670

Asp Leu Leu Val Glu Asn Ile Arg Arg Lys Tyr Ala Arg Leu Thr Glu
            675                 680                 685

Glu Asp Lys Arg Glu Glu Asn Thr Phe Glu Arg Lys Asn Val Asp Lys
690                 695                 700

His Pro Leu His Thr Asn Lys Asp Lys Asn Arg Thr Arg Gly Phe Asn
705                 710                 715                 720

Gln His Ser Pro Lys Asp Phe Ser Thr Thr Lys Lys Pro Trp Lys
                725                 730                 735

Asp Val Tyr Asp Phe Gln Phe Ser Ala Thr Asp Asn Pro Thr Ile Asn
            740                 745                 750

Leu Glu Val Ser Ala Pro Thr Val Ser Glu Arg Met Ser Ser Lys Ala
            755                 760                 765

Leu Ala Ile Gly Lys Lys Ser Thr Lys Asn Lys Gln Lys Gly Lys Thr
            770                 775                 780

Gly Thr Glu Ile Lys Thr Lys Ala His Gln Arg His Leu Phe Ser Asp
785                 790                 795                 800

Thr Glu Ser Glu Arg Gly Gly Asp Asp Thr Lys Ser Asn Leu Ser Trp
                805                 810                 815

Leu Gln Glu Gln His Ser Lys Thr Lys Pro Pro Ile Ala Thr Tyr Arg
                820                 825                 830

Arg Gln Lys Ala Gln Lys Gln Gln Thr Met Pro Tyr Lys Met
            835                 840                 845

Arg His Ile Thr Thr Asn Asn Ser Pro Glu Pro Lys Thr Gly Lys Lys
            850                 855                 860

Ser Tyr Asn Arg Ser Gly Gly Asn Lys His Asn Lys Leu Lys Arg Pro
865                 870                 875                 880

Cys Arg Thr Ala Ala Lys Ser Thr Asn Tyr Lys Asp Leu Ser Asn Ser
                885                 890                 895

Glu Ser Asp Ala Glu Val Pro Phe Ser Pro Pro Lys Arg Glu Glu Pro
                900                 905                 910

Val Arg Arg Arg Cys Leu Lys
            915

<210> SEQ ID NO 11
<211> LENGTH: 1530
<212> TYPE: PRT
<213> ORGANISM: Pan troglodytes
<220> FEATURE:
<221> NAME/KEY: misc_feature
<222> LOCATION: (1456)..(1459)
<223> OTHER INFORMATION: Xaa can be any naturally occurring amino acid

<400> SEQUENCE: 11

Met Pro Ile Arg Pro Asp Leu Gln Gln Leu Glu Lys Cys Ile Asp Asp
1               5                   10                  15

Ala Leu Arg Lys Asn Asp Phe Lys Pro Leu Lys Thr Leu Leu Gln Ile
                20                  25                  30

Asp Ile Cys Glu Asp Val Lys Ile Lys Cys Ser Lys Gln Phe Phe His
            35                  40                  45
```

```
Lys Val Asp Asn Leu Ile Cys Arg Glu Leu Asn Lys Glu Asp Ile His
    50                  55                  60

Asn Val Ser Ala Ile Leu Val Ser Val Gly Arg Cys Gly Lys Asn Ile
65                  70                  75                  80

Ser Val Leu Gly Gln Ala Gly Leu Leu Thr Met Ile Lys Gln Gly Leu
                85                  90                  95

Ile Gln Lys Met Val Ala Trp Phe Glu Lys Ser Lys Asp Ile Ile Gln
            100                 105                 110

Ser Gln Gly Asn Ser Lys Asp Glu Ala Val Leu Asn Met Ile Glu Asp
            115                 120                 125

Leu Val Asp Leu Leu Val Ile His Asp Val Ser Asp Glu Gly Lys
    130                 135                 140

Lys Gln Val Val Glu Ser Phe Val Pro Arg Ile Cys Ser Leu Val Ile
145                 150                 155                 160

Asp Ser Arg Val Asn Ile Cys Ile Gln Gln Glu Ile Ile Lys Arg Met
                165                 170                 175

Asn Ala Met Leu Asp Lys Met Pro Gln Asp Ala Arg Lys Ile Leu Ser
            180                 185                 190

Asn Gln Glu Met Leu Ile Leu Met Ser Ser Met Gly Glu Arg Ile Leu
            195                 200                 205

Asp Ala Gly Asp Tyr Asp Leu Gln Val Gly Ile Val Glu Ala Leu Cys
    210                 215                 220

Arg Met Thr Thr Glu Lys Gln Arg Gln Glu Leu Ala His Gln Trp Phe
225                 230                 235                 240

Ser Met Asp Phe Ile Ala Lys Ala Phe Lys Arg Ile Lys Asp Ser Glu
                245                 250                 255

Phe Glu Thr Asp Cys Arg Ile Phe Leu Asn Leu Val Asn Gly Met Leu
            260                 265                 270

Gly Asp Lys Arg Arg Val Phe Thr Phe Pro Cys Leu Ser Ala Phe Leu
            275                 280                 285

Asp Lys Tyr Glu Leu Gln Ile Pro Ser Asp Glu Lys Leu Glu Glu Phe
    290                 295                 300

Trp Ile Asp Phe Asn Leu Gly Ser Gln Thr Leu Ser Phe Tyr Ile Ala
305                 310                 315                 320

Gly Asp Asn Asp Asp His Gln Trp Glu Ala Val Thr Val Pro Glu Glu
                325                 330                 335

Lys Val Gln Ile Tyr Ser Ile Glu Val Arg Glu Ser Lys Lys Leu Leu
            340                 345                 350

Thr Ile Ile Leu Lys Asn Thr Val Lys Ile Ser Lys Arg Glu Gly Lys
            355                 360                 365

Glu Leu Leu Leu Tyr Phe Asp Ala Ser Leu Glu Ile Thr Asn Val Thr
    370                 375                 380

Gln Lys Ile Phe Gly Ala Asn Lys His Arg Glu Ser Ile Arg Lys Gln
385                 390                 395                 400

Gly Ile Ser Val Ala Lys Thr Ser Leu His Ile Leu Phe Asp Ala Ser
                405                 410                 415

Gly Ser Gln Ile Leu Val Pro Glu Ser Gln Ile Ser Pro Val Gly Glu
            420                 425                 430

Glu Leu Val Ser Leu Lys Glu Lys Ser Lys Ser Pro Lys Glu Phe Ala
            435                 440                 445

Lys Pro Ser Lys Tyr Ile Lys Asn Ser Asp Lys Gly Asn Arg Asn Asn
    450                 455                 460

Ser Gln Leu Glu Lys Ile Thr Pro Ser Lys Arg Lys Met Ser Glu Ala
```

```
              465                 470                 475                 480
        Ser Met Ile Val Ser Gly Ala Asp Arg Tyr Thr Met Arg Ser Pro Val
                            485                 490                 495
        Leu Phe Ser Asn Thr Ser Ile Pro Pro Arg Arg Arg Ile Lys Pro
                    500                 505                 510
        Pro Leu Gln Met Met Ser Ser Ala Glu Lys Pro Ser Val Ser Gln Thr
                        515                 520                 525
        Ser Glu Asn Arg Val Asp Asn Ala Ala Ser Leu Lys Ser Arg Ser Ser
                    530                 535                 540
        Glu Glu Arg His Arg Arg Asp Asn Thr Asp Lys His Ile Lys Thr Ala
        545                 550                 555                 560
        Lys Cys Val Glu Asn Thr Glu Asn Lys Asn Val Glu Phe Pro Asn Gln
                            565                 570                 575
        Asn Phe Ser Glu Leu Gln Asp Val Ile Pro Asp Ser Gln Pro Val Glu
                        580                 585                 590
        Lys Arg Asp His Ala Ile Leu Pro Gly Val Leu Asp Asn Ile Cys Gly
                    595                 600                 605
        Asn Lys Ile His Ser Lys Trp Ala Cys Trp Thr Pro Val Thr Asn Ile
                610                 615                 620
        Glu Leu Cys Asn Asn Gln Arg Ala Ser Thr Ser Ser Gly Asp Thr Leu
        625                 630                 635                 640
        Asn Gln Asp Ile Val Ile Asn Lys Lys Leu Thr Lys Gln Lys Ser Ser
                            645                 650                 655
        Ser Ser Ile Ser Asp His Asn Ser Glu Gly Thr Gly Lys Val Lys Tyr
                        660                 665                 670
        Lys Lys Glu Gln Thr Asp His Ile Lys Ile Asp Lys Ala Glu Val Glu
                    675                 680                 685
        Val Cys Lys Lys His Asn Gln Gln Asn His Pro Lys Tyr Ser Gly
                690                 695                 700
        Gln Lys Asn Thr Glu Asn Ala Lys Gln Ser Asp Trp Pro Val Glu Ser
        705                 710                 715                 720
        Glu Thr Thr Phe Lys Ser Val Leu Leu Asn Lys Thr Ile Glu Glu Ser
                            725                 730                 735
        Leu Ile Tyr Lys Lys Tyr Ile Leu Ser Lys Asp Val Asn Thr Ala
                        740                 745                 750
        Thr Cys Asp Lys Asn Pro Ser Ala Ser Lys Asn Val Gln Ser His Arg
                    755                 760                 765
        Lys Ala Glu Lys Glu Leu Thr Ser Glu Leu Asp Ser Trp Asp Leu Lys
                770                 775                 780
        Gln Lys Lys Met Arg Glu Lys Ser Lys Gly Lys Glu Phe Thr Asp Val
        785                 790                 795                 800
        Ala Glu Ser Leu Ile Ser Gln Ile Asn Lys Arg Tyr Lys Thr Lys Asp
                            805                 810                 815
        Asp Ile Lys Ser Thr Arg Lys Leu Lys Glu Ser Leu Ile Asn Ser Asp
                        820                 825                 830
        Phe Ser Asn Lys Pro Val Val Gln Leu Ser Lys Glu Lys Val Gln Lys
                    835                 840                 845
        Lys Ser Tyr Arg Lys Leu Lys Thr Thr Phe Val Asn Val Thr Ser Glu
                850                 855                 860
        Cys Pro Val Asn Asp Val Tyr Asn Phe Asn Leu Asn Gly Ala Asp Asp
        865                 870                 875                 880
        Pro Ile Ile Lys Leu Gly Ile Gln Glu Phe Gln Ala Thr Ala Lys Glu
                            885                 890                 895
```

-continued

```
Ala Cys Ala Asp Arg Ser Ile Arg Leu Val Gly Pro Arg Asn His Asp
            900                 905                 910

Glu Leu Lys Ser Ser Val Lys Thr Lys Asp Lys Lys Ile Ile Thr Asn
            915                 920                 925

His Gln Lys Lys Asn Leu Phe Ser Asp Thr Glu Thr Glu Tyr Arg Cys
            930                 935                 940

Asp Asp Ser Lys Thr Asp Ile Ser Trp Leu Arg Glu Pro Lys Ser Lys
945                 950                 955                 960

Pro Gln Leu Ile Asp Tyr Ser Arg Asn Lys Asn Val Arg Asn His Lys
                    965                 970                 975

Ser Gly Lys Ser Arg Ser Ser Leu Glu Lys Gly Gln Pro Ser Ser Lys
            980                 985                 990

Met Thr Pro Ser Lys Asn Ile Met Lys Lys Thr Asp Lys Thr Ile Pro
            995                 1000                1005

Glu Gly Arg Ile Arg Leu Pro Arg Lys Ala Thr Lys Thr Lys Lys
        1010                1015                1020

Asn Tyr Lys Asp Leu Ser Asn Ser Glu Ser Glu Cys Glu Gln Glu
        1025                1030                1035

Phe Ser His Ser Phe Lys Glu Asn Ile Pro Val Lys Glu Glu Asn
        1040                1045                1050

Ile His Ser Arg Met Lys Thr Val Lys Leu Pro Lys Lys Gln Gln
        1055                1060                1065

Lys Val Phe Cys Ala Glu Thr Glu Lys Glu Leu Ser Lys Gln Cys
        1070                1075                1080

Lys Asn Ser Ser Leu Leu Lys Asp Ala Ile Arg Asp Asn Cys Leu
        1085                1090                1095

Asp Leu Ser Pro Arg Ser Leu Ser Gly Ser Pro Ser Ser Ile Glu
        1100                1105                1110

Val Thr Arg Cys Ile Glu Lys Ile Thr Glu Lys Asp Phe Thr Gln
        1115                1120                1125

Asp Tyr Asp Cys Ile Thr Lys Ser Ile Ser Pro Tyr Pro Lys Thr
        1130                1135                1140

Ser Ser Leu Glu Ser Leu Asn Ser Asn Ser Gly Val Gly Gly Thr
        1145                1150                1155

Ile Lys Ser Pro Lys Asn Asn Glu Lys Asn Phe Leu Cys Ala Ser
        1160                1165                1170

Glu Ser Cys Ser Pro Ile Pro Arg Pro Leu Phe Leu Pro Arg His
        1175                1180                1185

Thr Pro Thr Lys Ser Asn Thr Ile Val Asn Arg Lys Lys Lys Ser
        1190                1195                1200

Ser Leu Val Leu Thr Gln Glu Thr Gln Asn Cys Asn Ser Tyr Ser
        1205                1210                1215

Asp Val Ser Ser Tyr Ser Ser Glu Glu Arg Phe Met Glu Ile Glu
        1220                1225                1230

Ser Pro His Ile Asn Glu Asn Tyr Ile Gln Ser Lys Arg Glu Glu
        1235                1240                1245

Ser His Leu Ala Ser Ser Leu Ser Lys Ser Ser Glu Gly Arg Glu
        1250                1255                1260

Lys Thr Trp Phe Asp Met Pro Cys Asp Ala Thr His Val Ser Gly
        1265                1270                1275

Pro Thr Gln His Leu Ser Arg Lys Arg Ile Tyr Ile Glu Asp Asn
        1280                1285                1290
```

| | | | | | | | | | | | |
|---|---|---|---|---|---|---|---|---|---|---|---|
| Leu | Ser | Asn | Ser | Asn | Glu | Val | Glu | Met | Glu | Glu | Lys | Gly | Glu | Arg |
| | 1295 | | | | 1300 | | | | 1305 | | |

Arg Ala Asn Leu Leu Pro Lys Lys Leu Cys Lys Ile Glu Asp Ala
    1310                1315                1320

Asp His His Ile His Lys Met Ser Glu Ser Val Ser Ser Leu Ser
    1325                1330                1335

Thr Asn Asp Phe Ser Ile Pro Trp Glu Thr Trp Arg Asn Glu Phe
    1340                1345                1350

Ala Gly Ile Glu Met Thr Tyr Glu Thr Tyr Glu Arg Leu Asn Ser
    1355                1360                1365

Glu Phe Lys Arg Arg Asn Asn Ile Arg His Lys Met Leu Ser Tyr
    1370                1375                1380

Phe Thr Thr Gln Ser Trp Lys Thr Ala Gln Gln His Leu Arg Thr
    1385                1390                1395

Ile Asn His Gln Ser Gln Asp Ser Arg Ile Lys Lys Leu Asp Lys
    1400                1405                1410

Phe Gln Phe Ile Ile Ile Glu Glu Leu Glu Asn Phe Glu Lys Asp
    1415                1420                1425

Ser Gln Ser Leu Lys Asp Leu Glu Lys Glu Phe Val Asp Phe Trp
    1430                1435                1440

Glu Lys Ile Phe Gln Met Phe Ser Ala Tyr Gln Lys Xaa Xaa Xaa
    1445                1450                1455

Xaa Arg Leu His Leu Leu Lys Thr Ser Leu Ala Lys Ser Val Phe
    1460                1465                1470

Cys Asn Thr Asp Asn Glu Glu Thr Val Phe Thr Ser Glu Met Cys
    1475                1480                1485

Leu Met Lys Glu Asp Met Lys Val Leu Gln Asp Arg Leu Leu Lys
    1490                1495                1500

Asp Met Leu Glu Glu Glu Leu Leu Asn Val Arg Arg Glu Leu Met
    1505                1510                1515

Ser Val Phe Met Ser His Glu Arg Asn Ala Asn Val
    1520                1525                1530

<210> SEQ ID NO 12
<211> LENGTH: 5497
<212> TYPE: DNA
<213> ORGANISM: Homo sapiens

<400> SEQUENCE: 12

```
atacacaatc atcatcttac tagttctctg tgttgctcgc taaccagtcc cccagttcag    60
tagactggag cccagagcct gcttacttgt caggtgttta ttttgtcttg ctttttttttt   120 tttttttaaat gaagtcaaaa tgccaataag accagatctc cagcagttgg aaaaatgcat   180
tgatgatgct ttaagaaaaa atgatttcaa acctttgaaa acactttgc aaattgatat    240 ttgtgaagat gtgaagatta aatgcagcaa acagttttc cacaaggtgg acaaccttat    300
atgcagggaa cttaataaag aggatatcca caatgtttca gccattttgg tttctgttgg   360
aagatgtggc aaaaatatca gtgtattggg gcaagctgga cttctaacga tgataaaaca    420
aggactaata caaagatgg ttgcctggtt tgaaaaatcc aaggacatta ttcagagtca    480
aggaaattca aaagatgaag ctgttctaaa tatgatagaa gacttagttg atcttctgct   540
ggtcatacat gatgtcagtg atgaaggtaa aaacaagta gtggaaagtt tcgtacctcg    600
catttgttcc ctggttattg actcaagagt gaatatttgt attcagcaag agattataaa   660
aaaaatgaat gctatgcttg acaaaatgcc tcaagatgcc cggaaaatac tctctaacca    720
```

```
agaaatgtta attctcatga gtagtatggg agaaaggatt ttagatgctg gagattatga    780
cttacaggta ggcattgtag aagctttgtg tagaatgacc acagaaaaac aaagacaaga    840
actggcacat cagtggtttt caatggattt tattgctaag gcatttaaaa gaattaagga    900
ctctgaattt gaaacagatt gcaggatatt tctcaacctt gtaaatggca tgcttggaga    960
caaaagaagg gtctttacat ttccttgttt atcagcattt cttgataaat atgagctgca   1020
aataccatca gatgaaaaac ttgaggaatt ttggattgat tttaatcttg ggagtcagac   1080
tctctcattc tacattgctg gagataatga tgatcatcaa tgggaagcag ttactgtgcc   1140
agaggaaaaa gtacaaatat acagcattga agtgagagaa tcaaagaagc tactgacaat   1200
aattctgaaa aatacagtaa aaattagcaa aagagaaggg aaagaattgc ttttgtattt   1260
tgacgcatca ctagaaatca ctaatgtaac tcaaaaaatt tttggtgcaa ctaaacatag   1320
ggaatctatc agaaaacaag gtatttcagt tgccaaaacg tcgctgcata cttttttga   1380 cgcaagtgga tcacagattc tagtgccaga aagtcaaatc tcaccagtcg gagaagagct   1440
cgttagttta aaggaaaaat caaagtcccc aaaggaattt gctaaacctt caaaatatat   1500
caaaaacagt gacaagggaa atagaaataa tagtcagctt gagaaaacta ctcctagcaa   1560
aagaaaaatg tctgaagcat caatgattgt ttctggtgca gatagataca ctatgagaag   1620
tccagtgctt ttcagcaaca catcaatacc accacgaaga agaagaatta aaccaccact   1680
gcaaatgacg agctctgcag agaaacctag tgtttctcaa acatcagaaa atagagtgga   1740
taatgctgca tcactgaaat ctagatcatc agaaggaaga catagaagag ataatataga   1800
caaacatatc aaaactgcta agtgtgtaga aaacacagaa ataagaatg ttgaattccc   1860 aaaccaaaat tttagtgaac tccaggatgt tataccagat tcacaggcag cggaaaaaag   1920
agatcatact atattacctg gtgttttaga caacatctgt ggaaataaaa tacacagcaa   1980
atgggcatgt tggacacctg taacaaacat tgaactatgt aataaccaaa gagcaagtac   2040
ttcgtcagga gacacattga atcaagatat tgttataaat aaaaaactta ctaaacaaaa   2100
atcatcctct tcaatatctg atcataattc tgaaggaaca ggaaaagtga atataagaa   2160 agaacaaacc gaccatatca aaatagataa agcagaagta gaagtttgca agaaacacaa   2220
tcagcaacaa aatcatccta aatattcagg gcagaaaaat actgaaaatg ccaagcagag   2280
tgattggcct gttgaatctg aaactacttt taaatcggtt ctcctaaata agacaattga   2340
agaatcgctg atatatagga agaaatacat attgtcaaaa gatgtgaata ctgctacttg   2400
cgataaaaat ccatctgcta gcaaaaatgt gcaaagtcat agaaaagcag agaaagaatt   2460
gacttctgag cttaattcct gggattcgaa acaaaaaaaa atgagagaaa agtcaaaagg   2520
gaaagaattt accaatgtag cagaatcctt gataagccaa atcaataaaa gatacaaaac   2580
aaaagatgac atcaagtcta caagaaaatt aaggagtct tgattaaca gtggttttc   2640 aaacaaacct gttgtacaac tcagtaagga aaagttcag aaaaaagct acagaaaact   2700 gaagactacc tttgttaatg ttacttctga atgcccagtg aatgatgttt acaattttaa   2760
tttgaatgga gctgatgacc ctatcataaa acttggaatc caagagtttc aagctacagc   2820
taaagaagct tgtgcggata ggtcaattag attggtaggt ccaggaatc atgatgaact   2880 taaatcttct gtcaaaacaa agataaaaa aattataaca aatcatcaaa agaaaaatct   2940
gtttagtgat actgaaacag agtacagatg tgatgacagc aagactgata ttagctggct   3000
aagagaaccg aaatcaaaac cacagctaat agactatagc agaaataaaa atgtgaagaa   3060
```

```
tcataaaagt ggaaaatcaa gatcatcctt ggaaaaggga cagccaagct ctaaaatgac    3120
acccagtaaa aatatcacaa aaaagatgga caagacaatt ccggaaggaa gaatcagact    3180
tccacgaaaa gcaaccaaaa caaaaaaaaa ctataaagat ctctcaaatt cagaatcaga    3240
gtgtgaacaa gaattttcac attcatttaa agagaacata ccagtaaagg aggagaatat    3300
ccattccaga atgaaaacgg taaagctacc aaagaaacaa cagaaagtct tctgtgctga    3360
aacagaaaag gaactatcaa aacaatggaa aaactcatct ctactaaaag atgctatacg    3420
agataattgc cttgacttat ctcccagatc tttatctggc agtccatcat ctatagaagt    3480
aacgagatgt atagagaaaa taacagaaaa ggattttact caggattatg actgcataac    3540
aaaatctata tcaccttatc caaaaacttc atcacttgaa tccttaaata gtaacagtgg    3600
agttggaggt acaataaagt cacccaaaaa caatgagaaa aacttcctgt gtgcaagtga    3660
aagttgttca ccaattccac gaccactgtt tttgcccaga catactccaa ctaagagtaa    3720
tactattgta aatagaaaaa aaataagttc tctggtactt acacaagaaa cacaaaacag    3780
taacagctat tcagatgtaa gcagttatag ttcagaagaa cggtttatgg aaattgaatc    3840
tccacatatc aatgaaaatt atatacaaag caaaagagag gaaagtcatt tagcatcttc    3900
attatccaag tctagtgaag gaagagagaa acgtggtttt gacatgccct gtgatgctac    3960
tcatgtatca ggccccaccc aacatcttag tcgcaaaaga atatatatag aagataatct    4020
aagtaattcc aatgaagtag aaatggaaga gaaggagaa aggagagcaa acttgcttcc    4080
caaaaaactg tgtaaaattg aagatgcaga tcatcatatc cacaaaatgt ctgaaagtgt    4140
atcttcatta tcaacaaatg acttttctat tccttgggag acctggcaaa atgaatttgc    4200
agggatagag atgacttatg agacttacga gaggctcaat tcagaattta gagaaggaa    4260 taatatccga cataaaatgt tgagttattt tactacgcag tcttggaaaa cagctcagca    4320
acatctgaga acaatgaatc atcaaagtca ggactctagg attaaaaaac ttgataaatt    4380
ccaattcatt atcatagagg agctggagaa ttttgaaaaa gattcacagt ctttaaaaga    4440
tttggaaaag gaatttgtgg acttttggga aaagatattt cagaagttca gtgcatatca    4500 aaaagcgaa caacagaggc ttcatctttt gaaaacttca ttggctaaaa gtgtcttctg    4560
taatactgat agtgaagaaa ctgttttttac atccgagatg tgtttgatga aagaagatat    4620
gaaagtgctg caagacaggc ttcttaagga catgctagaa gaggagcttc ttaatgtacg    4680
cagagaactg atgtcagtat tcatgtctca tgaaagaaat gctaatgtgt gaaatctagt    4740
ttttatcacc atactttatc taattattat tctctgtata taactgagga aataagaata    4800
gtcctacaaa gagaaaaata tacatgtcac cgaagcaagt gtacccttta taggaaccct    4860
caaattaaaa aaaaatgtct tttaatggat gagagggaac cactataaca tgagtccaag    4920
cccagaagac ttctgtctat acaatatttt ttttttaattt tggagataaa agctttaaga    4980 aacttttga gttaattata ctcataaaat gagtttcttt aataaattaa attttattgt    5040
gtaaaatgta ttattacata aaatgtgttt ttgaatcaat gcagtttggg gatgaatata    5100
attaaaatat gtttaataac ttagaattca actaataaaa atttagccac acttacaagg    5160
gggaggaagt ccctagttta aatgtgtaaa ctgagtggta gatcagtact ttcagcacac    5220
tgttggaaac atttattcag atatggctct aatgtattag gaagcactaa atggcctaaa    5280
aaagctacta cattgcctaa atatgttaat tcaatataga agtcctattt cataaccagg    5340
ctgtttgaca aatactttta atctagtagt cattgtaata tcttgctaga ttaattata    5400 aaaatgagta tacatttgat ttgcttttaa tgaagttgaa ataaatgctt atgtcacttg    5460
```
aataaatata aatcattata aaaaaaaaaa aaaaaaa 5497

<210> SEQ ID NO 13
<211> LENGTH: 5688
<212> TYPE: DNA
<213> ORGANISM: Mus musculus

<400> SEQUENCE: 13

| | | | | | |
|---|---|---|---|---|---|
| atcacttccg | gctgacccat | cgtggacagg | gcaggggtca | tcggaagtgg | ggcaaccgac | 60 |
| cgacccttcc | cagaagcgct | gcgtgtgcgc | ccacagccta | aagtgtctgc | gggtgtttgt | 120 |
| cttctcctat | tcttaaatga | gttcaaaatg | ccagtgagac | cagacctcca | acagttagaa | 180 |
| aagtgtattg | atgatgcttt | gagaaaaaat | gacttcaaac | ctttgttggc | acttttacaa | 240 |
| attgatattt | gtgaagatgt | gaagattaaa | tgcagcaaac | aattcctccg | caagttggat | 300 |
| gacttaatat | gcagggaact | taataaaaag | gatatccaaa | ctgtttcaag | catcttgata | 360 |
| tctattggaa | gatgtagcaa | gaatatcttt | atattgggac | aagctggact | tcaaaccatg | 420 |
| ataaaacaag | gattagtcca | aaagatggtt | tcctggtttg | aaaattccaa | ggagattatt | 480 |
| ctaaatcaac | aacaatcaaa | agatgaagct | gttatgaata | tgatagaaga | cttatttgat | 540 |
| cttttgatgg | tcatatatga | catcagtgat | gaaggtaaaa | accaagtatt | ggaaagtttc | 600 |
| atacctcaaa | tctgtgccct | ggttattgat | tcaagagtga | attttgcat | tcagcaggag | 660 |
| gctttaaaaa | aaatgaattt | gatgcttgac | agaatacctc | aagatgccaa | caaaatactt | 720 |
| tctaatcaag | aaatgttaac | tctcatgagt | aatatgggag | aaaggatttt | agatgtagga | 780 |
| gattatgaat | tacaggtagg | cattgtggaa | gctttgtgta | gaatgaccac | agaaaaacgg | 840 |
| agacaagaac | tggcatatga | atggtttca | atggacttta | ttgctaatgc | atttaaggaa | 900 |
| attaaagact | gtgaatttga | aacagattgc | agaatatttc | tcaacttggt | aaatggcatt | 960 |
| cttggtgata | aaagaagggt | ctatacattt | ccttgcttgt | cagcatttct | tggtaaaatat | 1020 |
| gagctgcaga | taccatcaga | tgaaaaactt | gaggaattct | ggatcgattt | taatcttggg | 1080 |
| agccacactc | tgtcattcta | cattgctgga | gatgaagaag | atcaccaatg | ggaagctgtc | 1140 |
| actgtacctg | aagaaaaagt | tcagatgtac | aacattgaag | tgagagaatc | aaagaagcta | 1200 |
| ctgactctaa | cttttgaaaaa | tatagtaaaa | attagtaaaa | aagaaggaaa | agagttactt | 1260 |
| ttttattttg | atgaatcatt | agaaatcacc | aacgtgacta | aaaaagtttt | tggtggaaat | 1320 |
| aagtataagg | aatttaccag | aaaacaaggt | atttcagttg | ccaaaacatc | tattcatgta | 1380 |
| cttttttgatg | caagtggatc | acagattcta | gtaccagaaa | gtcaaccatc | tccagtcaaa | 1440 |
| gaaaacctca | ttcatctaaa | agagaaatcc | gacatccaaa | agaaacttgt | aaaccctcta | 1500 |
| gaactaggca | atagcagcag | ccaggatgag | atcactacac | ctagcagaaa | gaaaatgtct | 1560 |
| gaagcatcaa | tgattgttcc | tgatacagac | agatacactg | tgcgaagccc | aatacttta | 1620 |
| atcaacacat | caacaccgcg | aagaagtagg | gaaccactgc | aagcaataaa | ttctgtggag | 1680 |
| aaagctgttt | ctaaaacatc | agaaagtgga | atggattatg | ctgcgtcacc | caaatctaga | 1740 |
| caatcagatg | gaagaaaaag | atggaataat | agagccaacc | ataacaaaac | tactgctgtc | 1800 |
| atacaaaaca | aacaatacga | ggataatgaa | tccccagacc | aaaatttcaa | tgaaattgag | 1860 |
| gacactctct | ctaatgtatc | ttctgcagtg | ggaaaagtag | acaagcctgt | attgcctggt | 1920 |
| gttttagaca | tctcaaaaaa | tacaacacac | tccagatggg | catgtggac | acctgtaaca | 1980 |
| actatcaaac | tctgcaataa | ccagagaagc | cgtgctttac | ctggagacac | ttgtacccaa | 2040 |

```
gatactggtg tcaacaaaaa atgcactaaa caaaaatcag tatcagatga tgattctgaa   2100
gaaacacaaa agggaaaata tagtaaagat gtaatcaagt gtaacaagtc agatgaagca   2160
gaattttgtg aaagaaacat tcaagaacaa aatcatccta aatattcaca aaagaaaaat   2220
actgcaaatg caagaagag tgattggcat attgaatctg aaactactta taaatctgta    2280
ctcctaaata agacaactga agaatctctc atctataaga agacatgtgt attgtcaaaa   2340
gatgtgaata ctactatctg tgataaaagc ccttctagaa aaagcaagag gaatcataca   2400
aaatcaagaa aggaactgat gtctgaactt acatcatgtg agctagaaga ataccagtg    2460 agagaaaatt caaagggaa aagatttact ggtgcatcag aatccttgat aaaccaaatt    2520
agtaggagat ataacccaag tgatagcatg atgtcaacaa gaaaactgaa ggagcctcag   2580
gatggcagtg gattttcaaa aaacctgat ctgcagttca ataaggttca gagaaagagt    2640
tacaggaaac tgaaggcaac tgttgtcaat gttacttctg aatgtccact ggatgatgta   2700
tataatttca gcttgaatgg tgccgatgaa cctgttataa aacttggaat ccaagaattt   2760
caagctacaa ctagagaagc cagtatggat aattcattaa aattggtaaa gaatcatgat   2820
gaacatgacc cttttctcaa aacaaaagat aaaagaatgt taagttatga gaagaaaact   2880
ctcttaagtg acactgaaac cgaatgtgga tgtgatgaca gcaagactga cattagctgg   2940
ctaaaagaac caaaaacaaa aagactaatg gattatagta gaaataaaaa cacaacaaaa   3000
tataaaagta gaaaatcaag atcatccatg gaaaaggac aaccaagacc cacaatggta   3060
ctcaataaaa acagtatgaa aaatgattat gaagtagttg tagatgggag aaccagactt   3120
ccacgaagag caacaaaaac aaaaaaaaat tataaagatc tttcaacttc agaatcagaa   3180
tcagagagtg aaaaagaatg ttcatatttg tttaaagata aactgccaac aaaggaggag   3240
actatccatt ccagagccca aacaaagaaa ctgcccgaga acaacagaaa agtcttcaat   3300
tcagaagcgc tgaaaggaca gccatcagaa gaacagaaaa actcctctcg gctgagagaa   3360
gggagagaag acagtctgtg cctgtcttct gcgtctgtgt ccaggagctc gtcctctgtg   3420
gaagtgatga gatgtacaga gaaaataaca gaaagggatt ttactcagga ttatgactat   3480
atcacaaaat ctctttcacc ttatccaaaa gctccatcac ctgaattctt aaatggaaac   3540
aatagcgttg taggtcgggg acaatcaccc agaattagtg agaccagtgc aatgtgtgta   3600
agaaagagtt actcacctgc ttcaggaccg cccttttcgc caagacacac tccgaccaag   3660
aataattctg ttgtgaatat gaaaaagca aattcagtga taaataatca gagaacccaa   3720
cattgtaaca gctattcaga tgtaagcagt aatagctcag agaaacttta tatggaacct   3780
gaatctccag agagctgtga caaccatatg caaaacaaga gagagggaaa tcatgcagca   3840
tctccattat cattgtctag tgaaaaaata gagaaaatgt ggtttgacat gcccagtgaa   3900
aatactcatg tatcaggtcc cagtcaacgt ggtagcaaaa ggcggatgta cctagaagat   3960
gatgagctaa gtaattccaa tgaagcagaa gtagaagagg cagaagaaag ggaacatttg   4020
ctttccaaaa aacgatgtca atgggaaaat tctgaccagc acaccttcaa aacttcatta   4080
tcgacaccag atttttctgt tcctaaggac tggcaacaag agttacaagg tgctggaatg   4140
ttttatgata acatcagctc agactataaa aggaaaactg atagccaaca taaaatcatg   4200
gatgatttta ctacaaagac attgaaattg actcaacaac atctgatggc aatgacctct   4260
caagctcagg gacgcaggga tgaaaatgtt gagaaattcc aagtcactct cctagatgag   4320
ctggaaaaag ttgaaaaaga ctcacagact ttgcagagact tggagaaaga gcttgtggac   4380
atcgaggaaa agttagttca gaagatgagg gcatatcacc gatgtgagcg agagaggttt   4440
```

```
cgtgttttga aaacttcact ggataaaagt tttcttgtct ataattctgt ttatgaagag    4500 tctgtttta catctgagat gtgtttgatg aaagcaaaca tgaaaatgct acaagacaag     4560
ctacttaagg agatgcatga agaggaagtt ctcaacatac gcagaggact acagtcatta    4620
ttcaaggctc atgaaggaaa tgatgcatga atctggctg ctgtcaatga attttatgat    4680
tagttttttg tgtataaata aagcactaat aaagtagctt tgcaaagatg catcatctaa    4740
gcacctctat tcttgtgtgc aagaacctcc cgactcaaat gttagagatg aaaaacatga    4800
ctccaaatgc agcttgtatg tcctatgagc aaacagtaaa aggagctgac tttccttgga    4860
tcatattttt atattaacta tgtctgtgaa agtagtgtct gtactaaagt atttatatat    4920
aaagtgtaat tttaaattaa tgcagttttg gaataaaata tactgaaatt tgcatgatgg    4980
tttgtaaata tacaagtatt aaatatttag caattctttg aaagaggaaa aggctctgct    5040
ttaagatctt taattgttag taccttcata ctttgagata tatagagtta cagtgcacta    5100
aaagtgttaa agtgacctaa agttatagct atttcataaa tattttatca cagtgtagaa    5160
gtcttaacta caaagcaggc tgcttgccat ttctttctaa gcacctggta ttcacctaat    5220
attttgttag attgtatttt aaataaatgc ttatttgagt aagtataatt actttacagt    5280
tactattatt gtgttttatg aaccatgact tacaagccac cttcagtcag acacttgaag    5340
gtaataccaa tctgaaggct gtagagtatt tgagcaatac cagcatttaa tattacagtg    5400
gtgaagtagt ttcttagtca agcacaaata cattcttggt gtattcaatt gacatcagct    5460
aagattttaa gatttatgag gaaaatgatg ggagtttcta gttttaagaa agagagagat    5520
tttacatttt attagcccctt agatgaactg tgtgtacaac aaagaactgc taagattaat    5580
tttgtaactc ttgttttttg agacatggtc tgtgtagacc tggctaacct caaattcagt    5640
tctgcctgca acattaaag ccatgggccc aaacaaatgt ccttcaaa              5688
```

<210> SEQ ID NO 14
<211> LENGTH: 4771
<212> TYPE: DNA
<213> ORGANISM: Rattus norvegicus

<400> SEQUENCE: 14

```
cgttggctcc caggagactg aggaggcgcc ataacactcg acggcccttg ccggcggagg      60
tggtcgccag gtcccgggtg tcctggctgc aggtggcgca ggtctacggg agaccgtggt     120
gtctgtcctc tcctattctt aaatgaagtc aaaatgccag tgagaccaga cccccaacag     180
ttagaaaagt gtattgatga tgcttttgaga aaaacgact tcaagccttt ggtgacactt     240
ttacaaattg atatttgtga agatgtgaag attaaatgca gcaaacaatt cctccgcaag     300
ttggatgact aatatgcag ggaacttcat aaaaaggata tccaaactat ttcaaacatc      360
ttgatatcta ttggaagatg tagcaagaat atctttatat tgggacaaac tggacttcaa     420
accatgataa acaaggatt agtccaaaag atggtttcct ggtttgaaaa ttccaaggag      480
attattctga gtcagcgaca atcaaaagat gaagctgtta tgaatatgat agaagactta    540
tttgatcttt tgatggtcgt atatgacgtc aatgatgaag gtaaaaacca agtattggaa     600
agtttcatac ctcacatctg tgccctggtt attgattcaa gagtgaattt ttgcattcag    660
caagaggctt taaaaaaaat gaatttgatg cttgacagaa taccttcaaga tgccaacaaa    720 atactttgta atcaagaaat attaactctc atgagtaata tggagaaaag gatttttagat    780 gtaggagatt atgaattaca ggtaggcatt gtggaagctt tgtgtagaat gactaccgaa     840
```

```
aaacggaggc aggagctggc atatgaatgg ttttcaatgg actttattgc taatgcattt    900
aagaaaatta aagactgtga atttgaaaca gattgcagaa tatttctcaa cttggtaaac    960
ggcatgctgg gtgacagaag aagggtcttt acatttcctt gcttgtcagc atttcttggt   1020
aaatatgagc tgcagatacc atcagatgaa aaacttgagg aattctggat tgattttaat   1080
ctcgggagcc acactctgtc attctacatt gctggagatg atgatgatca ccaatgggaa   1140
gctgtcactg tgcctgaaga aaagttgat atgtacaaca ttgaagtgag agaatcaaag   1200
aagctactga ctctaacttt gaaaaatata gtaaaaatta gtaaaaaaga aggaaaagag   1260
ttacttttgt attttgatgc agcattagaa atcaccaatg tgactaaaaa acttttttggt  1320
ggaaataagt ataaggaatt taccagaaaa caagatattt cagttgccaa aacatccatt   1380
catgtacttt ttgatgcaag tggatcacag attctagtac cagaaagtca accatctcca   1440
gtcaaagaaa acctcattca tctaaaagag aaatctaacc tccaaaagaa acttacaaac   1500
cctctagaac cagacaacag cagcagccag cgcgacagga aaacagcca ggatgagatc    1560
actacaccta gcagaaagaa aatgtctgaa gcatcaatga ttgttcccga tacagacaga   1620
tacactgtgc gaagtccaat actcttaatc aacacatcaa ccccgcgaag aagtagggca   1680
ccactgcaag caatacattc tgctgagaag gctgttttcta aaacatcaga aagtggagtg   1740
gattatgctg tgtcactcaa atctagacaa tctgatggaa gaaatagagg gaacaataga   1800
gccaatcata acaaaactgc tacagtacaa acaaaggac atgagcacca tgaatcccca   1860
gaccaaactt tcaatgaaat tgaggaaact ctctctgatg catatgcagt ggaaaaagta   1920
gacaagcctg tattacctgg tgttttagac atctcgaaaa ataaagcaca ttccagatgg   1980
gcatgttgga cacctgtaac aactatcaaa ctctgcaata accagagatc ctgtgcttta   2040
ccaggagata ctttttaccca agatactggt gtcaacaaaa aatgcactaa acaaaaatca   2100
gtatctgatg atgattctga agaaacacaa agggtaaaat atagtaaaga tgtcatcaag   2160
tgtaacaagt cagaagaagc agaagttttgt gaaagaaaca ttcaagaaca aaatcatcct   2220
aaatattcac aaaagaaaaa tactgcaaat gcaaagaaga atgattggca tattgaatct   2280
gaaacaactt ataaatcagt actcctaaat aagacaactg aagaatcact catctataag   2340
aagacgtgtg tattgtcaaa agatgtgaat actactatct gtgataaaag cccttctaga   2400
aaaagcatga ggagccatac aaagtcaagg aaagaactga tgtctgaagt tacttcatgt   2460
gagctagatg aaataccagt gagagaaaat tcaaagggga aagatttac tggtacagca   2520
gaatccttga taaacctaat taataagagg tataactcaa gtgatgacat gatatcaaca   2580
agaaaactga aggagcctcg ggatggcagt gggttttcaa agaaacctga actgcagttc   2640
aataaggttc agagaaagag ttacagaaaa ctgaagactg ttgttaatgt tacttctgaa   2700
tgtccactga atgatgtata aatttcagc ttgaatggag ccgatgagcc tgttataaaa   2760
cttggaatcc aagaatttca agctacaact agagaagcta gtatggataa ttcaataaaa   2820
ttggtagatg taaggaaccg tgatgaacgt gacctttctc tcaaaacaaa agatgaaaga   2880
atattaagtc atgagaggaa aactctcttc agtgacactg aaacagaatg tggttgggat   2940
gacagcaaga ctgacattag ctggctaagg aaaccaaaat caaaaagact aatggattat   3000
agtagaaata aaaacacaaa aaatgtaaa agtataaaat caaggtcatc cacggaaaag   3060
ggacagccaa gatccacagt ggtactcagt aaaaacattg cgaaaatga ttatgaagta   3120
attgtagatg ggagaaccag acttccacga agagcaacaa aaacaaaaaa aaattacaaa   3180
gatctctcaa cttcaggatc agaatcagag agtgaaaaag aaatttcata tttgtttaaa   3240
```

-continued

```
gataaactac caacaaagga ggagactgtc cattccagcg cccaaacaaa gaaactgccc    3300
aagaaacaac agaaagtctt caatacagaa gcgctgaaag gacagccttc agaagaacag    3360
aaaaattcat ctacgctaag aaatgggaga gaagacagtc tgtacttgtc ttctgcatct    3420
gtgtctggga gctcgtcatc tgtggaagtg atgagatgta cagagaaaat aacagaaagg    3480
gattttactc aggattatga ctacatcaca aagtctcttt caccatatcc aaaagctgca    3540
tcacctgaat tcttaaacag aagcaataga gtggtaggtc atggaaaatc accaagaatt    3600
agtgagacca gtgcagtatg tgtgagaaag agttgctcac ctgcttcagg actgcccttt    3660
tcgcccagac acacaaccaa gaataattct gttatgaata taaaaaatac aaattcagtg    3720
ataaataatc aaagaaccca acattgtaac agctattcag atgtaagcag taacagttca    3780
gagaaacttt atatggaacc cgaatctccg gatagctgtg aaaaccatgt gcaaagcaag    3840
agagaggaaa atcatgcagc ctctccattt tcattgtcta gtgaaaaaat agagaaaata    3900
tggtttgaca tgcccaatga caatactcat gtatcaggtc ccagtcaacg tggtagcaaa    3960
agacggatgt acctagaaga agatgagcta agtaatccca gtgaagcaga agtgcaagag    4020
gcagaagaaa gggaacattt ggtttccaaa aaactatgtc aaagggaaca tttcgatcag    4080
catacctctg aaacttcatt atcaacacca gagttttctg ttcctaagga ctggcaacag    4140
gagttacaag gtgctgggat gttttatgat aacatcaact cagattataa aaggaaaact    4200
gacacacaac ataaaatcat ggatgatttt actacaaaga cattgaaact gactcaacaa    4260
catctgttgg caatggcctg tcaagctcgg ggacacaggg atgaaaatat tgacaaattc    4320
caagtcactc tcctagatga gctggaaaaa gttgaaaaag actcacagac tttacgagac    4380
ttggagaaag agtttgtgga catcgaagaa aagatagttc acaagatgag ggcatttcac    4440
caaagtgagc gagaaaggtt tcgtgctttg aaaacttcat tggataaaag tttgcttgtc    4500
tataattctg tttatgaaga gaatgttctt acatctgaga tgtgtttgat gaaagcaaac    4560
atgaaaatgc tacaagacaa gctactgaag gagatgcatg aagaggaact tctcaacata    4620
cgcagaggac tggagtcatt attcaaggat catgaaggaa acaatgcatg aaatctggct    4680
gctgtcaaca cactttatct gattagtttt tgtgtatgaa tgaaaaaata ataaagtagc    4740
cttgcaaata tgaaaaaaaa aaaaaaaaa a                                    4771
```

<210> SEQ ID NO 15
<211> LENGTH: 208621
<212> TYPE: DNA
<213> ORGANISM: Sus scrofa

<400> SEQUENCE: 15

```
gatccttaac ccactgagca aggccaggga ttgaacctgc gttcccatgg atcctagttg      60
ggttcattaa ctgctaagcc atgatgggaa ctcctcatgg tgtaaacttt taatttatat     120
tcctggtgct tgtgctgagt gcttgcttta tctcatttaa tcgataaaac atccttataa     180
gggacatggt attatagctt gggttctagg acacggggct cccaggttct cagagccgtg     240
aagggagtgg ctcttggcct tgcaggttca atgagtggtg aggtggaatt cacccaggaa     300
gaccagtatc ccagctttgg ctctgtacca cctcgacatg aaccgtaaat catggatctg     360
cccctttagt cggagagctt cagagaagat gacttaggtg acacagagaa ttttgttgca     420
agcggttttt tttgttttgt tttgtttttgt tttacatcta agaaatccc                480 tgcaaaaatt caagacaccc aaatctctta aaaagctcct ggaattgatg tgcatctgat     540
```

```
tcgtgttcct tcaacttagc ggtagacaga gtcgccctgc ttggcagtgg cctcacgttc      600
tggagtggct ttcccaggag gagccttcat ggggcttggg gagaggtccc aggtgaagtt      660
acctggggttg gcagtgtcct catgcgttct tagaagctgg ggccggggcc ccttacaagt     720
tactgtgcaa acctatcttc ccttttctgt ctttggtccc gagaccttct tacttggaag      780
atttgagatg atgtccccaa ggccggggga gcaggcagtc gtgtcagcgg gcggggtgtt      840
cgctctctcc tactcgttga aagatgtccc aggccacctg gttcctctcc cagtcgctgc      900
gtggctgtgg ctgaccttgg accgaaatgc cccttactgc ccagaatttc catccggtcc      960
catcaggagg ggaaatgtgg atgctgcgtt tgtgtctgag cttcagcggg accccagccc     1020
cagaatcagt ggttccacct gcctggacca tcagcgggga cgtctcctcg tgtgcacctg     1080
tgcctgagag gtgacgagaa gggcagcagg ttccagcgtg aggaaagggg cggggctgaa     1140
atttggggat ggcacctata gatcacggaa gggcactctt ccccaggcaa tgccaatcgt     1200
ggtccgtctt cgttcatttc gttccagaag gagatctaat tttaatttct attaggtcga     1260
tcggtacgaa attcccactt ttgtagtttc gtgacagcca aactttggca aattcgaatg     1320
gctccattta gcacaacaaa ataatttaaa tctgaggaag aggccggtca gccctttgcg     1380
tggctcagtg ttttcaaaag gatgttgaca cggttcagcc gtacgtctct tgtgtgtggc     1440
gagcagctgt taatggttaa ggcgttgtgg ctgccctacg cgtggcctct tgtcaccaag     1500
agtctcctgc ctctccaagt ggcaggaatc tcattgcgag ggccattcct gatctagata     1560
agaacccatc agatctcatg aaaatttaat gtgtcaaagt gtatagttgc atgagttttt     1620
tttttaataa actatttcat agcccttggt aacgccagat aaatacattg ataataagcc     1680
tcctccaggg gctgtggggt tgccaggtgg cccactagga tgacctctgc tctctctctt     1740
atttgtggct tttccttaaa ggaattcctg ccttttgttt ttcttcctca agtagatttc     1800
aagtttgaca gattctgggg gttttaactg gattttgtgc tttttgcctg aaggatggag     1860
tgacagccct gtgtgcacct tcccctgggg ccacggttga cccacggtcc ccagctgagc     1920
ctcagtttgg gggtctttaa actggctttg ggggactcgt caggcttgcc caaatttggg     1980
tcttagtgat tggttcctct cccagtttca tcaggggcct ggctgaggtt gatatcaacc     2040
ttgtcacatg tcacaatcag ggaccccctag gtgacctgga gaggtccgtg acctgcctgt     2100
ggtcatggag ccagtatgac agggcgccac ccgccctccc tggcttcctc caggtcatct     2160
gatgagattg caaactcctt gaaagcaggg tgccgtgttg gagacccaac agccacgctc     2220
aggagactag cacctctggc caccaagctc accatttctt tgggtgagcc ccgcacagag     2280
tgggccacac cctgccaagt ggagtggcca ttctgggtgc acagacgtgt caataaacac     2340
gattaccacc caggaggtac ccacgggctc acgtgcacag gcccatggag actggagcag     2400
gtggagccgc ggcctctgag gtcccccaat ccctgtgctc tttgcttttg agaacactca     2460
ttgtgggcag tgccatgatg gtgtcttggg ccagccccac gggcgacaca cagctgaggg     2520
catccactga gcaaggggcc acgttctatg ttcccatatt tgtgcattta ggctgaccct     2580
gcccccccgtc cagccagagt cctcaaggag tgtgcccagc aagagctctc gatctttctt     2640
tgatctgagg ataccggttc tcctgaattt tgttcgctgt gcatcccccc caccgccctg     2700
ccacccaccg cccccagatc tttaaaaagt cttgttctcc ttccaagtgt cttaggctct     2760
tgccctaatg gccacttctc ctaaaagcct cgaacctggc ccttgcagct tccagaaggc     2820
accacagatt tttttttttt ttcatttgtc tttggtgttt tgcttgggg agagaatatt     2880
cattctgtgg acaattaaag acttgataaa aagtgccttt tatgagtccc ttgaaaaccg     2940
```

```
tgagatgtgg gccggggtct gtggagtctt gcactcatgc aacagaaact tattgagtgc   3000
ttatggtgtg ccagacgctg tgatccagga aggccaggaa aaactggagc ctagaaaaac   3060
tgacagcgga gaaggcgggg ttgggagcta acgcttatta aacacagctc tgtgccttcc   3120
aggtgcgtca actcatttca tcctcacaag agctgttggc ggtgggtgct aacgtcaccc   3180
ccgtgtcacc tatgtcagga aaccgagcct cagagaggcg aagtgccttg cccgagtttt   3240
cagccattaa taagagctgg cattggcacc cagtctattc tggcctgtgg aagcccagcg   3300
cggcaatgct acagtccgct ttgtaggcta aacccacagt ggccactgct ctttcaaggg   3360
tccttcctga gcactgactg tgtgcgagat tctgccctgc ctgatggtgg tgggcaaggc   3420
atacctgtct ccctgccttg atggactgag tccacaagaa atcccatgca tccagcaatt   3480
tggatgctgt gtgagatgtg atatcagggg ctgatgatag aggggctcag cgtgcccaga   3540
gcgggacccc cagtcccgag ctgggactgg cttttgagag gaagtgaaat ttaagctgtg   3600
acccagagca ggagttggcc aggccaggag aagagtctta taaggaaag catgaataga    3660 attcctgaag caaaagaaaa aagatgctgc agaactaagt aagagccagt ctagttgggc   3720
gagtgatgag gtggcgagaa ggcaggacca gaccccacgg ggagggcact ctgggcctct   3780
tgggctccct cctcagggca gcagatctgc acccaaaagt ttttgttttt gtttttcttt   3840
agggccatac ctgcagcata tgaacattcc tagagtcaaa ttccgaggag tcaaatcaga   3900
attgggactg ccggcctacg ccacagctac agcaatgcca gatctgagcc acctctgtga   3960
cctatgctgc agctcagggc aacactggat ccctaaccca ctgagcaagg ccagggatcg   4020
aacccgcaac ctcatggttc ctagttggat tcgttaacca ctgcgccacg acgggaactc   4080
actagttggg ttcttaacct gcagagccac aataggaact cctgcaccca agaggttgtt   4140
tttttttttt tttttttttc tgcactcata gcatgcagaa gttcccagga cagggatgga   4200
acctgagcta cagcagtgac aatgccaggt ctttaaccac ttggccacca ggaaactccc   4260
aagggaaatg cattgagccc tcacgaccct gggagaacaa tggtggacag acaggcagag   4320
tccccgctct caggggggctt gggttccagt agaacagcaa atggatacat acactgacag   4380
cggcagggag cagtgtgtac cccaaaggca gtgaaaaagg aggaagtggg ctgcgggagg   4440
tacaggaagg tagaggaagg agggagggc tttggagaag aggagccagc aatgtggcaa    4500
agttggggga cagcattcca ggcggagggg acggcaggtg caaaggccct gagacagcaa   4560
caaactgggc atgctcaggg aacacagcag ggttagcgtg gctggaacag agggaatgag   4620
gaggagcagg tgcccattga ggccagaggg tcctcagggg tcttgggttt gatcccaaag   4680
gcgggagaag ccactagaag gttaggcagg ggatggagag gcctgatttt acttttgacc   4740
agccctcggc ttctgcgcgg ttaatggact ggggagcagc aagaatggaa gttggaattt   4800
ggggcgggga cctgagctcc tgacgtcacc tatgctccag aagatgggga attgacttga   4860 gcggggccg tggggagtgg agcccagatg ggcttgggag atgctgcaga gcaagcttgc    4920
tttgcggaag agcttctggt gggaggggt gagggccgca gcttatggca ggcagtcctg    4980
ggtcctgggt tccctcccga aatcagaaag accccgtgg ttctcagcca gctcacagaa    5040
ggacctgaat gaggatgcca gcaggcccta agcatctagg ttttctttc tctctttttt    5100 ttttggcagc tcaatgagct ataattcaca tattatccaa gtgacccacc cagagtgcac   5160
aattcaatgg cctttagttt attcacagcg ttaggccaca tttaccacaa ttcaacttta   5220
ggacactttc gttacctccc aaagaaacct cattcccatt aagtaacccc attttcccct   5280
```

| | |
|---|---|
| cccccagccc ctggccacta ctaatccatt ttctgactct gcagatttac cgattctgaa | 5340 |
| tatttcactt aaatggactc ttaacaagaa gtgatctttt gtgactcgtt atttcacctg | 5400 |
| gcatcatgtt tttagggttt acccagaaac ctcctccctt tttatgacca aataatattc | 5460 |
| cactgagcag atgcaccacg tgctatgtat ctgtctgtgt gttgttggtg ttccctctgc | 5520 |
| tttttatgac gagggctgct gtgaacattc acaggcaagg tgcctggaca caagtgttca | 5580 |
| gtatttggcg tggaaaggga tacacccctg agtggagctg tcacctggta agtgggtttc | 5640 |
| actgggggaa gctgccggat ggttttctgg gcagcccct gtttctcatt cccaccagca | 5700 |
| gtgtgtcgat ggttctgatt tctcgcccac ccacccacac ttgtgactgt ccccagacac | 5760 |
| acccgggtcc acttacctga gcagttgccc acgatttata aaacaggtgc acagggatgg | 5820 |
| cacccgcccc cccccgggg gggggcgtg accaggacgt ttatctgctt ccgagagtca | 5880 |
| gggtgacttg gggaccaggt cctcttgttc tctcctctcc cgccttccct tcgtcccact | 5940 |
| ggagggaagg acacgagctc tcagccttaa cttcatgtac ttaatggacg aggaaggaaa | 6000 |
| taatttctga ggccgagacc tgaggggtcc ccaaggactc tgttttgaca atgcacttaa | 6060 |
| acttccacga gggcatttgc ctgttggctg ggaactgtgg ccaaggacct ttcagcattt | 6120 |
| tatggttata aaaggatctc gagagtaatg actcttgaaa aaggcgtttc agtggggagg | 6180 |
| acggggatgg ctttgggtcc acagcctcgc tgaggtttgc aaaaggctgt cagacgagtt | 6240 |
| tcgccttfgg catcacactc tggtctaggc accctcgggg gcaggtgagc aacgagacg | 6300 |
| cggtgcagaa atcccttct cttggtatga ttcgaagccc actctacacc cagagctgtc | 6360 |
| gcccttgctg tgggatcctg gataagtcac tctgccttcc tggtctctgc ttgtctcttt | 6420 |
| gccacatggt tcctgatggc cgtgagctca ggtgggctgg gagcccaggt aggcagtgag | 6480 |
| ctcgggtcag ccgtgagctt aggtagacaa tgagctcagg tgggctgaga gcccaggtgg | 6540 |
| gatgggagcc tgggaaggct gggagctcag tgaggacagg cacgtctagt tttctggtca | 6600 |
| ccgtcaccc agcacctcac cagagtagca ggttgtctta gtctgggctt tttgcaaggt | 6660 |
| gaccctgggg tgagggtttg agtggtctcc caggagacac tggttaaggg aacaggggca | 6720 |
| gccactcagg gaaggggaag gggaggccca ggcggagggt ggtcccaggc tgagtcctgc | 6780 |
| agagggcgct gcggcctgat cctgctcctc agaggctgag cccctcggag gggagggctg | 6840 |
| gatgctggct cctgtaaagc cagtcactgg ctcaggccgc caggccatgt tgacttcagc | 6900 |
| cctttcttct ctccacgctt gagggcaaag ggcaatgcat ccctgtgccc tccggggttg | 6960 |
| ggggtggggg gcagcgaggg tgcaggtttg ggccgtgaga ggcaagggca cacggaagcc | 7020 |
| gggtgaggcc acggccatgg tgaaggactc cagggcccag ggagaccgcg atggtgcctg | 7080 |
| cgggggggaca ggccccatcc tgcgtcctgt cctgatgggc cttgcaggac agggccgcca | 7140 |
| gcttcctcag tgtgcagttg gtatggtttt ccacgtgctc ggacaccagg agaacgtttc | 7200 |
| gattgtcagc tcaggtggtg cctccacgtg gccgtggttt gagccggggt gatgagtccc | 7260 |
| acagcgaaga cgctttgaaa tgtgtggtcc ctaacgagtt ttgcgtttag ggtgatggcg | 7320 |
| aggtttgcac cctgcatgag gctttctggt tttgtggctc tttcacacga gcatgaatcc | 7380 |
| cagtcctgat gtgtgtgtag gttcgtgttt ggcaccctga cccgccttct cccggacccc | 7440 |
| cgagtcctca ttctgcaaag gctggatcg acacgtgaac agagaggcca cgcccggaag | 7500 |
| cgagtcagcg ctagatgcct ggggagcctg ctctgcccag tgtggacctg ctggggctgg | 7560 |
| agtcattgca tcgtatattc cccaggacac tgggtatcat cggctcgagg ccaggcacct | 7620 |
| ccgctcagat gcaggtgggc aggaaaccgg aaaacccttg gctcctcatt ccacctgcgc | 7680 |

```
ttctgggtca gctttgcagg tttggcccca gcttgaggac gtgacaggga gcaccgctag    7740
gtcaggacat gccttggggt ttttaactgc tttggggttt ttaattgagg taaaagacac    7800
gtaacaggag ttcattcccc gggtggctca gcaggttaag aatccaatgt tgtctctgct    7860
gtggcttggg ttgcagctgt ggtgtgagtt cgacccctgg ccctagaact tccaaaaaaa    7920
aaagataaaa gacatgacat aaaattgagt gttttaacca ttttaaaggt acaattcagt    7980
ggcgtcaagt actttcacat gttgtgcgac caccctccca ctctcattcc agaactttcc    8040
agcaccagat ggaaactcta ggctctttta gtgctccctg cccagccccc tctcccacca    8100
gccttgacaa ccacgaattc atgttctgtc gcagtggatt tacctattct gggcgtttca    8160
tgtaaacgga agcctgcggt atgtggcctt ttgtgactcc aggtggtagc gggccagtgc    8220
ttccctctca gggggtggaa acagtgcagc cactccggag aatggacggc atttccccaa    8280
aaagtgaaag aggaaagtca ggggaaggga gaaattaggg gtctgggatt aacagataca    8340
cgctattgtg tataaaataa tcaacaagga cctactgcgg agcgcaggga actctactca    8400
atatcttgta ataacctgta aagaatggct tcagttttgc taaatcactg tgctctgcac    8460
ctgaaactaa cacaacattg tcaatcaacc aaacttcatt taaaaaaaaa aaagtggagt    8520
ttcgttgtgg ctcagtggaa atggatctgt caagcattca tgaggatgca gtcaattcct    8580
ggccttgctc tgtgggttaa ggatctcgtg ttgtcgtgag ctgtcgtgtg ggtgacacac    8640
atggctcaga tctggcgtgg ctgtggctgt ggctgtggtg gaggctggca gctgcagctc    8700
tcattggacc cctagcctgg gaacctccat gtgccacagg tgcagcccta aaaagaccaa    8760 aaaaaaaaa aaggggggtg aaacctagag ctaccatagg acccagcgat ttcactccta    8820
ggtatattcc taaagaact gaaaagacgt gttcaaacac tcatatgtag atatctatgg    8880
ctcactgttc acaaccagca agatgtggaa acaaccaaat ggccatcaca gggcggatga    8940
acagataaat aagacgtggt ccattcgtac cgtggatttt ttcctttta aaaagtatt    9000 taggagttcc cattgtggct cagcagtaac aacccaacta gtatccatga ggatgaggtt    9060
tgatccctgg gctcactcag tgggttaagg atccggtgtt gctgtgagct gtggtgcagg    9120
ctggccgctg cagctctgat tcgaccccta gcccgggaac ttccatatgc tgcaggtgcg    9180
accctaaaaa taaaaagcaa aaaacacaaa tttattagtg cttgcttaac tcctgctgat    9240
gctctaaagc taccccaggg taccctcact ttcccaggaa ggctttcccg agtccggagg    9300
ccggtcctct tcctgcccac agaatcctcg ctaagtcttg gtcatcgtgc ctcgtccatc    9360
atccattcat tcaccgcttc cagagtatct cctggaaccc ctgtgagcca gcctgcatc    9420 tctccatcgg gcagaggtgg tgacgtcaga tcaactcagg gaggagcccg gtccctgcac    9480
agcgggcccg tgcctgggtc tcactgtggc tgagtgcgcc tccctgcgga ggagactgtg    9540
gcaccaaaac cctggggacc agaggaggca gctttgcaaa ggcagaaggg cacgggatct    9600
cccaggggcc acagagtgca ggggtccaga gatcagatgt gtgtagaagc tgaaggcccc    9660
cagggcctga gctgctggtg aggggagagg tcacgaggca tgaggaacca tgtgggaagt    9720
tcccggccta aggctcgaag ccaagtcaca gcagtgactg cagatgctta acctgccacca   9780 ccagggaact ccccacgtgg gattttaatc caggtacaga cggaaggcac tggagggggtt   9840 tcggcagcta aggtggaggt aaggggccgc ggtgtgacat gattcagggg tagacattgc    9900
aggaacctga cagtgacgag ggcgaagagg gcgaccagga cagggtgtga ggcaggggag    9960
ggcggagtgg caaagtcacc ctgtcctaat tgcccagtca ctcgactgtt accacaccc    10020
```

```
accccaaatc ctgggactgg gtgggcaggg gccagctttc aggacagagt aggtgctcag    10080
ggagctggac tgaagtgagt cggtcagccc cgtgtgggtg cagtggggag tggccctag    10140 tgtggctccc cagtggccca gcttgatgga ggatggtggc tgggaccggg cagtgggcat    10200
gcatctgcca ctgggaccc cagaggggc catcttccaa ccacagcagg aggtcttag    10260 ggatgttctg agcagacatg tgtcaactgc tccagagcag gttcccggga ctggtccgtc    10320
accagctggt gcttgtttcc agaaagcgtg cgctgtatgg acttgtgggc ttgtcccatc    10380
tccatctcgc tctgtcgctt ccgtgacagt taccagggcc gggacagggc ctgtggagaa    10440
gcaggagcca tggtgacagc agaattgcag acacttgcag atgtttgggc gtcacgtcct    10500
tggctcttgg gtgaaagttc tccgtgaggc atcacagctc agctgctgag gtggcagcgg    10560
gaagctgggc tggagaagca catcggatcc acgaggagg cccacgtggt acatgctgag    10620
acccgagcct tgttccagca ggataataaa ctccaggtgt cctggatgcg ctgccccagg    10680
caggggctgt gaacttgagc acagaagacc gggcagctcc tgtcaaacac ctgcagagcc    10740
cttgctgggc ctcccgggct gtgtttcagg gcctcaggag gcaggatata ggacgtgctt    10800
ggtctctgct tgtgacagga gagaaccttt gtgtcctgcc gcaagtcgct caccaaaggg    10860 aaggggctg taagcttaaa atatatttga tggcccgtct ctgggaaccc tccctcccag    10920
gcagtgagca ttaagctaag aaacctcctg accaggccct cctgtgaatg ctacaggga    10980 ggcagaaatg gacacctcct gtccaagaga ctgatgggaa ccaggaaatg gttaactttg    11040
cttcctcccc ttttcgtata aagaagcca gaattctaac tcaggcaaaa cggttctttg    11100
ggacacgagt ccaccctctt gtctgccagc tttccgaata gtcactcttc cttgccccga    11160
tctcttagtt tattggcctg ttgtgccgta agcagtatga gcttggactc ggtaacatgc    11220
tctcctggtc aatttgccaa gatgcacatt taaactaatt ataaattgtg ctgaagattg    11280
ttgtggaaaa aaaacaagga aacataacag gtgggtatgg aggatggggc tgtgaggaat    11340
gagtaggagt tcatcaggga atagtgttac ctccagaggg tttggcctgg gaggcagccc    11400
tagggtggga gagagttgat gagtgaggag ccgaaagaga cagaactaga gcacagcagg    11460
tgaggggtgt ggcatgagat aagcagagac taggactctg gggtcacagc tggggttttg    11520
tgtttcatcc tagaagcccg atagggtctt aagcagagaa gtgaggcaag gccctatttg    11580
ctaagggggg gccagggtta gtggaggcct ggaaaccagg gaggaagctg ctgagttggg    11640
tgggcagagt gatgctggcc gggagcccag agatgagaag tgggggtgaa ggtcagggct    11700
caggatcaga aaatgtcctt ttcctccctg tactttgtgg gatgtgtccc atggtgtgtt    11760
ttctctgacg acatcgccaa agggaccatt taaggcaggc aggagttggc aagggaccat    11820
gcctggacta aatcctcctg ccactggttt gtgtaaagaa agttttattt aaatatagcc    11880
ccgcccatta acttacggcg gctttcctat tgcagcggca gagttaggta attgtgacaa    11940
agattttctg gcggtccaag cccacgatat gcactactga agcccgagat ttctctctga    12000
cccattccag aaaatatttg cccatccgtg acctcagcga aatgagactg ggacacattt    12060
gcaaaagaca gatctcttgg ctcagactct tccagcactg aaaatgtgtt taattcctat    12120
gaaaaaatgc taacgtatgc atattttaa attaacattt gtacgtcctc aagctttgac    12180
tgacattatt taagaacctc gtcttgtact tgaggtttat aaagtcagtg ttggaacttg    12240
ggctttgaag atgttgcgcg atgttatttg tctaaattta tacgccgagg cgaaaatctc    12300
ccgatgcatt atttcactgt ttatcttctc tctgaaacac tcattttct cctctctgta    12360 aaataagatc tctaggcgga tgtctctaaa gccagctttt agtctttgca aagtctttgg    12420
```

```
cctgcttgca aaataatttt tgtgagagtt tgccgagttg cagatgaagc ccaatggcag   12480
caaagccaat ttcccagctt ctacctttt ccttccctga tcctgttgtc tccatgtttc   12540
aactcctggt tccaaactcc gtgcagcatt tttggatcca cttgatttac agattggagc   12600
tgatttcact tggagaactg gccatatgtc tggcagacac cagccgccat ggcagaatt   12660 atggggttga tgcgaagcag atgggctttc tagttagatg tgctgttttt tccatgatac   12720
atatgaggaa aaaagaagcc actttagtaa tgtcttgatt tttttccact ggtgtcggag   12780
gcataaaaga cacccattta tctagtctta atttcagcat cattgctctg caggggggtag   12840 ccttagacag ctgaagagg cccagagact tgggaaatat tgaggcctga cttctgttaa   12900
tgacgcagag aatcctatta ccttgggaat acagttttg gggaagaggt ttttatattt    12960
ccaaaataaa tggtcactaa cgccatttag ctggagtaca ttcaaactgc ttaagctcag   13020
gtttattgct caaactccac ttgacagctt ttgtgtggtt attgctgcct gggaagcaag   13080
gtgtaaatag ggattggctg gtccatctgt ttaggagaag ctggccaagt ggctgaatgg   13140
gtttgcttgc tgcaggactt ctcagagcct ttactatgac aacacgtggc ggggctcttt   13200
ggggaaggct tttcgggtag atggtatctt cgcaaatgtc ttccttcaca agcctctcct   13260
gtgctagggt tccatgggac gtgcttgggg aaacactgaa gtcatgccca gatggtaagc   13320
ttccggtcag aggaccgggg ctccaatgcc agaccagtca cttgccagtc gtgtgactgt   13380
ccttctacgt gccccccacc ccacagcctc cacttcctaa atgtaaaacg gagctgaaaa   13440
tggaaatcct gcctccgaga ttgtttgctt ggaatgaaca cccgaaagaa tgtggtggcc   13500
tccccacaag cactgacaga tatgttctcc tatgatgcag cattcgttca attcacaggg   13560
ttccagggac tggttattcg cgctgaagct cagccagact ctcgtacttc cttctgtatg   13620
ttccttagca cctcgactaa tgaggaagga agaggaagga gatgccgtct gtttaggtgg   13680
cagccaggaa aaataaatga tggggcactg tgagcccagg aagtcgctta ggaattacag   13740
ggatggctcg ctgtcaaggg gcacacaggt ggctcaggtc gttgttaata acctgcattt   13800
tgattccact tctgtggttg tatcacagat caaacgcttt cattcattct ctcctttgtt   13860
cattcacccc tgtgcccagc gcagtgctgg gccctgagga gggagagcct gctgcggggg   13920
ggtctctgcg tcttccaggc tgaaaaggca gcaattttc catcccaggg ggtgtcagcg   13980
ttgccgggtt ctgatgatac actcacagag ctgtaggaaa gagtctgcag aatggctggg   14040
aatagggcca tgggtctta ggaattcttt cctccccctt ttcagtaaat tcatccttct   14100
tcctacatcc ctgctccatc agcaaccagc ttcttcctgc attcagagca gtgtggttct   14160
ggggcgtggt ctcccctctt cctggaagct gtcccagggt ggcccagct ctgcttgggt    14220 ggattggctc tccccagaca tcctgcttct caggcctcac tccggaattt tccaggagaa   14280
gtagagaagg tcaaaccaag agtacttttg tatctgggag actttacatc cattttgtaa   14340
atttggtttt ggagattcag acccatcagg tgggagtct atgaacacac ccagaaaaat    14400
cttcttagca gacggtcgtc aagccacatc tctcacagcg tggacacggg ccattggcct   14460
ttggacccca aatgccatga ttcgagtata tgtggctttg atcttcttct ccgccccatt   14520 cctccaccctt cagcccatat cccagacgac cgcgcggtca tcgtctgctt gctgcaggga   14580
gtctaacggg gggaggggg ggaggacgag ggcttcggga gcaggtgtcc tgatttccag    14640
gcccgctctg tcacacgagc cgcgcgaccg cgcgagaacgg gtccgcctct ctgcttccat    14700
tctcctcgtc ataatgtgag tgatgaagac aaggcctgat gggaacgagc cgattcatgt   14760
```

```
cgggtgctca gggcacagct tgtcacacag caagcgccca gcagatgctg ctgttgctga    14820
tgaccgtgac cgcaaaacaa cccttgccct gcttgactcc tccgtgtgag ttacaggccc    14880
gcataggcat caggtgaggg ctctgcccca gcatcgtctc tgggttcctg cctcctttct    14940
ctgctgtccg catggtcctt gccctgctgt cctctctcag cgggcctcct agccttcagc    15000
ctcattcctc tgcagttggc acccgcatcg actgtctctg cagcccttct ctcagtgctg    15060
accatgtacc ccagtggtcc ccaggccctc aaggctcctc tggtggctgc acacggccct    15120
ccttggctgg gtcccaacct cccctccggc ctctccagcc caaaacccag agctccagcc    15180
taagggttct caggttcaag tacacagacc catgccagca aattcggaat gcctaggaca    15240
acacagcatt gctatttttt ttttcattta tcggtatatt gattgatata tcaataataa    15300
cgtttcctct gttttaaaat ttttattgga gtagagctaa caatgctacg ttaatctcag    15360
gtgtacagca aagcgagtca gatatgtgta catataacat acaccccgt tctctttcag     15420 attcctttcc catgtaggct ctctcagagc gctgcgtaga ttttcccgtg ccacacagtg    15480
gctccctact tatctgcttt atctacagtt gcgtgtagat gccagtccca acctcccaat    15540
ttttccgtcc ttgcaacgtt tcccctttac taaccttaag tttagtttca aaatcattaa    15600
gtctatttct gttttgtgaa taagttcttt tgtatcattt ttaattaggt tccccttatt    15660
agtgatctcc tatgatgttt gcctttctct cttagtgtga taacctctac gatgatgttt    15720
cctgttattt gtagtcaggg gtgatgctga caatgataat ttgtgtctag gtatttgtgt    15780
gtgtttgttg gccatcagtt ggcgccgttg aaatttggag tctcagtgtg catgccaggt    15840
ttatacatgg aggccgtaca gcttctgaac cttggagact gaggcattgg atctggctcc    15900
cctgcatcgt ttgttatctg ccaaacacca catgctttta tggtatttta ctcaactcct    15960
actcaacctc caaggcccag ctccaatatt accctgaccc ccagtagcct tctgaatttt    16020
cccaccccag gcagggagaa tggcttcctc tgcagttgta atccctgtct gggttctttc    16080
tggtgattcc acacacctag attttctttg tggtcagttc accaggcagg agagtgtcca    16140
gtacctcttt ttttgttttg ttttgttttt tagctacacc caaggcctgt ggaagttcct    16200
gggccagggg acaaacctgc accacagcag ccacccgagc cactgcattg acaaggccag    16260
atccttaacc tgctgcacca ccagggaact ccaagcacct ctatgtgctg ccccatgcct    16320
ggcatggtgt ttggttcaca gaagatggtc actatgtgtt gctggatgtt tctttgggga    16380
cagggaagga ctcgtcaaag aaatagaagc cacgctctgt gatccacgtc cccacctctc    16440
gttttcctct ttcagagcct gtaaagcatg ctggagtcac ctccttgttc ccttcctcct    16500
ccgtaagcag gtgagcctca tgctgagcaa gacagcatgt cgcctgtgtt tactgctctg    16560
tgtcaaatgc agggcagccc tggcccacag cgggcctcag ctgatgcttg acgagtgaac    16620
ttgtgaatga acgtgtgaaa caaacaagcc taaagtcaca ttccagtatc gcctgataag    16680
gacagtgcct gtctgtccgg gaggccaagc cactcagcat gtggcatctg ggaatctgag    16740
tgggggctgt ccttccattg tgttttagcc taggtgaccc agtgacatgg aaggagacag    16800
gggcaggaga gtggatagaa gacaaggaag cagaaatgcc cagtgtcact aaggtgaggg    16860
ctttggagtc agacggatgc gggaggggct ggatcctggc tccagcactg gcacctacct    16920
ctgcctccca aattcacagg tcaagcaggt gtttattcaa gtgccagtca agatgacagg    16980
gacccaggtg gacaagacag ccaccttcc tgtcctcaca cagcttaacc tttgttccag     17040
ggtggaagac agatgctaac catagataac acatcccagg gcactatctg agcgtgatga    17100
gagcaggatg gagggaacgt taggaatcag gagttggccc tgggccaggc atggaaatta    17160
```

```
gcccacaagt tccgtgacct tagccatgac agtggtgtcc ctcgctgtct tgttctagga    17220
gcacctaatt tgtaggtggg atccatcgat ggtggaagtc gatggggttg ccctggggg    17280 acaagtccac agactgcctc agaggggacc gggggagggt tgctgtggtc gagggaccag    17340
agatggcagg gagctaagcc ggcacccttta gctccaggt ggggcaccta ccccccctcca    17400 tcatgggtgg gagggggct cccgcctgcc ctataggtag gtggtgcctc ctcagcagat    17460
gtggaaaaca gttttcatta attaactgct aatgcctcac aggtggcaga ggtgcccctt    17520
caacttcgca cctccgagct gttccaaggc tggagggatc tgctgggtct gcacctgctg    17580
ggtgtgggaa ggtggttccc ccgccacggc cgagcagact cacaggctgg ggatccaggg    17640
aagcggcggt ccacgcagcc tcccttctgt ctgcatgaca cacacatagg ggtgcacaca    17700
cgccacccac aggtgtgcac acattcacat acagatacac cctctctcct agatacatgc    17760
ctgccgcgtt cacacccact ctccagggag gggcggggc aggcgccagg gcacaggagg    17820
acccacccca cctttgctgg tccggacccc caggcacagt ccgtggcacg cccatgccct    17880
tgagtaagtg gttcctttcc cggggcagca tctgttttga agtttctggc cttgggttct    17940
aagtcgcagc cctgaggaat cgcactggcc ctgggctcga ggcgcctgca ggcagctggg    18000
ggcagagggc gcttcctccc atgggagcac tggaggcgca gttttcagac tgatggagcc    18060
tgtccccacc tgggcttggg gatcctcacg gcccctgaca gcaggccctg gggagtcact    18120
cagaactagg ggtctttctg gtcacgcact tcggatgttt ggtaaatgaa caaatcgggt    18180
catttgagct gaggagcccc aggggctccc tgctgaatgt tgaatcaagt tcaagcccca    18240
gctacggccc tggcccctca tccactgcat tcttcctcca agcccttgac cccactcttc    18300
ctctgactgg caccttcgtc cctgcccag ctcctgtcta caccgccggc tcccgtcat    18360 ccaggcttct gctccaatag ctcctctcag agcagctttt cataacctct ctttacagtc    18420 agcccccgg gttccccaga ctccctgagc aggtgttggg ttccgtccgt ctgtcctgtg    18480
tggacgcacg caggtgtgtg caaacaccag ccatagatgt gatgggaaaa ataaggagag    18540
gaaggcagca gagaacgccg gggtgtgcag gctgattgtt ctcacccatc gtctgtcgcc    18600
tgcaggcaac tagaagcccc acaagggcag gcatttttct cttctgttca cctctgtaca    18660
ttctgctgga gcgattccca gcacgtggct ggtatcaata agttttttgtt gaatgaatga    18720 atgaatggat ggatgaattc tctaaggag aatagcgggt gatttgttca ggagtgcccc    18780 gccccctgccc caggctgtgt tgtgaggact caggcggcag aatgaggtgg gaaacccagg    18840
acctgctcca gccactaggg ggcagcgggg gggggcagg ggcagcggca gcggcagggc    18900
aggggcagtg ggaggcagca cattacagtg gtgacggtgg tgatggtgca agaggggag    18960 gggagatgag gaggggccg cactatccct tctgtccacc ttccatccgt tcagacaagc    19020
acttggaggt ccctgtccc cattccccca gcagagcggt ggcaaaagtg aggacacagg    19080
gagcagggaa gtggcctcaa cacttgagcc ccccatgatg agcaagggag acagggtgtg    19140
agcctggatg cctggttcta gcgcctgtgt tcccagcagc tcaccagact ggtttccatg    19200
gcgtgccata gacactaatg caaaatgatg gtgctaaagt gaagccgggg ctggggcaga    19260
ggtgaggtgg gcaggggttg ggagcagacc tcggagaccg tacaggcttg gccattaatt    19320 gaccttttgtc caaaatgagg aaggaggcca tggggagtca ggaggaagtg atctgatcag    19380
attacgtttg taggggtca tggggatgcc agttagaagg cttgtgtggg catctggtgt    19440
ggccgtgctg gtggcctgga ctaaagtgac agtgatgcag tggcagatgg agtgaggttc    19500
```

```
ggggtctgat ttgtggttta ttttatgcgt tgttccttt tgctttggct gctaggaagc    19560
tcagagccac ctgtgtaccc atgtggagtc tctaacccca gaggctgtgg tcctgtccag    19620
acgccccttc ctctggactt cctcaggcac tcattttatc ttggtgggca tgtttccgta    19680
cccaaccttt gtggcgcgag atgagggcta aaccaagcag tgacaaagcc gccttgtccc    19740
cgtgcacatc tccagggatc ttcgtcttta tcttcagacc agccggaagc ttgggggac     19800 ctggccagtt cttttccctt tgtgccaaaa ttgcctccag gacggccagc cttcctgggg    19860
ccatgtggca gccatgtggc actggcagtc ccgctcccat ctggcgtccg tgggcggagg    19920
aaggaaagaa ggggataata acacggggta acagtctct ggggagagaa gggccgtctg     19980
caggctgcac gcctggtgtg tggagctggg gacctgcgac cggtccttgg acctccccga    20040
gtccctcgcc cgaacttcct ggttcctact gggtgctggc cactgggtc acagctgaac     20100 acaagatgga gcgtgtcact ggcttaggag tctcgctggt ctgctgtctc tgtaagaagt    20160
cctcgcacga gactcctccg ggctgtctgt ctgcacaggg gaggggcttg ctgtgtggac    20220
gctgcagacc cagcctgggt gtacccaagg cgcagttctt aaccactggg agagggtggc    20280
cgcacaccct gggtggctgg gatggcctgt gctgtgtccc attccctcat gtcctgccct    20340
gcctggtaca gtcatataat caccctagaa gcagcttagg gctgcgagag ggagtcaggc    20400
tgcccagagc cagcatttcc tagctccgat agccgacaga atggctctga gcctcagtgt    20460
gctcatctgt aaaatgggta taactgtctc caccgcatag atttcctgtg agggtacaac    20520
acagtggtaa ctggcccaga acaagcagtg actaatttca ttccagaata attattgtat    20580
catgtatata atataaatta acgcaatgaa aatgtctacc agggagttcc cgtcatggcg    20640
cagtggttaa cgaatctgac taggaaccat gaggttgcgg gtttgatccc catcctcgct    20700
cagtggctta aggatccagc attgccgtga gctgtggtgt aggtcgcaga cgtggctcgg    20760
atcccacgtt gctgtggctc tggcgtaggc tggcggctac agctccgatt cgatccctag    20820
cctgggaacc tcccatatgc cgtgagagtg gcccaagaaa tggcaaaaag acaaaaaaaa    20880
tagaaaaaaa gaaaagtcca ccaaaaggta cccctgccga tggggcatgt taattagtgt    20940
ggctatacag ttttttgttg ttctttgttt ttctcatttt ttagagtttt attgaggcgt    21000
tcccattttg gctcagcagt aatgaacctg actagtatcc atgaggatgc gggttcaatc    21060
cccggccttg ctcattgggt taaggatctg gtgtggctgt ggctgtggtg tgggccggca    21120
gctgcagctc tgctttgact cctcgccagg gaatgtgcca tgggtgtggc cctaaagaga    21180 caaaacaaa acaaaaaaag ttttattttt atttttaaaa tgttaaaatt ttaattacat     21240
tttatttaat aaatattaaa taaatttatg tttatttaa aaataaattt aaaagtaaag    21300
tttgattttt attttcaaaa cactatcatt gatttacaat tttaaaacag atgatatgac    21360
ttcgcagggg ttgtaacata ctatcgagaa actgtgtgtt ctgtatgttt gcctatggtc    21420
acacagactc ttccactcac ccctagggat caggtggagt gattattta ctgaggtgga     21480 aactgagggt ccgaggggct gagtggccta agctgctgag agatgcagcc ctttgtaagt    21540
cagaccacgt ggggcattgg gcggggtctg acggtgacca gccatcccag gtccagtccc    21600
ctgccggccg gggcctcct tcagcctggt cctcgctcgc tccagctcgg ctcttcctgc     21660
gtccttgggt ctctgtgggg cttcttggct cgagagggac tcaggcttcc ggcccttctt    21720
cccaggcagc agcaggtgaa tgaacccacc gggcgtggag ctgagcgtgt gctggacctg    21780
accccacgga gccccggct ttggaaggtc actggtggcc ccaggacagg ggagtcacgt     21840
cgggtcccca gggccccctg tgggctcggt agcactgacc cctccctggg cttcgtcttc    21900
```

```
cagatgagac ggaacaaacc ccccggcgc gctccgagta tctggtctca gggattcgaa    21960
ctccgcccgc gaggaggagc agcaaactgg ccaccctggg caggatcttc aaaccctgga    22020
agtggcggaa aaagaaaaat gaaaaactga agcagacgac gtcgggtgag cagcggggac    22080
ggggcctgct gtttgccctc ccgcgggtcc cctgcgggtc cctggtgggg gcgggtcagc    22140
accaggcaca cctggagccc actccccgcc cagaccctca ggggcccacg agtcaccctg    22200
gatcccgtta gacacccaga atccgggtca gtgctggccc caggcctgag actcagcttg    22260
taacgacctc ccctcgctga ccacagagta gaaagtgccc agcaccccgg catctggacc    22320
ctccctcgaa gggcccacca ctccacccc accccggct gatgccaagg gccctcggtt    22380
tggcctcagc accctgcggc ttctcctact ggggcctcct catccccatg ccctcccta    22440 aacgatccag aagcttctct cactcacctc cagctgcagc cttacacccc accagtccca    22500
gctctctggg gggttgggtt atgacaggtg gtacccttgc ctctacccct cgaggtccat    22560
gtcaggaact ctggccatga ggccgagcca gtcactgagc ctggggtaac tgtgcctgaa    22620
ctggctacga gagtgaaaat cgacccagca caattccaac catccaaagc ctgagaagca    22680
cccctctcgc cagcgccctg accacccgg ggacaggaag tgggctctgc gatgggcagc    22740
cgctccaggg tccagcagca gtgggtcgtg gggctggggt ttgggtccag ctccaaggac    22800
agggtgccct tgatgaagag gaggtcagtg tcctgagagg ccaacccag ggagcagcat    22860 cctagctccc ccaggcctat atccacggcc ggaaagaatt agtgagaggg ctgccgtgtg    22920
gagggagccc tgggccttgg ggacctgtcc tgtgagcgcc cgtctcaggc tgttgcctct    22980
ggcggtcccc ggagtcccta ttcccttccc agccttgaag aagcacagat gccagggcgc    23040
agaggatggc agaggcaaag ccagtggggg cggggggtgg gggctgcttc ttatagcagc    23100
agctggtcct ccactcacac tttttaatgt tttatgaaat cacgtgtttc actacccaaa    23160
aaggtgattg acaaattctc caagtcaaga atgaaagcag aacaagcact gttattcagt    23220
gaatctcgtg aggcccctgc gtgccaggca cagagcaggt gggggcca ggtcccgccc    23280 acagagcttt ctgccaggtg ggggctcagg ccacagacaa gcaaacacgt ggacgagctc    23340
gtgagataga ccttcccctg gcaggctgtg gaggaggag tcagcaggtg ctggggtggg    23400
ggggtgggtg agggtgggtg ttgccttggg ttgcgtggcc tgagaggacc caggtgagaa    23460
ggtgacactg agctgaccct taattggccc cctggggaa aagcatcgca gcagcaggaa    23520
cagccatgcg gacgcactga gttggggaag gctcaccttt gcgccagtga aaggctccag    23580
gggctggggc agcatgacct ctgtgacctt ggggaacccc gatattctct gggccatggg    23640
attggaaggg gagctgcatg ctctcaggac cctgtgcccc tggccccttg accctgggct    23700
gtggggagca ccctgtgagt tcatcgggat gctgggacc ctgccagggg gtgagtgtca    23760
ccaggttaat cccggcaggg tccccaactt caggttcctt atcaagtatt tggaagactg    23820
gaaacggtgc tgtgttttat ttatttattc taagccattc ccctcccctc caagtgcggg    23880
atattattta tttcagcata tcaaatcctg gatttcacag gcttccttgg ctagggtgag    23940
atgaagtcaa taagaagatg gtttagagaa aaaaatgat gcaggagttc ccgtcgtggt    24000
gcagtggtta atacatccga ctaggaacca tgaggttgtg ggttcgatcc ctgcccttgc    24060
tcagtgggtt aacgatccgg tgttaccgtg agctgtggtg taggttgtag acgcggctcc    24120
catcccgcgt tgctgtggct ctggtgtagg ccggtggcta cagctccgat tcaaccctta    24180
cttagcctag gaacctccat atgccatggg agcagcccaa gaaatggcaa aaagacaaaa    24240
```

```
aaaaaaaaaa aaagatgcag acaggggttt gggcgcgggg ggactggccg ataccacaga   24300
gatggctttc agaagcctgc agtctgggac gtggcatctg gtccctgctg gctctggggc   24360
gtggcctggg cggtggggca tgtccctgag atgcgggcag cagccctggc ccctgcctct   24420
tccagtagct ggggtgtgtc caagtcactg gggtgagtcc aagtcccgca tcggagccgg   24480
cccctgtgag tgccacccag tgctggctgg acgacgcggc ccctcagttc taggaccttc   24540
accctcgttc tgctcacctc tgttttcaga ctagacggca gtcctttgct cacctcccaa   24600
agccagggtt ccacttctca gttttatcca cacttctggc gcctggaaac tggattggaa   24660
attggactca gaaaggaaat tatgcccoct tgtccccaa atgtcatctc tctgatgttt   24720
gggttttccc attcacccct cagatggcag cgtaaacacc ctcaggggtg ccctcccac    24780 cccacccca cctccgccct gtgcccttct gcttgaggcc acttgcctgc ttgttgatgt    24840
ttgtcatctg ctccatgcac catcctcccc gaggctggca cacagtaggt gctcagtaaa   24900
tgtttctgaa taaacgaaat aacttcagtc cccttgcctg tttgtcctca gccactagac   24960
tttaagctcc accggccggg ccactctttc ttttcccatc ccaacccgcg ccgggcagag   25020
agctcccacg cgtgcctgac ccaggcccct tggcgaccca ggcttgtagc caggactttg   25080
catcttttaa agggaggatc tgagggatga cggttcatat ttggaaagtg gattctactg   25140
gaggcaggta gttttctgga tggttaggag aagaaggagc ttgtcaagcg gagtgagccc   25200
gccccaggag gggagaggca ggggcggagg gcgaggtgct ggggcccaaa gggctattct   25260
gaaggaggaa tgagaaggct cagcacattg aggacggtgg aggggtggg ggcctggcct    25320 ccatcctgtt tatctgggga attcttggaa agcacgaacg tggggttcat gggaggagcc   25380
tcccgtgcca tagttgtgca gaagcctgat ctgtggacag gtggaagggt ggccaggatg   25440
tagttaacga acaataatag agccacaaaa gagcatcccg gggtattggg gacagagaga   25500
ggatgcagtc ctgggctgga acatgaaggg atttctgcag gggatgggac gggcgctgga   25560
agaggctgag cagaggccgt cgtacggggc tccctttcag gtgcgtcatg caaccatca    25620 ccctaaacca tactccccct ccgccctgct ttccgctggt accggcaga ttgttcaggg    25680 agggagctcg ggatacctga ccgcgcgca cacacacaca cacacacatg cacatgcaca    25740 caccccggtgg ccccctaacc tgcggtcacc tgccaccttg ctgccctctc cctgacctgg   25800
aggtggcatt ggtggggctc aggcagggcc acacggcacc tctgcccgtg actcacctga   25860
tgtttgtgtg tcctgcagcc ttggagaaga agatggccgg caggcagggg cgggacgacc   25920
tcatcaagaa agggctgctg gagatgatgg agcagggtga gtggggccgg ggcaggaggg   25980
ctggagcgca gggctgggcg tctgacgggg cccaggaagc ccactggcgg ggaggggag    26040 gtggaagagt ccagatgtgg cagctggacc tgaaagaggc ctgcatgcct agagaaacgc   26100
cccaagtgag gacccggggc tcagccccca ggcctctgag gaccattggt gagtctaagc   26160
tcagctactc ccaggctggg tgtggatgga gctggtggtg agtcctgatt cctctgaggt   26220
ggtagcactg cctcttggtt tttttggtat tcatatttc agcgtagatt tggggagtt    26280 actcatcccc catttttcccc tagtcccggg gctgccgttt attaagcatc agtgatgaga   26340
ttatatgcca ggtgctgagc cgggcggcg ctctactcac ctccacccct tcgtcgtcac    26400
agcctccttg ggactggggg tggtgttact ccccgtttcc aggtgaggga tgtgagggtc   26460
tgggaggtgg ctgtcctagt cgcgcagctg gaggacccag aggctgtgtg gactctggtc   26520
cagagacctt aatcaccgca gtacgggggcc acctgggggtg gcctcttttgc gaaacaccag   26580 gttttatcgc tggcacagtg aattttcaga attctcgagt tccctcatct ccctctcttg   26640
```

```
gggacggtgt gaggcgcggg ctcgggtcct gatgctcacc cttcctgctt tctagttctc   26700
tgagtctctg aagcgtgggg acgggagcgg gtatcaggaa acctccatac tgcttataag   26760
tctctgggga gctgaaccaa gcacttgctc ctgattgaag aaagctggcc tcccagagcc   26820
acaggtcccc gaggacacga gaataaacgg gaattcccat ctcccttaag cctgcgaata   26880
tcactagtgt ctttgtgatt ttccaggtat cagaaactgg ggagggagcc cctggagtca   26940 gtgacccag atttataaca caggccctcc gaagtcctcc ctctccttta gcttcaaagg    27000
gaaagtcagc tgctgatgct gttttcggag gaaaactatg tgggaaattg cttagggtat   27060
gaatcaaact ttgcctgtaa aaaaaacaaa aacaaccttt ggtgtcaagt cctgtgacct   27120
tcagatggtc aaggtcccgg cctgactctg gggtttggag gaatgtcatg gctgggatgg   27180
aaatcggact gttttaattt ggacgggaca gaaaaactcc caactgcggc cttttgaata   27240
cctagccaac aaactttccc ttaaatcttg gggaaggagg agggaaacaa agcaatatga   27300
aggcctgttt atcatctatt tattttagag cctcacccaa aacacatgga ggtgcccagg   27360 ctaggggcg aatcggagct gcagctgctg ccgacacca cggccacagc aatgccagat    27420
ccaagccaca tctgtaacct atgccacggc ttgtggcagc tccagatcct taacccactg   27480
agcaaggcca gggatggaac ccgcatcctc atggatgctg gtcaggttct taacccacca   27540
agccacaatg ggaactccta tcatctattt tttaaaaata ttattgacgt tcctgtcatg   27600
gctcagtggt caatgaatcc gactaggaac cacgaggttg caggttcgat ccctgacctc   27660
gctcagtggg ttaaggatcc catgttgcca tgagctgtgg tgtaggtccc agaagcggct   27720
cagatcctgc atggctgtgg catacccggt ggctccagct ctgattcgac ccctagcctg   27780
ggaacctcca tatgccacgg gtgcggccct gaaaagacaa taaataaata aataaatata   27840
ttattttgct gaggaaagag ttactaaaga catggctttg attcccttga taaggaggct   27900
ggtgagtcat ttaaggggag aacttccagg agaagggcag tttgccttcc ctcatctccg   27960
catcatggca aaacaatgtt gcctgacagc ctgagcagcg agccagcagt caaattgatg   28020
gggtgggcgc ggggccgagg tgccgggggc cagctctcct ggcttccgtg aggctggtgg   28080
gaggtctcat gccagcccgc ctgcggtctt gcgctagatg ggggtcagcg agccttttt    28140 ggagagagcc agacagtggg tattttcggc ttagatggcc gtcctgtgct gtaatcaggc   28200
aaaaactgcc acagacacta cttgaaggag tgggcgtggc tgggttccag gaccacttta   28260
tttagggacg ttgaaatttg aatttcatat cactttcctg tgtcgtcagt tattagtttc   28320
ctttcaattt tttccccacc attgaaagag gtaaacccc tttgaaactc cacgctctag    28380
gaaacaggtg gcggctggat gaggccaggg tgtaggttgc caacccgac gttagatgat    28440 ttttctcttg ctcagtgatt atggaccagg agctcgaggg gcctgaacca gtctctttgc   28500
tcaggaacgg acagcacgct cgttaatggt tctcccccaa ttttattgag cacatgctat   28560
gggccagggt ctgtgttagc tgctgaggat gcggtgagca aatactttc tcccaggact    28620 catagtctgg tgaggaacaa gccttaaaca tcccacaaac aaatgtaaga ccacagctga   28680
gatcagtgtg gcgcaggaga ggcacctgca aaacaggagt tggggccccg acctggtcag   28740
ggccttgggt cgggtgggg agggtggtga ggctggcgtg gtctgaagg caggaggagc     28800 caataggctt ctctcagaac ttgccagcat caggatcacc tgggcagctc ttgcgtcaaa   28860
ggcgctgggg gtgggccca ggcatcatac tttataagcc tccccagctg cttccaactt    28920
tggtgccacg gaggttgaga agcggaggga gccggtgagc tgggggtgg gagcagcccg    28980
```

```
cgtgcatccc tgcttctccc tgcaaggtgg acagagccag gaaaactaga ctccccagga   29040
aggaagcggc tgggtgacaa agcctcctct ggggctgtgg gggcccagga cagccacagg   29100
gtgcgtgggc agggtgcctg cccagggcat cgctgcagtg ggggtggggg gtgttagaag   29160
cagggcagca gggattgccc ctgggaaggg ccctggggag ggagaggggg cagggaggtg   29220
ggctcaccac ccacgtggac cccaggggc tttactgcgt gtattccctc caacaggcag    29280
acagacagcg ataagaggag ttgtgaaatg tttgatcaca ggctccttgc agggttgttt   29340
ccttcctgca tttgctcaga aaatgccttt tctctctggg ggtgaagtca aagctctagg   29400
tccgtcctgt ccctcatttg tcctggtgtt gggaccgcag ggttcctgct gggtgcgtag   29460
caatccgtgg ccttgggagt tggtccttgg tttggattca gaaatcgccc acctgggctg   29520
gacatctttg tggccaggag cgcccccctg tggccggccg ccctccgtcc ccgctgagcc   29580
tgtacttcac acccagtgaa gccctggcg gctcagtgag cctccagctg tgaccgataa    29640
cctaggggct cagagcagcc cccgcaggcc agggccccgg accctcccag agctgcccgg   29700
agtcctccac agccccagga cctcacactt gaacttcctt ggccaggaca cacctgggaa   29760
gggcctctgc ccagcgcagg tgtgcacaca gacacgccct ggagtcagtc ccctggagtt   29820
tgcccacaat gcagtcagga gccagccctg gacgagcct gtgggagagc cccacgtccc    29880
gggcacccct ctctaggggg caccctctc cagggggtgt gttatcttgt gatgctctga    29940
acacgtgttt tatgaactcc tctgacctct cctctggttt ctgagagtcc ggccatccgc   30000
cgggcccagg aaggaccctg tgtgtggtgg gagatgggac cagctctgcc cgggaacggg   30060
cagctgctga cctttctcct cactccgcct tcactgctct ggctggtgac acatctgtga   30120
caggcaaggg ccggtgtccc acccctcca tagggtcccc gacccagaca ggctgcttga    30180
gggcagaagc ttgcccgttt ctctgtccac atgccctgtg tgctcctaaa ggacttcccg   30240
catcctctgt gtgtatctgc ctggcacagt cttcagtgat ttaaggaatt gcattctctg   30300
tcgttggaca taagaggaag ttgttagcct ggcgctgtgt tcagtgacct gagagacttg   30360
aggtctctct ccttggggaa gctggcagtg acaaatcgtg tcagtctggt ttctgtgtgg   30420
cagaaacgct gggagcagcg tgtgtgtctg tatgtgtgtc tacgtgcatg cttgtacacg   30480
catgtgtgtg tttgcacagt gcatgtgcac gcatgtgtgt gcatgtctgg ggcacgtccc   30540
cttccctctc accatggctg ctctgggtat aaccctggca tctggcttgt gtgcccccct   30600
gccgccctcg ggggagaagg gcctggaggg agggccgacc gtctgtgaga ggcgcagggg   30660
accagctgcc cacagctccc ccgccccgcc agcgttgctt agcaacgacc ctgccacggg   30720
gctattttgg gaaccgtaag ttttcattga aggtgattat gagccgcagc ccaggaaagt   30780
ccagcaagtc cactaaggtg ggaagcgggt ggaggaatcc agaaaccctg ggtgttttgc   30840
caagcctggg gcagggagcg ggcgggcgca ggggaggag gctgggacc ttccggcctt     30900
tcaggctctg atcacttgat ggaggggagg atggagacgc cgttataagt atcgacatca   30960
ttattagtaa tcaccagcag caaatgacct gccccttcta agacctggtg tccccgcctg   31020
taaagggcgg gtagcagtct ctcctaaggc cgtggagagc tgtccactca gctgggacag   31080
cgccgtgcgc tgtctccggc tcatgcatgg gtgctggctg tcaccccagc cacgaaaggc   31140
cgtgtgagcc agtggcacag acggtcacag ctgtgtgtca ggatgggtaa gctagttgtg   31200
agaaagggcc aagaagttgc tgagcgtggt ggctctgat cggttcaca gggtgaattc      31260
tcttgacttg tgtctcagtc ttttcctggg tcaggactgg tgggctgctg gtcaaatcag   31320
gcccaggacc tgttttttgta gagcccttcg agctaagaag aggtttggac cttcaaggat   31380
```

```
tttataaaac tgaaaaatcg ggtgttcccg ttgtggttca gtgggttaag aacccgacat    31440
agtgtctgtg aggatgtggg taggatccct ggcattgctc cgtgagttaa ggatcccgcg    31500
ttgccgtgag ctgtggtgta ggttggcagc tgtggctccg attcgacccc ccagcctgag    31560
gacttccacg tgccgcctta gaaaggtggt ggggaggggt tctcaggtg tataggagca    31620 aaaggtctac cacaccgggc ctggggtggc gtcctggcca ggaagtcact ttgtgtgaat    31680
gaaaagcagg aaggagggag tctggcctgg ctgacagctg gatttctttg cagacgctga    31740
gagcaaagca ggcagccctg atggaggccc ccgagctgcg cagagcgaac cttccacgcc    31800
caggcaggag cccctgactt cagaggaagc ccagccggga agcccttcag ccgctgggac    31860
agaccaggct tccctggatg aaccgctgtc ctcggaaacc cattcagatg atgcaggtac    31920
tggctggctc ctggagttga gctgttccca ggatggcatc gggcctgggt ggtgactggg    31980
gtccctggtc caggctgtgc agcagctctg gcagaagact gtcccagag gtgcagccac    32040 acccctggtt ccgagccctg ccgcgctcca ctgtgtggct gagtttcaag gtttgctggg    32100
cgttctccct cagcatcttc ccaagtcggg cagggctgtg gatagaggtg ctaacagatg    32160
ggcacaggtg acttaccacc aaccttcctc ccaggacgtc tttgcttgtt ctcttgggac    32220
ttctgaccaa ggaaatgctc tctaaagggg ccctgtccag tgggagcatc tttgctaccc    32280
caaggccaca gggcaggatg gaggcagggg gcctccccgg tggcctgact ccctagggga    32340
tggctgcccc tccagagggc agcctgtctc cctgggccac cctggggctg gcagtgctgg    32400
tggtggcgcg gccagcctac tcctcacctt ctctgccagg tgtgcctggc acatgcccga    32460
agcctcattc ctccctctgg caaatggggg aagaatggtc tgtctggggt tatctgcagg    32520
gtgcgaggag ccccaggtgg tgtctgctgc gttgaatgat tcttggtgag ggcggtggag    32580
gccgaggtgg tggttctagt ggagttgaat tgaacagaca gttgccgcag tgaagcagga    32640
ggagagagaa ggagagaggg atggtgggaa ctaactgtgg ccccaccaca gaaacctacc    32700
tgtaggtgct ttgaaacacc caccgtgca ccctctgacc tgttagcttc cacagaattc    32760
ccccgggaga ccttgtggtc cagcaggaac cctgttccct cataaaacca aagctataaa    32820 tatcccagc atggggctg ggacgtgaac tgggttccca cagcatggag cagggagtt    32880 agggcctctg gggtcagctc tctggcttca gagctgggga cagggacagc tgtgctcggc    32940
ccctgcttct ccagaggagg ctccctccta tgcttccccc gctgccccat ccacggcact    33000
ctctggctta gcaggcacct gccaagagct gtgctctgct ctctctaggg gtggctgtga    33060
gtctccagtc tcagtctcac cccagcttgg agacgtgata ggagtttggg atccaagagc    33120
tgtatttctt gggacagtcc tggcctttcc cgcagaggtc cactcggcac gcctgtgtcc    33180
ccgtgggctg tgtcatcaga cttcaggca gtggttggcg ggttcttgtc gcccacctgt    33240
ggttctagca gccgagctgc tctctgtcca ccagcttggt gggggatgga ttcttgggtc    33300
caggcttggc tttttgagat cacacatttg tattggagct cccgctgtgg caccacagga    33360
ttggcagtgt ctgcgcagcg ccaggacgca ggtttggtcc ccagcccagc atggcaggtt    33420
aaaggatcca ccatcattgc cgtagctgca gcataggtcg caactacagc tcaggtctga    33480
tccctggacc aggaattgca catgttacgg tgcagcccaa tgtgaaaaat aaaaacaaaa    33540
accaaattaa ggacttttcc caaggtggga catgcttttg ggtctggggt catgatggta    33600
gtgtgtctga aactgtcttc ccagagggat tggggggga gcaaacctgg tggcccctag    33660
agccgagtcc acggcagccc agctggtgcg aagggatgag aggaattgtc ggcacagaga    33720
```

```
tggagggata gagcaggctg gacggggag ggacccttgt tggacccgtg tgagactggg    33780
agcagtaaat atcattgact ttgtggctca gaaggtctca cctccaccaa gtagcacaga    33840
aggagccaca gagcatgtgc cgaggaagag tgagggctgg gtgccagtgg tctttcatca    33900
caaagagcct acaggctgca ttttggtgga ctgtggttgg cttgggaaca agaggggtcg    33960
ggggacttgg gcagagctga aggtttatag atgtggacag gcctgggcag accagccctt    34020
ccctgagcca cactggggtt tgccctgtaa gagcaccggc tggtgggcgg ggcaaggcct    34080
gggggagtga gaccctggtc ggagtgtggt cggcgtgtgg tccatggtaa cacagtgacg    34140
ctcatccctc acctgggctc ttccttccct cctgcccagt gtggtcctga ccccagggt     34200 gtgagaggtg atgttttgtg ggtggtacat gcaaacaact taaacacctt catagtgatg    34260 cttatttca ttaattagag caagtggtac gggtttctca ttcaggccaa tgatagcttc     34320
ttaataaaca aattgaagta agaagtagga ctgtaagtac agcagacaga aatatacaga    34380
gggccgggca gtggccagta tccagagcag ggctgatggt ctccttagcg ctgcagttag    34440
tgtattagca gctagtgatg cttagcacac tgctgatgac aacaagagcc agcatgcaca    34500 gcccttgtg tgcaggacac tgttcaaagg gctccatgta catttcacca tggaaacccc     34560
cccaagacga tcgatgctct ggccccgtct tgctcatgag gagctcaagg tgcacaggtt    34620
aagcatctca cccaagggaa cagaattggg gaactgacag cagcatatgg tctttgacat    34680
caggctggcc cgagtttcag atttgaccga actcctcgcg aagccgtgtg accatggaca    34740
agccacgcag cctctctgaa cctgcctcac caactaaatg gggatcatgc cctaccctgc    34800
tcttggggtt gctaaaattg aaccacttgg ttgtgacccg cgctgagtgc gcagagagcg    34860
tttgctgctg cagctgagga cccttgtcac cgtctttatc atcatcatca tcactttcgt    34920
catcgtcatc atgaaaagc agccctggaa ggagggcgat gcattaactc catatttggc    34980
tgcccacaca cgcccctag gggccatgcc tctctctgcg tgtgctgggg ctgagggtgc     35040
acctgcattt tgctcttgag ctgggacacc cccaccccca ccccacgggc ctcttgcagc    35100
cctgcagcag gaacactgat catgacttcg gctccgagtc tccgctgaga agcctgacct    35160
ggagcaaagc cccttccgtg agggagcgct tgtaatctaa tgcagagatt ttaaactcac    35220
cgttgaaaac tgaagtttaa acatcaggag cttcacaaa aatccacatg tgcaactagc     35280
tgcttttctt taaaaatttt tgttttctta cggtatggtt gatttacagt gctccttcaa    35340
tttctgctgt ccggcaaagt gacccagcca tacatatacc tatatacaca cattctttt     35400 ttttgttttt gtatcatctt ccatcatgtt ctagcccaag agattggaca taggtccctg    35460
ggctgtacgg taagactcca tcgcttgtcc attctaaatg gagtagtttg cgtctaccaa    35520
ccccaaactc ccagccctct ccctgtctcc cccttcccc tggcaaacac acgtcggttc     35580
tccgtgccca tgatctggtt ctgttctgta gagaagattg tctgtgccat atcttagatt    35640
ccacgtataa gcgatatcat ggaatatttg ttttctgtc tgacttcact tagtatgaga     35700
gtctctagtt ccatccacgc tgctgtaaat ggcattgttt tgtccttttt gtgaccgagt    35760
agtattccac tgtgcatata taccacagct tctttttttt ttgtctcttt tccttttcca    35820
gggccactcc cgcagcatat ggaggttccc aggctagggg tcgaattgga gctgtagcca    35880
tcggcctgcg ccagagccac agcaacacgg gatccgagcc gcgtctgcaa cctacaccac    35940
agctcacggc aacgccggat ccttaaccca ctgagcaagg gcagggatcg aaccgcaac     36000 ctcatggttt ctagtcggat tcgttaacca ctgtgccatg acgggaactc caatatacca    36060
cagcttctta atccattcat ctggctagct gttttttcaac caccagagtc caggcccacc    36120
```

```
tacgcagcca cggtctctcg gagcaaggcg aggtccctcc cttcgggggt cttaccccc   36180 agtgcctgcc tggcccattg ggtgtgagct ggccatccct tccatggcag gaaagagcct  36240
ggctctagga gccaacccct gtgctgcact gggctgctgc ttccgggcgc cccacactgt  36300
ggagtggggt tttgttttta gcttttgctt tttagggcca cacccaaggc atatggaggt  36360
tcccaggcta ggggtcaaat cagagctgta gccgccagcc tacaccacag ccacagcaat  36420
gctgcatctg agctatgtgt gcgaccctga ccacagctca cggcaacatt ggatccttaa  36480
cccactgagc aaggccaggg atcgaacctt cagcctcatg gttattagtc agatccgttt  36540
ccgtgttata tctaatgatg gcaaacatct cggtaggaaa cgtggtcaga ctatgaccat  36600
ggttttcttt gatcctctgt ttgcgttcag tgatttgggt tgactttggg gtgatttgtg  36660
tttggggtgc ttgctggttt tgtcctcttg gtgtggcatc aaccacagaa cttgccctaa  36720
aaagcccagg agggtttgtt gttttgatgt taagtgggac aggatcccgt tcagggtgtc  36780
tgtcgggcag aggctgagct ctgggcttcc caagagtgtt ctcattaaaa ggaaaagtgg  36840
ccttcagtga gcatgttctc cctatgcaat attatcttag ccctgctttg ggttttgctt  36900
ttgttttgag atgagaaagc aggagcccag agaggttaag tcacttgccc gaagccacag  36960
agcatataag cggtaaagct gggatttgtt cttaacttta acactctaca gcccaaacta  37020
gagccaagct tttctctgct tctggaatgc tctggaatgt ggcttgtttc tgcagtcttg  37080
aagatggtta gcaaattgca ggctacaggt cagacccagc ccacctgtgt ctgtatgacc  37140
agctcaagtg tgttggcacc gtaagcctgg ggaccatgca gagatggccc cctccttgcc  37200
cccagcctct gcctcccagc tggtgccaca cttgaccaat gtccagggtc tgtgctggtc  37260
ccacctacac ctgggatttg gctgtgggca cctgctgggc tctgagctgt ggaacctcct  37320
tgcaggaatc atccagggcc agccatccat gagatcaagg acttgggggt gtccctgggg  37380
tgggatgaca ctgaccacgg cacctccagc ccaccagctc cctcctccag gctggtctct  37440
ctgggtctca gaatgtgtcc agtgggtggt cactgggtgt taaggcgagc ccacccagca  37500 ctacaccccca gcaggaaagg ccttggctgg ctgggagctc agttgatgag cagcgacctc  37560
tgctggccag ggcaggacag gacaaccccg agggatccta aatgttggag caccacaaag  37620
ctgactctgg cttcttcagc gttaaaataa aatttgacat agcacttgag acttttaaca  37680
gatgttagca tttcagtttt gacaagattc tgaaatgcaa aggcagctgc accgtcacat  37740
ggcactcgcg tgagatgtgg aggaagatgt agataagaaa gaaatggaaa caccaggttc  37800
ccagaccagg gaccctcag acaggttggg gtgtgagggg tcagtgtgtg ggtttggagg  37860
aggggcattg gaggagggggt ctgatgtgag ttcctgggtc ctgggctct cagagcagag  37920 ggtagggcct ccacactcca cctggggctg gttggtgggg gggccaccat ggggctgtta  37980
gaagcttacc ctgccatctc tctggttgaa ggggtgtggc tgtgaccacc aactcaggct  38040
caaacccaga gttgccctgt ccactacctg catggagatt tgaatgaatg aagactaaat  38100
aaaatgaaaa atccagctcc ccacttgcac cagccacttt ccaggtgctc cttggccagt  38160
gtggctagtg gctgcccta aagagcgagag aggacacatc tccatcatgt cagggctact  38220
gggcagcact gagggtgaga cgtggccaca catccacttt ggtgcaaagc cagtggagtt  38280
ggctggcttg gccagccctt ccagagtttt ctgcatcaag cagggacctt ataacctgca  38340
atgccaaagc cctttacagg aaaagtttgc catcccctca tttagagtgg acttaggcga  38400
tcatgggcag aaggggaaga gcttgaaggc cttgctgagg tccaggggag gctgtggcag  38460
```

```
ctgacactgg gagaacaggc aaaaggacgg tatttctgag aaatattttg gaggcagagt    38520
gcccaggatt tatctatgca ttagatccaa gagtcaggtc tgaggtggag agggcaggag    38580
gggaatggag catggggtcc agtctggctg daccgctgag gggatggggg accatgtaga    38640
aagtctggtg acagtggggc tctgtcttgg tcaaagccat gtccacagct cctggaaggg    38700
tgcctggacc ccataattgt tcagggaccc ttgtggatgg atgaatggat ggacggatgg    38760
atggatggag aagtgagaga gaagaggaac tggggagggc tttctcatgg gaaatcaaga    38820
gatgcgtttg catgtgtttt attttgatta tttgacctcc tgacggaagt gtcaaagtgg    38880
ccagtgatgg atgtgtctgg agttctgagg aagggtcaag ggtcgacaga gatgggattg    38940
gttctgaagc cagaggactg actggatgag agaattggat gagagaatta aatgagagag    39000
tgagccaatg gggaggagca ccaagggcgg gtcctgggc ggcccagcgg gagcctgaga    39060
ggggctgagc aggagtggta ggggtaccgg gggatgtggt ttccagaagc actagaggaa    39120
ggtactggcc tggacagatg gagggacttt gctgccacag agccaagtgg accagccctg    39180
gctgacgcag gtgtgggaac gcggatccac ggctgccctg tctccctgtt caccctcgc    39240 gtggaactat tcagccctt ggacagttat aggcaccttg ccagggaaaa aggcagtctt    39300
ttggaacatg gatgcatttt tcttcatct taggtcaagg gttctcggcc ttggcagtat    39360
tgatatttgg ggccagagaa ttcttgcct gtaagagccc agttcaaaca ctgcccactt    39420
tgtccagact cccaggtcca tgggggggaga ccaaggccca gtgggagcaa ctggcctgtc    39480
tgggtttcca gggtagcagg acccagactt gttccaagag cctgtgtcac agctgcgcgt    39540
ctcaccgtgg gcctccttg ccaagcagac accgcaacgc atccccatgg aaatctaagt    39600
agtgtctgcc tcaagcaggg gctctcggcc gtgggcattc tgcccccag gggcagtagc    39660 tggagaccgt tttggtggtc acactggcat ctggcagata gaacccaggc ttgctgctat    39720
gtatcgtata ggcagagatt tatctggaag gagaggaaag tgcatccatg cttcaaacca    39780
cagctcttag ccctgaggat aatgtgcaaa gtgccgaaga gtccagacct cccctccgtg    39840
gcctccatca atctccctgc cttggaatgg gcagaatcgg gcatgttacc caaatatttg    39900
tgtagatgag gaaaccgggc ctcacagagg tggagactaa ggcgcttgtc tagaaatgag    39960
tcagtcatca cagaggaaaa ggatgggtgg aggtgggaga cgggtgtgtc agcgggccat    40020
tcctgtgcca gccttccccc caaaaccttg acattgggga cctactgatg cccagggag    40080 ggatactgag cctgtcctga gcactgcgag ctcacgccgg ccctgtgcct ggtgcttctg    40140
gctgcaggct tggctgctga gggcctgggt ctgggagcgt ggcctctgaa gggtcggggt    40200
ccactgcctg gcactgattt gcaggaaccg ggagccaaca gagtcacagg acaggtgccc    40260
acatggagaa aaagagcctc tgcacacgca caaggaaacc acacaaccgc ttttacctgg    40320
aagcaccaaa tgtttgcttt aatgttatca tttgtgcaaa acgtattaac caagtctcag    40380
tggtggactc ttagaagtta caggttgcag ttcataggcc ataacaatag tcttagagtc    40440 tagggggtctt tgaaaaattc ctatgaacaa gtaacccttc tgaggacggt tttattatta    40500
ctcgtaggag taataataat aaaaccagag tgtttccggg tgcgtgtctt tgctggacag    40560
aagagtaagg agcccactct catgcctgtt ctcagctcag actgagacct gccatctgcc    40620
gtgggcgggc agggggcgtt tcttagatcc ttttcatcgg gatttgggag gagccctttg    40680
aaggcaaggg ctgcatttcc atgagtatca cgagggagag gacctggcct gagaggtctt    40740
gaacttccaa cgtggatgat ggaatcacag aaatggtgat gagccctggg acccgcggga    40800
cgtgcaggcg tccttctccc aagcttggta ggaccgggag cgggtggcct cagtcagcac    40860
```

```
cacggacagc gccatctctt tggtcaggca ccagccgcgt tccctgactg atggatgaac  40920
ctgtcaggct gttcctaggg gttgttggta tcttcccctt gggtggttgc aaagataaaa  40980
tgagattaag tggggccagg gccttgccag ggccaggcac ctgggctgc tccaagaggg    41040
caggaaggct ggggtcccaa ggtgaggatg ggaggccacc cctcttttg cgtcagggtg   41100
gaaggaaggg tgtgttgggg cccataggtt tgtgtctgag gccccccgc ccctgccccc   41160
agcccagttt ccctgtaaag ctggaggtga ggtggcctgg gaggggagt gagaagctgg   41220
acagagaaga gccatggatg tattttcctt tgcatccatg gaaggaaagg gacagaagag  41280
ggtttgacgc agagtggctg caggatggag cagagcccag ggccctgagg gtgtggtcct  41340
gggatggcca ggacggggc ttctgtgtca ctttcttctg cagcactgtg cctcggcagg   41400
gactggcaga tggaggcttc atccagaggt gggactttcc cagtggggca gaggacttgg  41460
gggtactggt gaggtggttg ttgctgcggt ggatggtgga acttgagctg gataaagaga  41520
gaaggggaaa ggagagggct gatgggttgg gagaaggcgc aggtgacagg ctgaagtggg  41580
ggtggagcag tgccccagga ggtggaggca ctgttctaga tgagcctgca ccaggcgagg  41640
ggacggggct cggggggctc aaagctgaac ctccctgatc ctcccctgcc actcacctgt  41700
cttgctcgcc tggggcagtg atgttgaaaa gcaggcgtgt aaagtcaata gctgcccaac  41760
ttgagggtct gcgacatgcc aggcacacat ctcatggttg cttcttcttc ttcttcttct  41820
tcttcttttt tttttttttg tcttttaggg ctacaccca tggcatatgg aagttcctag   41880
gctaggggtc tattccgggt ctaattggag ctacagctgc cagcctacac cacagccaca  41940
gcaacacggg atccaaggag tgtctgcaac ctacaccaca gccacggcaa tgccggatcc  42000
ttaaccccct gagcgaggcc agggatcgaa cctccaactt catggttcct agtcaggttg   42060
gtttccgctg cactgcgata ggaactcctc attgtcactt cttagttaaa cctcccagcc  42120
atcctgtgag ggactcttgt tcgcctgacg tcatccgtga caaatggtga cacaggagtt  42180
tagtaactta tccaaggtcc cagggtgagc tcagggacca attggagtct gattccaaag  42240
cctgtgttg tgaccagctg cccaggtgag gtgggagctt cagtgacacc tgttgagtgg    42300
aaaagggaca gaatcccctc cactggcgca cctccctccc ccttccgcct ccgtcgtcct  42360
ctctctgctt ctgatgtatc tgttgacagc ggaattcaca agtgtcatgt ccatgggcca  42420
ggccaccccc tgtactcagc tctgcaataa caaccccacc caaccaaggc ccttgcagtc  42480
ctcacaccca ccccaagcgt gtctcaactc tcttgccttt gaaccagcca agacgtcatc  42540
agcatccaga ggtgacgaag cagacgccgc cggcagccgc ccacctgcca tggacgagcc  42600
gtctcaagcc ttagctgggc ccgatgccct ggacagtcct cccagacccc tggacagatc  42660
catgggccag cttcccagcc ctccgctgct gcccaccccg ccacccaagg caggctccac  42720
agcctcaaga agcaccccag gtgggtccgc ctgcatcccc cttcctgccc tccatccatc  42780
cgtgcctccc accagccctg ctgggcctgt gaccaggact tcagactcac acctgccct   42840
ctgggtccag gaacctaagg acatcagggg gattttctga cgcgtcaccc actggtctgg  42900
ggactgaact aggagtgcga ggggacaggc gggtcatgag ctttggactt tggcctggat  42960
cgcttagagc tgagatattt tttgtgattg atttaatttt cttagggggg aaaggtttgc  43020
ttcggcaagt ggacgctagg tggcagcaga aaggagaaa gccccctcact tgggcttaac   43080
tggggcccaa ggggacagag gccacaggct gagtctccct ggggcccccc atcggagaca  43140
gccgagcggc ccccgcccg agagcttcct caccccactc tccacccaaa tcccacttgc   43200
```

```
agacttgctt tgctgggcct gcatgatatt taatacttaa agaaaatgt gtggccacat    43260 ttaaaatata tcaaaacata tttaaatatt aaacatatta catatgttta aggggtggcc    43320
tgcggacccc tgggccttgt catcattagc ccagaccttg tctgaagggg gatgggagag    43380
ccatggtcag aaagctcctg ctgggcaagg cacagggtgg gaggcagacg tgaatgagga    43440
agcagagggg cccctgtggt ccaggctggg ccaggcctct ggaggacttg tggcttcggg    43500
gagccaagtt cgtagcagag aaatgggaag gagggcttca ggcgcctgag accttgcagg    43560
gagctgtggg tactaatgtc tgcagctcag gggtcacgag gacggatcgg aactgctcat    43620
ggctggaccc cttctccggc tctggggaca aggaggcctc atgcagcatc acagggttgt    43680
gtgagtgggc tcacctggcc acgagccctg cattctcttt gcttacgggc tcctatcttt    43740
cagcaaagcc ccacttccct gcttccaaag acttatattc tttttttataa agttatttta    43800 ttttatggcc tcattcccag caggatatat ggacattccc aggccaggga ttaaattgga    43860
gccatagttg ggcaacacca gatccttgaa cccactgtgc tgggccattg attgaaccct    43920
tgcctctaca gccacctgat ctgctgcagt ttgattctta acccactctg ccacagcagg    43980
aactcaagac ttatgctcgt gtttgtcctt ctcccacccc aggccaggcc acgctcttcc    44040
aaggctctgg cgggaagaat actgaccctc cgctccgagg acagctttcc acgcccacgg    44100
ggtctccgca tctccccacc gtccaccggc cgctgccccc cagccgcgtg atcgaggagc    44160
tgcatagggc gctggccacc aagcaccgcc aggacaggtg aggcccctct cctggcaggg    44220
ggtcctgtgt gcccaaattc ccactggggc ccagcctcgt gggggtcacc tatgcagtta    44280 tggggggtgcc cgctctgggt gggcttaatg ctgtgcagtc acagtcttga aattctcagt    44340
ttttgagcaa gaagctcacg ttttcatctt gtaccggact ctgcagctgg tctgtagctg    44400
gtctcggctg ccacattcca ggtggggtca gctgggagga gtgcactgtg aggacaagcc    44460 acaaaccca cgtgtcccct ggaccatccg gggtcaggtg ggagcctcct gagggagcca    44520
atagtgaggg agttgtagat gtcgcgttgt ccccggactc tgccggcttt gggtttgcat    44580
caggcaggag cacaggtaag cctgctgtga tgctgcctct aagtcctcat ctcctgtgcc    44640
tcacagccct gaggacaggt gagtccttgg agggccaaac agataatgca acacacgtgc    44700
ggcttggcaa atattgctc aaataaaagc cctcttcagt tcttaggaaa tcctggctct    44760
gagcgtttgc tgcactaagt gttggtggat tttattccat acccgtctgc cattcaagac    44820
agcatgttct cagtgccatt tgccttggcc tccaagccgt gtgctcctct ggagcttcta    44880
gcccagtgta ccggctgtac ctacttggga gctgtctctg cggcccctgc tataaacctg    44940
atataagccc ccgagtcaac tccgcacggt tgcctgggga agctggacca ctgacaatgt    45000
gacctgcctt tctgattcag tttccaagga cgggacagta aagggtcccc gaagaagcgt    45060
gtggatgtcc ggctgtccag gacgtccagt gtggagcggg gcaaggagcg ggaggaggct    45120
tggagcttcg atggggcctc cgacgtcaag cgggccgccg ccaaggagtc cgaggagaac    45180
aaggagaact tgctgatgaa ttccgagctc aaggacgacc tgcttttgta tcaggacgaa    45240
gaggcgctga acgactccat cgtctccggt gagtgcaggg cggatcccgg ccgtgggaac    45300
ttctcgccgg aggcaccacg cccacgtcga gggggtgctt ctgtagctag catgtggggg    45360
ggggtggagg gacaccctct ctgtccgtga acagggcgtc agcaggcggg cacggggcac    45420
aattagccag ggaccgaggg agctggtttt attctgatca ttgcatattt tcatgtgtgt    45480
tcgaaccaac aaaagtggct cagctatcga ctaagcatc gtggcgtggg gatgacgtgt    45540
cagatggtgg caggggggggc cctgagatgg ccagtgttgg aagatgtggc caaagatgct    45600
```

```
catagaggga gatgaggtgg ggccgatgcc agtggccatc tcagaaatac acaaacctgc   45660
tgtgtctgct ttgctcgggg ccacatctgc acgaggccct tagaggcctg gtctgtcctc   45720
acagtgtcct caagatcaga gggattgctc tgccctaccc gtgaggacct ggggctcagg   45780
gaggcagagc gttgtagacc ccccgtgatg aatgtaaaag gaactcagcc ctggtgtggg   45840
ctgtgctgag ctgcatccct tgcaaaggtc aaggacggat gtggccataa agccttgtgg   45900 cgggggtgg tgattgtccc cgagcgaggg gttcctagaa gcatctcgtg gtgaccatca    45960
ccacattggg cagaggtctg ggtggaggct ctggggaact tgcctgctgc tcgtgccagg   46020
tggggaaggg gatggcattg accctgccct ggctggtatg acggggcac aggcagtggg    46080 cactgtgccc aggtgggcag accgggaccc ccggattaga cactgacctt ggctgtcacc   46140
ctgcccggga ccttgcatac gtctgggcct ttcccgccct ggtctggtga agctcttctg   46200
gaagagcagg tgacagtgct tccaactggg tctgttgctg aaattcagcc tctgtctgcc   46260
agtgtcaaat agacgcagag acagagcttt gggtgaaggt gaaaaggta actttattgc     46320 tttgccagga aaaggggcca tagcaggcta atgccttata gattgtgccc ccgttggagg   46380
gggttaggag gtggttttat agtttggggc gtggaaaata gggccacacg taaggatcac   46440
gttgaggcaa gcttgccttg tcttttcaaag ctggtgttta gtggccccag gactggttct   46500
ggtggttctc ctccttccgg gaatgaagat gcttcatcac gtagttcttc cattgtgggg   46560
ctgggggttt cgttctgcaga aaggctcaaa ggtactgtta tctatattcc ttgaggagac   46620
accaggacct gtcccaaggc tgcgctcttg tctctgacgg ctcctccctg gtctctgcat   46680
cccctccctt ccctgaagag caactgccct ttggaactca gggaaggtca cggaggctga   46740
ggcttattcc ctaaaaacaa gaaacgaggg acacagaaag acttgtgtgc ccaggagccc   46800
cacagggctc tgctcggttg caggtcttca tggcagaaac gccaagccag tcattggcca   46860
agaagccctg gacatctagg aagaggcttc tgaagcctgt gtgttcccca aacttatctg   46920
gccccggggc tttcccttaa acacccatca gcctcctgca ggacaggtgg cgtgggacac   46980
acctgagagt ggctggtgga ggcagggatc tcggctgga gcaggtgcct aaacatcggg     47040
accagtgatg ctgagggctg gagggttctc tgccgtgggg ctgccctgag ctttgcaggg   47100
tgtttggcct ctacccgcca gactgcgctc cctccagctc taggggaggg tccttcctgc   47160
ctcttccagc tgctgtggct gcaggtggtc cttgccttga ggctacgtcc ctgctgccct   47220
cttcacattg ctgtccctgt cctcttgcta ataaggacac tctcactggg ttaaggaccc   47280
atccgcataa tcctgcatga tcctcatttt gagttcctta tcttaattac atctgcaaaa   47340
gcaaattaca tcttttttt tttccctcag agaaggtact ttcccaggtt cccagtgcac    47400
tctttggggt cactcttctc tctcccctgt cactcctgat ggtgtaccat gttcctcttg   47460
ttgagccaag gtcacccctg gggccttttca tggccccca gccccatccc tgggtcctcg   47520
gcagcagggc cagtccactg cctcagcggg agctcccatg ggaaggtgcc ctgctctgtc   47580
cctgcagcct gggtaggtcc cctgcctcgc tccctcctca gagatcagat caaccatccc   47640
tcagagctcg acgcagtcgc aatttcaccc tgattttgt tattattcct ctgttgtccg   47700
tctccctcta aaccatcaat tattcgatga tgatggatca tctgacatgt gtgtttgacg   47760
gctgtccgga tgggggacgg tggccttttcg tccacacagt gcctggttct aaggaagagt   47820
caggaagtag cttctggata atataatggc tgtgattctg tctgccgatc tgatgggtcc   47880
ctggtgaggt cccccagccc acgtgctcca aggtgtcacc ccatagacgc agcatgtcca   47940
```

```
cctgggtct cagacgtgtc gctgacctga ggtctctggc tctgagctct tgatctttgc   48000
ttccaaaacc aaattgtcct tgtgaacaag ggccctgacc ctctgggccc cgggccacct   48060
cacccctctc ttggctttgc acctgacgca cagacggctc ttcctcaggg aaatctggcc   48120
atttctcctc tgctccatcc tctcctgccc agagtcagcc tcccacgggc ccctgccac    48180 caccaaggcc cctgttgtag cccctccctc cagacgccac ccctcgcttg tgtccctcca   48240
gcggcttcct gaaggctgaa acgccacttc ccaccaggac ctgggtggcc tgtccctgtc   48300
acccaggctt atctccttcc aagctccttg ggacccagcc atgggccctc tgtgctcctt   48360
acacacacca accacagtcc acccaccact gggctctcgt gcccacccag gaagaggtgt   48420
gtgtggctgc accgtgttta aaacaccgct tcctccgaga agccaacagg cctaagcgag   48480
tgacgccccc ctcacacggc tctgcagccc ctccctctcg ttgcatcccc tgagacgccc   48540
ctgaggtcag gggcttcacc aggcagctcc cgctttgtct gcagtcccg cttcagtgct    48600 gctacgtgta caataaaggt cagttaggaa agactgggtg tccccggggg attaaaggag   48660
gggtgattgt ggcctcagat ggaggagcag catatgatgt ctcccagggt gtgggccaaa   48720
cacgcatctc ttgttatttg tctcctaaaa cctggagtttt gacgacagtg acaggagcag  48780
gagagtagaa ctcattctag aaactcgctg ttgtggccct gccctggctc ccctggacgg   48840
cgctgggctg tgcttatggt atttgcaaac cccagcaaag ccacctctcc tcctgggcct   48900
tccttgcgta ccagcctctg gggtcaaggt caaggtcaag ggctcacaac cagccctaag   48960
atcatcctgt ggagcgcccg gcccactgca cagtcaggcg ggtctggaga tcgagtcccg   49020
acaccccggg cctggcccct gccaactgca gctgaggcca gggtgcaggg tctgggggcc   49080
ccaaacccct ggaaccccaa gtagaaactg aggtctttgc ttttatcaca ttctcataag   49140
tgtccggaac tccctccaag ttgtgaattt ctggaacaaa atgcttggag gagaaaacgc   49200
aatgctggtt ctggagaaag cgtacagatc tcactttagg gggaaaacca gtcatagtgg   49260
gagaagccca tacaagtatt ttgcccggta ggagagtagc acagatccgt ttttcttggc   49320
ttttctcgag ttcagacccc ctcccaccat ggcggatggc accttatttg tagatcgctg   49380
gggtgcgacc tacaaataaa agaagtagaa acacgcccgg cagcagcttc atcagttgtc   49440
aatcttagaa actgcactgg tgtttcttat ttatttatcc tcataactca ctgtccccgg   49500
agcctttgca ggtggtgtcc catccatcac gaacccccca ggacgttttc attagcatct   49560
cattaccctg aattctctag aagcagcagc tactttaggg tgtgatttct ggagctgatg   49620
gaagccccac ccaaggcaga tctgccctgg catcggctgg aagcttgtcc tgtaggatcc   49680
tgttgcagtg acaaatgtat ttgtttcagt ctagggctga cagtggatttt ccatgcaggg  49740 caaagacaat gtcttgatca atacagcgtc acaggccgtg tgtttccgcc tcgagctggc   49800
tgccccggct tgccgtgtgc acacacactc ccccaatatg cgtgctcagt acctgccagc   49860
acatagggca ccttttgtggg catgcgtggt cagcgccagg aagaaacagg acactgggga   49920
ccttctcaag tccatcaaag gtgattcttt acaagatttt gttttttcaga gcaatttaag   49980 tccatagcaa attaagactc aatacagaca tcccctggcc ccgcaactgc aaagcctgga   50040
cacagcgtca cccaaagctc ataactgaca ttagggttta ttctcggtgt tggagggtct   50100
gtgtgtttgg acaaatgtat aaggaggtgt ccatccttgt atagtgtcag agagagaatt   50160
ttccgggtct tagcagtccc ctgggctctg cctgtcaccc cattcgtcac cccaacccct   50220
ggcaaccact gatcttctta ctgtctctgt agttttgcct tttctaaagg gtcacacttg   50280
gaaccatcca gtaggtaggg ggctttcctt ccctcaggac taggcatttg tgttcctgcc   50340
```

```
atgccaccac atggctggat aacccgtctg gttttttttcc tttttttttct gccggtttca    50400 ctgagatata atcaagacat aacactgtaa atttaaggta tacagcataa tgttttttcac    50460 ttaggtagta tcctcaaatc atgaccacag taagtacagt aaaaatttat catctcatat    50520
agatacacct ggtattttga ttttcaaaga aatagaaaaa ttattttttc ctagggatga    50580
gaactcttac gatttactct ttttcatttt tttactttt tgtcttttgt cttttgggg    50640 ccgcacctgc agcatctgga ggttcccaaa ctagggtct aatcagaact acgccagagc    50700
catagcaacg ccagatctga gccgtgtctg tgacgtacac cacagctcac agcaacactg    50760
gatccttaac ccactgagca aggccagggg tcaaacccac aacctcatgg ttcctcatcg    50820
gatttgttcc tgctgcacca caacagaaac tccctcgatt tactctttta aactttctc    50880 tctctctctc ttttttttt tttttttttt ttttgtcttt ttagggctgc acccacggca    50940
tacggaggtt cctaggctgg ggtcaaattg gagctgtagc tgccggcctc taccacagcc    51000
acagcaacgc gggatccttg ccccactgaa tgaggccagg ggtcgaactg agtcctcatg    51060
gatcctcgtc agattcgtgt ccgctgagcc atggcgggaa ctccaggacc ttcatatgta    51120
acatacaaca gtgtgaactg ttttgatcac gttgttcatg acatcccgt gctcggctgt    51180 tttgttggtg gaagcttgga ccttttgact gccttcatcc aatccctacc acccccctctg    51240 gtcaccacaa accagatctc cttttcaatg cgtttgtttg tctttggagt ataattgccc    51300
tacactactc tgttagttcc tgttacacaa cacagtcatt tgatacgtct atgcatttca    51360
aagcgatcgc cgcagtaagt ctagtcccct ctgctatcat acggagaaat tatatcatta    51420
ttggctctat tccccacacg ccacgtttct gacccacgac tcatttattt tttgactgga    51480
ggtttgcacc tcctaatctc cacctattcc tctcccccc acccgcctcc cttcttttg    51540 atggagacta gtatcccact gttgacacct gccccacctt ctgcattcct tcacctatta    51600
gaggacctct ccgttgtttc ttagtcttgg caactacgaa tacatctgct ctaaacatcc    51660
atgtgcaggt ttttgtgtgg ctgtaagttc tcaactctat tgggaaaata ccagaaggca    51720
attgttggat cacgtgggaa gagtatattt agttttgtaa aagaaatcca gtcttccaaa    51780
gtggctgcac catttacccc cctccccgc caccggccgt gacagttcct gtggctccac    51840
attctcgcca gcatctggag ttgtcagtgt tctgggattt gaccatattc attctaagag    51900
gtgtgcagtg gtgtcccctt gttgttttaa tttgcatgac atatactatg gagctacagt    51960
tactggccta caccacagcc acagcaacgc aggatctgag ccacatcttc aacctacacc    52020
acagctcaca gcaacgccag aatccttaac ccactgagcg aggccaggga tcaaacctgc    52080
agcttcatgg ttactaggca gattcatttc tgctgcaccg caaagggaac tcctgttttt    52140
aatttcaaat tccatttgtt tattgttggt ataatggaga gcaattggct tttgtatgtt    52200
aaccttgtat cctacaacct ttatgtaaat cactaattag ttctgggagt ttttcattga    52260
ttccttagga ttttctacat agacgtttgt gtcatctgca agcaaagaca cgtttatgtt    52320
ttctttctca ctctgcctac cttttatttc cttttcttct cttattgcat gaactacttc    52380
ttccagtatg atgttgaaaa ggagtgatgg agaagaaaga catcttgcct tgttcctgat    52440
cttagtaaga aagctctgag tgtctcacct ttacatgtga ggttaactag aggttttgt    52500 agatattcct tatcaaggtg aggaagttcc tctctattga cagtttacag aggagttccc    52560
attgtggctc agtgataatg aacccaacta gtatcatgcg gatgtggatt caatctgcct    52620
cactcagtgg attagggatc tggcattgcc atgagctgtg gtgtaggtca gcagctgcag    52680
```

```
ctccaatttg acccctagcc ttggaaactc catatgctgt gggtgtggcc ctaaaaagca    52740
ataaaacaaa caaacaaaaa cagtttacta aggtgattct tttaaatgga ggtaacatta    52800
taacacatgg gtttcacata gacaacatta tactttatt tctgtctaca ttacagcatg    52860
ctcaccaccc aaaatttaga ttctagccat caccatgcag ttgaccctct gtgtccattt    52920
tacttcctcc ccattctcat ctggtaacca ctgctctgct ctctgtatct acattttggt    52980
ttggtttggt ttattttgt tgttgttttt tatgttgcac atatgagtga tttcatatgg    53040
tatttgtctt tttttgtcac atttatctca ctttgcataa tatcctccat atccattcat    53100
acccttccaa atggcaggat tttacctttt tttttatgac tgagtaggtt ctggtgtgta    53160
tatgtgtgtg tgtgtgtgta tacatgtgta tatatatgta catatatcta tatatgtata    53220
cacacatatg tataccccaa cttctttatc cttcatttgt tgtctacaca tcttggtact    53280
gtaaataata ctatgaagaa cacaggaggg catttatctt tttgaattag tgttttgta    53340 ttcttcagat acataaccag aagtagcata gctggattgt atggtagttc tcttcttatt    53400
tctttgaggg ttctccatac tgttttccat agtggctgca ccaatttaca ttctcaccaa    53460
caatgcacaa gggttccctt tcttcacatc ctcgctaacg tttgttattt cttgcttttc    53520
tgataatagc cattctgata ggcatgaagt gatattttat tgtggttttg atttgcattt    53580
ctctaataat tagtgatgtt gaacatcttt ttatggtcct gttggccatc tgtgtgtctt    53640
tttagaaaaa tgtctattca gatcttctgc gcatttttt taaattgctc aatgaatttt    53700
attacattta tagttgtaca acgatcatca caaccaaatt ttatagcatt tccattccaa    53760
acctgcagcg cctctcccca cccccaacc tgtctcattt ggaaacaagt ttttcaaagt    53820
ctgagtcagt atctgttctg caaagaagtt cattgtgtcc ttttttaga ttccacatgt    53880 aagtgatagt atttgatggt gtttcaccat ctgactgact tcaattagca tgttaatttc    53940
taggtccatc catgttgctg caaatgccat tatttctttc cttttaatgg ctaagtaata    54000
ttctgttgtg tataggtacc acatcttctt tatccactcc tctcaatgga cattcaggtt    54060
gcttccatat cttggctatt atatatagtg ctacaatgaa cactgaaata catgtatctt    54120
ctcaagtcat gttttttttt tttttttct ggatagatgc ccaggagtgg gactgctgga    54180
tcaaatggta attctatttt tagtttcctg aggaatcttc atattgtttt ccacagtgat    54240
tgcaccaatt tacatccca ccaacagtgt aatagggttc ccttttctcc acccctctc    54300 cagcacttat tgtttgtaga cttttggatg gcagccattc tggctggtgt gaggtggtac    54360
ctcatagtgg ttttgatttg catttctcta ataatgagtg atgttgaaca tcttttcatg    54420
tgtttgtttt ttggttttgg ttttggtttt tgcttttta tttgtttttg ttttgtttt    54480 ttggccatct gtatgtcttc attggagaat tgtctattta gatcttctgc ccatttttt    54540 tgatggggtt gtgggttttt tttttggta ttgagctgca gaaggtgttt ataaattta    54600 gagattgatc ccttgtcagt cgcttcattt gcaaatattt tctcccattc tgtgggttgt    54660
cttttcattt tgttcagggt ttcttttgct gtgcagaaac tattaagttt aattaagtcc    54720
catttgtttt tattatcttt actctaggag gtggatctga aagatgttg ctgtggttta    54780 tgtcggagag tgtttggtct atgttttcct caaagaattt tctagtatct ggtcttatat    54840
ttaggtcttt aatccatttt gagtttattt ttgtgtatgg tgtcaggaag tgttctaatt    54900
tcattctttt acatgtggct gtccagtttc cccagtacca tttattgaag gggctgtctt    54960
ttctccattg tatattcttg cctcctttgt catagataag ttgactgtag gtgtgtgggt    55020
tttattctgg gctttctatc ctgttccact gatctatatt tctgtctttg tgccagtacc    55080
```

-continued

```
atacagtttt gatgattgtt gcttttgtag tatagtctga agtctgggag cctgattcct   55140
ccagctccat ttttctttt caggatgtat ttggctattc agggtctttt gtgcttccaa    55200
acaaacttta aaatatttgt tctagttctg tgaaaaatgt tcttggtaat ttgaactgaa   55260
tcattagatt gccttgggta gtatagtcat tttgatgata ttgatccttc cagtccaaga   55320
gcatggtatg tctttccatc tagttgtgtc atctttgatt tctttcatca gtggctaata   55380
attttcagag tacaggtctt ttgtctcttt agataggttt attcctaagt attctatttt   55440
attttatttt gttttgtttt gttttttggt ctatttttag ggacgtaccc atagcatatg   55500
gagattccct ggctaggggt ccaatcagag ctgtagctgc tggccttcac cacagccaca   55560
gccacccagt atttgagccg catctgtggc ctacaccaca gctcatggca atgcaagatc   55620
ctcaacccac tgagcgcatc ttcatgaatg ctagttgggt tcattaactg ctgagccaca   55680
gtgggaactc ctaagtattt tattctttt gatgcagtgg taaatggaat tgtttcccta   55740
atttctcttt ctgatatttt gttgttagtg tgtggaaatg cagttgattt ttgtgtatta   55800
attttgtatc ctgtgactgc caaattcatg gatgagctct aatagttttc tggtagagtc   55860
tttaggattc tctaggtata ttatcatgtc atctgcaaat agtgatagtt ttacttcttc   55920
ctttccaatt tcgattcctt ttatttcttt tcttctctg attgccgtgg ctaggacttc    55980
caaaactatg ttgaagggta gtggcgagag cagacatcct tgtcttgttc ctgatttcag   56040
tgggaattct ttcagctttt caccattgag aatgatgtta gctgtaggtt tgtcatatat   56100
ggcctttatt atgttgaggt tggttccctc tatgcccact ttctgaaggg ttttttataag 56160
aaatgggcat tagaacttcc caccatggca cagcggaaac aaatctgact aggaaccatg   56220
aggttgcagg tccaatctct ggccttgctc agtgggtaag gatccggggt tgccatgagc   56280
tgtggtgtaa gtcacagacg tggctcagat ccctcattgc tcgctccaat tagaccccta   56340
gcctgggaac ctctatatgc tgtctgtgca gccctcaaaa agacaaaaaa aaaaaaaaa    56400
aaaaagaat gttggatttt gtcaaaggct ttgtctgcat ctattgagaa ggtcataagg    56460
ttttattct tcagtttgtt aatgtggtgt attacactga ttgatttgcg gagattgaag    56520
agtccttgca tccctgggat aaatcccact tgatcatgat gtacaatcct tttaatgtat   56580
tgttggattt ggtttgatag tattttgttg aggattttg cgtctgtgtt catcagtgaa    56640
aatggcctgt aattttcttt ttttgtggta tccttgtctg gttttggtat cagggtgatg   56700
gtggcttcag agaatgagtt tgggagtgtt ccttcctctg caattttttg gaataatttc   56760
agaaagatag gtgttagctc ttctctaaat gtttgataga atttgcctgt gaagccatct   56820
ggtcctgact tttgtttgat ggaagttttt aaatcacagt ttaaatttca gtacttgtgt   56880
ttgatctatt catattttct atattgtctt agtttagtct tggaagattg tacttttcta   56940
agaatttgtc catttgttct atgttgatca ttttattggc atatagttgc ttatagtagt   57000
ctcttatgat cctttgtatt tttgtgatgc ctgttgtaac ttctcctttt tcatttctaa   57060
ttttattgat ttgaaacctc tctcttcttt tcttgatgag tctggctaag ggtttatcaa   57120
ttttgttgat cttttcaaag aaccagattt tagtttcatt aatcttttca actgttttca   57180
tttctactca aatacttatg attactttcc ttctgctaac tttgggtttt gtctgttctt   57240
ctttagttgc tttaggtgta gagttaggtt atttgagctt ttccttgatt ctttaggtag   57300
gatttttattg ctataaactt ccctcttaaa actgcttttg ctgcatccca taggttttgt  57360
actgttgtat ctttgttgtc atttgcttct aggtgttttt taatttcttc tttgatttct   57420
```

```
tcagtgagcc attggttgtt tagtagtgtg ttgtttattc gccacatgtt tctgtttttt    57480 gaagttttt  tctggttgtt gattttcagt catatagcat tgtggtcaaa aaagatgat    57540 tgataagatt tcaattttt  taaatttatc aaggcttgat ttgtggccca gaatgtgatc    57600
tatcccaaag aatgttccat gtgcacttga gaagaatgtg tactctgctg ctttttgatg    57660
gaatgttcta taaatatctg gtccaatgca tcatttaaag ctgtgtttcc ttgttgattg    57720
tctatatagg tgatctgtcc attgctataa gtggggtgtt aaagtctgcc tctgttattg    57780
ttttgttgtc aatttctcct tgttagcagt tgccttatat attgtggtga tcctatgttg    57840
ggtgcatata tatttaaaat tgttacatct tcttcttgga ttgatccttt gatcattatg    57900
taatgtcctt ccttgtctct taaaatattc tttatttcaa ggtctatttt gtttgagtat    57960
tgctactcca gctttctttc aattcccatt tgtgcggaat attttcttcc atcctctcac    58020
tttaaatttg tatacgtccc tagaagtgaa gtgggtctct tgaagacaac atatatatat    58080
gggtcttgtt ttttaatcta ttcaacagtc tatgtctttt ggttggggtt tagtccattt    58140
acatttaagg taattactga tatgtatgtt cttattgcca ttttatgaat tgctttggat    58200
ttgtttttgt tgctcttttt tcttctcttg ttctctcctc ttgtggtttg atgactatct    58260
ttagtgttgt atttgaattg atttttctta tttgtgtgtg tatcagttgt aaattttgg     58320 tttgccgtta cactgaagtt ttgatatagg agtctgtgtg tgtgtgtgtg tgtgtgtgta    58380
tgagattgtt ttaagttgtt ggcctcttaa ctgcaagtgc atctccagtg tcctgcattt    58440
gtaccctcct cttctcacaa tttctgattt tggtagtgta attgtacatg gatagtttcc    58500
tatctttact gtatatatgt ctttactggt gagccttatc atttgtggta tttttgtttc    58560
tagttgtagc cttttttttt ctgcctaaag aagttccttt ggtatttgat gtaaagctgg    58620
tttagtgttg ctgaattctc tcagcttttg cttatctgta aagcttttga tttctccttc    58680
aaatctgaat gacagacctg ctgcgtaaag taatcttggt tggaggtttt tttccttca    58740 tcacattaag tatatcatgc cactcccttc tggcctgaag agtttctgct gaaaaatctg    58800
ctgataacct tattggggtt cccttgtgtg ctatttgttt cttttctcta gctgctttca    58860
gtacattccc tttgtcttta attttgatca gtttgattaa tatgtgtctt ggggtgttcc    58920
tccttgggtt tattttatat ggtactcgtt gcacttcctg gatttgagtg agtggttccc    58980
ttcccatgtt aggaagtttt tggctattat ctccttggaat attttttctg tcccttcc     59040 tctctctctt ctccttctgg tactcctata atgtggatgt tgatgcattt aacgttgtcc    59100
cagagttctc tgagactctc ttcatttctt ttcaatcttt tttctctttt ctgttctgca    59160
tccgtaattt ccactagtct gtcctccatc ttgcttattc attcttttgc ctcctatatt    59220
ctactgttgg ttgcttctaa tgaattttt  atttcagtta ttgtattttg catcactgct    59280
tgcttaagtt ttaaatcttg tatttctttg ctcagtgttt gctgtaaatt atcaatcttt    59340
gcctccagtt tatttccagt gtcttgcatc accttcagca tcatcagtct aaagtttttt    59400
cctggaggtc gataatctcc agatcactta gatgttttc  tgggtttttt tctttctccc    59460
ttatctgagc tacagctcat tttcattttt ataggtcttt ggtgtggtgt cttttttgcag   59520 ataagtgagt taaagcatct cttacttctg gtatctgccc tccttctggc cgaagttggt    59580
atgggcttac tgtaagctcc ctgatgaagg gactgctacc cgcccactgg tagttggagc    59640
tgattcctat ccttctggtg ggtggggctt tgtctctggg tgagattaga ggctggctgt    59700
gtgcctgggg gtctttgggc agcctgttta ctaatggatg gggctgtgat cccacctgga    59760
ttattgttgg gcctggggct tctcagtgct gatgggtggg gccagatttt cccaaaatgg    59820
```

```
ccacctctag aggaacactc actgatgaat attcccaaaa gctttgcctg caatgtcctt    59880
cccccacgag gagccacagt cacccctgt tttcccagga gatcctccaa gaactgcagt    59940
caggtctgac tcaggttcct atgaagcctc tgctttgtcc tgagacccag tgcacatgaa    60000
agtctgtgtg cacctttcaa gaatggggtc tctgtttccc acaatcccct ggagctccta    60060
ggcacagtcc ccaatggcct tcaatgccag atgctctggg ggctcttct tccaatgcca     60120 gatccccagg catggggact tgatatgggg ttcagaactc tcactcttgt aggtgagtct    60180
ctgtgaacca gttactttcc agtctgtggg cttcccacct gggagggatt gcttatatca    60240
tgtaatcacc cctcctacct tctgatgtgg ctgctctgtc ttctggagta ggatatcttt    60300
ttgaaagttt ccagtccatt tggttgaagg ttgttcagca tttggttgta attttgttgt    60360
ttttatgaga gaaggtgagc tcctgtcctt ctattctgtc atcttaatcc catctcttct    60420
gcccattttc tcaatcaggt tttgtgtttc ggagttgttg tgttgtatgt gttcttcata    60480
tgttttggat attaacccct attggatata tgattaacac atatcttctc tcattggata    60540
ggttgtcttt tagttttttt gatagttccc tttgctgtgc agaagttttt tagtttgatg    60600
tagccctatt tgtttatttt tgcttttgtt tcccatgctt gaggagacat atacagaacg    60660
atattgctaa gacttatta agaagagcaa ccttcttatg tttccttcta ggagttttat     60720
gcttacatgt cttatgttca agtctccaat ctattttgag ttagtttttg tgtatggtat    60780
gaaatagtga tttttctctc attctttgca tgtggctatc cagttttctc agctccattt    60840
attgaatgga gctatccttt gtctatagta tagggtttgc tctttggtta taaattaatt    60900
gtccatgtgt gtgggtatat ttctgggctc gcaattctgt tcttttttg atctatggac     60960 ctgttttcct gccaataccg tgttgttttg atgactatag ctttgtaatc tattttgaaa    61020
acaggcagta tgatatatcc agcttttattc tttttctca gatttgattt ctcaggtatg    61080
tgtgatcttt tgttgttcca tataaattta aaaaatttt gattctattt ctgtgaaaag     61140
tgtcattggg attttgatag ggattacact gaatctgtac actactttag gtaatatgga    61200 cttttttaaca atgttaattc ttttagtcca gtgagaacgg agtatcttta tcttttttt    61260 tttcacttttt tttgaattaa tgtatagttg gtttacaatg ttgtgccaat ttctgctgta    61320
cagcaaagca acccagtcac atatgtatgt atatacacat gtgcgtatat atatgcatta    61380
cctttcttat attacctccc atcatggtct atcccaagag actagatata gttccctgtg    61440
ctctacagta gggactcatt gcttatccat tctaaatgta atagtttgca tctactaagc    61500
ctaaacttcc aatccatctc attctctcac ttctggcaac cacaagtctg gagaacagag    61560
tatctttctt tcttccctt tttttttccc ccttttagg gccacacttg cagtatatgg       61620
aagttcttag gctagggtt gaattggagc tgcagctgca agcctatgcc acagccacag     61680
caacatggga tctgagcagc atctgcagcc tacaccacag ctcaccacaa tgctggatcc    61740
ccaacccact gcaaggccag ggattgaacc tgcatcctcg tggatactag cctcatttgt    61800
ttgcactgcg ccacattgga aactcccaga gtatctattt ctttgtgact ctgcagttta    61860
tttccacaat gtcttgtatt ttcagtttta caggtctttc actttcttgg ttaagttct     61920 tcctagattt ttttttgcag caattgtaaa cagaattgta aattttctc tctgcttact     61980 tattgttagt gtatagcaat gcgatagatt ttaatgtatt gattttatac cctgcaactt    62040
ctctgtaatt cttattatt ttgagtagtt tttagtgga gtctttggag ctttctatat      62100
ataaaattat gtcatctgca gaacagtgac agttttactt cttcctttcc aatttggatg    62160
```

```
tctttcattt cttttctta cctaatttat ctggctagga cttccaatac tatgttgaac    62220
aagagtggtg agagtggacc tccttgcttg ttcctaatct tagagtgata actttcagtt    62280
ttccactgtt gagtatgatg ttagctgtgg gcttgtcacc tgtgattgct attaggttga    62340
ggtacattcc ttccacaccc attttattga aattttttat cataaattgt tgttgaattt    62400
ttatcataaa ttgttgaata ttgtcatatg cttggtcata tgattttat ccctcattt    62460 attaatgtag tatgttgtat tgattgactc tgtggatatt ggaccatcct tgcatccctg    62520
gaataaaccc cacttgatca tggtgtatgc tcttttaat gtatcattgt gttcagtttg    62580
ctaatatttc attaaggggtt tttgcgtcta tgctcaccag agatattggc ttgtagtgtg    62640
tgtgtgagtg tgtgtgtgtg ttgtctggtt ttggtataag aatgatgttg atcttgtaaa    62700
atgagttagg aaacattcca acctcttcaa ttttttgaaa gagttgagaa ggatagataa    62760
taaaatcttt gaatatttgc taggattcac ctatgaagct gtatgcccct ggacctttt    62820 tttagaggaa attttattta ctctttcaat ttccttacta gttattagtg tattcagatt    62880
ttctacttct tcatgattca gtcttggaag tttgtttgct tctaagaatt ttcccatttt    62940
tttctaggtt gcccaattta ttgagtgtac agctattcct agtattgtct cataattctt    63000
tgcatttctg tgatattcat tgttatttct cctctttcgt ttctgagttt attcgtcaga    63060
gcattctctc tttttaataa tgagtctacc tataggtttg tcagtttatt tattttttcaa    63120 aaaaccagct cttagtttca ttcatctttt ctgttatctt ttagtctcta tttagttatt    63180
tcttctctaa ttttttgttat ttcctcccgt ttactgacat tgggctttgt tcttttttt    63240 ctgtttcctt taggtataaa gttagattgt ttatttgata gttcattgtt tcctgaggtg    63300
ggcctgtatt gctataaatt tccctcttaa taccactttt gctgtacctc ataaattttg    63360
gtatgccata ttttcatttg tctccaggta ttcttttatt tcttaatttc tttttttttt    63420
tttttttttt ttttttttgg tgacccagtt gtatggcgtg taatagcata ttgttcagcc    63480
tccacgtgtt tgtgacttct ccagctttct tcttgtagtt gagttttttgt ttcagaacgt    63540 cgtggtcaga aaagatgctt gatatcaatc tttttaaatt tgccttgttt tgtgtcccag    63600
tacatgaccc ctctctcctc gagcatgttc catgtgcact gtgggagaat gtgaattctt    63660
ctgcatttgg atagactgtt ctgcacaaat atgtaaaatc catatagtct aatgtttcat    63720
ttaaggccac ttccttattg acattccgtc tggatgatct gtccagagat gtaaatggga    63780
tgttaactgc tgttgtgttg ctgtcaattt ctccctttag gtcagttaat aattgcttca    63840
cgtattttgg tgctcctgtg ttaggtgcat actcgttaat aacttttata tcttttttgct    63900 gaattgtccc ctttatcctt atataatatc tgtatttgtc tcctgttgcc ttttttgggct    63960 tgaagtctgt tttgtctgat ataaatatgg ctatatcccc tttctttcga ctggtatttt    64020
tcttgtagaa tcatcttcca tgctccgact ttgatcctat atttgtcttt agagctgagg    64080
tgtgtctcct ggaggcagca tatagttggg tcttgttttc gtttgtttgt ttgttttta    64140 aacacagcca gccactctgt gtcttttgat tggtaagttc agtccattta catttagggt    64200
gattactgat aaatgagaac ttagtaaaag cattttgttt gtttctttgc tttctggtag    64260
ctctgtatcg ccactgtttc ttttttcttg tgtttctctt cttttggctt ggtaattttc    64320
tatggcactt ttttggtttc ttcttttatt actttgtgtc tctgctccag atttatgctt    64380
tatgctttct atgatgtttg tttaaaacat atcatagata aaactgtcct ttttctgctg    64440
ataacatctt atcttcattt gcctatatga tttctctcct ttcctctcctc cctttatgt    64500 ttttattgtc tcaaatgatc ccttttttatg gttgtgagtt tgttaccaaa gtgaagtgta    64560
```

```
gttatttttc ctactttttt cctctttgac tttttttcctg tagtacatgt ttaaaaacct   64620
attttgatcg atagttgcaa tttctgatat tgtctgttac tactttactc aaatatttgt   64680
gtacttttgc cttttttag gtagaaaagc tcctttcaat atggcttata aggcaggcct    64740
agtacagaag ttatgactcc ttcagctttt gtttgtttcg gaaaacctttt accttccttc  64800 acacctgaag gataacttgg ctggatggac taatcttggg tgacagtttt tatctttcag   64860
cctttggaga atgtcttcct actccctcct gggccgtggg gctcctgatg ggcagtctgc   64920
tgatggcctg gtagggggctc cttcagagat taccctcctt ttcccttggc tgcctttaaa  64980
gttttctttg ttggagttcc cattgtggct cagtggtaac aaacctgact agcatctatg   65040
aggacgcagg ttcagtccct ggccctgctc agtgggttaa ggatccagca ttgccatgag   65100
ctgtggtaga tgtcatagac atggctcaga tcgtaagtgg ctgtggtgta ggctggggct   65160
gtagctctga attgaccccg agtctgggaa cttgcatatg ccacaggtgc agccctaaaa   65220
agaaaagaaa aaaaaaaaaa ctttgtcatt gattgtgac  agttttgata taatgtcttg   65280
gagacggtct tcttgcattg aggcagttag gtgttctctc agcttcctga acttgtgtat   65340
ctggttcctt ccccagggtt gggatgttct cagattttct ttaaacaatc ggtctgctcc   65400
cctttgcgtc tcttcccttc tggattacct gttatcctaa tattgctctt cctaaaaagt   65460
catactgttc tcacagtttc ctcatttttta aagatgtgct cccacctctt ctccctgaat   65520
gatgtccaga tgtccgtcat caagtccact aattctgttt gaggtggtct gctctatttc   65580
cagcactttg tgtcgtattc ttcatctggt tttctcagtt atacacctcc ctaatttcca   65640
tttggttctc ttctcgagtt tcaatttctt tggtaaagta ttccttctgc tcttcagttt   65700
tcttctcgaa tttgttgagc tgcctttctg agcttttctt gtggctcatg tgttttttttc  65760 ctgacagcta ttttgaattc tctatcagtt tgataacact atgctgtgac ttcgagtttg   65820
gcttctagaa aactgtcatt ttcttttctgt ggcacagtgt ttctgattgt tcctggtgca   65880
tttgaagcag tgagcaccat tcaactttag gtaaagcttt ttctttttac agttgtacct   65940
gtggcatatg gaatttccca ggctcgaggt caaattggat ctgtagctgc cggcctacac   66000
cacagccacg gcaacaccag atccaaacca cacctgcaac ctgcgctgca gcttgcagca   66060
acactgaatg tttaacccaa tgaacgagac cagggatcta acgcacatcc tcatggatac   66120
tagtcgctga gccacgctgg gaactccaaa gcttttttat ttttaaact tggttctaac    66180 tgttcaacag gttagaaatc agaggacttt cttttctctt ccagcaggtg gtgctgtggc   66240
acaggttcta acagttcaac aggttagaaa gcagaggcgc ttcttttcat ttccagcagg   66300
tggtgctgtg gcacaagttt ttggtgtctc ttacctgagg tcgcatttga gaactgggac   66360
tttgcaacct ccaccctgta cccttcttgc cccaactgtg tgtccggagt ccttggtgcc   66420
ttgctgctgc tgacctccaa gcccccgcca tctgtcccca tcagggctgt gccccacgcc   66480
ctgccactcc cttgcccagc tctgtgctct ctctccagga ctgtcctcac ggctgccccc   66540
gtgtaagtgc acgggctcaa gtcttcaccc ctggcgccag tgctcaccca ggctgaggcc   66600
ttacatgtcc actgcccact gcttgtgccc ctgtagaggg cccactgacc cacaacccag   66660
gaaacccgcc caaccgccga ggtccccact ctcaatgtct tcgccacgtt tcgagacact   66720
gaagccacag ccgtccctct ttccgctctg tcctcatcac acaccgcttt gttcatccag   66780
aaaatattag tcacaccgtg tgtcgggcac gggggaaagt gatgggtggg agggggtact   66840
tgtccccaag actcggtctg tggctgcatt tatgaggatc actgtccttt acagaagggg   66900
```

```
tcagccactg ctgcttctgg cctgggcaga acaagggtag ctgcccttct cctaaaccag    66960
ctataaaacc actgtgtagg ggcgatgagc agcaagcagt gtggactgtt gaccagggaa    67020
gtcgagggga cacacagagt gagccccaca gtggccgtcc agcttgctgc ctggagcctc    67080
ttcccagaga gggtgcaggg aggtggcccc cgagcagagg ggtggccaca tcttccatga    67140
ggcagattgc aacatggaag cagctggagt ttgtaggaca ggtcctgggg gctgtgggaa    67200
gagggcccag aagttccggt ggacactcag ctggccgagg gctgggtgtg tctgggaagg    67260
tgggattccc ggagattaag cagcagtcac ctgtaggagt gagggaggaa ggtgacgcca    67320
gaagccaggg atgctgggat ccggcccagc ccgcggagag acctcgctga gcacccggac    67380
catacgctga accccagaa aggtcgggcc tcggagtaa ggagctggcc gtggagtaga     67440
cgaccacgat caaaaccgaa atagacctgc tgtccttgtg aacatgttct gggcgctaag    67500 gacgggatg aatgaacaga tggagaatct tagcagagaa ccagaaagca gaaagagggg    67560
ccaaatgccg attctagaat taaaaagcat aatgtctgga atgaaaaatc cacggtgggt    67620
taaagatggc cccacagtgt ccctgcttgt gctgggacag ctatcagggc tcttgacaca    67680
gggcccctgc agccaggcgg gggcatcctt gccctgcctc ttctctctcg gggcacccac    67740
gccttcatcc tcctcctcct cctccaagcc tcgtgtgccc ccgccctgg ccctcccctc     67800 cctgggttct aggatggctg gtctggacat gcagtttcag aggggtgtg gctgcattgg     67860 cgccatgggg atacgcttct tgcagctaa ggctttgtgc atctctgcag ttttgtcttc     67920
aggataaatt ccaaagtgtg actaattgag aaaagatct cgtgctgtgt gtattttaa      67980 ctccggagcc tctcactcag ccttctgttc ctctttacac gcggtcccct gtgagggtcc    68040
ctccctcttc caagagggc actcaagcct gtggttctgg aagcagcggc gcagcgatgg    68100 tccaggtgg actgggcga ggagcacctg tctgcaccta gaatacatgg cgacgtggc      68160 tcagcgatgc tcccacgtcc agggatggag cattcatccc acatgagtat gggggtgttc    68220
gtttatgtgc agggaagtcc aggaaggagg gcagtccctg aggttttggc taaaagagca    68280
agaagcagct ttaaccggga cccgcaggtg atgggattac gccacgtcca ctctcgggga    68340
ttatgtgcag ccgttgttgg aaagagctgg ctccggtccg ctttcgaagc tcgtgagtga    68400
gccagctcac tgccctgctg ggcgtggtgt gttccctcgg tgctgtaatt ggaaatgtca    68460
gttgttaatg gcagagaaat aggtctggaa ggaaatagcc ggaacctcag gagtggtttc    68520 ctctggggt gagatgtggg cggggaaagg ggttctttc atctcgatgc tgccgctggg      68580
catccgttgt ctgcactgag tgcattgttc ctgtagcgga ggcagagatc aaacctctct    68640
gagcccgaag gcagccacct ggggctctgc gctccctgca cttggggcag ctcccacctc    68700
ggggaactta accttccctc tcttcacgtt gctggcgagg caggcgggca gatcccgccg    68760
ctggggccag tctgctctgg tagagggagc ccccggtaca tggaagaatg gtctaatgac    68820 atggttttt tcctttttaa cgtttgttaa tttggcaaat tacatcgact gcttctcaaa    68880
tgataaactg ccttgcctcc cagttggttg ggactgttac catgtttcta aattattggg    68940
ctcgatctgc tacaatttta tttagggtgt tatgtccaca ttcacgaggg ctcttcatct    69000
tcgggatctt ctctggtttt gacatcacgg taaattctag cttcatgaca cgcgttttaa    69060 cgtcttcct tctttcaat tttccgaaat catttgtata gaattggaat tatttacatc      69120
ttacatgctt catagaattc atcagtgcat ccatcttgcc cggctggggt tttttctttc    69180
gacgggggaa gcgttttca gtagaaattg taattcttta gtacagatgg ttctatttta    69240
gttacatgtt tcttctaaag tgagtcttgg aagttgatgt tgaatcacat ggagatatgg    69300
```

```
cccctccttc ctgacactgg tagtgtgtgt gtgtgtgtgt gtgtgtgtgt gtgtgtgtgt    69360
gtgtgtgtgt gtttcttcct ccccttctca ccgttgcctc cttacttccc cggtgagcct    69420
gcctggagtt ttatctgtct tacgactgtc ctccaagtat tcacttttat tgctcctctg    69480
ttttcagttc catcagtttc tactctggtc tacatttctt ctcttctcct tcgttggttt    69540
taattcactt tttattttct agtttcttaa gatggattct gaggtcagtg atttgagagt    69600 cttcttttt ttctcacata ggcatttgat gctgtaaatt ttccctaaca tcattttgat    69660
aagctgtatt ttttttttct tttcttta gggctgcacc tgcagcatgt gcaagttccc     69720
aggctagggg tcaaatcaga gctacagctg ctggcctcca gcacagccac agcaaccca    69780 gaacccagcc acatctgtga ccacagctca cagcaacact ggatccttaa cccactgagc    69840
agctccaggg atcgaaccca catcctcata gatactaatc agtgtcgtta ccactgagcc    69900
acagcaggaa ctctataagc tgtatttttt tttttttacc tcaaaatact ttctaatttc    69960
ccttttggtt tcttcttggg atgggtgat tcggaattta aaattttagt ttccaaatta    70020
tatgggtata tttctagaac tcttttggtt attggtttcc catgtaattc cactctggtc    70080
gaagaacata cttggtatgg ctcgagtcct gtttaattta ttgagacttg ttttatggcc    70140
tcgagcatgg tctgtcttgg taaatgttgc atgtgttctt ttgtgggtag acaacacccc    70200
actaactatt aatcggacca catcgctcgg tagtgttgtt tcggcttcct cagccttgca    70260
cgttttctgt cgtcgtatca gtcacttacg gagaggtctg aaatcgccag ctgcagctct    70320
ctccgtctgc tgcttctctc cgttccgtga gttcttcttc ttggattcca tcatcttcag    70380
aggtgtgtga acacttaggg ttgttctgtc ttcccgacgc aggtgtccct ctggcatttg    70440
gaatgaccct ctttgtcccc gagaagcatc tttgctccgg aatctacctg gtctgacacg    70500
gaaataccac ttccgctttc tcttgattcg tcactcgtct tgtacgtttc atcgatgtgc    70560 tgcttttat ttcgagcgca tgcttttaa cagcacacag tctgctcttg cttttttgtc     70620
catcctgaga accctggcct tcggttaaga tgctctggct gttcacactt catgcgatca    70680
tggatttcat taggtttaag tccaaccctg tccatggcct agaaactcac tagaggcagc    70740
aagctgggtg atcatagggc tcaacctgtc ctggctcaag gatcgtcatc ctttccagtg    70800
tcatcaaaac tgttgtctcg tatattttga cttttcgtttg ttttattgt gggcgggaaa    70860 ctcagcgtgt atcactctgt cttcgtcaga agtagacatc aaagtcaccc cttttgcttt    70920
ggagccaagc tctcagagca cgtcccttct ctggaaggag ctgtgttctg atgtgacgtg    70980
tccccaggag ggactctctt caggtcccag ctcagaggct gcttcctcca ggaagccttc    71040
cttgatggtg acctcaagcc cccttcccca cgtggcctat tcgctcttcc ctgctgtgtg    71100
caattcagca gacatttccc gagtttgttc aggggaagaa tgagcaaggc agagtcttct    71160
ctatggatga gctcatcaga tttgtttttcc tccatcgcgc gaaaatgttt cgagcttgga    71220
taatgactgc ggttagggaa gagccacaca aacagacaat taggatgcgt tgggaggatg    71280
agcaagagga acacacatga caagtttcag atcattccag gtgcttgttt tcacgtctgc    71340
ctccctcccc tgagcgagct cagcggggtg tgcctcctgg tttctgctct tgggggccag    71400
gtgtgtgaca ggcgcattat agatggtgcc ttactgaact tagcagatcc gtgaggtcac    71460
agccaagggt ggatgccggg gtcagccctg ggtgtgcata ttggctctgt cgcttaacct    71520
gttggcactt cagcaggaaa agaggagctc agttgtggga agggctgagt ttgagatgcc    71580
tcatggggac cctaggggag acctcctgaa gggagcagaa gatgtggtgc agattcagga    71640
```

```
gagaggacat ggctagagag ggagattcgg agcccgcagc agtggacttg tagtgtcatg   71700
ggctggagat cccctagaaa gcaagtgtgg acagagggt ttgagaactg agtcctgggt    71760
gcacccacat ccagagggga ggtgatgaag agccagcgga cggctgagat gtggccatgg   71820
aggtgggagg acgctggcca gtgtggtgcg tggggagaga aagggagcc tttcacaagg    71880 aagagcgtgg atgttctgag tcccacccttt gctggtgggt cggcctgggt ggagcccggg  71940
agcctgcccc ccacttggtg aggtggagcc cgagccctga ggtcagcagc tgtctgggct   72000
gcgctgggtc ctgggagaag agccagcatt gcccaccctg cctcctgagc cctgtgcact   72060
ggaaaatctc tccagcattg gctgcacttg aactggctct gctaacatca aggtcttcct   72120
tttaattgac tgaattttttt gccctgtgca ttgcttttta ttggcttttg ccgggaaaga  72180
actctccagt ctattgagca agactggtgt caagaaatat gagggtcctg cgccgttacc   72240
gttctggagc aatgcccctg ggagagggcc cttcccgccg ggccagctct gggtcagacc   72300
caaagcaggc agcctcgcag tggggacctg agggttccag tgacaggtca gaggcctgtt   72360
cccttccctc tgggggcttc caggcccctg gtcttcatga gagagcagac tgcttcagcg   72420
ctgccacagg gctggagaga ggggcaggcg gctggacgga gcaacacctt cttactgaaa   72480
ttcagcctac ttttttcttga gttaattaat actccctgtg ctgcagccct ggggttactt   72540
cacagagttc tgaaaaagag cccgataatt tttgcagttt ccttgttgaa tcgtgcagtg   72600
acttcttcac cctctctcca caaagttcct tcttttttctt ttctgttttt ttggttttg   72660 ggggcatcct gcggcatatg gaagttcccg ggtcagggat cagatcggag ccacagccac   72720
agcaacgccg catcctcaac ccactgtgcc gggcccatg gaacctgcgt cccagcgctg    72780
gagacgctgc ccatcctgtt acaccacagc gggaatccag ttcgttcttt ttaaataatt   72840 acttttttatc caaggaaact gtgtttatga taaaaaaaaa taaagtacgg acaaccaagc  72900
ttaataagta aaatcaattc ctggcgtttc tgttgccagt ttataagact atatattctt   72960
acaatatgag atgcaagcac atatacaggt atgctgatat gcatcttata catccttcct   73020
acaagttgct tctcttagca acatgtcctg aatgtctttt tgtccctcag tggcgtatgc   73080
accatcgttc ttcttagtcc gcaattctca gatgatacag aatcaccttc tgtgaacaag   73140
ggctgtcttg ttggccgttc cggctgttta attttttcct ttcataaata aggctggatg   73200
aacatactat gtgttggggt gcttgtcgcc tttgttttgg gaggcagact cttagaagtg   73260
tggtttctgg gcccacagca tgtttggggg agcatctggg gagagggtgg tctgctccct   73320
gcccctgggg acaggaagtt tcctggcccc cgtttctcag cttgtaccca tcctgcctgt   73380
ggtagacgtg tgctctgggt cacgtgctca tttaggttaa ttctgtcatg tgggtagaag   73440
tgctgttcaa gttcatgcaa aagccctcat tttaagttat ttgtctggaa atgtcctttt   73500
ctggctttta agtagcaaaa cctagtaacc tgatgcctcg ggaagactga cagcccagga   73560
gttttctttc tttttttcttt tttttttttt ttttttttt ttgcttttttt agggctgaac   73620 ctgcagcata tggaagttcc caggctggag tccatttgga actgcagctg ccggcctaca   73680
tctcagccca cagcaatgcc agatccctga cccctgagc gagacccggg atcgaacccc    73740
atcctcatgg acactggtcg ggtttgtagc tgctgagcca tgatgggagc gccccaggag   73800
ctttcagtgt ggccctactg ggtgctcatg ttgtggtcac agaggctgga ttaataagca   73860
gaggagaatt ccttgctctg agcccagagg cttcatgcgg gatgaattct cattacctct   73920
ggaaacctct ggtggaagga tctttctcgc ttaagaacaa gtatgattag agtgtgtaag   73980
ggcaagcctg agacatttgc agtgggctta aggatgttct ttatcaaaag ctaaaaagat   74040
```

| | | | | |
|---|---|---|---|---|
| taaaccacac | ccagtgtagt | gttatggtga | cgctattaca | cgcgtccgaa aatggcaatc 74100 |
| cctctcgcca | cacatcagac | ccttgacatc | cacaagggat | ttgtccccg agaacttcga 74160 |
| gagccccacc | cactcccaaa | cgccggctta | gcttcccgtt | tccccagaa catgcgggag 74220 |
| agaccaactg | aacaatgcat | gtggctgctt | caagcttttt | atgactctat aaacacagca 74280 |
| ttctgatcgt | ttagaatgct | attaaaacaa | aatcaggctg | gagcccttgc tgaaatggtt 74340 |
| ttgggggtca | ctattttct | ctttctctat | aaaacacagc | aaacaggttc atatgagaaa 74400 |
| tccaagcctc | agttgagtcc | aactgtttgt | ttttttttt | ttttccggtc ttttgccat 74460 |
| ttcttgggcc | gctcccacag | catatggagg | ttcccaggct | aggggtcgaa tcggagcttg 74520 |
| tagccgctga | cctacgccag | agccacagca | acacgggatc | tgagccgcgt ctgcaaccta 74580 |
| caccacagct | cacggcaacg | ccggatggtt | aacccactga | gcaagggcag gggtcgaacc 74640 |
| cacaacctca | tggttcctgg | taggattcgt | taaccactgt | gccacgatgg gaactcccca 74700 |
| agtccaactg | ttaatatctt | tatggcaaat | tcctgctcaa | ctggcaggtt agagacatac 74760 |
| ttcttgctgt | gtattctgca | tcccacacaa | actgactttc | ttggggagtc gttttcttg 74820 |
| tgaaatgaag | tttgcctcca | cctgcgtgca | tggccctgtt | ggatggtggt ttgggcccca 74880 |
| agatttaaac | ccaaccccta | gtcaaccggc | aaaaccccac | cctgcaaaac cgcaaccgac 74940 |
| cttatacttt | ggagtttctc | gccagttgtc | atctgcactt | ggtggcgggg ttgtcggggg 75000 |
| gggggcacgt | cgggactccc | tcattcagaa | aactcagagc | catctcctgg caccctggag 75060 |
| aatgaccctc | ctctgcccgc | gaatgcagcc | aaccccatt | tctgctcaaa ccaatataag 75120 |
| catcgttcct | tgagatctta | cacgcgccct | gatgtcccctt | ggctgattct gggcgtgtgg 75180 |
| agagatgagg | tcaatgtcag | cctcaccata | ttccttgata | acctgcaatg tcagcactgt 75240 |
| tcctggacca | gcagaacaga | ctcttgttgg | actcaaaggc | tagtggagga gacgaatgat 75300 |
| caactcgcga | gggagaaaga | gaccagatga | ggggagaatt | cgtagggcgg gtgatggtga 75360 |
| ctggagaatc | gcttgggctg | ttgagaacag | ggttcaaggc | cagcggcggg gctcaggagg 75420 |
| tggccagccc | cggtggtgca | aacgagcag | ggtggcgggc | gatggaaaga caacggtgct 75480 |
| gagatcctga | gttgggatgt | tccaggcgcg | aaaggagacc | cgcatggcgg ggggtggggg 75540 |
| gcagtgggg | gaggcgggag | ggagagtcgg | gggagggcc | gctatgggta aagttaactg 75600 |
| taattttta | tctgaacgtg | gacacttttg | aaagaaaaat | ggacctattg atagtcaccc 75660 |
| tgggcaatag | gtgccaacca | ggtctgtccc | tggagacccc | agatgcataa ttgatccccc 75720 |
| acccgtggca | ggcgtggctg | cgggtggggg | gctttaggaa | ggcaggcgca ttgcccacca 75780 |
| ttcgctggag | gcaccacagc | tgctggacct | gccctggcg | ttcaggtcca gattctgtcc 75840 |
| tgcggcgggg | ggtgggggc | tacactgaca | gccagcgcct | cactgacacc tgttttctct 75900 |
| ctgcctctga | acggctctct | taggaaccct | gccgaggaaa | tgcaagaagg agctgctggc 75960 |
| agtgaagctg | aggaaccggc | ccagcaagca | ggaactagaa | gacagaaaca tcttccccag 76020 |
| gaggacggac | gaggagaggc | aggaaatccg | gcagcagatt | gaactgaagc tctccaagta 76080 |
| agtagcctgt | gtagacacgg | gcagaggctg | aggccagacc | cctctgccac cccacccttc 76140 |
| ccgccccgtg | acgtcccccg | cccgccatca | ccactgtcag | tgctggggac cagacggttc 76200 |
| ttcgctgtgg | gccccgtcca | tggcgctgtc | ggatgctggg | cagcctccct ggcctccgca 76260 |
| ccttatgtcc | cctgtgacag | cctacgctgt | cccagacat | ggctgaatgc ccctgggggc 76320 |
| cagtgggaaa | gcagtggaca | cagaaatctc | ataaggcctg | cgtttgggcc aagccccggg 76380 |

```
gctgccggtg ctgctggtct ctggccgcac ctggaggaac ggatctcccg ggcttggcgc    76440
tgctgctgtt tgggtgactc tgtgattggg tggcctgtgt gtggcgggat atttagcagc    76500
gtctctggcc tctaccctag agatgctcat ccccccgcc agctgtgaca accaagtgta     76560
tcgtaattgc caagtgtccc ctggggtggg ggtggacccg tggccttacc tccccgggtc    76620
ttagttttct catctataaa gcgctccggt cgttgtgagt ttgggggat tcggtaagga    76680 aggcacattg cagggctctg cgcacagta ggggtgcagg aaccccccagg ctggtggtg    76740 gctggggagg cccagggccg gtccttgcag cccctcctcc tgcctcggct cggctcggct    76800
cgcgtggtga gggtgcccac ggcccagacg gctgtcaagg tgcctgtggt tacctgtggc    76860
tttgaaccca gaacaggcct cccccccagac ctgggtcaga ctcgggcggg gcaggatttg    76920
agtgaatccc ctgatttcca cggggttggg gaccttctcc cttttggacct tcttagcccg    76980 atggcagtga gattgtcgga cccaccaagc acttatccgc ctgcatctgg tccctcaaca    77040
aaggctgatt ttactcgcat gaggagcggg cgccgaggcg ctgctggaga taggctgcgg    77100
ggagcgaggc tgaccgcgcc tgagagcgcg ggttccggga gagcaggctc agacctcttc    77160
tgtgcggctg gtacccactc tggggctcgg tacagatgag atgctggaac acaggcagca    77220
cagccggggg cagtaggaag ggcagggcca aggaagccag cacagtactg gggccccagc    77280
gcggaggtca ggccctgcca caggcgtgac ctctcagagc tcccctgcag aaaaggctgg    77340
ggacaagcat ttcctaaagg gatgtcccac ctagtgtgac gtccgccgtc agggtgaacg    77400
ggctctccat ggtcaaggga gttagggaaa ccatcgcaca agcggtttat ttgctgctgg    77460
acttgtcaga acctttaatg tgattaaacc cccatggttc tgcaagaggg ggtgtgggac    77520
tttgtcctgt aactgtgaga tctttcctcc tctggcacct cgggtacctt ggggcccctt    77580
tggggaggtg ccactgtagt cacaaaggtg tgggaggaac ctgagggtgc tgggaccgcc    77640
cactttgcag ccacgtgggg tgtgtcacac ctggcgttgg cccctggtcc ccactgcagc    77700 tggagggggtc cttggtgggc tgtgggggt ctgcatggac ccctgtggcc agacctcgcc    77760
cacactgggc aggatggtgc ttggatttct cagggagttg ctggtgcagt gcaaggagtg    77820
tgtgaccttg ggccagggga gatgacgggc agcatctcaa cgtcctaggg tgacgtgggg    77880
gactcggtgc caccaccaca atcaggacta tgatggctga tgcttcaagg tggccctgtc    77940
agcctctgcc tgtgagcaag gcccccagtt ctggtctgga ccacaggctg ccgtgatggc    78000
ttctggtcag ggtgggacag gaccccccgga gtgcagtccc agcactggct gacgactggt    78060
agcgcctgcc tctctctgga ccccccagatc cggcatgaaa agtgaagaac aggagaatca    78120
gtgcttcccc aacagtagtc actgcggagg taccaagaag aagctatagg gtctatagag    78180
ccccagggac ccaataacgt tcattttcct aagtcagcat tgccttgtgt tcagtcatcc    78240
aaatccatgg tcatcctggg tctgatgctc ttagtttttt gttgttgttg tttttaaat    78300 aaagaagaag agctggtctt cttgtctgtc cacctgggta ttctgaagct caaaggaaaa    78360
gccacaggga aaggggcat cgttaataaa gcttcctgcc tacctgctgg agtcatgatg    78420
gatggtctgt ttggatcctc tctgtcacct ccacctcttt gtaaacttcc cctttctttt    78480
cactggtaca caggccatct gctgaataac agtgacatgc caggacacta gggctcacaa    78540
catttgtgta tgcttcaggc atgccttgat ccaggtgctg tacatggcat tgactggaat    78600
ttctctattg ctgtttctgg actctgcttt gctctgtatg gattcactct cttgactgtc    78660
ccattccacg tccttgcctg ggaagctcca ggcttacata ggagcagcag aaagataagt    78720
actctttcct cctcaggaaa agctccagga tcgagtctga ttcaattgcc cggggggcagg    78780
```

| | |
|---|---|
| cacccagtcc ttaatcaatc accttggccc aagggatgc aagggctgt tggccaagtt | 78840 |
| tggatcacat gctggtccct aagcccatcc catggccaag gggatgtgct ggccctccag | 78900 |
| gcttagtgtc ttacggtatc cttgttgtca tcaggtggct ggcatatgcc ttccccagag | 78960 |
| gctgggttct ctgtctcttg tttctagtga gattgaagtt cctttttctt tttttttta | 79020 |
| atttttattt tgacttctag ggccgcacct gtggcttatg ggagttccct ggttaggggt | 79080 |
| cgaatcagag ctgcagctgc cagcctacac caccgccaca gcagcacagg atctgagcca | 79140 |
| catctgtgac ctacactgca gcttgcacca atgcaggatc cttaacccac tgagcaaggc | 79200 |
| cagggatcga acccgcaacc tcatggttcc tagctggatt tgttaaccac tgcgccacga | 79260 |
| cgggaactcc tcttttttctg cgtttatttc tttttggttt cttctgttct ttttatatac | 79320 |
| tttacctggt tcttctttct cgtgatgatt ttaggagttt actctgggaaa ttgcagcttc | 79380 |
| cagtcctttc cagtctgtgc gattcccctc tcctctgtct tctgggctca gtactgtcag | 79440 |
| gtgcttctgg ctttccttttg ctgtgcaagt ggtttcattg ttaagttcat caggttgtca | 79500 |
| atcagatact tcaggtgtcc ccagactttt cctgtgaaag accagagact gaatatttcc | 79560 |
| ggctctgggg actccactgc gtctgctatg accacacaac tctgttgttg ccctgacgca | 79620 |
| gccaaagcca acacgtggtg agtgggtaca gctgtgaaac catacgaaca cgagcagcgg | 79680 |
| cccaatggtg acaaaatttc acagccccga tgcgctatgg ttcacactat ttgttcgtgt | 79740 |
| tttaaaacat ctttccctgt ccagaagcca aaaaaaccc ttacttttac ctgcattact | 79800 |
| tttgcagtta tcttctaacc atgccggtcg agaatggttt tctatttgct aaacaaacca | 79860 |
| agttctcttt caaaatagaa tattgagtga actaagaaa aattaggaat tcccgttgtg | 79920 |
| gctcagcgga cacaaatctg gctagcatcc atgaggatgc aggtctgatc cctggcctcg | 79980 |
| ctcagtgagt taaaggatcc ggggtggccg tgagctgtgg tgtgtgtagg tcacaggctc | 80040 |
| aactcgaatc tggtaatgct gtggctgtgg tgtaggccgg cagctgcagc tcggatttga | 80100 |
| cccctagtct gggaacctcc atatgccgtg ggcgtggccc taaaatgaaa gaaaaacatt | 80160 |
| gtagtacatg tgattcaaga aaaacaaaat tatccccatg acgcttgata tcagacaact | 80220 |
| ctggggacca caccctgcct cccagggcag agggaggtgg gcgaaggtgg ggtgaccgga | 80280 |
| agccacggcc gagggtctcc cagggccccct catgaagagg ttcccagagc acagaccccct | 80340 |
| ggtctggatt tcctccatca ctcactgagt ctgtaactaa ttttaaaccc tgggctggaa | 80400 |
| cgtggtggct ccttggacgt gtgtcatcgt gttgaaaagc ggaaacgtat ccccagaatc | 80460 |
| aggcacggag agttccgtgg ttgggaaatc gcgtcccagg atggcagttt gtttccctgc | 80520 |
| agacgaggct taattggatc ctttgtcttt gctttgcctc ctttcagaga ttcttctgcc | 80580 |
| atcacttgct gaataattca gcctctggtt gccatggtga cgcaccatcc accgtatcct | 80640 |
| caaatgcagt tggcgttttt ggtttgttta ttttttttaat ctccagacct ttactgtttg | 80700 |
| tctttggggc gcctctaggg cttttctgcc gcagggggtca cagggtcccc tgagtctttg | 80760 |
| tgctggccct gcggattcat gtgccggtgg agtcagcgtg gcggactata gccccggtg | 80820 |
| actgtcgccg cctttctgta caggagccca actcacctttt accgcccgtg gagatgtacc | 80880 |
| tacagagtgt tactgaccta aggttctgtg cctggaaaat tactgaaaca ctcccaacct | 80940 |
| actgtgcgcc caccactcaa gggaaaccca taaggatgtc tgacagcttt cttcttgttg | 81000 |
| ttattaaggg tttcaagggt ccagcattat aattcagcat ctgagtgcac tgcaaaggga | 81060 |
| tcagatgaca gcttttactt ttaagtgcag agctcgggcg gtagcagtaa gttttgcttc | 81120 |

```
ctttcctttg tgtcatcttc acaggcaccg atagagtagg tgttgtcatt gtctctggtt    81180
atacggacga gaaaacgaag gcttgatgag acagggtaag gaacttgccc aggatcacac    81240
agctcacgga ctgggaatca ggccgcgggc ggtccccgag agcaccaggc ggggccgcag    81300
gtgcagggga tcctgggagg tggcctccgt gcctggcgta tctgagtctc tgctttgcat    81360
tttctcttct tggtgtggct tccatcaggg cgcagtcagg cctccggcca acactctggg    81420
cctcagagcg aaatacctca cgtctttaac cctgtagtta gggaaaacat ccagagaggg    81480
gccgtcggcc ggccacgggc tttggggaaa tgtagacggg cgggttcgaa tcccagcctt    81540
tccgtcacag ccctgtgggc ttgggccagc accgccacct ctgaatctcg ccctggcccg    81600
gacaccgtgc ttggcagcac cttcctccca gggccctttg gaaggttcca ggtcagtccc    81660
tgcacgacag gtagaagtgc atccccacag gaggtgctca gaggggcaga gcagctgctg    81720
tatggtccct tgtcacctga gcaggggcgc aggccgccca gcaggccagg ctaggtcagt    81780
gagctgcgcc tggagggcca aggagtgtaa gcatagctgt taatgatgat acgttgtgct    81840
tatccgtgac cgtggtgtca tctgcctgga gacagtggag ggatgcacga accttctatt    81900
aaatctccct tgggtgcccc ctgcccgggg acgacatcgt ggaagctgat taatgctcag    81960
cggtggtgtc ctccaggagc tgggagctgg catatgttaa atgatcctcg agctggtcct    82020
ttcgtacagg gtgttctgct gcatccagaa caggctgcca ccattcaggg ctccaggaaa    82080
acacaaattc ctagggggggg aaaaaaaaag gttgtgtgct gctgctccca tccccgtgc    82140
ttgctttgga atctgcagaa tcttgaggag aaggctcgat gcctctgagc atggcgtgga    82200
ggctgacatg ccttataagc acagggctgg ctggctggac cgagccttag tctggtactt    82260
tctttcagct gaagtcccag gaaaaccggg gccgagagca gggtctccgt tctgcggatg    82320
cagagttttg aaaaatacag aaaccttagt tggcctgggc tttgcaggaa aaaaaagtga    82380
ctcagttgct agaaaggaag ccactgcttt aggaagtttt gagccttcat tgcacagcgt    82440
ggaagattgc ctcataacag attccgataa ataattcgcc aatttcccta ttcccgacct    82500
gcagtgctgg gtaggagccc agcttatcct gggtggctgg aatccaacct tgtaggcatc    82560
atctaagagg gacagaaaag cgaagttatt aaaaatggtc gctgctaaca tttatttcat    82620
gccttctggg taccagcttc ctgctatgtg ctctgtgcat cttacctcct cggggctttt    82680
cgagagccct ccagggtgga tgctcttaac ggtggggccg ggggtagctg ctcatctgaa    82740
ccacaccact tcccacacct gagtgcccat ccagatcacc agggagcgtg aaaacacaga    82800
ttcccagacc acgcgccaat cccgtgaata ggaatctgta ttttaacaga acccttctct    82860
cctgtgtcac tgctgcctcc tgtccccttc ttcatgacct gtcttctgag cctcaggatc    82920
aaaacaaact atttctgtgg aacagatgcc acagaatagt tagcgtctta aggagaatgc    82980
acgtttggta gttaagtttg tttctgattt tgccttgccc accaggaagc tcagagccaa    83040
gtgtacctct acctgttgca gctgggttgt gtcatttggg ctgtgtgtct gtgtttgacc    83100
ttctgttgta cgaccttggc cttcatttcc tcaactcttt tctttttttg gaaagaggaa    83160
gtctcatatt tattgatcat gccacgtaat aattctttca cttacgttgc attccatagt    83220
gtagctctcc ggaagctctg gtagtattct ttttgtaaat tgaagtatag ttgatttacc    83280
acattgtgtt aattttcggt gtacagcctg gtgattctgt attttgcag atcatactcc    83340
attataggtt gttacaagat agtggggata attccctgtg ccacacagta ggtccttgca    83400
gtttatctgc tttatgtata tattagtgtg tatctgtgaa cccccaatt tgtctctgcc    83460
cttctccctc tcccccttg gtaaccacaa gtttgttttc tatgtctggg agtctgtttc    83520
```

```
tgctttgtaa atacagtcat ttctattatt ttttacttct tatttatttt tatttattac    83580
tattattatt attttgtctt tctaaggctg taccagcagc atatggaagt tcccaggcta    83640
ggagtcgaat tggggctgta gccaccggcc taccccacag ccacagcaat ggcagttctg    83700
agccgcatct gcgacctaca ccacagctca cagcaacacc ggatccttaa cccactgagc    83760
aaggctaggg accgaacctg cgtcctcacg gatactggtc agattcattg actgagccac    83820
gatgggaact tctgtattat tttctagatt ccacatataa gtggtatcat atagtgcttg    83880
tctttctctc tctgacttat ttcactaagc attaataatc tctagaagtt cccgtcgtgg    83940
agcagtggtt aacgaatccg actaggaacc atgaggttgc gggttcgatc tctgcccttg    84000
ctcagtgggt taaggatccg gcattgccgt gagctgtggt gtaggttgca gatgcggctc    84060
agatcccgcg ttgctgtggc tgtgatgtag gcgggtggct acagtctga ttggacccct    84120 agcctgggaa cctccatatg ccgtgagagc ggcccaagaa atggcaaaaa gacaaaaaaa    84180
ttaaaaaatt aaaaaatctc taggtccatc tacactgctg ccaatgtcag tacttcattc    84240
tttttatggc tgaataatac tccagagtgt gtgtgtgtgt gtgtgtgtgt ggacacatca    84300
catcttacgt cttctcaagc catttatctg ttgatggaca agtaggttgc ttcccagtct    84360
tgtgtcatgt atcttttga attggagttt ttgccacatg cccaggagta ggaatgctgg    84420
atcatatggt agttctcttt tttgttttt aagagacctc tgtactgttc atagtggctg    84480
caccaattta cattcccacc aacagagtag gagggtcccc ttttctccac gccctctcta    84540
atactgattg tttgtggact tttaattaat ggccattcgg actggtgtga ggtgatacct    84600
cattgtggtt ttgatttgcg tttctctaaa aattagcagt gttcgagagt tcctgccgtg    84660
gctcagtggt aacgaacccg actagcatcc atgagaacac agatttgatc cctggcctca    84720
ctcagtgggt tccggacctg gtattgccgt gagctgtggt ataggttgca gatgtggctt    84780
ggatctggca tggccgtggc tgtggtgtag accagcagct gcagctccaa tttgacccct    84840
agcctaggaa cctccatatg ccgtgggcat ggtgctcaaa agaccaacaa aaatcgaata    84900
aaaacagcaa catcaagcat cttctcatgt gcctgttgcc catctgcacg tcgtctttgg    84960
agaaagtcta ttgacgtctt ccgcccattt ttggttggg ttgtttgatt tttttgatat    85020
tgagttgtat gagctgttgg tatagtttgg gtgttaactc cctgtcagcc gtatcatttg    85080
caaatatttc ttccagttct gtgtgttgtc ttctcatttt gttgatggtt tccttgctgt    85140
tgccaacgat tttaattagg tcccatttgt ttctttctgc ctttattcct tttgccttag    85200
gagacagacc caagaaaata gtgctatgac gtatatctaa gagggttctg cttacattct    85260
cttctaggag ttttatggtt tcaggtctta aaattaggcc tttacaccat tttgagttta    85320
tttttgtata cgtccagtga gggagtgttc taatctcctt aacttacaag tggctgtcca    85380
gttttcccag caccacttgc tgaaaatgct cttttcccta ttgtgtattc ttgcctcctt    85440
tgtcatagat taattgactt taggggtca gtttgtttct gggctctcac ttctattcca    85500
ttgacctatg tgccagtgcc atactggttc tattactgta gctttgtagt atagtctgaa    85560
gtctagcagg ttatgcctcc aggttggttc tttttgcttg ggattgcttt aatttgttca    85620
actcttaatt ttgtctttgc aatacatcat ttcaaatcca tttctagatg ttaactttaa    85680
aaatgtgagt agccattcct gtggtggctc agcaggttaa gaacccgact ggcatccctg    85740
aagatgcggg ttgatccttg gtctcactca gtggatgaag gatccggcat tgccgtgagc    85800
tgtggtgtag gtggcagatg caacctggat ctggcattgc tgtggctgta atgtaggcag    85860
```

```
ctccgatttg accectagec tgggaacttt catatgetgt gggtgtggac ctaaaaagac   85920
aaaaaaaaaa tgtgagtaaa tatatatata tatatatttt aatggagccc ctcttcacac   85980
acctgagega tttcgccacc tcacatcatg tcagaagggc tttctctgct tccacgaagt   86040
atttgaatgt tggtttttaa cagtggcctg gtgtgtaggg agtggacaga cattctatag   86100
ctttgcttct ccctccctca atcagcagac ttttagtcct gctgcaaaat ctttactttt   86160
aaaatcaaac tacatgcaat gcttatttcc atgcatcagt gggttttttc ctttctgtgg   86220
attatttata tgagccacag ttccaaaatg caaaaagaa gaggaagaaa aatgcactga    86280
attagacaat gtcatcattc aagaatgaag cccagtgttc agcagaaacc ggcagatcac   86340
tgggcaaaaa cagcctggaa ttcctggtgc aagaggaagg gggcgaaatt tctaaacaaa   86400
tatatgaaaa taattcaact tcactggtaa gtgcaggtat taagaattca tagtaacagg   86460
agttcccgtt gtggctcagc agtaacgaac ctgactggta tccatgagga tgcaggttcg   86520
atccctggcc tccctcagtg ggttaaggat ccggtgttgc cgtgagctgt ggtataaggc   86580
gcagatgtgg ctcagattcc atgtggctgt ggcgtaggcc ggcagctgta tctccagtga   86640
gaccectage ctgggaccet ccgtatgcta tgggtgcggc cctaaaaaga cagaaagaaa   86700
aaaaagaatt cgtagtaaca gggaactttt catcccccat taaaaatgac aataaaactt   86760
ttaattatta attttccctt atacgtcact aatataaata ctgataatgg actgaaaaca   86820
ccctgccctg gcgggtggtg ctttacctgc catcctctgc tggcagccag gtgactcaaa   86880
ataatgggac agaggaagag ccaggatgac agtctgcaca gattaaccaa cccttttttg   86940
cgcttctggg agttatgcta tggaatttag aggaaggtca gtgttgtgat ggtaacacag   87000
agcccagcgg tggactttgc tcgtgcacgg tcggcagctt ctgcttggcg gagggggtg    87060
gcggccaggc cacttgggga acagacacgg atgcccctgt taactttgcg agcctccccg   87120
gttctttgct ttcgggacct cgtggagaga tgggaagtcc tgtcagtatc agatggtacc   87180
tgggctgctt ctgcccggag atgctgttct cgacacatca cacccaccca gccgatgagg   87240
tcgacagcct ttcacccaat tggaggtgag gccgtgggaa ccactgcaaa tgccttggcg   87300
caaggcaccc actgctgagt gggtcgggat ccagcactgc cctggagcag ggtccccgga   87360
gcaggttgat ctgggcctgg ccgggctgcg tggccctggg aaggtcctta actgcctgtc   87420
tcctcccagc tcccctgggg gggcaccttt gagcacctgc ccctctgagc ctctgccagt   87480
ggccccagtg ctgtcgccca ctcgaccttt gcctgtgccc cccatcact catggcctcg    87540
tggggacaag gccttgctgt ggtggggtct cagccctgcg acccctttag tgtctgtggg   87600
gggaagggtc aggacacagc gtgacagcca agagcctcca tccctggctg ggctgtcggt   87660
ggggcaggtc tgttttgagt cctgcggatg gaatatgctg agactgtttc cggagaagct   87720
gtcactcggg ctgtgaaggg gacgtggcgc tgggctagct gggggtgggt ttggtccctc   87780
tgggcctttg ttctgcggca catttgtacc caaacctgtg cagacaatgg ctctcacttt   87840
tcagaagtgt cctttggcca agttcaggcc agttgaggtg gggagccagc ttccgacgcc   87900
aggtttcgtg acactgtgaa ttgcagcagt gaatcgtgaa ggttgaccct gacctctggc   87960
ggggacccag ctgctcgtgt ctccagcctg ttgctgcgtt ggtcagggac ggtcctcctc   88020
cccgctttgc agaggagggg gccgggcggt gaagcggggt cccagcgtct gttaggagcc   88080
tccagaccat gggttccagg gccccccgc tccctgccg aggagcatcc tgtgctcatc     88140
ttgcacacag gggcagaggg cacatgatga gctacagccc aatctgatgt ctttctttct   88200
ttctttttag attataggac ttcggttgac tcagattgtt gtgttggttt caggtgcaca   88260
```

```
gcaaagtgaa tcagttatat acacccatgg atccattctt ttttcagatt ctttccccac    88320
attggttatt acagaatatt gaagagagtt ccctgtgctg tacagcaggt cctcattggt    88380
tacctatttt atatattgta gcatgtaaat cgttaatccc aaactcctac tttagccctg    88440
tccctgtgtt cccctttggt aagcaaaagt ttgctttcga atctgtgag tctgtttctg     88500 tttggtaaat aagctctttt gtatcatttt taaaattaga tcccacatat aggtgatatc    88560
atgtggtgtt tgtctttctg tgactgatgg acttcactta gtatgagagt ctctagttcc    88620
atccaggttg ctgcaaatgg cattattgtg ttcttttta tggctgagta gtattccatt     88680
gggtatatgt accacatctt cttcatcgac tcctctgtca atggacattt cagttgctcc    88740
atgtcttggc tcttgtgaat agtgctgaaa ggagcatcgg ggcgtcagtc cagtttctgg    88800
tgcttcagaa ctaactagaa ggtaacctct acatccttca ctggttcttt gtctgctgca    88860
gcatgggcag ccctagagcc ttccctctgt gttctgcatc ttgtggggcc ttgtaagcgc    88920
agcacggccc ccaccccac ccccgatgcc cacgttgcag cctctgagga cgcagcacat     88980 ggcacccta aatcagggct ggcacagctg ctgccgactg tgctcgggta ataacagcta     89040
ttaccgccac ccttagaatt ccttggagat actgcctcct tcctacccca cgtcttgtgc    89100
acggttgctg tgacacaagg caatgctgta aacgactttc cgggaaggtc gtgactgcag    89160
gagagcagcc ggcttcctct gtgcccctg ggggcacagc ccccagtcac agacttccct     89220
tcctgtggga gcacaggggc tggggttgg ggagtggcgg tgcatctaga tcacccactg     89280
tgcctgataa aatacgcacc aaagtaaata caaaccagac gcagaagtgg agggctcggg    89340
agggagggtt aatccagcag gagggaggcc gagctggggg tgcaggccgc acaggggtg     89400 ccatggagca cggtttggac ggctggcctc acaggtggca gtgcaggtgt caggctggag    89460
tgcaaggatg tcccagacag aggggccaca agagcctacc acggcctgcc ctgcattgcc    89520
cctcagagaa caaggcgggg ctgagaaggg cggcctggga ggcgggtggg ctccgcaggg    89580
ccgggtgctg ggctctccct gctctccatc cgcactcagc tgcctctggt cattcagggc    89640
tcagctcgtg tcacctcggc agaagggcct tcctcgatgc ccctgtcctc cccaggggcc    89700
tggcctcaca ccagctccct ctgcatctcg tcatcccctg ctgtctgcgt gacactttct    89760
gctgcctgag gtcacccttt tggatcccctt tctgtgcctc gtcagggtct gtctgctgct    89820
agagcctgcc tgtgtccttc atccgatgtg ccctggtgcc gtttattccc attttttgagc   89880 agccgcttga gaaataggcc taaatggtga atagacatgt ctggcctcta ctgagaagca    89940
gcgagggtcc ctggaggggt catgcgcagg ggcgtggcag agggggggcca cccggcctgc    90000 acgtgggggc tcaggtgggg acctgctggg ggcaggtgac agtggacttg gaagtgctgc    90060
aggaaaggca tgtcatcagg tggccctgag gctggagagg gtggactcgg ccgctggggg    90120
aggacgagga gcaggacccc cgggtgagga cttgaggagg tggcctggtc gggcggagcc    90180
ggtatgctgg gcacagggga gggggctcag gaggaaggga gggaggcgtg gcggaaagct    90240
tctgtgtcca gacccttgtt ggcgtgtctc tggcacatcc acgactctgg cgccgttagc    90300
ggcggtccga tccacaaacg gggcgcgcgt cgactgcgtg gaggatggca gatacaggca    90360
gtgccggctc aagaccaaag gcagtgaaga cccagcatgg agttttacgg ggtcctgtgg    90420
gtccttttat catgggggtca tttcctaccc cagtgttctc cctcggacct cacatcacag    90480
ctgcagaagg agacggggtg gccggctgtt ttcttggcga cagagcaggt ttaataagcc    90540
ccgtccatct aaggaaacag ggcagcgtta aatgcaaccc cccggaggac gtgagatcca    90600
```

```
cttttctcgg ttctgcaagc ccgcagggtt caagctgtgg gacgttgttg atgctgggct   90660
ggcccatcag gggccaggct tctgtttagg acaagggaca ggctgagacc tttctcacat   90720
gctgaggagg agccgggcca gggctccccc acttaggggg tggagtctcg cagccgggct   90780
ggggctgcag tccgtggggc ccagctggac agagtcaggc cgggtctgcg gagagaggct   90840
cgtggttact gaacagccat ccatgaggaa ggcacacgct gttctcccgg cctcagcccg   90900
gctgcacgac gagaaccctc agagggctga actcaatgtc ctggtacgtg aaggtacctt   90960
gtcctgctca gtctctgaag tgaccagtgg ggcaacttcc agagggatgt tcagacagta   91020
gacggaagaa ccaagatgag taatgagagg acgaataact cattatgccc gagatgatct   91080
tgaacagaaa actaatagca gggcccctgc ggcaggaaga agcacagctg tgctcgaggc   91140
gggaggtgcg ggtgtaggta taacagcctc tcactttaca gcgaaccctc agtctgcaaa   91200
gtggatggtt acgcctgtga ttgtgcacct ttggggactg ggaatttaag aatttgatgg   91260
aagccttaat aaaactgggt ataataatat ctcccatgat ttctggaatt ttgccacttg   91320
tctagtgcag tctgcacgtg taaggactgg tggctctccc ttcctgagtg gtgggtctga   91380 caccteccgt tttgcatgcg aggaaactga ggctcgggat tgctggtggc cagtgagtag   91440
ctgggcaagg acgtgaactg ccgagctcag agtcattctc tcagtaccca ctgcctgagg   91500
tagcctgctc tgtaactcct tgaggctggt ccggttcaga accactgaat tgtttgtatg   91560
accctccacc tgtgcagtag ttgttccttg aaggaaggat cttacttgtt cagttttatc   91620
tgcagtgccc accacagtgc ctggtgcaag gtaggcgccc agctaacaac tgctgaatgg   91680
atgggttact tggatgaata gatggagatt gagagatggg tggttgggag gttagttaga   91740
tggatgggtt ggcagatgga gaggtgggta gatggacagt taagtggttg caatgttgga   91800
tggatgggtg gatggatatg tgggtgggtg gatgggtggg tagatggaag gatgtgtgga   91860
tggttggatg gaaggacgga tggatagatg gatgatgtgt ggatgtacag atggatgtgg   91920
ggatagacag atggatgggt ggatggatgg aagaatggat gtgtgatgaa tggatatata   91980
ggtggatgga taggtggatg gatggatgtg tggatggatg gatagatgga tgggtgggtg   92040
gatggataga tggatgggtg ggtggatgga tggatagatg gatgggtggg tggatggatg   92100
gatagatgga tgggtgggtg gatggatggg tggatggatg ggtgggtgga tggatagatg   92160
gatgggtggg tggatgaatg gatagatgga tgggtgagtg gatggaagga tgtgtggatg   92220
gttggatgga aggacggatg gatagatgga tgatgtgtgg atgtacagat ggatgtgggg   92280
atagacagat ggatgggtgg atggatgaat gaatggatgt gtgatgaatg gatatatagg   92340
tggatggata ggtggatgga tggatgtgtg gatggatgga tagatggatg ggtggtggga   92400
tggatggata gatggatggg tgggtggatg gatggataga tggatgggtg ggtggatgga   92460
tggatagatg gtggatggga tgggtgggtg gatggatggg tggtggatg gatggatgga   92520 tggatggatg ggtgggtgga tggatgggtg gatggatggg tggtggatg gatagatgga   92580 tgggtgggtg gatgaatgga tagatggatg cgtgggtgga tggatagatg gatgggtggg   92640
tggatgaatg gatagatgga tgggtggatg gatggatgga tggatggatg ggtgggtgga   92700
tggatggatg gatggatggg tgggtggatg gatagatgga tgggtgggtg gatgaatgga   92760
tagatggatg ggtgggtgga tggatagatg gatgggtggg tggatgaatg gatagatgga   92820
tgggtgggtg gatggataga tggatgggtg ggtggatgaa tggatagatg gatgggtggg   92880
tggatggata gatggatggg tgggtggatg gatagatgga tgggtgggtg gatggatgga   92940
tagatggatg ggtgggtgga tggatagatg gatgggtggg tggatgaatg gatagatgga   93000
```

```
tgggtgggtg datggataga tggatgggtg ggtggatgga tagatggatg ggtgggtgga    93060
tggatggatg gatgggtggg tggatggatg gatgggcagg cagatgatta gatgatcaca    93120
tagttaaatg aataggtaga tgggtatata gcgttggata aatggatggt tatatgaaca    93180
ccacggtaca caaggcagag ggtagggtac agtcagtaag aatgtagtta aacaaagtag    93240
atgtgctttg aataaatgtc ttcctgtggg tagtagagtc ttaagatacc tgatttatcc    93300
accaatttca ggtagatctt tcaaggcgta tttgtgggta atgtgaactt acagatctat    93360
ggtgagtgtt gctaatttgg gggttttttct gtctctggga tgcatctagg ccagggactg    93420
aatgttcctc ctgttgcatc atggctctct ggccagctgc ccagacgggg ctacctccag    93480
gctacaggtc ccctggctct tgggaggggg taccgcccaa ctcccccttc tccatccggg    93540
gaaggctggt ggatgttgaa gctcccaaag cttcctgagc actttcgtgg ggagaggaga    93600
ggagctctcc ctggatggcg atggctccag aaggacactg gcctgtcctc acagctcatt    93660
tccgagtagg actcacaagc tcaaatgctc tgagagtgac ttggggcagg tgggaactgt    93720
ggcaggttgg ggcatgcacg tccttgcggc aggggccacc tgccgttcag caactgtggg    93780
tgtcacctct gcagatgcca gatccgtgtg ggcagggttt tctaacagaa actggaaatg    93840
tttattttga tgccaaattt ccttcattta aatgttggaa gcctactcac attttacaaa    93900
cagaaagggt gaacccccata aaacatgttt gtgggctgta tttggcctgg gggggtggt    93960 caccatttgt cacctgtgat acaacaaagt cacttgtttt atgagaagct caatcttgtc    94020
tgtgctgaga acgggggactt ttgactgcgg aatgaacgta gggaaaacaa tgggtcagac    94080
tctgaatcga tggtccccag tggaaacatc acgacccagg actgggacca tcagtgccct    94140
gtgcagcccg gtgcatcctt tctcttcctc tggcctctga ggtgctgctc aggaagagct    94200
tgtgtgtgac ccccgccccct ggctctgacc ttgatccaag gaagcatctc tgtggcggtg    94260
aaagtgcgga ctctgggcag ggaaccttgg ttcctgtccc agctctgctg ttttccagct    94320
gtgtgaccac aggcaggtga cctccctgac atgtgcctca cggtcctctt ctgtagaatg    94380
ggggtaatta caacagagcc catctcctag ggctgcggaa aggacgcaaa gagacaagac    94440
acataaatgc ctagaattgt gcccggcagg gaggaagcac gagggaataa aacaaataca    94500
tgtgagatct gtgggggcgg gaaatttgtt ccaatagttt gagatagaat atccacacca    94560
tacgattcac cctttcaaag tatgtgatcc agggctctag tttatccatg gagtcgtgcg    94620
tccatcacta cagtctgttt tgggacattt ttgtcactcc caaaggagc cgctcacccc    94680 tttgccgtat ctctgatccc tagcacctgg gccacatggt cactcagtaa ttctccagct    94740
cctgttgcaa ggacggaggg aggtaccctg tgcaaagagc cacggccaca gtttagcctc    94800
atcatccttt tcttcatctt tgtcgtcacc gacgtgaaca tctttctgag catcttcatc    94860
actgtcaccg tcttcgtcaa catcttctct gtccttctct tctttgtctc tgtccgtctg    94920
tcttcttcat tgttgtcctt agttccttcg ttatcttctt tgccgtcgtc ttggcaacgt    94980
cttcatccat gtctttgtgg tcatcaccat tatcttcgcg gtccctcttt gatacaaagt    95040
gagcacttag gagacactgg ctcttcactc cgtggggacc agcggcccca cttccaggac    95100
aatgacgccc acgtctgacg ttgggtcagg agcttcaggc tgattcctgc ctccaggaga    95160
agggagcctc caaagaggtg gcaggttgag ggtggggtgg ggccaggacc tttctgaccc    95220
tgcaggtccg gctcaggacc cgcccagtgc agtgacggtt gggtaccagc gacccctcag    95280
tggggatgtg caggacacag ctctctacaa ccctcttgag aggattttga gatcccagga    95340
```

```
gcagggagtc tttgtgttta gcggttcctc tgctttcttg cctttttttgg tgaagcagat    95400 gtgcctggct gactcccact ggcctccagg gagtccaggg catcttcctg gggctttcag    95460
tctccctctg tttagaagcc tcggagcaca ctgaggtccg tctggtctat cagataaccc    95520
cgcgcccggg acctcagctg ggtacagccc cctgctccac tgcggagtg agtgccttga     95580 gtactgcgta gcctccaagg tcaagaggca tctggggctt atttagctga ggtttcaagg    95640
atccgttgct aaacacaaaa gggatccgtg gggcggggct gtgagcaggc cctgtggggt    95700
ctgtggggag ggcaagacaa gaccccgacc ctggaggag gggctcggtg gccctgcgag     95760
gctgcggagg tgggcgaggc agctccagcg gtaggtcttg ctgcctgctt ttagatggaa    95820
gtacctgggc aacagaaaac agcgcttcca agtcaggaaa agtttgccaa aatcggagcc    95880
ttagaggaca tgaatataag tcttggtcct tgatggagag cgtgctgtgc agaggggag     95940 gggcagtggg gggggagggc tccgtgaccc ccccgtgggt agtgctcagg cccctcgctg    96000
gtgtctattg aagtggcgca agctcctggc cttcccgtcc ttcgtggggt cggctgctct    96060
ttgtttctct tggttacttg ggagtctgtc aaggaaagta cagcatgttt tgtgagaaaa    96120
ggcaaaacaa caaaccccct tcggtaccaa taaaacacag atcccatgca caggggagca    96180
ggtggcctgg cagatttgag ctcacctggc tgagggaacc caggcacatg gccccatctg    96240
cctgagctgt gaagtgggta tgtgacacct gccagcttta cccagagtca gggcttttcc    96300
cctctgagtg agtagttgtc atagcagtag cgctgtggta gcaaacattt attaaatctg    96360
tgttgtgtgc caaggactgc gctttgtgta tttgccgaag cccaagatgt aaatgctatt    96420
attaggtgta tttcataggc tacagaaatg gtggctcaga gaggtcaggc aagatgttca    96480
aagtcataca actagtatgt catggagcta agatttgacc caggcaggcc ggttctggac    96540
actgggccta aaggcatcct gctttgttga atggttgcag acatacaagc ctggcttggt    96600
tattccacag tcatcgagga cccaggcttc tttctatctt cctgctcagc tatcctcacg    96660
ttggcattta ccctctatgg tcccaggtgg ctgcgggagc acctgacatc acattccagt    96720
tccgagggtg cacagatccc agctgagtca gctcttccaa aagacccttc tcagaggctt    96780
tcagcacacc tctccctaca gctccttggt cagaacctct tcatgtggcc acgcttcgtt    96840
agaaaagagg ctttcctgaa cagaatccac tttctgatgc taccaaagaa gagagagtgg    96900
aggattgggt aggaaaccag cagtctctgc tacgtaggtg ctcaagttaa ttttgtgttg    96960
agttagcctg aagcaagaaa ggaaggaagg agcaaacaga tggacaagtg gaagaaaaac    97020
cctgtgtctg tgagatgaga gccagcgatt ccctgggcag tctggtccga gaagcctgtg    97080
tggagccctg ataggctctg ggaggtttat aagtgcctca tgttcctgtc cagtgctggg    97140
cccagggact tgggcaggtg gcgggaagct gggaaagggg aggagggggac agagctgcaa    97200 ggggcccctg gagtgatgag gacagacaca gctgtcccctt cctcagtggt accttcacct    97260
caggacggtg cagttcaagg acagacactt cctgggcaat ctctgtgtgc cacctgcagc    97320
ccagggcact gggggtggag gaaggaacca ggtggatgca ggagctgcct tcaggaccgg    97380
gggatggggg aaggtcacct aagagagggt gtgatacctg tggcctgggg gaggggatg     97440 caggaagtag cacaccttgg tgcagagggc gctatccgtc cagcgtcccc cttcccaccc    97500
ccaggcagct cctcacctcc cctgtctggg ccggcgaggc gcaagctccc tggtagcact    97560
gatggagttc cggggcctgt ggaaattatt tggtgtgtag gctggtgccc tatcctttta    97620
aaaatcgagg cagtgttaag tggaatttgt gcttctcttg gccctggtat ttccttgccc    97680
agtatttgct tgtttcctgg aggagcccgg gagcccccaa gccctgggga agcgacactg    97740
```

```
gggaagtgtc agaggaggga ggggatggcc agggcctggc acgcagcagg tgctccatgt    97800
ttggggacca gaaatcaaat catcccgatg ccaggggcca ggcaatggga agcattatat    97860
attactttca ttttccaaat ctgaataagg gactgattta cgtgcaaaaa caaatggtgt    97920
gtctccctcc caccctgtct cggcccagag gctgccgctg gccgtgggct gtttgcagcc    97980
actcagaggc ggtgttacac aagcagccat aagcacaccg gtaactagtg tgctcggggg    98040
aggtgacgcc cgtgagggag gggcctggag tcccctcctc aagggcaac aacaaagcca    98100 gtcagaagaa gaaattaaaa tgcgatttgt tcgagctcag aacacttaat tttaacctgt    98160
cattgagatg tgccttaact tgggcttctt ctgctgggaa accaaagact tttccctgca    98220
gaaggaccaa cagttagtgt tcttccttgc ttgagacaaa cgctggttct ttgcagagga    98280
gtgagaagga gacacttggc agcagtcgcg cacagagtcc ttccagagac ggagccctgc    98340
tgtctacacg ctcctctccc acactcacgc ggacagctgg gttccaacat ctagccttta    98400
ctgccttcaa agcagtccat ttggttattg tagaaatatg ttttctttt ccatccacat     98460 tgagtcattc catccctgtg tgtaaagtct gattagatca cctgatacag gcacaggtcc    98520
acctggcgca cgtagctggg gaagaaggga cccacgcccg acaggtgcac aggtcaccac    98580
gggaacagat ggcacggggc ggggggctgcc ttgccacgcg tgcgtgctcc gcgggtctgg   98640
ttcgccagaa ggaccgggag ggtcagttaa tctggggtca ggtaagtgga ggtaacagga    98700
cagcactcct cccacgggac tgtcatcctc atttagggag gaggctgcgt ctgagacgac    98760
agcggtccag agccgggggg aggtgtctct caagggattt attgcaaggt gttggtggcg    98820
gtggctgtgg ggctggctat gcaggtctgg catcgatggg acaggccgtt aggaagggct    98880
ggaactccct ggtagggacc gaggctgctg tccacaggca gaagtgcctc ttcattcagg    98940
gagccccagc cctgctcgtg aggtccttct cctgattgga ccaggccac cagaccattg     99000 gtgacaatgc cccacactta aagtcacctg gttatggatg ttaatcacat ccacctttac    99060
cccagtacct agatgagtga ttgattgaag aacagggat gaggcctctc cgggtggaca     99120
gataacacaa gatccggtgc tggaggtgaa ggataggcct ctctttccag cttgaggtct    99180
tcccagagga ggtgaggtat ctgcccagga gcccagggct taggccagct gttcctgtgg    99240
cccctggtga gcctggggag cttcgtgtgt cctgtcactg tgaccggatg tctgtgtttt    99300
tgggccaggc cccggtgtcc tgcagtcaag gacacctcct gagcagggaa gacttgcccc    99360
gctccaccca ctcagctttc tgtgtcccct ggacactcat acagaaggat ccagagccgt    99420
gggaaggacc tgaacctgca tcctgggtgt acagcggaca cgccgagggg tttggtggag    99480
tttggtcaca gtctgaattc tccccaaatg cacgtgccgg ggaaattgat ggaaatggac    99540
gtgccttgtt tcattcagaa ctttaccaag aaccacgcat tttgggaaac agctcccgtg    99600
tggctgcatt gctagtggtg tgcgaatcac cggaaggacc ctggtccctc cgtgctggtg    99660
gctgaggtca tcgtggtgac cgtgtggacg cctttgcccc gtcgcctgat gtgctctggt    99720
ctgaacaccc gtgtgtggac tgtgtgttat tgggttaaaa cgccctgcct tcctcctgcg    99780
cgttacagct gagcatcaca ttgactttt ttttttttt tttgtctttt tgccattcct      99840
tgggccgctc ccgtggcata tggaggttcc caggctaggg gtccaatcgg agctgtagcc    99900
accggcctac gccagagcca cagcaacgcg ggatccgagc cgcgtctgcg acctacacca    99960
cagctcacgg caatgccgga tccttaaccc actgagcaag ggcagggacc gaacccgcaa   100020
cctcatggtt cctagttgga attgttaacc actgcgcccg acgggaactc ccacattggc   100080
```

```
tttaaaact  tgtgcacgtg  ggtgggttgc  agtaaaggga  cgggatgcaa  tactcgatgt  100140
aagggggtgt  aggtggctgt  gcccgagggg  gccggtgtaa  gcagctcggt  gtggggggcca  100200
cggggcacag  agttggggga  tgggtgtcca  cggactcgct  ggcctcgcgg  ccctggactt  100260
tgtcctgagt  tcactgggga  tcccagattc  gagctctttg  tgggactggg  gatatgtttc  100320
agaaggtcca  cacgtggctg  tgggggcagc  aggatgccga  gggcccctgg  aggctggtgg  100380
cctgggtcag  gcggtgggggg  gatggggagg  cagatggaca  agtgaggtgt  cgacgcctgg  100440
gaccccacag  acttggagac  tcctcggggc  tgggagtggg  cagtgggagg  ggcagagggt  100500
ggttctgggg  tgagtgtgtg  gacgacggcc  agcctctgag  gcggaccctg  gacgatgagg  100560
aaggggacga  ggtggggatg  gggtgcgagg  cagctttgga  cgagcacatc  ttgagtgccg  100620
gggtcacaag  atgctgtgac  gggggcggct  gcacttcccc  aggcaaggcc  tccacgggct  100680
gatcattcgt  cccagggcgg  aggcggctga  ggctgggggc  ggctgctgtt  ccctgacgtg  100740
gacaagctct  gctcttggag  cccccggccc  atctctgggc  tttccatggc  tttgtctccg  100800
catcacatcc  tggagaggcc  ccctcccttc  cctgaccctc  tctcccaggg  ccgcccactt  100860
gtccctggtg  gcccctgcc   ctgacagcgc  ccatcgggtc  agaggagcca  ccctctgttc  100920
acgattcgcg  agcccacgc   ccagcacagt  ctggcacagt  ctcccctgat  gatgggagga  100980
cgttgccccg  ctgggggaat  ccctgcccgg  cggggactcc  cgccttcctt  ggtgactcaa  101040
ggctggcggt  ggagccggat  cggtgttccc  aggaaggagc  tcccaaaata  gccggcgtcc  101100
ccgtgggcgg  ggagctgtct  gttctgcagc  tgcggcttct  ctctccagga  aggcgttttg  101160
ccttgtttga  cgggattgct  tctcagctca  gttcttgctt  gatgctgagt  tgatttgaga  101220
tgtttattgg  agccccgcgg  ggatgaggga  gacctggggc  ccatgagccg  aggggacag   101280
agctggctgc  ggatctggag  ccagacaggc  cattcctccc  gtgtcccccgg  aattacctgc  101340
agcctcggag  ccctaccagg  tctgcagtcc  tgagaggcgg  agagggtgt   gcaaagggcg  101400
attcagaaac  gggccatatg  ccaggcacct  agcttggcac  ttcttgggcc  atgtcgccat  101460
cctcacggca  agcccaagag  gtgacagttg  tcatcagccc  atttggggag  agacaggaga  101520
aatacaggga  gtaacagggt  cgggatggag  ggtcttgagt  gacgggccaa  gatgtgggcc  101580
cccgccccat  ggtgttggcc  tcgccaccaa  agcacttttc  ggggcaaggt  gagccacctg  101640
gagcccagge  tcaggaggcc  tggggtgggg  gggtgaac   aggggacaa   gccttggcca  101700
aggtgggagg  agtcacctgg  aggggtgact  catggagggt  gtcgtccccc  ccgcccccac  101760
gcccccacc   atagccggct  tccagggtga  ggtgggggat  gggaagcatc  ctcacagggt  101820
gagtcccctg  tgctggcagg  tcctccccac  ctgaggtgag  ggctgggccc  tgcgcagact  101880
ccaagcagct  gatggggaga  ggtgagctca  cagaggtcaa  gggtcacatg  gtgagacggg  101940
gcttccctgg  ttgatcagga  actgtttggc  aaggacctcg  gtttgggggct  ttcgttggtt  102000
ttctaactcc  ctgtgctcat  cagtcgacgg  cagggacgga  ggccgggggtc  aggggaggc   102060
ttagcgagtc  ggggtccggg  gagagcctgg  gctttcgggc  tgatcgctgg  cctctgctct  102120
ccactgcact  gccaccttag  agagctttcg  cgatgaagag  agaaccatgg  caagagtgct  102180
gaagctggag  ctttgcgtgg  cggcccatga  gatgggagtt  tgcaattccc  gcgacacagt  102240
gtcccaccta  gtggatggaa  ggtggctgga  cagcaaggac  agaagaaagt  cactgaaaac  102300
aggggtcacc  aggctcgtga  aagccttgtg  gcctgtggta  ctggggaggg  ggtgcctggt  102360
ggcactgttc  ccagcaccct  cctggcacca  gcccctcagc  agtggcaggc  cgcgtggccc  102420
tggttcttga  agccccttga  tcacagctgg  ggggctgggg  gtgcaggatg  gggtggcggt  102480
```

```
tctccctgac ggagaagccc agcagctgga tgctcccctg ggacactcag ccagggccat    102540 ctgtccccg ctgacctcag aaaggagatc aagacctgct ttctccttgg gccaccctcc    102600
caccatgcca ggcactccag ggaacttggg ccacctgccc cacgtgtgtc tgggaggcag    102660
aaggggtcct tgggacaagg agaggttccc tccctcagga gcctggtccc acaggtgaca    102720
tagaagaaga ggggtccctg gggccagccg tgaggatgac aaggagccag gcgcccctc    102780 agcccagacg ctgttccact ccagcctttg ctctgtatct tcaagggcag ccagaaagct    102840
gatgttttaa agtgagaact ccctgttgat taatatttgc ttcatattcg tgttttaaaa    102900
gtatggcgtg agccaaaaat gcaactgctt gctggatttg gaccagcgca ccagtgggtc    102960
tggtagccag cctgtccccc atgccagctg gccgagtgag tgtctgatgg aggaggaggg    103020
gctgtctgac agagggaggt ctgggtgggt gtctgatggg gactttctgg gggatcctgg    103080
ctggcaggga ggctaccagc agggtggtga gggtggctct gttggctgag tgaggctgga    103140
cgagacctgg cgagggatat aaatgctgac agtcaggaca ccaccaccca cttgtgcgcc    103200
agcctccgcc ttgtcttagt ttctccaccc cctccgcacc cctggggtcc ctgggggcagg    103260 ggaggagcag gggattggag gctcatgtgg gagggtggta tcctctgtca ccctgctggc    103320
ccggggccga gctgggactt gaattcagac tctgcctgtg tcgtggcctc ggtgctggtc    103380
caggggatgg gaatttgcag cctgacagat gtggatggta caaccgcttc accgcatctc    103440
cttcagcccc ctcggggcat cctggtcacc cagctggcgg tggcctcctg gctcccccgc    103500
cctccaccgt gcctcctctt tcgtctccat ctgctcgctg accaagctct ccgtcctcag    103560
tcatgtccca cgttcagagc acagggttgg gtgtggcgtt cggccgtcac cacagactgg    103620
ctcagaggag acacaggagg gcaggggagc ctctttgggc tggttctcct ctcccgacag    103680
ctgggggccc tgactacgac acacacccac actgcacagg gaccccaggt gccatgaccc    103740
catcctgtcc tgtccccggt ggcccatgcc tttacctcct gctcaggtcc ccagggcctg    103800
tccggtgtgc tcctgctgcc cgcctctgtc cctgcctctc ctggggggcac aggccgggac    103860 caggctgggg gacaggcagg agcctctctc taccctggtc tccttccctg gtgtggctcc    103920
cacacccaca cggcgctgtg attggctgcc acactcctgc tttctcagcg gggagagtca    103980
gaaatagact gtggcttccc cagttccagg aggcaccaga gcagcagttt ctgaatcagg    104040
ggtgggagcg gctgtgggcg gagccgggga atccctcggg cgctggactg aggctgcccc    104100
gccccgcctc tcctgaggct ccacccaccc cgcctgaggc tccgcccct caccaccaaa    104160 gcccagcccc tggggctgtg gggctgggtc tctgcaggtc ctggagaacc ccttgctgct    104220
gaggctccaa agcagggttg ctgtggctgc acacgcctcg gggagggaga gaagccggcg    104280
tccatttgct cctctcgtca ggctctggga tctacgcaga gaatgagacc tggtcccaca    104340
ggtgacacag gtgccagtgt ggattctcca ctttggcctc ctgagcccct atggcctcat    104400
ctgtaaagtg ggtataatcc cacgtgctgt ccgcttggat atgagggttg tcgttcatca    104460
ctcctgcttt gggaagaccc agcccacat ggagagcgag ccgagtctcg ggtagcaaat    104520
ggatggaata ttgtgtttaa tgtatattta gttcagtgtg tattaatttg gagctggcag    104580
tgttcttact ctagagccag tatctttgcc ttgcctcgaa catttcacag gcccttgat    104640 ggctcacggg cctgtggcac ctgtgcttgt ctgatgtccc ccctccaagt ggctctatat    104700
ctcctggtgg taggttctgc actgttcttc cctggacagc agtctggaag agtctagaag    104760
tgctcccaca ggcaaatcca gtcctggcct gccctcacgc catcctgccc cgcctgctcc    104820
```

```
ccaccccttga gagccttccc ggcttctctg gaaagaaacc cagacctcag cagggcctgc    104880
aggttgggtg ggtcctgccc caggagcagc acccgtcacc gcaggagtcc tgagctcagg    104940
acctttgcac acgctcttcc ttccccgctc ggcttagccc tccccactgg agcctgtgct    105000
ccctgaggac agggctgggc cgcaccacag catcagggcc gggcaggttc tcaggtgctc    105060
actaatatct gactgggagg gtcaggttaa ctcacattag accttctcag cctcatacag    105120
gggggtgtct gcacagtagg ggcaagtcca gactcaccgc acaccaccc cccatgacta     105180 gggtcccaca gggaggtgct cgggctggcg gtcctctcgt ccagcctctc tgggtagaga    105240
gacagttggt gccaagccgg ccggctgtgc tctggtggca gctacagacc tacagggctt    105300
tgaccagagg ataccccttt ctgcttcgtt cagaggtgct ccgaggatcc gctgtggccc    105360
cgcagtggga agtaggactc ggcaccaggc ttgccagctg cataggtttt gagggtgaga    105420
tgtccgcact ttgctgagac gtgtgacttg gacaaaatgg ctttctggga actcagccca    105480
tgatcagctg acaacccaca ggttgggttt tctcaagaca tttttgaaga aactactgtc    105540
ccaggccagc atggtaacgg tgggtttgtg cgttttctct caatgccctc ggctctgtga    105600
gggtctattg ctagacagtt tggaagagaa gtggggatcc agcaataaaa agcctctctg    105660
ggggcagagt gagtggaggc ttggtgttgg tttcaggttt gaggggatgc gtggccttgg    105720
tgctcaggtg gccctgcggg caccccggctg gccaggtggc accagtaggc acctggctct    105780
gcaccccgtg tggattctcc acacctccgc ccaaagggtc ctcttccaga agcttggctt    105840
gcccactcct cccagctgtc cccaacccag ccagtgagca aataggagac acagtccaga    105900
gatgggacct ccctgtggct gtggcgggct cctcctcttc ctgctgggtc cccatggcaa    105960
tgcaccccca agtgcccag cccatcactc agcttccaca gcccaccttt tgtttcctcc      106020
tggccttgac cactccctgg gttgttctgg tttgtttact gtttgtctgc ttcctcttta    106080
gagggtgact ttccaagggc agggaccact gcgtcctggg atttagaaca gtgcctggca    106140
cagagcacgt gctccatggt cacatattga gtgagtggca ttgggggggt ggggttgac     106200 caggctgagg caccccaccc aaagagctgg gtttatgccc tttgcttggg agggagctgg    106260
aggttctggc ccttggtccc agccaggagt tgtgtttttt gttttgttt ttggagggaa      106320 ggtaggttca agccccagca gacatccaga tgagatgtta atcaaccacc caccagccag    106380
cagacacaca aaaccccaa aggagcagac ggcacactgt cgctttgagt gtggaggag       106440 gagcagctga gccctggggc cgccctgggc tttgtgctgg gacagggtta taaataggag    106500
acaagtattt ctggaggtga caaccgcttt ggggcagagt attacggccc cacattgtgg    106560
ccccattcaa atgctcagcc tggtgtctct gcgctgaggc taaaggatcc ggaagtggga    106620
aggtttctgg cttggcccca aagacaacat tattggagtt acaaaaataa ttggagcttg    106680
gctttaattt tggctaatta tgcctccctc tcctgacaag ccttttattt atttatgtgt    106740 tgttttttt ttcttttga ctgcgtcctc caactccctc cctgagaagc catttcaaag       106800
gaaatgataa tttgtcttcc tatctcgcaa accgtgtgtg tctcttgggc tggtgggacg    106860
gcaggcggga gccgtgggcg tggcaggcgg gagccgtggg cgtggctggc agctgtgggc    106920
gtggccgggc tcgcgctctc ggcccaggag attccgggcc tggattggct gcgctcgctc    106980
cctcctggcg gtgctccctg cgggtagagg caggagctcc ctccatcacc ccgcagctgg    107040
cgggtgtcca ctgaggctga acggggcaga aacaggacca gggccggagc ccgtgtctgg    107100
ggcgctggga tacggaagcg ggagtctcgc ccgcccgccc ctccctccgc ccgcgagcag    107160
gggaccgtct cccgggtgga gctcctgctg ctcctacgcc gcctggggag ccgtccagcc    107220
```

```
ccgcgggctg gcagcagatc tggacatgaa gagctgcccg tccagggggg gcgcggggac    107280
tgccccagcc gcccggtgac ggagggcccc ctccctcccg cgtggaggtc tgactcgcca    107340
gcaagaggca gccaccggag gaggctcccc ttccctctcg cttttgggga ggtgctcttc    107400 aggggggtgcg ccagccacct ctgaccctcg cagacccagg gcggaattcg ccggcagcca   107460
ccatggtgca aaatgtaatt ctagtgtttt tccgcagacg gctgagccaa agacccgccg    107520
tggaggaact ggagagaaga aacatcctga aacgtgagta gcgggtgacc ccctagggct    107580
ctcctcaaga gtgctgatgc tcaggttgct gcaggatccc agcgtgggcg gtgggcggtg    107640
cagtgactcc ggtccttcgg ctgagccctc ctgtgtgtct gagctgccca ggaatctgaa    107700
agcaaccccg gggaaagttg aaacacccag aagcatccca tttaaaattg agagggaaaa    107760
aaaaaaaaaa aagactctct tggcatggta aaagatgtcc ctacttcagc gttatctaat    107820
gagtcagccc cataggtcta agggagatga ttctgtatcc tttcgcaggc tgggtctcag    107880
caggtttccc tggcagtttg gacagggtt tctgatggcc gcagtcacca caggcaggtg     107940
tggacaaggg atgaactcac cccttagcgg ttacacctgg ggaatcaaat agccccaagg    108000
aagcgagaaa cctttgggaa tgttgccggt ggctttcaac tccacagtgt gatgcgattc    108060
cagaccaccc cccccaccc cccccccccc cgccccagc cttctgggct ctccagtta       108120 ggtgtgtggt tgtgaccagt gctgagcatc actgtccagg aagaaccccc gaagtgtaga    108180
gagcactgtt ccatctcatt aaagccattg atgagtcggg tggtaaaacc cttgcagaag    108240
tgttttcgca gatacttctt atgtatctgg tcaatgcatt tcagctttcg agacattttg    108300
tatgaaaagt gtcttctaag gcctgtattt ttgaactatt ttcctttccc tcctctcttt    108360
atgatggatg gacactgcag acattctctg agcttgggtt tcattgcatg gccatctttc    108420
tacaaagagg gtcccgaggc tgagctgtca gaaagtgggt gccagggccc ctgctccagg    108480
tgtggagccc taacccattc ctctgcccag caccttcatt aactgcctag aaatcccctc    108540
tctgtccacc gttggaaata cttaaaccct aagatccaga attcttggtt ttattgtttt    108600
aatttaaaat tatagttgat ttacactgtt gtgtcaattt ctgctgaaca gcgaagtgac    108660
ccagtcctac atgtatatac attcttttc tcatattatc ttccatcctg ttctatcgca    108720
tgagattggc tatagttccc tgggctgtgc aggaggacct cattgcttat ccattttaaa    108780
tggaatagtt cacatgttta attttttaaa cctaggatac ggcgactgct gttctatttt    108840
acccaaacta ggccacatct gaggatttaa agaaaagctt ttcattgata acaatcttca    108900
gcacgtgagc ggatacaaaa gtcaagctat ttgtgacaca tatttgaatt ttaaaaaatg    108960
aagtcactta cgatggaaag cgcctaagtc tgatgcccct gaagaaaatc taagacttga    109020
gtggggcaag ttcacgcccc tcagcctggc ctgccgccca gagtgggcag aggctttct    109080 cctgggaacc gttcctccca tccgtgggga ccccctctct gctctggtgg atggccagga   109140
cccccagccg gtcagtgccc ctaagggagt tagtcttggc acagaagccc tgggagcagg    109200
gtggggcctg gcgggcagag gtggcaggtg gtcccgggat ggacagagct cgcttctgcg    109260
cacagaagag gcaggaaaac aagccccgcc aacccccact gcagcccga catcccttcc     109320 tcaccacctg gccaggcggg tccatccctg gtcgacgcc tcgtgccccc gggcagcagc     109380
gcctgagaat ttcgctggat agtggtgggc ggtgctttgg tttggttttg tgccgggaga    109440
agcgaaggga ggaactgtgt gagatgccgc ccagggcgtc atcctcgcag gcccttgacc    109500
caggctcatg ctccatggtg gcgtctgctt ttcatcagtt cttaggctgt cagcacattg    109560
```

```
tatttgctcc ctttaagtgg ggagctcatg actaacgcca tcctgtcggg ggaacacgca   109620
gagctgggcc tgcgtgttga tggagacaag agcgtaagac agagcggccc tgtacctgtg   109680
atgacactaa aaatgatcct gtggcattgg gcccacgcta tgccaggcct cggactcagc   109740
gcgtccggtc ctcattcagt ccttggagca cagtcgccag ctttgctcgg cgtccccatt   109800
tccctagtga ggcagctcgg actccgggag gtaataggac tttttatcag gcgtctcggc   109860
acagggaaag gaaccgcagt tcacgcccat gtgtcctgga ttagactcag gcacactcta   109920
atcactgtct caggagcaat agtgcaggtc tgatgattta cagaagatgc acgtgtgact   109980
gtcccagctc ctgccactat ttctggaaaa tctgggcgtg gaggctgtgg tcatggctcc   110040
cttgttttgc acaaggcacc gtgttttccg ggtctgggag ttagacatcc cgaacccagc   110100
actgagtggc gctcagagag tctgtagctt aacatctcag gagggacttc taagagttgg   110160
tgccccacca agcgcctggc ccggagacga tcctaccaga cactttcaaa gatcagctct   110220
ccaaagcccg tgctgtgccc gtgtgccctt gtcatgcaga tggtacccat gattttaaaa   110280
aaggaaagat ctgatcttgt ttccgtgttt tcacatgagg gctgtactgg gggtttgttc   110340
gtggcctatt tttgagaact ctgaagaatt agtttcatat cattgtttga atccctcatg   110400
gttggcccag gtggtacttt catcactttt ttctaattgt atcatcagct ttctgattag   110460
agcttataac tgtggtttct tctggctttt cacttggatt aagacccccag gacataacag   110520
ggtttggttt cctttcttaa aacagccaaa tgtaagctgc atcttccgtc ttaacgaaag   110580
ttacagaaga gtacgatggc taagtataca aagcacctag ataccaaacc ccccaggcgc   110640
acaaatgtta ggagtgtttt aaatagaggc agacatgtga acttatgtta actgcaagga   110700
gcaggcttcc cctttctcaa acctggcggt gtgtctagga gtgctgacag acgaagtcct   110760
tttcctagga gtggaatgct gggtcccctc cagggacctg aggctttatt tagcaacaga   110820
gagccagaaa taggacatcc attatctcgt atcccagggc agagcctaca ttttacacta   110880
cagctcagca ttctgctcca ttttttagcta caaagtgtag gtgtgagcac ggcttgaatg   110940
ttaatagcca cactcaccaa gcaaagccaa ttttggcgaa agatcctcgg ggtcccttga   111000
aaggcagctc acgtgtcttg cttctgcagt ggagaggcag ctgggttccc gggtatgttt   111060
cgagttgaaa tatattctga aaatacgcat tccaggcaag catatgctgc ccacaatctg   111120
aaatgggtgt ttcttatctt acgttggttg gctgaaagca tgtgtgccta ttacgtggaa   111180
aagggggggga aaggcagtga cagttctatt aatattcatt tactcattca catatacgaa   111240
gatattatat atgtgtatct agctcatcct aaatctgttt ttgtttgcca tctatgttcc   111300
tagatgtaaa tacacacaga gagagagttg attagaggga gagggagaga gagagcgagc   111360
ttttttcctgg ttctcctgca aataaatgcc caacaacaat cgatgcggtt atttctgacc   111420
cagaggaagc ggggatgctg gcaaagcgtc cacatacaag gctttctgtg tgacagtgag   111480
gccacggtct cccgagcagt gatgggcaaa gtggggaaaa acaaagtgat gtggacaaaa   111540
gcgtcttcta cgtcgtgtcc ttcgtcctcc accccccagca tccaggtttt gaggacactt   111600
cctgctaaag agaagaaagt ctcaacctgc ttcttccttt tcttttcttt gttttgtttt   111660
gctttaatttt ttcacagaaa ggaatgatca gacggagcag gaagaaagaa gagaaatcaa   111720
gcaaagattg acaagaaagg tactatcatt gaagcacctg attccggacg attcgaggga   111780
gaaagctgct tctgcagcgg tcgggatggg cgatgcaggc cctcactctg tgagggcagg   111840
tgccaggaat tcactcacca gacgccagga gagcagggcc ttttgccacg tcctggcatg   111900
taactgacat gcctgccaat agtgtcctcg cctggcaccc gagcccgcgg ccctgatgac   111960
```

```
acttcgcttt gtttccaggg ggtgagctct ttacacagtt cctgggcaca gcgcccggac   112020
agcagagctg ccctttcctt tgggacactg gttacctcac tctgtctaga agctctggat   112080
ggcagaacat tttattagcc tcaaggattt gtatcggggg gtctctagta gttaagtcaa   112140
tcaaaatgga ctgtggccaa tataggtagc aactccataa gcgctgatct ccttctaaag   112200
ccctgcccat ctctaaatcc aggtgttctg gtgttgccct ttttctactg tgttctccaa   112260
ttattactat tctaacaatt attattctat taataataat tctattaatt attattatta   112320
ttattgtcct acttgaagtt catggagtgt cttcctgagc ttgacttatg agtaccagta   112380
gtatttagca ttttaacttt ctctaccttt ttcgtaaaag cttccctaat gatagcagaa   112440
aagaagccgc tgctactgta aaatctttcc taagttcatt cacctatggt tccttgagct   112500
gtgctgtgaa cagggcactg ctgggctcct ggagcttagg gtccagagaa gaggtgctga   112560 gggcagggggg ctggaataga agaggtgtac tttaaacccc tcatacttga ggttttttgc   112620 atcaggggttc catttcacag cttcagggtg ctttaagaat gctaatttgg cacgggacac   112680
ctgacagtgg tgatcttttta ttttttcagct taatcagaga cccacggttg atgaactgag   112740
agacagaaaa attctgatac gattcagtga ttacgtggag gtggcaaagg cacaagacta   112800
tgacagacgg gccgacaagc cctggacgag actgtcggca gcagacaagg taccgagcag   112860
gccggtctgt gccgccgggg tgggtcggtg tgaaaggagc agagcgcgtc ctgccagcag   112920
gtttctatcc ttggtgggca ctgtccactg ttgtggtcga ggctgtgcct tcccagatgc   112980
tggctttgta aatacaagct ggcggtaggg acatgctttc acctggggga cactttgcct   113040
ttagggactc tggcagtggc tggggacagt cttggtggtc agcagtggtg gtcgctgctg   113100
gtgtctagtg agtggagccc aggggtgccg ctcccccctg tggcaatgca caggatagcc   113160 gccccccaccc cgagactgtt gaggacgtga aactctggcc tgggtgcgag tcacagtagg   113220
caggtgggca aaaagagct ggacaacatg ggtttacaca aagcgagcca cagccgggtg   113280
ggggaaggga ggagatggga gaagccttca ggctgcaggt ggaggcggct ctggactcgg   113340
tcctgggctg gtcccgtttg aggtgtccct ggggatcctg agcagtctca accaaagggc   113400
caggaggaga gcaagggggt tgcggggggc tgaggctatg gggtgaagca gagggaatta   113460
acatccccta gcccgtacac tcccccgtac tggacccagc ctgccaggcg ttatttcact   113520
taatcctcag caacatccca aagagagagg tgttgtcatt atccctgcag aggtgaccag   113580
gagaggctgg gggagtagtc ttgaccgtgg gcaaacgcta ttgaccagca gaacttaaac   113640
ccaggaacgt ctgttggcag agtctgtcct gccttcctgc ctctggtgat tttcagaacc   113700
tcaaagcctt taggaagagg aactattata catccagcca atacatttgc aggattttct   113760
cattgttcct cctccttcat atgctgagtg tgagtctgga gcttttaagt gaacacacac   113820
gggcatagca tcagcttgga gaagtccaga caggctgtag ttggaccaac tcagttaccc   113880
ttggcgaggg gcttggaggg gcccgggcac ggggggagagg gtgggcctct ttggtggcag   113940
gcctggtgac gatgggcgta gcctgcccct gacattctgg aggcagagtc tttccttgcc   114000
ctgaaggctg atgttttttg tctcccctgg tcctggaggg tttatctgag agaagcacac   114060
gatgaaagtg ggcgttggga agctggaggc gggccaggag agaggccccg gatgggcggc   114120
gatgcgcgtc tcacccacag gcaaccggga ggttcttttt caaaatgcag aacataaacc   114180
tgcagtgacg tcagaatgac ttcttcctac attgtctagt tgcagagttc caagtaattt   114240
caccaaaagc tgaagtttgc tcgttgtctt gaggcttggg gctcttagaa agcaggacca   114300
```

```
tcagaataag gagtgacgtt cagcttttgg tgacgatagc cccgcattta tctatttatt   114360
acgtatcgtg gctgggtggg gagggctggt atcttccctc ttgggcacag cagataaatt   114420
ccctgaacac ttcctgaata ccagccatgc actagctcgg tgggactgta aacatgagca   114480
agtaagagtc ggaatgctga acaaaaagct tttctgcctg tcgcaccagc accgaagtca   114540
acatgtgttc gaagtggctg tccatccgca gccatgacac cagtttcctc tgctaatgtt   114600
gtaatgttct gaaaaatgat atgctggttt tcaattccag gcagcgattc gtaaagaact   114660
gaatgaatac aaaagcaatg aaatggaagt acacgcctca agcaagcacc tgacaaggtc   114720
agatttctat ttgtatgaag ttcgtgatac ttacaatatg gtgtttattt aaaaggaaaa   114780
ttaacatgcc acaaagaact atgtgttcac gttaaaaaaa aaaaaattca gtatctctgc   114840
agagaactgt attgaacaga cagaaggcac ctcaattaaa agctctgttc gctcccctgg   114900
tttctcgtag ggctcggtgg aaggtggttt taggaggaca ctgctacgca gatcactggt   114960
tatctgagca gttagtgtat atttaaggaa atgagcctca aagcactgaa agtaatttgc   115020
ctgtgtgttt aattcccctt tgctaacgtc cagaactctc tcgtttatga gctccctgat   115080
tcattgatac gtagaggagt ggtgtgaaac aaccctctcc attcctgttt tcccacctta   115140
tttaaatctg tattcatttc tttaacacaa gctaatgctc cctcgaagct cttccaaaga   115200
gctggtgttt ccccggcaaa tgtttgaatg acgctgtgcg ccgttcttgg cactgagaat   115260
acaactacag ataagatcaa ggaggtcctt gtcatcatgg ggcttatgtg ccagtggggc   115320
tgtgctggct gatgcctctg taatcgaggc gtttcacatg aggggaacat ccactctgcc   115380
cacgtgaccg tagcagcgat ggggtgtctt gctgatcatg acctgctcac tggctgcatg   115440
ttctttcagc atctccctct gtccgtggcc gtgacagtca ggatggtgtg aggttctcac   115500
acacctttaa tccaaggggg tggccgtgat gccataagcc ttcaactgca gctgctgctt   115560
cgtcatctct cccttggtct gatgatgctt gggccccaga tacaaagaga aggacggtc    115620 tgaatggaga tactgccttc agctaaaaga acggattccc tcccttttcc gtttgtcaca   115680
aagtggccac tgcaattgtt atttaaaaga tctactctgg agttcctgtg gtggcttagc   115740
ggaaacagat ctgactagca tttatgagga cacaggttcg atccctgggc ttgctcagtg   115800
ggttaaggat ccggtgttgt ggctgtggtg taggccagca gctagagctc taattcagcc   115860
cctagcttgg gaacttccat atgttgtggg tgcggcccta aaaaaaaaaa aaaaaaaaa    115920 aagattaact ctgcaagcac aatgaggttg tagaacagaa accaggtctc acaagatagt   115980
tttactttga ctatttcaag ggaggaagag gaggttgatg ggcaagaaaa aaacgaggca   116040
agtatatagt ttgtttaaaa acgtttaagg gttttcccct actttggggt aggaataaat   116100
catcttattt ttgagtgttc aaaacgctga aaaatgttta ggaaataaac attctcctta   116160
aaacattttt taatgttcag tctatgtttt taaaaaagag atataattgc taccattcta   116220
tgtatggtga tagcaaatat ttaatacacc ttcttattct ttagatgttt actaaagaca   116280
tgtattttct ctcataagtc cttgataact ttccttagaag atggaacttt aagagagagc   116340
ccaaaacgta gacatcagga catataagat ttttgtgcta ccacagttta gcacttaatg   116400
ccaactttta ccagaacagt attttttagtc atatgaggtt ttcttaagca tatgggacat   116460
taccacaaac acattaccag ttctttaagt gcaaaactat aactctactg tattatccaa   116520
taatttgctt tattaatcag ttcattactt ccactgattt agtgaagccc tggtctttct   116580
gtgtactcaa gggcttaatg ggctgttttc agacgaagtt ttaggtagtc ttaagaattc   116640
agtgtctagg agttcccttc gtggcacagt ggttaatgaa tctgactaga aaccttgagg   116700
```

```
ttttgggtcc gattcctggc cttgctcagt gggttaacga tccggcgttg ccgtgagctg   116760
tggtgtaggt tgcagacgcg gctcggatcc cgcgttgctg tggctgtgac ataggccggc   116820
agctacggct ccgattggac ccctagcctg ggaatctcca tatgtcatgg gagtggccct   116880
agaaaagcca aaaagacaaa aaaaaaaaaa aagaattcag tgtctactat tcacaagagc   116940
caagaagaca tggaagcaac caaaatgtgc attgacagag gagtggatta agaagacgtg   117000
gtacatgtat acaacgggat accactccgt cataaaaaaa agaaggaata atgccatttg   117060
cagcaacaca gatgcaactt cagattatca taccaagtga agtaagtcag agaaagacaa   117120
ataccatata atatcactta tacgtagaat ctaaaacatg gcacaaatga atctatctac   117180
agaacagaaa cagactcaca atcgtggaga acagacttgt ggttgccaag gggagggccg   117240
agggagtggg atggactggg agtttggggt tcgtggatgc aaactctcac atttagactg   117300
gataagcaat gaggtcctgc tatacagcac agggaacgat acccagtctc tcgcgttgac   117360
cgtgatggaa gatcacataa gggaatgagc tgggtcactt tgctgcacag cagaaattgg   117420
cacaacattg taaatcaact gtacttcaaa aaaaagaag aattcaggct ctagttcccg   117480
aacaggtggc cccaccatta ctttaaccca aacaggtcca tcctcatctt ttacctgttg   117540
gacttctgag acgcttgtaa tggcaacagc attatttgtg gaagattttg gcagtgttaa   117600
cgtaggaatg tgtaaccttc aattcatttt ctctttgtga tttctagatt ccacaggcca   117660
tagagatttt cttctgagaa gaattgtgtt taattttga taccaacact gaacattcat   117720
cagggaactt tcctgacgct catgaccacc tgctgtgttt gcgaaggagc aggaccacag   117780
gcaggtgaaa tgtgggtcgc tctcacctgt aagaggagga agcgggggac ggcctccact   117840
ctctggtgtc tgaggagtgt gaacagttgg ggtcgataca gccccagga actctcccag   117900 aagaaaactc agttttgctt tgcagctctg cggtgcgaag gaggacgcgg tgtgcatgtg   117960
caggtcaccg ccgaggctct gagtgccgga cgagtgacgc agcgtcgtca gtaccatgtg   118020
gccgagacgt ttttattctg atcacgatta atttgagact ctttaagttc ctgttataca   118080
aaatgattta ctgtattata cttttctctt tttttatata atgtctaaca aaaatacagc   118140
tgcgacattt tgattcctgt taattttgtt ctttcattaa atgactactt attgcaggaa   118200
attaatctgg ccagtacagt ttcttggggt tggggtgtga gatgttttta gcacaggggt   118260
ctgtgaaaca agtccaattt tattactttt gagccatcag aagccaacca catcaaagag   118320
cattcaaacg ttttgtgtat tttgttttgt aaattctgtt agtatatgtg atttcgtgcc   118380
ctggaaaatc aaagtattct tttcaagtga agtttatgga ttattgagta atgaacctag   118440
aaataagtga tagcttgttg aaaaagtctg ccaagatgaa aattatgcct tatttaagag   118500
tattttgaag ttcgcatttg cagacagtat taaaaacgca ttataagaag cagaggttta   118560
aatggaggtg cgatcgtaaa gaggaaattt ccctcctcca gcacaaaaag gtaaaaagta   118620
atcttgcaca aagggggaaa gtaagttaaa taaaaataaa tattccaagt aaatatgttt   118680
tggcttggcc tttgagtaag tgtcctcgag aatgagccca ccctctctgc tggtccatcc   118740
aggcagcgag cacagtgcgt ggactttggg acctgggccc caatcccagc tctgcacctt   118800
gcagcgagat atttatttcc tccgcaggaa catctccccg ccccccaac acggctgtaa    118860 tcttttgaatg agatgaagga ggtcaggtgc cagcgcagtg gccagcacat tctcagcctg   118920
accaggtggc cctggagcag ctgaatgtcc ctgtgacttc tcaccgcaca tgttacctca   118980
ttgccttccg tgacctttcc tgttccgctg cttaaggct gcgatgggtc agctgcccat   119040
```

```
ggaaactgct cagcctttga ggtagcactt tgtgctgagg gacttatgac cagtcctggg  119100
tgctagacaa cctactgtga gttgaactgg ggtcttttag aagaaatcac tgcatggtag  119160
aaaaagtcca gctctacctc ttacttgctg tataaccttt tgtgaattgt ttgacttctc  119220
tgagcctcag tttctgtgtc tgaaatgaga tgatttctaa atcctttcta accagaagtc  119280
aatcccttaa ttttataagc atttatgtgt atgcatatat actgtgtatt taatgtatat  119340
ttatatgtgt ggactctatt ttatacgagc cgttacttgt tgccaatcaa cccctcaaa   119400 tactgatttt ctactttaag ctacgtatta gcagctccct attttatatt ttattcaatt  119460
taaaataata tttggagcca gactagggaa aagatttcac tctcctgtac aaatatccac  119520
ataactactt actatgaagc aaagcaaaga aaaggcctcc cttattctag aaaccaccct  119580
ggcccctaaa gcaaaaagat tcagtggtta agaaataact gcacctatag ttagagataa  119640
cctgatggat gggacacatg cttaggtttt tttcccaagt acagacccat agctaataaa  119700
tacatttgaa aataaagtac aagataccaa aagaaggttt ggctgggtcc agccccaaag  119760
gttctatgat attatagaac cagaagacat tttcattgta atcaaaatgt ttgcaataac  119820
agctaacttc taccactgta tttttattaa tcttgaatta ttctaaattt tatttctgta  119880
tttcatgtcc ttagcaggtg tcatagaggt caagataaac taaaactatg tgttaagtag  119940
gtatgtctac tctgcaccta ctaagagtgt gtaatcctgc actaaatacg ttgatgacat  120000
ggcatctcac atctctctca tccagttagc tggaggaaca acattaaaaa gcagttcgta  120060
aatcacatgg tactggtgat atgcatgcat aaatttacat atgtcgtata aatttgaaga  120120
gaaagtttat atactgagga gcctgaagac ttagaaaaaa caatcctaca gagttgccgt  120180
tgtggctcag tgggttggga atccaaccgc agcagctcag ccgctgtgaa ggcacaggtt  120240 tgaccccag gccgacctca tgggttaaag gatctggcat tgccacggct gccgcttgga  120300
tttagtcttt gacccaggac cttccatatg ctgcaggtat gaccattaaa aagaaaattc  120360
tgccttcttg ttcagtaaca gatataggat ctgaattatc aacactcttc atgactagta  120420
gtagtcattg atggagtttt taacgcactg attttataaa tcatttaaca aaatatgatt  120480
attaaagtaa caacattaag tcattaaaga gattgttttt aaggagttta aaagatttaa  120540
aaaacttact tggtaatttg gtgagaagaa attgagttat gtcctgaagc atcaagtttt  120600
aagccagtct gatggggaa tgctgcattg tatgactttg taaaaagtac attttttaaa   120660
attcaaaggg gttttgaatt tatgtaatgt tttggacaca tggatttaaa aaagcaccta  120720
acatcaagag gtccaccttg tggaaatata tggtaattac aagtctaaat ttatatttga  120780
ggtgtgtgaa gtcagtgttc tttgacagca aactcaagtc cagaaatgca aaattctaat  120840
taaaatgact agtctcacat gattcgtctt tatttaccca gattttttgtc cagaagtttt  120900 tcagttttttc atatgaaagc agtttcagaa gatgctcata cacaactgaa tatattgaaa  120960
gtcaggctga atatcggaaa atattttaaa atagtgaatt actataaatt acatttcttc  121020 atttttttggc aaacgtattg ataatgatgg tgttaggaac ttatcgctag ttcatatttta 121080 gacaaacgat atttattaga ctgaacagcg gaagagctac ctgttaccag ttctatgaaa  121140
acagaacggg cattctcttg tgggacacgc tgggttaaca cccaccccg cccaaaaaag   121200 aagaatagca atattttata tttggagtaa taaaaaaact tttaagtctt tatctcaact  121260
gtaaatctct tcaaaggatg tgagcaggga aactaaaaat tacattgtct tgactgtgag  121320
cagttataca tgctgataat tttaaaaatt gaaaatatgc tgttacacat gcatcattac  121380
tttcgaaacg caactgattc tccttttttca aaggcacacg tgctgaaaat gtggccacga  121440
```

```
tacaggtgtg tgccctgaac aactggtctg caccgcatgg tccactccct gcttcccacc    121500
ccgagagttc ctgggttatg ctggtgactc caggtgtggc agagcacagg ctcaggaagg    121560
acttaactcc ttgctccaat ctttgcagtc caagttaggt gggtttgttg ctcagcattc    121620
tatcttgggt gtttaatcac cgcaccagat tcttccatgc ttactcccgt tttcatgcaa    121680
cctattagtg agcctgaact cacgtctgag agctgtgact gggctcattg cccataggtg    121740
acggtgcaga ggcggaagac ctacccggag caaccgctga gcttcacgct aggcaggccc    121800
tgaggtcagg ggtggcagcc ctcatccccc tggactgcca gggtgaccaa gaatcaagaa    121860
gtagctgagg gcccagtgta ctgtccactc gaggacctcc cgtgcattta tggagtcagg    121920
actgggcggc atttaggtct cttcagtcgc gtctgtaggt ttggcattta tggttctgcc    121980
cagctgtact aacgctgcaa aacgttctct ctctccgtct ttccccgtg ttctttttgga    122040 acagtgacca ctgtaccgct ccgtttggtc gaggaagtgt ggcagacctg taccagtagg    122100
gtgtgaaact gtgatctagg taagaattgg atgtcattag caacaatgat tgtttatttt    122160
ttgatatgct tggcacagga aaatcaaaac gtgttaatta acacaaccat aaacccttcc    122220
caatgcaatc ttgatttaaa ccactatgtc ttttaagtag taagataaat tgaagaatac    122280
attttgtact taagaacaga gaggtctagg agttccagtt gtggtgcagt gggttcatga    122340
tccagcttgt ctctggggct ttaccggttc aatgcctggc ccagcacaat aggttaagga    122400
tcttgcattg ctgtagctat ggcataggtg gcagatgcag ctcagatttg attcctggcc    122460
aaggaacttc catatggtga gggtgccact gaaggagaaa aaaaaaaaaa ggaacagaga    122520
tttgatcttc aaactgtttc ttctaagcta ggggtcttgc aagctatagc ccacagacca    122580
aatctggcct gcctcccttt ttttttaatgg tctgcgagct aagaatggtc cttacatttt    122640
taaatggtta catttgacgt gtttatatta gtttctacat gatctcctca agtttacctt    122700
ttggtccaca aagcctaaaa catttaccat atagcccttt aaaagacagt ttgcctgctc    122760
ctgctctaaa aacttttttt aaagtgtaag taaatatata atagaaaatg ttgaattatg    122820
cagaacaaat agctaacttt tgtttctaag taagcttaaa attttaaca tcaaatctgt    122880 ttcagggagt tccattgtgg ctcagcggaa acgaacctga ctagtaccca tgaggatgcg    122940
ggtttgatcc ctggcctcgc tcagtgggtt aaggatctga cattgctgtg agctgtggtg    123000
gaggtcccag acacagctta cttagatctg gcgtcgctgt ggcataggct gcagctccaa    123060
ttcgacccct agcctgggaa cttccacatg cgtggcccta aaagaaaaa atctgtttc     123120 attttcagac tcattataag ctcacatgac agtagctgtg tgacatgcag agaaggcaca    123180
tcgagtcagg taaataataa agggctaagt gatattaaag aattatttc tcactgtgac     123240 aacccactgc tccagcttcc tttcatttaa aattattgct atcatagcat aaaccaaaat    123300
taaattgtct actgttcaag atggtataac atacagatct cattgaacac atctgcattc    123360
ctgaaagaca accggattat ttccctctag atgttgtttt agaatatttc catgggcttt    123420
ttggacctaa tttaaaaaaa aaaaaaacag taagcaagca ttacaaatgt agcgtctttg    123480
gcagtgaagc ctgtgcacat ttgatttgcc tgcatactct tcaaaggcac gaatgaaagg    123540
aaatctgatg ctgaacgacg gctttaaaac agagatctaa aagcccaaaa gggccacaga    123600
gacctcattt tattagtttt tcttttttagg gctgcatctg cagcatatgg aagttcccag    123660
gccaggcatc aaattcgagc tgcagctgca acctgcacca caacttatgg caatgccaga    123720
tccttaaccc cccgcgtgaa gattggcatt gaacctgctt cctcatggac actgtgtcag    123780
```

```
cttcttaacc cactgagcca taatgggaac tcctagatct cattttttaag tacaaggaaa   123840
gggttctttt cttacctctg catgtagagc taagtacagt gtatgtcata tactagacac   123900
tcaaatggct atttgactaa tactctgtta tcaattttaa tagaaatgcc aacactatgc   123960
aagatttgag gatctgaggg ttttaggagg cacattggcc ctctccaaac gtagcaaatt   124020
tctacctaga aatactacat ttgttcaatc atttattcac tgtgcaggtc aacttttcca   124080
ggcactcgtt ttaggaagta gaacctagac aaaccaggct cttgttccca tagaatttac   124140
aggggtgata ccaaaaaatg ctgtatgata gagggtgata attgcattaa taggattgtg   124200
aaggaagtcc tttctaaaga attactattt aaatgggaac ctgaagaaga gtaagagttc   124260
ccaggaaaat tgaatcacat aaacaaagac tctaaaactg gaataaggag ttctgttgtg   124320
gctcagttca tgatgtggtt cattgctcag aggtcatgaa cctgactagt acccatgagg   124380
acacggattc aatccccggc ctcgctcagt gggttaagga tctggcgttg ctgtgaactg   124440
tggtgtaggt caaaaatgtg gcttggctct ggcattgctg tggctgcggt gtaggccagt   124500
ggttacagct ctgattcaac ccctagcctg gaacttcct tatgcctcag gtgcggccct   124560
aaaaagacaa ataataaat aaatataaaac aaaacagaaa taatactggt taaggaacaa   124620
ggcttgaagt atatgtacaa gaggagagga gtaagaagaa ggaagagtga gaaacgaggc   124680
agaggccagc tcacatccac ctgtgggggc catgtgctat aaaacttaca ttttaagggc   124740
acaggaaacc cctggagagg ttctgtgttg ctgctggttt ttttttttt tttttttag   124800
ttcaggtgaa atgcagataa catgaaagag tacagttcaa tggcattgaa tatacccaca   124860
gagtcataca accaccacat ctctctagtt ccgaaacgtt ttcacacctg aagaggaccc   124920
catgctctca aggtggctac tccccactgt ccccttttcca aacatctcct ctgctttctg   124980
tttacaagga ttcacacagt ctggatagtg catgtaaact gaatcacaca acatgttacc   125040
ttccgtgtct acttctttca cttagcataa tacatcggag gttcatccac tgtaataaga   125100
atcaatactt ctctccttt ttggctgaaa aacattccag tgcatagaca gactacttgt   125160
ttgttggcca cacccatggc atgtggacgt tcctgggcca gggatggaac ctgagttgct   125220
gcagtgacga tgctggctcc ttaacccact gcaccaccag ggaaaagcac cactacatac   125280
gtacttagct gatggccgtt tgggctgtct ccccctgttg gctattatga acagtgcact   125340
tgtgaacatt cttgtacaaa agtatttgtt gaatatgttt ttaattctta cgggcgtatg   125400
acgaaaagtg gaatcatacg gtaatttctt cttttaatttt ctgaggaacc accaaactat   125460
tttccatagt ggctgcatta ttttacattc tcttagaaat gcacacgttt tccaattcct   125520
gaacagtctt gccgatcttt agtgttttt gattctagcc atcctagtgg gtataaaggg   125580
acatcagtat tgttttggtt ttcattttcc taatgattaa tggtgctcag tatatgttca   125640
tgtgtttgtt ggtcatttgt gtatcttctc tggagaaggg tttatccaag tcctttgccc   125700
attttttcagt cagattttt tgtcactttg ttgaactgta agaattctct gtatattctg   125760
gatactagac tctacagatg gatcatttgt aaatatttta tcccattcta caggttgttc   125820
tcttttactt ttataaaagt attctttgat gcacagaagt tttttttttt tatttttgatg   125880
aagtacaatt tacacttttt aatgttgttt cttgtttcat tttgtttttt tcttttttgg   125940
ccgccctgca tggcatatgg agttcatggg cctgggtcag atctgagctg cagttgtgac   126000
ctacaccaca gccgtggcaa gtccagatcc tttaacccac tgagctgggc caggaattga   126060
acctgtgtcc cagcgctcta gagacaccac ttattccatt gcactaaagt gggagctcct   126120
gttgttggtg tttttggtgt catatctaag actccattgc caaatctaag gtcgtgaaga   126180
```

-continued

```
tttgctccta tgttttttcc taagagtttt atagttttaa ctctttagg ttcttgatcc   126240 atttaaagtc aatttttaca tttggttaa ggtaagggca tccagcttta ttgttttgca   126300
tgtggctata tggttgtccc aaaaccattt gttgaagaaa ctgttatttc cccatcaaat   126360
ggccttggca cctttgatga aactcgactg accatagcta aataggttca tttctagaat   126420
ctcagttcta ttccatttgt ctttatgtct atccttatgt aggtactata ctgtgtgttt   126480
tgtgggtttt ttggttttgg ttttggtttt tccttctta gggctgcacc cgtggcatat    126540
ggaagttccc aggctaaggg tggaatcaga gctacagctg ccagcctacg ccatagccac   126600
agcaacgtca gatccaagcc acgtctctga catacaccat agctcactga gtgaggccaa   126660
ggatcacacc acatcctcat gggtactagt caggtttgtt accactgagc caccatggga   126720
actcctggta ttatactgtt ttaatttagc tttgtagtaa gtatgaaatt gggaactgtg   126780
agtcctccaa ctttattatt cttttttaa gattgttttg ctctgttggg tctcttacat    126840
ttccatgtga ttttttagg accggcttt ttcatttccg tagaaaggac ttggaatttt     126900
gtgagagact gcattaaatc tgtagcttgg ttcagaatat tgccattttg accgtattaa   126960
gtctaacaat cacgtgggat gtcttttccac ttgtttggga cttctttaat gtccttcagc  127020
aatgttttgt agttttcagt gttcagatct ttcaactcct tcataaaatg tactcccttc   127080
gatatgctgc tggacttggc ttcccagaat ttcgttgagg attttgcatg catattctac   127140
tggtctgtaa ttttcttttc ttgtgatgtc tctatctgac tttgggagca aggtaatgct   127200
ggcctcgaat gagttaggaa tgctccctcc tcttctgttt tctggaagca tttgagaagg   127260
gctggttaat tctgaaaatg tttggtagaa ttctgtcttg ggaggttttt aattactgat   127320
taaatctctt gttataaatc tgttcagatt ttctgctgct tcttgagtca gttttttgtag 127380 attgtgtttt taggcattta tccatttaat gtgagttatc taatttgttg gcatacagtt   127440
gtccatagaa ttctcttaga agcctttcta tttctctaac atcagtagta atgttcccag   127500
ttttcatttc tgcttttaga cattttagtc ttctattgat cgtaatctga caagtcagtc   127560
aggtttatca attttcttga tctcttcaat gaaccaacct ttggttatat tgattttctg   127620 ttgttttct attctctttt attttatttt ttttatttt tagtctttt gctatttctt      127680 tggggccgct cccacggcat atggaggttc ccaggctagg ggtctaatcg gagctgtagc   127740
caccggccta cgccagggcc acagcaacgc gggatccgag ccacgtctgc aacctacacc   127800
acagctcacg gcaacgccgg atccttaacc cactgagcaa gggcagggac tgaacccgca   127860
acctcatggt tcctagtcgg attcgttaac cactgcgcca cgacgggaat gccgtccttt   127920 tttttttt ttttttttgg tctattctct tttaaaaagc tttactatct attatttcct     127980
tccttctgac agctttgggt atagcttttt ctagttcttt aaagttaggt gattgagatt   128040
tccatcactt ttaatgtata taaatgtaca gctataaata tctctgagca ttgctttcag   128100
taagtttcat cttcatttgt tccaaagtat cttttttttt aaaaaatctt tttccttttt   128160
ttaatggctg tacctgtggt atatggaagt tcccaggcta ggggttaaat tggaactgta   128220
gctgccagcc tggccatagc cacagccact gccggatccg agctgcacct gcgacctacc   128280
ccacaggtgg cggcaatgct ggatccttaa cccactgagt gaagccaggg attgaacctg   128340
catccttacg gacacaatgt ttggtttctt aacccactga gccacaacag gaactcccca   128400
aagtatcttc caatttccct tgtgattct tcttgactc actagttact tatgaatgtg     128460
ctgtcactgg agagttttac ataagggagt cacaagctgg gtatatgatt tacgatttaa   128520
```

```
caagactata ctggctgcta tgtgaatcag gggttgtaaa aaggggagca cgagtgctgg 128580
gaagcaattt agcagctgtt gccattgtct ctgtgagtca atgatgtaaa taaacactgt 128640
caaaggtgag tgatggcaag aaagtatatg gacctacttt ggcggtaaaa tctgcaggac 128700
ttatcagcta actggccaaa ggaaaaggaa caatcaggaa atgcttctag gtttgggctt 128760
gaatagttgg gtggatagaa gggcatttac tgagatggaa gtacaggttt attttttct  128820 tcggtggcga gaacgctgag agagaaaaga gaggtgtttt gagaacagct gtttattgaa 128880
ctgtcaataa aacaatgtat atgacatgct aatgttcaaa gtcagaatgt ttctacacgt 128940
gggagttagc aagacaacga cagttactgc atgggaccaa atgaaattac caagagaaa  129000 gtgcagacta aagagacgtg acagactaag aggtaaaagg ggaacgagac aagaaagagt 129060
ggaaaacatg tgccagccaa aggttttaag tgtggaatgg cactgcgaag cttaagacga 129120
caggtaagat ttgataaaat ggacgactgg tgattttgac aaaagctgta gggacaggag 129180
ttcccgtcgt ggcacagtgg ttaacaaatc ctactaggaa ccatgaggtt ttgggttgga 129240
tccctggcct tgctcagtgg gttaaggatc cggtgttgct gtgagctgtg gtgtaggtca 129300
cagacgcagc tcggatcccg cggttcgctg tgggtctggc gtaagccggc ggctacgget 129360 ccgattggac ccctaacctg gaaccctcca tatgccatgg gagtggccct aaaaaaggca 129420
aaaagccaac aaaaaaaaaa aaaaaaaaaa aaagctgtag ggacaaaaag tgggactggg 129480
gcaaataggt agtgtgtaag ttgagacagt acctaaagaa cattcttttg atatggtctg 129540
tgtaaaggag catagatgat ctcacgggg  ggcagtaagt aaaggggaac ttgatgttaa 129600
catctttttt tttttttttt tagtaaatgt gggctataca caccggtaag agaagtcata 129660
gacaacaggc ttcagaaggg ggattacagt gtcctgaaat aatgagtcta atttgccact 129720
ggaacatgtg agaaatcagg aagtgccggt attgatgcag gcaagctgtc agaggagatg 129780
aggaaagtag aaggtaaggc cacctcctaa aaggcaatga attaagggat gaggtactga 129840
tgtacagtaa caccctggaa atggggcaaa atcaattaag acagaataag ggttgctgag 129900
caatgctttg tagccactgg aaatatgcag tcacagattc taaccttgat tatatgctat 129960
ttctcgagtg atgtgcgcat tgaggggtct gaaccagtgg gtaaagttga agacaggaca 130020
gagggcaaga gagtattatt ttggcctaag gactctagaa tcggtgaggg gcatggcaag 130080
acagtggtag agtaagcatc cgggctcctc tgaaaagcag gttggggagt tcctgctgtg 130140
gctcagcaga aacgaatctt gactggcaac catgaggatg caggctccat ccttggcctc 130200
cctcgctcag tgggttaagg atccagcttt gccgtgaact gtggtgtagg tcactgacac 130260
agctcagatc ttgcgtcact gtggctgtga tggagcattg ctgtagctcc aatttgaccc 130320
cttgactggg aacctccgta tgtcacgggt gcggccctaa aaagacaaaa aaataaaaa  130380 agcagttgga gtgatcatgt cagaagtgag agtcagtgcc caacttttgg ttatgacaag 130440
gtcaaaggag gcagatttaa agagctgaga agaagtagga acctggggttg gatcggagtc 130500 ttctaagtct ggccatgggt gaggtaaact ggggaaatgt gtcatgatgg gactgcttct 130560
caagtctcac aaggcaacgt ggagttacaa ctgctggtcg tatttaaaat tacagcagtt 130620
tttaaaaata ctgccactat tgcttgaaat agaatcccga tgctaacaac agaataaagc 130680
tgaagtatgt aggatttccc tttgcttatt cagactgaga agccactttc accactgttt 130740
ttcgtttttt ttgtttttt tttttttaagg gttgctctca tggtatatgg aggttcccag 130800
gctagaggtc aaatcggaac tgtagcttcc agcctatgcc acagctcacg gcaacgccgg 130860
atcctcaacc tactgagcga ggtcaggaat cgaacccaca acctcatggt tcctagtcgg 130920
```

```
attcgtttcc actgtgccac aatgggaact cctggttttc gttttgacc atgcccttgg    130980
catgtggaat ttctgggcc agggactgaa gccatgtcac agcagtgtcc tcagccacac    131040
cagcgacaac accagatccg tacccactga gcctccaggg aactcctttc cactgtactg    131100
aaatactggc agtattcaaa tactctgcta ccattaagca ggttaagtga tagtgtgtga    131160
ggctgtgtgg taatactgtg gatgtctgac tggagaagga tgttttgttt gatccaatgt    131220
tcataaacta gaaaagagt gattcataaa ataactgtaa tatccaagtg acagagcatt    131280
tatttcaact ttattataca attaaactgt attatttcat aaattaatct agcaaaatat    131340
tattacaaag aacactaggg cttaaaaagt acttgtcaaa acagcctgct tatgagttaa    131400
taatgtctcc acctagaatt aaaatgtttc gataacaaag taaccatctt aggctacttt    131460
gtgccttcta gcataatgga gctgaagcag aacaaatata ctctccaaca gtatcctcaa    131520
agtactgatt tacactcagg taagtatttt aaatcaaatg ttctatgtgt cactaaaatt    131580
tttaatagtt gtagtatatt ctgaactagt aaataaattt tattaataat ttatatctgt    131640
agttaaaact tatttaaaat atatgataaa ttttagtttg ttaaagaaat aactagtttt    131700
gagtacagtt aactcagtaa tattgtctca tgcaagtatt accataaaaa caattccttt    131760
gactgtttgg cttcccaaaa cttttcttaa aaaaagcagt actgtataga caagactttg    131820
gggctcggag tatgttaaag tgattatagg gtcttttta tccataaaat gacatttctt    131880
tgaatttgga ggttcctaca aaggtgctct tgccagggtg acatatattt tctccttgta    131940
gagctacttt gggtatttcc tcagttatac acaaatattg gataaaacct gttgatagca    132000
actagacatc acacattgtt tctttcatga gccatgaata atgactttag ccctctgcgc    132060
acattaagaa gctcctcttc ttgctatggc caagaaaaaa agacagattt taaattatca    132120
ctgtaaaact atcaaataaa ataggaaaaa aatcaagatg ttatgaataa atatactgtg    132180
tatcagtgtc caatctccca ggatatattc ctagctatct acagaattat gtgctcatca    132240
ctgatgtttt agatgatcaa ttgagagaag accttcagac ttaaatccca aatccacaaa    132300
atttatttt ttcatttaaa tattaaatct atactccaga aaataatttc agtaagggtc    132360
agtccagtta gattacttgc ttcaagctaa gctggctaag ccacaacatc ctgctcctct    132420
actatttcag catactgagg tgctattaaa atttactagg tgcattaata ctaatacttt    132480
agaggggatg ttttaaagtt aacctaaaat tcctccatct tggagaaaac accaaaggca    132540
tgctcacttg gaaaagcacc ttaaagcacc ctcccctctc ccaatcttag tgtacttttc    132600
ccagaatgca gttagttgct ggtctactag actttgcaaa gtcagcttat tttatcccca    132660
cgtctaagta gatgaagcct tgttgtccaa gtaatcaata attctttcta ggtaactctg    132720
cctgacacat catctccttc agaagccaca acaggacaga ggtctgctac agtgcacact    132780
gctaagatac atacaaataa atcattcttc tagctaattt taaaattttc aaattgacct    132840
ctcctttttc cttaggaggg actctttatt tgtttagttt tttagggcca tacccacagc    132900
atatagagag tcccaggcta gggggtgaaa aggatctgta gctgctggct gacaccacag    132960
ctcatggcca cgttggattc ttaacccact gagcaaggcc agggatagaa cctggggcct    133020
catggatgcc agtcagattc gtttaccgct gagctacgat gggaactcct tggactcaat    133080
atttaaatca cccctgttat tctactataa atttgctccc attttaattt aagaactta    133140
cagtactaga agaaccctaa tggggctaaa actgccttct ctgaatccga aaacaaagaa    133200
agaagaaaag cctatggaag aaattcccat ttaaatatgt aaaagcatga ctgattattc    133260
```

```
catttgaaaa atccaaacta gatagttgac ttaccatttc cttaagaagc ctgtcttgta   133320
tcattttcat gttttctttc attgaacaca tctgtgaata agtaattttc cccatgaaat   133380
ttactataaa gttttcacag caaaaagact gaccaatagt gagcgattat atataaaaat   133440
ataaaattga tacctcagaa gtaaaaatag tttcttcata atcagtattg tagaagacat   133500
tcttgttcaa cgaagctttt aaaaggtgaa gccttaacaa gtaaataat gaagtcacct    133560 ttgaagttac cttttgtatt tcactttaac aaattacgtt gctatatgta tataattaca   133620
tatgtataat atataatta gctcataata aaaaaaaatc cagtgttata gatgccaatc    133680
attaagaatg tcacactaac ctctgctgtt cactttttg ataggcactg aacttctgaa    133740
atatcttctc ccaaaagccc taaatttcaa aatacaaaat tagttatact ttaattatga   133800
ctaaaaatta acacttgaaa gaatatactc tatttctact attcctaatt taaataaaca   133860
actcagctgc atgctaagaa tattcagatt catacactct tttagacaaa aagaatgtat   133920
caaaggtatt catcaactat ctgcatattt ttatggaagt atagtgactt acacagtttt   133980
aggtgtacag cagagtgatt cagttttta taggttttcc attataagtt attacaagat    134040
attaaatgca gttccctgtg ctatatgtag tttctggttc atctatttta tatatagtat   134100
ggtatatctg ttaatcccaa attcccaatt tatccctccc cccattataa acttaaatct   134160
gtattttaag tgtgtgtgta agaaattaac taaaaactta agataaaata agttatcttt   134220
taaaaatgaa acacaagttt aaaacaggtt ttcctgagtg tagctcttta aaaataattt   134280
taaagcctca tttttaaact cttaaaagca caaaccacta attccttctc caaatctttt   134340
aaggactgtg aatcttttc aaaattctcc agctccttta tgatgatgaa ttggaatttg    134400
tcaagttttt tgattctagt aaagaaacaa aatgagattt ttttcaaaat gatagcactc   134460 agaatacca gcacttataa tatttcagaa gggatttca gtacagacct atactcctga     134520
atctgatgat tcattgtttt tatatgttgt tgagctgttt tccaagaatg cttcgtaaaa   134580
taatccatta ttttgtggcg gatctgaaaa atactcattt ttaacttgaa aaaaatcttt   134640 acaaataat aatctaacca agattatatt aagaccaaag cctttctat gaaatataaa    134700 cgactaagaa gaacttagca aagtgaaaaa ttgaaaactc agtgatttaa agtgaagggt   134760
taataaataa gctcagtcag agcacggcct ggttctacca ggaacgctct ggctgagagt   134820
tgaactggca attaatcatt ttcataacta catcacattc tatagtattt acaaaatgct   134880
ggttaataca atttttttt ttttaggagt gcagcctaag agtcacactc aaaattattt    134940
attactattt ttcataaaaa cattttcaca tctagccaca gataagtaac agaatatatg   135000
aatcagggct tctctgttag gctagattaa atcacagcaa aataaatata tacgctctta   135060
aataatttca ggttttaccc ctgaagataa gaaaaataat ttcaggttta cccttgaaga   135120
taagaaaaag aaaaggaaga gatatggctg ataacctgtg caaaaagaac tgtctgtcct   135180
aaataaagac atgtgagaag atgggtggag aaaataataa aattattttc gaaagcattt   135240
ttgcaaacat cacctcacaa gcctcagtaa caaaggatac ataagtacag agctggtgaa   135300
acaaaatgaa atggatttct ctggctgagg ttgctcatcc tttacacttt attatgtacc   135360
ctcactagca atcacttctg tgagataaat gtattgatta aaaagaccag gcatgaaaag   135420
aaaattgttc caaaaaataa agaaaaataa gctaagagtc aaaatattaa attgaaaagg   135480
aagataggac aaagagacag aacccacaga agaagaatac agagaatgca cagatttag    135540 aagacaaact tggctcatga gataaaaggt ttttttgcc taggaatcat gccagttttc     135600
accagcacac gaagaaagct gagttcatga atggatgttt tgttgccaag agttcacact   135660
```

```
gatagtctag cagaaagtgt ggcatactgt catattattg gttataagtt gtaaatcatg    135720
atttaaaaat gacaactcac atgaactttc ctcctaaatt ctgtattgag ctgctcatac    135780
atcattccga catctgacat ttcatttccc cagttctccc caggaataga aaagtcattt    135840
gttgataatg gagatatact ttcagacact aaaaaatgaa gacaatcaac taaaattaag    135900
atatgcattg ttagatattt agccttttg tcatgaggcc aagaacaaaa tctcttattt     135960
tcagattctc tacataatct aagtattatg aaatcaaagg cagactattt tttttttttt    136020
ttgtcttttt agggccgcac ctgtggcata tggaggttct caggctaagg gttgaattga    136080
agctgtagct ggccgtccta taccacagcc acagcaatgc cagactgagc ctcgtctgcg    136140
acctacacca cagctcatgg caacgccaga tccttaaccc tttgagcaag gcctgggatc    136200
gaacctacat cctcatggat ggcagtcaga ttcacttctg ctaatccatg acaggaacgc    136260
ctatattttt taatttaaaa tattttgagg aatcccgtca tgactcagtg gtaacaaact    136320
gactagtatc cattaggatt caggtttgat ccctggcctc actcagagag ttaaagatct    136380
ggcattgctg agagctgtgt tgcaggttgc agaatcggct tggatcccaa gttgctgtag    136440
gccggcagct acacctccaa ttcgacccct agcctgagaa aacttccata tgctgcagat    136500
gccgccataa aagcaaaaaa taaaataaat aaaatatttt gacttataaa taaaaagtc     136560 ttttagcatg ggtattaagt tcaaaacagg taacattaaa atggaacata tttggactgt    136620 ttttttaaaac cagttttttaa ctacttccat attagtaact caagtattta gtatttacca  136680
gtaaattctc tagtaaaact tataagtggt aatcagtgat agaatgatga gagaaatgta    136740
tgagtaagac cctcagtata atattattca gataaagtga actgcgtaat aaagcaccat    136800
ccttgggttt atccaatgtc gttacaaagg aatttgtctt gtgaatggag tcactcaaga    136860
tctaagaaac caccttcgac agtaactgaa ttttgacaga ggcatttgat ctacctacct    136920
ttgtaagttt gaaaatccgt accttcactt ttagataatt ttttgggaag caagcttgct    136980 cttcctcct ctctctctcc caatgctact tcatcagaat tactcagatc cttttctatg     137040
tacattcgtt tccgactaac atgtagtgta gggccttagg aacagtttaa agtaatgaa     137100 taaagctaca atcttaattt aaaacaccta atattttctt gcttttatca aaaaaaggc     137160 atttgcttca gttatttgta tagttttagg cacctgtgca ttaaattcta ctgtattttt    137220
ttcattttca ctaaaattgc aataactaaa ttgaataatg gtatgattta aagtatatag    137280
ctcctttaga tgagacatca ccatagtatt tcagtaatta atacgttttt aaaaagcaag    137340
tctatgacta caaacctgat ccatgagtgg agtcacaggg caggccaccc catattttct    137400
ctcttccttc actagccatg gagagtggag atgctgaatg actttcctaa aatttattag    137460
aaattggaaa aaattctata agtactcttg gattcatctc ctacttccaa attcgtatta    137520
tgattttgat ttctttgagt caggatatgg gaggccgtag aaactgaaag tctaaactac    137580
tttttcacgc tctattttta acgtctttgt cctctaacct tgtttcactg ctccaataca    137640
caagtctctt tgttccagtc aaatcagtct ttttccttt ttttttttaa atctttttgt     137700
ctttttaggg ctacacctcc agcatacgga ggttccccgg ctaggggttt aatcagaact    137760
gcagctgcag gcctacacca cagccacagc aaacaggatc caagctgcag ctgtgaccta    137820
caccacagct cacagcaatg ctggatcctt aacctactga gcgaggccag ggatggaccc    137880
tgcgtcctca tggatgctac tcatgttcat taaccactgg gccacgacgg gaactcccag    137940
tctttttcct tttttagaaa aatgtatgtc tacttccagt tcccttgtg gacttaggtt     138000
```

```
actgttctttt ctccattcag ccggatatat gaacctaccc actccagtcc agatcaaatc   138060
ccagcccact tcaaactgtg aaattctgcc ttaactttct gtattttata ggtcattaaa   138120
atcttttata gaggaaaaaa ggtcaaccaa actcctgtat aatcatgaaa ctataaagtc   138180
ctgattatga atatgtaagc tagtggttaa cagtgacagc ctatttaaga ccttctcatt   138240
ttaaaatttt caactttttt ttgtcttttta tcttttttagg gctgcaccca tggcatatgg   138300
aggttcccag gctaggggtc gaatcagagt gtagctgctg gcctatgcca cagccacagc   138360
aatgccagat ccgagctgca tctgcaaact acaccaaagc tcacagcaac accggatcct   138420
taacccactg agcgaggcca gggtttgtac ctgcaacctc atcgttccta gttggatttg   138480
tttccactgt gccatgatgg gaactcccct caactttttt ttccatgatc aaaccatcct   138540
aaatatttta aacatcacat ttttagacaa ctgaaaaata ctaaattatt ataaccatta   138600
ttaaaggccc ataatctgat tcttataaga accaccttag tttaagtaaa gtctgatggc   138660
cacataacac atatactctc cttaacttta aatatgattt tcatatttgg aggttcaatt   138720
tccatacatt ttttctgaac tataactgct taatctgaat agctactgca attttgtgtt   138780
tcttacgaaa ggacactctt ctctcagtat ctgtggaggg ggattgcctt caggacccctt   138840 tgcaaatacc acaatccact gatgttcatg tcccatgtgt aaaacagtga tctgcaattg   138900
actgaattca ctgttgggca aatccacaga tgtggaatcc atggatatgg agagtcaact   138960
gcatcacaaa gtttatattg tttctttttac agtagtattc ttaactgggc aatgaacaag   139020
acatacagaa atccagagga aattagaaaa ctaagaaag aaaaacacaa tagtaaacca   139080
aaactagcta aattttaaga gaataattga tttgctgcta aaactcaaac atattcctaa   139140
ttgaaaaaaa gcacttaaca cctaaaatat taatttgata acaagtatcc accaaaacct   139200
atagataagc atgcatgcta gcacagtatc aattaaacac tgttccaagg gtcatggtca   139260
acttaaaaat gaaaacgtca tgaagtataa ggactggaac agaaaaatgc aaaaaatata   139320
catacattgt ttttttttctt accaaaaagc ctgattgtgg aattggtgag caactttctc   139380
ctccacacag taagttttttc tcactgttat tgggtgaatt tattggactt tcaactccac   139440
tgtttaagga ttcaggtgat gaagtttttg gataaggtga tagtgatttt gttacatagt   139500
caaaatcttg agtaaaatct ctttcggtcg ttttctctgt acctatattg cctcatgaaa   139560
cagaaagaaa aagagatgac aggtgttatc attgatattt actttagaaa cagtatgatt   139620 aattttaaatt ctaaaaaata gtaatttacc aagtcctcaa atcctagctg tacttaggat   139680
aaactttcaa taaattaaga tcaaattata tgtaaaatat tttaataaga ctttttaaaat   139740 actaatggct tgatttaaaa tgtaactgta ggagttcctg tcgtggcgca gtggttaacg   139800
aatccaacta ggagccatga ggttgcgggt tcgatccctg gccttgctca gtgggttaag   139860
gatccggcgt tgccatgagc tgtgatgtag gtcacagacg cggctcggat cccgcgttgc   139920
tgtggctctg gtgtaggctg ttggcaccgc tctgataaga cccctagcct gggaacctcc   139980 ataccacg gatgtggctc taaaaagaca aaacaaaaac aaaaacttcc taacatttag   140040
taaagcttca gtgtcataac agtttactta gcaaagacca agttactagc attaactagt   140100
ttaaaaataa agttttgact actgaaaatc ttaaatacac ccctcaaaat tagtcttcaa   140160
attatatttc cacatagttg taacagaaaa ttactaaata ttcaactaaa gaaaaaaaat   140220
gatactgaca tctcattact tctatagatg atggactccc agataaagat acaggagatt   140280
tgtcaaggct attatctctt atagtatctt ttagtagaga tgagttttttc cattcttttg   140340 atatatcctt ttgcatttcg gaagagaagg aattctgttt ctttggcggc ttcatggttt   140400
```

```
tgcttctgga atggatattc tcctaaatgt attggtaata tacaaattat atttgaatac    140460
aaataattta tacttgaaca cacaaaataa tttaattaaa ctacactgaa atctttacta    140520
aatgctttat accactacat acaggcaaaa taggagcctc aaatgagtag agaaagactt    140580
taaaagtaaa attgttggag ttcccgtcat ggagtggtgg aaatgaatcc gactaggaac    140640
catgaggttg agggttcaat ccctggcctt gctcagtggg ttaagaatct ggtgttgcag    140700
tgagctgtgg tatggttcgc agatgtggct cagatctggc attgctatga ctgtgcggtg    140760
tagaccccta gcctgggaac ctccatatgc tgcgggtgcg gccctaaaaa gaaaaaaaaa    140820
attgtttatg gccacaccca cggcatatgt aagttcctgg gccaggggt ctaatccaag     140880 ccccagctgt gacctaggcc acagatgtag caataccaga tccttttaac ccactgagcc    140940
aggaaatcga acctgtgcag ccagagacac cacctgctac accatagtgg gaactccgtg    141000
aaagaccttc taatatacta gaaagcacat gacaaattca caggaaaata taaacataga    141060
ttataataaa tatcctaata gatacaaata aaatgctata acagttgaaa gattatttc    141120 agtttaggga aatgagaaag agttcctagg tttcctgtta ctcaacatgc tcaggagttt    141180
gtaaaggaag atggcatgct gagaatgtgg aggactactg atgggagaag agaagcaagg    141240
ctttgtttgg gaaccacagg ttattttatt ttattttgc ttcttagggt cacacccgag     141300
gcatagagaa gttcccaggc taagagtcaa gttggagctg tagcccccga cctacaccac    141360
agccaaagca acatggggcc caagctgtgt cttcgaccga caccacagct cacgacaatg    141420
ccggctcctt aacccactga gtgagggcag ggatcaaacc cgcaacctca tggttaccag    141480
tgggattccg ctgtaccaca aagggaactc caagggagtc acaggttatc ctatctgact    141540
gttacagctc tgggtatata ccggggaaac aagaaaataa gcttggaaag gcatttgatg    141600
cgctgaatgt ctatttggat attttcaggg ttcttctttg aaggttaaag tgagcgagga    141660
ctgcgcaaga tgtacctaac taaatgtata gtagattaaa ttaagaactg atagaaaatg    141720
tgaaaagtta caaagtcctt aaggtcttcc agataagagg cgacaggggg atatggaggt    141780
ttaatgattt aaaatgggaa cagtgtaatg caataattgc agagacctac ctctactgcc    141840
tctcttttga gttcaaacct ttttaaaaa atttttcaac acttcctagc tgtgtgacct     141900
tgggcaagtt ccttcatctc tctgagcctc aattttctca tttgcaaaat gagatgtcaa    141960
taatagtaat agtcacctat gatacttaag atattttaag aaattagcac ctggcacatt    142020
ataagcacta tattctttca ctttgttaaa aaagctttca agctagggta tgtctataat    142080
attaagatgt aaggaagaag tcaggaatga acaacggtgg ggcagtgtat gggaagaagc    142140
tcacatccag tcattttact ttcattcaag aaaagatcc acggcttccc aacagtgtac      142200
tttcttgaag cataattttg aaaagaccaa gtacttctct aattcaaaga tattatctta    142260
aagttataat tttactagtg ctttgtaaca caccaattta ttacaaattt taacattata    142320
tggcctaagg ctcaatttca gaagattaaa tcttaaaaga agtgatgaaa taaatcttat    142380 attttacaa aaatatatac actatttaat attttaagaa gctgttagaa attattaatc      142440
tgaattgaat ctatttacct ttattagcaa tttctcttta aatgaatgtg aaaattcttg    142500
ttcactctct gattctgaat tgagagatc tttataattt ttttggtttt tgctgctct      142560 tcgtggaagt ctgattctcc catctggaac tgtttcatcg accttttggg tgatgttttt    142620
gtcgggtgtc tttaggagaa aaattcctga atatattaga tcaatatttt gagatacaag    142680
ctatctgcta taaaattggc accatgacaa aatatgcatg aatatttgta ggaataaaaa    142740
```

```
gattcctgat caatacttttt aaaatgactga gattttatct ttccaaatac attctttatc  142800 acttttttaat ccttatcatt aaagctctga gatgtcttat atatattacc taactttagt  142860
aagacagaga gaaaggaaaa gatagcaaaa atacccataa ccacagaata aaatagactt  142920
aaaacaggcc agcttcaaaa aggcagaagt aagtgtgcaa agttttgaac aattatggaa  142980
aataaggaac tgataacaaa gataaaatta tgagatgaca aatgatattt ttcatgacag  143040
aaaaataatt taaagggat gttgaggag ttcctgtcgt ggtgcagtgg ttaacaaatc  143100
cgactaggaa ccatgaggtt gagggttcaa tccctggcct tgctcagtgg gttgaggatc  143160
cgtcgttgct gtgagctgtg gtgtaggttg cagacgtggc tcagatcccg agctgctgtg  143220
gccctggcgt aggccgtcgg cttacagctc caattcgacc cctagcctgg gaacctccat  143280
atgccacagg agcggcccta gaaaagacaa aaagataaaa aaaaaaaaa aaaaaaaaa  143340 aaaaagggat gtttgaacac aaacttcctg gttttaccat tttagatctt ggttgttccc  143400
tttccaaaga tgatcctgta atttaagaaa ataaggttaa aattttcaaa tagataagtg  143460
acattaaaca attattaaac aatttctgca tataagttaa tatcacaaaa gcaacaagac  143520
tgcatggtta ttttgatat cttttcctct ctctctgtct tacaaaagtt aggaatatat  143580
atcagacctc ttagtcactt gctcttaaaa gttttacttc agagatatat atccctaaac  143640
aatacaatga actttataaa acagtattat gtcatattcc atgatttgct ttattttca  143700 tccatcatct taagatttag ccatcttaat gagagtagct tcagtccta ttccgttttt  143760 ttcatttcca gcacaactgc tactttctaa atattctctg aagcctaaga tttgggatta  143820
tccaagctaa ggaaggaaca gagctctcgt agaaaggtcc ttcgatcctg gcaataagcc  143880
agctcgtact tactgactga ctcatcattc agccgtttaa acaaaacaat tcagggagtt  143940 ccatttttaag agtaattact gactacagtc ttctaacttt actaattcct caagatttct  144000
gtgttataaa tgtctttact tgtacatctt cccattgtaa gcttgctgag agtatgtgaa  144060
tctaatcctg tttctccttg tctttcaaag tctacaccct gactagaccc agccacatct  144120
gtcagcattt tcccacaagt ctgagctacg ttccaacccc tccaatactg cacttcctga  144180
gttcgtatgt cacttgtact gtcactttta tatatgataa cgcttttgct tctcttcctc  144240
atgtatatga ttgaactctc atctgtttcc aagaatcagc ctcatttcaa attacaagcc  144300
caaattaatt tccatgtctc tattttttact tcttttttctt tttagggcca cacctgcagc  144360
ataaggaagt tcctaggctc gaggttgaat tagagcgaca gctgccagcc catgtcacag  144420
acacagcaac atgcgatctg agtcgcatct gcaatcctat gccacagcct gcagcagtgc  144480
tggatcttta acccactgag tgaggccggg gattgaacct gcatcctcat ggataccagt  144540
cgggttctta acccagtgag ctataacagg aactattttt actttttta aagccatcat  144600 ttcttccccc aactccaaga ggccactaac aattattttt atcctgaaat aaaataagaa  144660
gtgattccct taaatataaa agttaagggt tatcgtatct tctttgaaaa taaaatacat  144720
aaaatctttg ttttaataac cattaaaact gatgttaagc tatgaaaacg gtcattatgt  144780
ctagcccaaa ctccatactt caaactctta tccaactact tcaagagatt caccagagaa  144840
agtagaatat ttaggctggg aaaacatttt gtggaggatt taggcaaagt atttctgtaa  144900
gaaaattgtt tacctttcaa taaatttgta ttgcatctat tagaattcct aaaagtatgt  144960
gtattggatg tggcagggag tagggtgttg tccaaggttt gattttgttt agggtgttag  145020
gttcatgagt acttaacaca tattcacaat tagccaaata accaaacagt aggctaggag  145080
ttgacaaatg accagagtgt gtcatgaacc aaagattatg atcaatcata ctttatgtcc  145140
```

```
ctgagatccc aatgaaaata aaatttaaat ataaccatat tgccaaaaat aataaaacaa 145200
aaaaataaaa accactgtag tgctttggtg tatttgcttt catactttt ttcctattca 145260 taaggatatg tagttataaa cactatctac acacaaaaat atattcaacc aacaaagcat 145320
ttcatatagc tgaaatggta aaaccatgag cagcatttct ctataaaagt gatttcttac 145380
ttgatttccc acttttatgt ttcttcacat ttttatttct gctgtagcct attaactgtg 145440
gtttcgattt tgattctctt agccagctaa tatcagtttt gctgtcatca catttgtatt 145500
ctgtgtcagt atcactaaag agagtttct tcttatgatt tgttacagtc tattaaaaaa 145560
aaaaaacaat ccttgtaaga gatgaagaca tctgtcttaa tatatgtcat gcaaagaata 145620
tgtcatagca ccccccccc caaaaaaaac cccaccaaaa taatgaaaaa actaacttgc 145680 catttttag cgtgctaatc tatctggcat taaggacctt tccaacagtc actcagaaat 145740
ccagatcaga gattgagatt tatatttgc tgccaatgtt gctgtaaatc aagctaaaac 145800
agctcacttc cacagagaca taacttaata gcactgaaga gagtaactac agttgttaca 145860
tattactaga tgattacaaa tagctcagac accataagaa aagacaattg gaacatggat 145920
atttcctaca attaaaaaaa tgacccaaat atttttgttt ccaattctgt gataatcttg 145980
ggcattgaaa aattatatac tgattttaat agacatattg ggatattaaa acttactcgt 146040
ttatctttgg ttttgagaga agtttcaagt tcatcatgat tccttaaacc tacccttgaa 146100 caaaatatg cattcatttt aatctcaatt acttgtgttc ttaaagtagc atacaatggg 146160
acacttgggt ttcctgccta aactctttac taactcccta tataactgtg gccaagtcac 146220
ttgttctgac ttctatttat tataaaataa ggttagatca aacaactatc aagttttc 146280 agttttatca tctgagttat gcaactaata ttaaagtgt acagaatctc tagattactt 146340
ttagaatggt gaaataagag aatcctaaag gtgtattcat gacattcagt aacatttta 146400 ttcactctt tcatatgtta aaaactctca agtgggagg aattatttaa gaaagtaac 146460 aactgataaa agtatatttt aaacaaaccc atctgattat aataaaaata cctacaatgt 146520
tattgtacta tccacgcagg cttctctagc tgtagcttga aattcctgga tctatattgt 146580
gaaaaagcat taaaaatttt tcttagtgtt aaaaaaaatt aaaagaaata agcatgaaaa 146640
atctcatcac attcaacaga agatgtgaca ataaaattaa gctttgaaaa agtttaataa 146700
tataaactat accaaaacca aaatgagtat tattttatat ttaatttaaa aaatttta 146760 aggagttccc gtcgtggctc agtgcttaat gaatccgact aggagccatg aggttgcggg 146820
tttgatccct gccttgctc agtgggtaa ggatccagcg ttgccatgag ctgtgatgta 146880
ggttgcagac gcagctcgga tcccgcgttg ctgtggctct ggtgtaggcc cgtagctaca 146940
gctccgattt gaccctagc ctgggaacct ccatatgccg caggagtggt cctagaaaag 147000
gcaaaaagac acacacacac acaaaaattt taagagtaat tattttaaat ctgttgcatc 147060
agtaaggaaa gtagttttct tgatgcctct attactcatt tttctctact ttggtatagt 147120
gggagaaaga aaagatttga atgaaaacca aatataccta cgttggtatc aaataaattt 147180
tgaggaattt agtaatataa atattttaaa gcatatctat aagaggatga aaataaaaag 147240
gcatactcta gtaactgcat ggtaaataca aaataactac ttatttctag cttaccccaa 147300
gttttataac aggctcatca gctccactca aattaaaatt gtaaacatca ttcctgtaaa 147360
gatgagaaga aatattaact ccattataca taaataaatt tattttttc aaacatgagg 147420 aaaactttaa gctttataaa aagttactta caatgggcat tcagaagtaa cattaacaaa 147480
```

```
agtagtcttc aattgtctgt aacttttttt ctgaaccttt tcctaaatac aaagaaattt  147540
tacataaaac cattcaaact tgtacagtat gatatgtggt aaacagatac cgtgcaatta  147600
aatttcatat attatctact tgtgttttca tcaatataaa ttttatactt gtaaagttt   147660 ccttaaacat ccacactttt aaaaatattg aagactggag ttgccatcgt ggctcagtgg  147720
ttaacaaatc cgactaggaa ccatgaggtt gcagggtcca tccctggcct cgctcagtgg  147780
cttaaggatc cagcgttgct gtgagctgtg gtgtaggtca cagacttggc tcagatgcca  147840
cgttgctgtg gctgtggtgt aggccatcgg ctacagctcc aattagaccc ctagcctggg  147900
aacctccata tgccgcaggt gtggccctag aaagacaaaa aagacaaaaa aagacaaaaa  147960
aaaaaaaaaa attgaagact taagtatcta ctgagaacaa atattgtaa atcaaataca   148020 aaataaaaat aagatgctta tatctttaat atttattgac aatatatagg taaatgaccc   148080
cactggtata ctacaggcta atcttagtg atgctaggat cacaaaacaa gcatgcttct    148140
acttttttac caccccacct ccccgactct catttgtttt aaaactctta aatagaaaaa  148200
ctttgggaga ggctactatt tatgtaaaat atcatgcgaa aaagtcaaaa ttctgtcaat  148260
caaatagtat gattagggga aaatatgtgt aaggttattc ctatagcata ttgttcaaag  148320
tatattcaat ctgatcaaaa agtaggcaga gaataagcta aataaaattt taacatatta  148380
aatgaataat tgttattaaa ataatttaac tacaattaca aaatgactac tgatcagaaa  148440
taattagaag tctaatttaa tatctggaga ttggaaatac taaactaaaa tattcatttt  148500
aggtgatatt catctccagt tttattactt cttttggcta ctttataata aaattctttg  148560
cattattcca aaaataatgc tattccaaaa agtttatccc ttaatatatt actcctctga  148620
tcatttatct cgcttattct ttccattatg attttacca gtgtttagat acctttgctc   148680
aattcatctt ctgcatgcca gtgtgtgcta ggtatttaca aaagatacaa aaatgagcaa  148740
agatattaaa gaaggtgcag aaatgagaaa aggtcttata taggatacaa agatgattct  148800
aaacagctgc attctagaag aggacagaag agagaaaaaa ggaactccaa ctgtgaataa  148860
aatatcaaaa ataaggtata aagacattgt tgcatagatt cagagttctt gtccatttgg  148920
attttgagtc aggacacctt agaaagtttt tataaagaag gcagactctt aacaaagact  148980
tgcaaggagg aatgaagttc tgacaacgag aaaagagggt gaaagaacct ggtaactcac  149040
tcttaatttc ttttcaaagg ggggaagaaa aaaataaact taggaaagac acatcaggga  149100
atctcaagtt atttcgtttc agctaaaaaa gacatgtcta aggaagtagt tttaggaaat  149160
aagacatact tttaggaggt ctagggagcc agcctacgtt cccacttaat tcaataagga  149220
acagagacca aaggaggatt ttgaacaaga gagtgacagg attgaagcta tgtgctttac  149280
aaagtccaaa agctagtact gaaagtaatg aatggattgg cacaaagaaa cactagcagt  149340 gaaagaatt acataaaggt gaacctaata tgtcttccca cagaaaagaa actcatggac  149400
atgaacagac ttgtggttgc caaggggaa ggggagggag tgggacggac tgggaatttg   149460
gggttaatag atgcaaacta ttgcctttgg aatgggtaaa caatgacatc ctgctgtata  149520
gcactgggaa ctatatctag tcacttaaga tggagcatga taatgtgaga aaaaaagaa   149580 tgtatatata tatatgtgtg actgggtcac cttgctgaac agtagaaaat tgacataaca  149640
ctgtaaacca gctataatgg aaaaaaataa aaatcattaa aaggaaaaaa aaggtaaatt  149700
catatataaa ttttaaactt ctgtacaata gagcaaaagc ataaacaaca aagaaaaga   149760 attacataaa ggcaattgta aaaatccagg gatgagaaat tagaactcaa aaaaacagga  149820
gttggcacaa gcagaagagg gaagatgcga gaggaatttc ctgagggcaa acctcaaaac  149880
```

```
ttgaaattaa ttggagataa ctatgaagaa taaagcaaag ataactgata tttaaagcct  149940
gtatgaatag taaatgtttt taacaaaaac aaacaaagaa aaaaaacccc aaaaaaacaa  150000
aggacttaag gagtttcctc atggttcagt gggtaaagga tctggcacat tgtcactgtt  150060
gtggctctgg ttacagctgt ggcacaggtt cagtccctga ccctgtaact tccacatgcc  150120
atgggtgtag ccccaatttt cttttttta aatagggact taataatttt actgtcagga  150180
gagatggagt aagctagaaa aaaaaaatgg tactgaatca tgtaccgaaa agtaaaaata  150240
acacacatac acataaaaga ggcattttct ttgaaaagta gaacagaaag ttaggggcta  150300
ttttgagtac ttgccactaa aagttgtcag ttatttaaca caattatcaa tatgttgaaa  150360
acattaaata tacttccatt ctactattat tctattttag tgtttacagt caaatatcat  150420
aaagtttgac tacacatctg gtgtagttaa atagatgaaa cctacctttc tgagctgtag  150480
atcagacttg tttgaaaaac cactataaaa aaggttttgt caaaattaaa aaagtgaata  150540
tcagtagaat gttttcata aaagccagtg tatataaggt aaaacatatt tgggtcacta  150600
agtccacatt caatatgcta caaataactg aaatgacggt actagtccag tattttgca  150660 ccttcatcca tagccaacag ttcaataata gttaagtcta agttgaatca tttatgcagc  150720
aggaggtgcc aagcaatata agatgaatgg ttctgccata agagtatttt ttttcatgcc  150780
atttaaggcc agaattaatt taaacaccaa ctggcagcct acaaggagat acttctcaat  150840 aaagaaaat cttcagaaag actgcaaaca aggaatctac atttactatt atgaaatagc  150900
taaggagttc ccgttgtggt gcaggggaaa tgaatctgac taggaaccat gaggttgcgg  150960
gtttgattaa ggatctggca ttgccgtgag ctgtggtgta ggtcgcagac atggctcaga  151020
tcctgcgtgg ctgtggcata ggccagcagc tgtagctccg attagacccc tagcctggga  151080
acctccctat gccgagggtt cggccctaaa aagcaaaaac aaacaaaac aaaacaaaac  151140 aaaaaaacaa aaaaaaccac cctcacctca gctcatttac atttcatact ttattaaata  151200
atatatttaa aatatttagt tttactcatc actaggctca ataaataaaa ttttgaaaat  151260
atctatatac taaagattta tttctgaaat gttatgctgc atcaatatgg tcttttgat  151320 actttataaa atgtactcag atattagaat aattcaaat tgagttccct ttatgtataa  151380
tttgaacaga tactatttat aaaagtaacc aagcaactgt attctctaat ggaaagttaa  151440
gttatttaaa cacatgttta aaaactaact gtaaaactat gtaaataat ttatttgtat  151500 ctgtcaaaac atattaattt ctaaaattta agaacatacc tgtcaattaa agactccttt  151560
aattttcttg tagactttgt gccatccttt ggtttgtatc tcttattaat ctgacttatc  151620
aatgattcgg ctgcatcatt aaatcctttc ccttttgact tttctctctg aaacagttta  151680
caagttacat aaaactgtt aaccttgaaa ggtaaaaaaa ggctgaaaag aaaatttgag  151740
aaaaatctag ttctgtaaaa taagtgcaaa gagaaataaa ggggtcaga aattttttta  151800 aagaaattat ttaataaaca cttgggcttt gttttgcagt aaaacaactt ataagttttt  151860
ttaacataca gaactgtgca gggtgctctg tttttttaa agtttctatc catgggaaaa  151920
aaattattaa aaaactgaag gaaccaaaag ttggctcttt gaaatgctca ataaaattga  151980
taagcctcta gccaagttaa ttaagaaaaa aagaaaatta ctagtatcag aaatgaaaga  152040
gaggttagca ttattgatca catgaataat aaatcacaaa gaattttaaa aacattatga  152100
acaactctat gctcattaat ttgataacct agattaaaag gaccaattcc ttgaaggaca  152160
agttttacta aaactgacac agggagaaat aaatcatcta attaggatta taaatattaa  152220
```

```
ataaacttaa tgaataaaat ttttttttggt cttttagggc tgcatctgca gtatatggaa   152280
gttcccaggc tagggggctga attggagctg tagctgccag cctacaccac agccacagca   152340
atgccagatc tgagccacgt ttgcaaccta cactgcagct caaggatact acaccacaac   152400
tcacagatcc ttaacccact tagcaaggcc agggatcaaa cccatgtcct tgtggatact   152460
ggtcgggttt gttaccgctg agccacaaca ggaacaccaa ttgaataata cctgtcaaaa   152520
cagaaagcac caggcccaaa gaggctgagt tttagcaaac atttacagac gaattataca   152580
attttttcaca acccttcaga agatagaagc aaagggaata cttcctaatt cattctatga  152640
agtcaatgta tcctaataac aaaatcaaag acattacaag aaaggaggac tgtagaccac   152700
tatctctcat aaatataaat gcaaaaccct caacaaaaat attaacaaat cggaggtacc   152760
atcatggcac agtggttaac gaatccgact aggaaccatg aggttgcagg tttgatccct   152820
ggccttgctc agtgggttaa ggatctggca ttgccgtgag ctgtggtgtg ggtcgaagac   152880
tctgctccaa tcccatgttg ctgtggctct ggcataggcc ggtggctaca gctccaattc   152940
gactcctagc ctgggaacct ccatatgccg cgggagaggc cctagaaaag acaaaaagac   153000
aaaaaaaaaa aaaaaaatta acaaatcaaa tccataatg tataaaacaa gaattatgta   153060
tcatgactat gagaaattaa ttccaggcat gcaatgttga ttcaacattt gaaaatcaac   153120
taatataatc caggctaaga aagaaaaatt acaagatcat atcaatatat gcacaaaagc   153180
atttcacaga atccaatacc catttgtgat aacaattcgc agaaaactag aaatagagag   153240
gaatgtcctc aatctgataa ataacatctg caacaaaatc atagctaatg gagaggaacc   153300
agatactttc ccaggaatat cagaaacaag gaagggatgc ctgctttcac tacttctaat   153360
caacatcatt ctagaagtct tactaattcc gtaagacatg aaaagtaaat acactgtata   153420
catattggga aggaaggaat aaaactattt cttcacagat gagatcactg tctatgtaga   153480
aaatctcgaa gaatcaaaaa aaatatccct ggaactaaaa tacaattaca gcacaactga   153540
ggggtaaaga gtttatatac agaagtcaat cgccttctta taaatcagta atgaacaact   153600
cgaatctgaa attacattcc acttacatta gcgccctccc taaaatgaaa tatttagcta   153660
taaacctaac aaaacatgta gaacatctgt ttgggaaaaa catgactgat gaaaaatctt   153720
aaaaaatgga gagaggatcc atgttcatgg ataaggaggc tcaatactgt caagatgtca   153780
ggtcttttcca cttgatctaa aagtcagtgt aatcccaaag tcccagcaag ttattctgtg  153840
gttaacgaca aaatgactct aaagttcaca tggagaagta agagaccctg agtggccaaa   153900
caatattaaa ggagaataaa gttggaggat tgaccctact ttaagactta ataaaaagat   153960
attaataatc aatatagtgt ggtattggtg aaggaataga caaatagaat ggaacaaaac   154020
agagggcccc aaataggtcc acataaatac ataagaacaa aggcaataca atcttgaaaa   154080
gttggtcttc tcaacaaatg gtgttggtga gctcccgctg tggcacaagg ggatccctgg   154140
cctggaagct ccatatactg tggggcagcc aaaaatgatc aaaaaaaaaa aaagctaaaa   154200
aaccaaatg gtgtcacaac atcaccgtgc cctgcccaga tctttcaccc ttcacaacaa   154260
ttacctcaaa atggataata gacctacatg taaaatgcaa actataaaac taatataaaa   154320
tctaggtaaa cttgagtttg gcaatgcatt tttacataca acaccaaaag caccatcaat   154380
gaaagaaaaa aattgctaag aattcattca ttaggagttc ccgtcgtggc gcagtggtta   154440
acgaatccaa ctaggaacca tgaggttgcg ggttcggtcc ctgcccttgc tcagtgggtt   154500
gacgatccga agttgccgtg agctgtggtg taggttgcag acgcggctcg gatcccgcgt   154560
tgctgtggct ctggcgtagg ctggcggcta cagctccgat tcaaccccta gcctgggaac   154620
```

```
ctccatatgc ctcgggagcg gcccaagaaa tggcaaaaag acaaaaaaaa aaaaaaaaaa  154680
aaaagaattc attcgttaaa attaaacatt tctggagttc ctattgtggc acagtggaaa  154740
tgaatccgac taggaaccat gaggttgtgg gttcgatccc tggcctcgct cagtaggtta  154800
aggacctggt gttgcatgag ctgtggtata ggttgcagac acggcttgga tctggcattg  154860
tgtggctgtg cacaggctg gcagctacag ctctgattta gaccctagc ctgggaacct  154920 ccatatgctg cggggtggc cttaagaaa agcccaaaaa aaaaaaaaaa aaaaaaaaaa  154980
agtaaacaat aatatactta atgccccaga gcggttcatt taaacatggt taaaatggag  155040
ttcctactgc ggcacaacag gatcggcagc atctctgaag tgctgggatg cacgtttgat  155100
cttggcacaa tgggttaagg atccaacgtt gctgcagctg gggcaaagga acttcatatg  155160
ccacgaggtg accaaaaaag aaaaaaaaag aaaaaaaatt taaatttctg ctctgcaaaa  155220
gatactgttt agagaatgaa agaaaggat acagattggg agaaaacata tgcaaaatac  155280
atatctgata aagaactcat atccaaaaca cacaaagaat ggttgaaact caacaattag  155340
aaaacaaccc aattaaaaat tgggcaaaag atctgaacag acaattcacc aagaagata  155400 tacatatggt aaataaaaac atgaaaagat gctcaacacc atctgtcatt tgggaattgc  155460
aaattaaaac agcaatgaga taccaccaag catccctaag aatggctaaa atccaaaaca  155520
ccgacaacac caaatactgg aaaggatagc cgatcaatag gaactctccc attcattgct  155580
actgaaatgg aaaaatggtg cagacactt ttccactttt ggaagacagg cagtttcttt  155640 tcttttttt tttgccttt ctaggcccgc tcccgcagca tatggaggtt cccagaattg  155700
gagctgtagc cgctggccta tgccagagcc acagcaactc gggatctgag cagagtcttc  155760
gacccacacc acagctcatg gcaacgccgg atccttaacc cactgagcaa ggccagggac  155820
cgaacccgca acctcatggt tcctagcagg attcgttaac cactgcacca agatgggaac  155880
tcccgaagac aggcagttc ttacaaaact aaaaatactc ttatcatatg accctgctcc  155940
ttggtatttt cccaaatgag ttgaaagttt atgtccacac aaaacctgca cacgaatgtt  156000
tttggaggca ttattcataa ctgtcaaaac agggaaacac caagatgtcc ttactgatgg  156060
atgaacaaat attggtacat ccatacaatg aactcagcgt tttaaaaaa aaaaaaaaaa  156120 aaaaaaaagg tagttcccgt tgaggctcag cagattatga atctgactaa tatctatgaa  156180
gatgtgggtt cgatccctgg ccttgctcag tggcttaagg atctagtgtt gccatgagct  156240
ctggtgtaag tcacagacat ggcttggatt tggtgttgct gtggctgtgg cacaggccag  156300
cagctgcagc tccaacttga cccctagcct gggaactttc atatgccaca ggtgtgcccc  156360 taaaagaaa aaaaaaaag ctattgagcc acgaaaacac atggaggaac agtcaatgca  156420
cactgctaag ggaaaaaagc caatctgaaa agactgcatg tatgattcca actttatggc  156480
attctagaaa aggcaaaacc atggagatag taaaagatca gtgacagcca ggagtttggc  156540
agaggaggag gaagtaaagg agggatggag cacaggggaa tctgggggtg gtgaaactaa  156600
tatgcatgat attgtaaggg tggatacctg ttatacatct gtcaaaacac agcagaaaga  156660
gggatctaaa atgtaactat ggaatagagt taatatgtca caggggctca tcatttatt  156720 cggaacaaat gcagcactaa tgtaagatgt taatgacagg ggaaactggg atgatggaaa  156780
ggggtatatg ggaactctct gggtagctgt agacctcaaa tgcttttgaa aaattctatt  156840 actttttta atgaaagac tgcaaagtag gaattattat ctgcatagct ttaaataatt  156900
tggttaaaag aaaacttgat gacactctta aagatatgag ttctcttgat tttagctttt  156960
```

```
cttttttttct gggaatcagg catatgaggt ttttaaaatt aggacaaaaa caacaaataa    157020
aacctgacat aaaatttact ttttaaccat ttttaagttc atatatatat tttttttttg    157080 gtctttttt tttttctagg gccacttccc gcagcatgtg gaggttccca ggccagggt    157140 ctgatcagaa ctgcagccgc tggcctatgc cagagccaca gcaactcggg atccgagcca    157200
cgtctgcgac ctacaccaca gctcatggca atgccggatc ctttatccac tgagcaaggc    157260
cagggaccga acccacaacc tcatggttcc tagttggatt cgttaaccac tgcgccacga    157320
cgacaggaac ttccaagatc atatgttttt atttatgata gataataagt tattacttct    157380
tatcccttct tttttttttt ttttgtcttt gttgctattt cttgggctgc tcccgcggca    157440
tatggaggtt cccaggctag gggtcgaatc agagctgcag ccaccagcct acgccagagc    157500
cacagcaacg cgggatccga gccgcatctg caacctacac cacagctcac ggcaacgccg    157560
gatcattaac ccactgagca agggcaggga ccgaacccgc aacctcatgg ttcctagttg    157620
gattcgttaa ccactgcgcc acgacgacag gaactcccaa gatcatatgt ttttattat    157680 gatagataat aagttattac ttcttatccc ttcttgagat taccagaaca aaagattac    157740 cagaagaaag ggagggtata cttgccttga taaaaacaaa cctcccttaa aacagtgtat    157800
cattaagaac ttagacataa ctggagtcaa tgtggaaaat ctgtaccttt gaaacacaaa    157860
ggtcctattt ctcttgattt atccagtgat cagaaagaca ggaccaggat ttcctgttgt    157920
ggctcagcag taatgacccc aaccagtatc catgaggatg caggtttgat ccttgacccc    157980
tctcagtgag ttaaggatct ggtattgctg tgagcttcaa tgtaggtcac ggacgcggct    158040
tggatctggt gtggctgtgg ctcaggccag cagctgcagc tctgatttga cccttagcct    158100
gggaacttcc atatgccaca aatgtggccc taaaaaaaag accaaaaaaa aaaaaaaaa    158160 aaaaaaaaaa aaaaaagaca ggaagacaag accagacaga tgacagatga ctagcttaga    158220
ggagagtgat ccatgaatga gagtggcagg aaatcctgca taataaaaaa gggagtcaca    158280
ctattaaaag agtgaaaaga acttccgaat acaggaagtt gatttaaaaa aaatcagagc    158340
acagcttaga aaagatgatt aagagtctgt gctctcatga agaaatgatg gctagatgag    158400
aaaaattctg tagaatgatt ctaaattcca aagaaaacag tttaaaatta aaatcgaagg    158460
gcagatcagc attcagacaa aaacaatgtt acttccactg gatctgaagg aactaaatag    158520
cagtttaagc ctagaataaa gaatagtaca ctaaaaacca agaaaaagt gacccaacag    158580 gatctgctta aaaagaaag ttgcaaaatt aggaagaaaa ggtaaattgc aggttaaaaa    158640
caaagagtaa gtagcctggt caagataaac gaaataatgt ctacatacaa gtgaaaaatt    158700
acctattaaa tattttactt gcacactaag atgctccaat atatgaacat tttcactgcc    158760
tcctaggtgt taagaagacg acaaatgaaa atgaaggcct gtgaaacctg gatcttctag    158820
ggcatagaga aaagggactg cattattgcc agtggatatg tattttataa gattttcatt    158880
ttttccatta tatagtgttc tgtcaatttc tactctacag gaaaatgacc cagtcataca    158940
tatataatac attctttttc tctcattatt ctccatcaca tttcgtcaca agtgaccaga    159000
catagttgcc cttgttatgc agcaggatcc cattgcctat ccattccaaa ggcaagagtt    159060
tgcatctatt aagcccaaat tcccagtccc tcctagtccc tcccctccc tatgggcaac    159120 catagtctgt tctccaagtc catgattttc ttttctgtgg aaaggttaat ttgtgccata    159180
cattagattc cagatacaaa tgaagtcata cggtgtttgt cttttctga cttacttcac    159240 tcagtatgaa agtatctagt tccatccata ttgctgcaaa tggcattatt ttgttctttt    159300
tatggctgag tagtcgtcca ttgtgtatat atacatcttc ttagtctgtc gatggacatt    159360
```

```
taagttgttt ccatgtcttg gctgttgtga atagcgctgc aatgaacata ggggtatatg  159420
tatcttgttc aagggaagtt ttgtccagac atatgcccaa gagtgggatt gctgggtcat  159480
gtggtagttc tatatttagc tttccgaggt acctccatac tgttctccat agtggttgta  159540
ccaatttaca ttcccaccaa cgtgcaggag ggttctcttt tctccacgcc ctctccagca  159600
tgtgttattt gttgacttgt taatgatggc cattctgact aatgtgaggt ggtatctcga  159660
tgtagttttg atttgcattt ctcaaataat cagtgatgtt gagcattttt tcacgtgcct  159720
gttggccatc tgtatatcct cttcagagaa atgtctgttc aggtcttttg cccatttttc  159780
aattggattg ttggctttt tgctgttgag tttataaact gtttgtatat tttagagatt  159840
aagcccttgt cagttgcatc ctttgaaact atattttctc ccattctgta agttgtcttg  159900
ttttttttgt tttttatgg tttccttttgc tgtgcaaaag cttgtcagtt tgattaggcc  159960
ccattgcttt tgttttcgct tttatttctg ttgctttggg agactgacct gagaaaacat  160020
ttgttaaggt tgatatcaga ggatgttttg cttatgttct cttctgggag tttgatggtg  160080
tctcgtctta catttaagtc tttaagccat tttgagtttg gtttttttttt gtgtgtgcat  160140 ggtgttaggg tgtgttccag tttcactgac ttacatgtga ctgtccagtt ctcccagcac  160200
catttgctga aaagactgtc ttttagccat tttatattct tgcctccttt gtcgaagatt  160260
aattgaccat aggtgtctgg gtttatttct gggttctctg ttctgttcca ttggtctgta  160320
tgtctgtttt ggtaccagta ccacactgtc ttgatgactg tggctttgta atattgccta  160380
aagtctggga gagtgatgcc tcctgcttgg ttttttgttct tgagattgct gtggcaattc  160440
tggatctttt gtggttccat ataaattttc ggactgtttg ttctagttct gtgaaaaatg  160500
tcatgggtaa tttgataggg attgcactga atctgtagat tgccttgggt agtatggcca  160560 ttttttacaat attaattttt ccaactcagg agcatggaat atctttccat ttctttgcat  160620
cctcttttat agttctcagc atgtaagtct ttcaccttcc tgtcaggttt attcctaggt  160680 atttaattttt ggggggtgta attttaaaag gcattatatt tttgttttcc ttctctggta  160740
tttcattgtt agtatacaga aatgtgactg atttctgaat gttaatctta tatcctgcta  160800
cttggctgaa tttgttgatc agtttgagta gttttttgtgt ggcgtcccta gggtttccta  160860
tgtatagtat catgtcatct gcacacagtg acacttttac ctcttctctt ccaatttgga  160920 tacctttgt ttcttttgtt tgttgattgc tgtggctagg actttcaata catgttgaat  160980
aaaagtggtg aggtgggcat ccttgtctag ttccagattt tcgtgggtag gctttcagct  161040
tttctccatt gagtagtata tttgctctgg gtttgtcata aacagcttct gttatattaa  161100
ggtatgtgcc ctctataccc actttggtaa aagttttgat catgaatgga tgttgggctt  161160
ggtcggatgc ttttctgca tctactgaga tgatcatgtg gttttgact ttcctttgt  161220 taatgtggtg tatgacattg attgatttgc gtacgttgaa ccgtccttgt gaacctgggc  161280
tgaatcccac ttggtcgtgg tgtgtgatct ttcttctatg ttgttggatt cagttggcta  161340
aaattttgtt gagaattttt gagtctatat tcatcagaga tattggcata tcatcttctt  161400
tttggggagt atcttttgtct ggttttggta ttagggtgat ggtggcttca gagagtcctt  161460
gggagtgctc ctcctccttc aacctttcag aaaaattcaa gaaagatggg ttataagttc  161520
tttgtatatt tggcagaatt cgcctgtgaa gccatctggt cctggacttt tgtttatagg  161580
gaatgttttt attacatact ctgtttcagt tctaacgatc agtctattca attgatttct  161640
tcttgattca gttttggcgg gctgtatgcc tctacaaagt tgtccatttc ttccaggttg  161700
```

```
tcaaattggt tggcatataa ttgttcatcg tattctctta tggtgttttg tatctctgca    161760
gtatctgttg agttttctgc cttttgattt cttgttttct ttgatttctt tctctctttg    161820
gtgagtctgg ccagagcttt gtcaattgtt tacccttca aagaaccagc tcttggtttt    161880
atcgatttt tcgattgttt cttgaatctc tattttgtga tttccttcct tctgctgatt     161940
tgggttttgt ttgttctttt tctaattctt tttaggtggt aagttaagtt gttgatttga    162000
gattttctt cttttctgag gaaggcctgt attgcaatga acttccctct aagcaccact     162060
tttgtggcat cccatagatt ttgaatggtt ctgttttctt tatcatctct ctggaggtat    162120
tttttaattt cccttttat ttcctctttg acccactggt tttttagtag catgttattt     162180
agttttcatg tagtcagttt tttctcatat cttgtcctgc ggttgatttc tagcttcatg    162240
ccattgtggt cagagaagat acctgaaatg atctctagac tcttaagttt gttggttagt    162300
tttgtggccc agtatgtggt caatctttga gtatgttcca tgtgcacttg aaaagatgta    162360
cattatgatt attttggatg taatgacctg aatatgtcta ttgtgccact taggatcttt    162420
gttgctttat tgattttctc tgcagaggat ctgtccattg acgtgagtgg ggtattaaag    162480
tctcctactc ttaattatat tcccatcaat ttctcctttt atatctgtta gtatttgttg    162540
tatgtacctg ggtgctccta cgttaggggc atatatattg acaatcctaa tacccttattc   162600
ttgaatggat cctttatca ttaaatgctg tccttctttg tctttatggc ctttgttta      162660
aagtctattt tgtctgatat gagttttgca acttctgctt tcctgtcttt cccattggca    162720
tgaaatatct tttcccatct cctcactttc aatttatatt gtgtcctgtg ccctaaggtg    162780
agtctcttgt agacagcata ttgtaggccc ttgcttttt atccactctg ccacactatg     162840
tcttttgatg aagcattcag tccattgaca tttaaggtaa ttattgataa atgcgtattt    162900
actgccattc gaaaccttgt tttccagttg attctatgtt tctcttttgt tcctttcttt    162960
ttttggttgg atgatttcct tggaaatgta ctctgattag aaaaatctta atctgcatct    163020
tgataacaat gaccaaagaa accacttaca gtaactgcct caaaaagtaa acttttcaaa    163080
gtatcgggca gacttgctaa aactgtcctg gagatgttct acacatgatt cacctgaaga    163140
agaaagtgaa gacttcaatg gggacaaaca atagttacaa cagaagataa gtctccttca    163200
ccccactttc atcttttctt gaaaagcttt gtcaacttta aggcaataat tcaagaaatg    163260
tttcagaggc tactatgtgc aaagctgtgc taggccatga aggaaaacaa atgttgaata   163320
aaagagtctt tacaccctaa taggttaaaa tggggaaaaa cacaaaataa ccatttatta    163380
acaagaaagg taagcacata agacaggcac agatagttct atatgcatgt tcaaaagaac    163440
ctgagggaca ttagtgggag agacccaacc ctaggagaca aggaactata aggttcactc    163500
ttgctatacc tatttacata cctgctatgc accagcaggc acaggggttc tgtcagggct    163560
gggactggaa agaggtcaga aagggggttca ggaggcactc actctcagag ttgaagctga   163620
attaaagaag agggtattgc taatagttac cagtggtgag agggaaaagg agaggggcaa    163680
gataagagta cagtattaag agatataggia gtttctgttg tgttcagtgg aaataaatct   163740
aactagtaac catgaggatg cagattcaat ccctggcctt gctcagtgga ttaaggatct    163800
ggcgttgctg tgagctgtgg tgtaggttac aggtacaggt tgggtctggc attgctgtgg    163860
ctgtggtgta ggctggcagc tgcagctctg attcaacgct tagagtggga acctccacat    163920
gccatcgatg tggccctaaa aaagaccaaa ccaaaaaaaa aaaaaaaag agagagagag     163980
agatacaaac cgctatgtat aaaacagata agcaacaaac ataagttgta cagcacagag    164040
aaatacagcc attattttgt aataaacttta agtggaatat aatctataaa aatcactgca   164100
```

```
ttacacacct gaaactaatg caatttgtaa atcaactata cttcaattaa aaaaaaaact   164160
cagggcatta caaatactga attcacagca attaatcaag cttcactttt tgttattaag   164220
taggatatta tgagtatgaa gaaataaaac acattgaaag ctcaccattt cttttgttt    164280 caaatcccag gaattaagtt cagacgtcaa tcttttccct gattttctat gacttttgt    164340 attttttcta ggagaagggc ttttatcaca aatagcagta ttcacatctt ttgacaacgt   164400
gtacttcttc ctatagatca cagattcttc aactgtctta tttaggagta ctgatttaaa   164460
agtagtttca gattcaatac gccaatcatt ctgcttggta ttttcagtat ttttctcctc   164520
tgaatgttta gaatgatcta gttgttgttg tttgtttctt ttgcaagctt ctgcttctgc   164580
tttatctatt ttgttatgct gcattagttc tttcccatac tgcaccttac tcgtttcctc   164640
agaattatca tcagacattg aagaggatga ttttttttta gtaaggtttt tgttgataat   164700
aatatctagt gggaaaatga gaattaatc cttattaaat ttataaactg atcatattta    164760
aaatttgtta aaaccaaaat atttgttcag acatttcaga aacgagtatt tccctgaacc   164820
cttgttttat atacagagaa aactatgttt caccttgatt aaatgtgtct tctgatgaag   164880
aacttgctct taggttatta cacagcttaa tatttgttac aggtgtccaa catgcccatt   164940
tggagtgcat tttatttcca cagatattgt ctaaaatacc aggtaacctg gaaaataaat   165000
tcatttgctt atttcaaaac atcactagcc tatgactcta agaccttgat tttattagtc   165060
aatgtttatt gacagaaatt tgttaagtat gaagatattt tcttaagtca tgatgaaagc   165120
tgaaatttcc tatataattg ttcagattga agaatattac aaaaaagttc cattattgct   165180
acaattttgt atctacttaa ggcatgtgga agttccaggc tagggtcaa attggagctg     165240 cagctgccag cctatgccac agccatagca atgccagatc caaggtgtgc ctgcaactta   165300
caccacagtt caccacaaca caggatcatt aacccactga gcaaggccag gaaccaaacc   165360
cacatcctca tggatactag ctggattctt aacctgctgg gccacaacgg gaactccagt   165420
atctacctaa ttatacctca catatcttac atgtgtattt tttatggcca tacccatggc   165480
atgtggaagt tcccaggcca ggggtagaat ccaaactgta gctgcagcaa taccagatcc   165540
tttacccctc tgagttgggc tgaggtttga atctacacta ctgcggccac ctcagcccct   165600
gcagttggat tcttaaccca ctgcactaca gcaggaacta cttacaagtg tatttaaact    165660
catattcata ttttattatt taaaaatct tattcatttt aagtttctca atgtgaatac      165720
agttatgttg gttgatatgg aaaaaacata taggctactt taccattgtg ctatcataat   165780
aatacttgaa aattattaat tctaaaacca atactacatt ctaagtctat taagacctct   165840
tcctttaaat tttgatttga tgggttttct catacttaca caggtttatc tatttttccc   165900
actgcctgtg aatcaggaac tatctcctgg agttcatcta aataaaaaaa aaattacagt   165960
attttcattt tttcatgcag ttggcagggt gaaatggaag ccagtataga acttgatcaa   166020
tgttcacata ctggaatgga gagattgatc tcatcttccc catccctgac ccaaactttt   166080
tgggaacaaa ggctactatt atatttcctt gtaactacta gttttttgc ataaagctaa     166140 atatattcat tataaatctt ttttaaaat aaatgaaagc tagtgggatt aaaggcaagt      166200 ataagacaa gtatatgaat atattttaca agaatgacta aaattaaacc aaaaagtact     166260
tactaaaatt ttggtttggg tattcaatgt ccttattttc tgccttttct ataactttag   166320
ttttgatatg ctataaatac aggagaaatt tcaatataag ttttaattaa ggaattacat   166380
aaaagcaact tttaaaagtc agagtattaa agtttaaaac ttttaaaatt tgccttatta   166440
```

```
aaagttagat agcatttcta tttatttcat aagtattatg cccattctag aatactgcat   166500
atcctaaaac acaagaaagt aactttcatt gcagatgagg caaaagatcc tacaaattgt   166560
ctgttctcag ccacagctag aggagtaatt cacttttcat ctcaagaatt tctagaacat   166620
ccatggcaca tctcctattg gtactgctct cacagcctgc atacattctg cctcttcact   166680
aacatacact ggaattggaa attatcaagt gtcaaatgat ttgataaaag ttttggccat   166740
tgcacaggtt aacttcttga ctacagcaag cttccctctt tccatatcca cagatacaca   166800
ctagcccaga tcaaacgaaa atttgccgtc actactggga aaacataccc tctagctaaa   166860
ataccttgct tcatcctgca tgtcttccct gcttactcca gccagtggtc ctttacactg   166920 ggagggagc agtaggaaaa tgcacaggtg taattttgct tgtcacagtg accgaagggt    166980
tctcctgacg atgagtaagc acaggcctag gacactcatc ctttcatatt cagaaccata   167040
tgctacacaa ctgaagaaca gtgcccccta ttaagaaaca ctctgaacca ctactttttt   167100
tccctagtat cttcaactct tgacccctttt aatgtttctg ccacatatcc attaaaattt   167160
tttaaatcta ccatctattc ttctttacta taacaccaag gctgctcaac ttttttggaag  167220 aaattacata tgtttcttaa ctaacgccat aataaaattc atggtcttaa ctctgaactg   167280
ggccctaaca ttgcctaatg cttgtactta ttctcagcct tttccattat ctcttatcag   167340
ttactccaaa tctttgtgtg tcactgagcc tctacttcaa ggatccgtat ccaagagaag   167400
ttcgccatcc tcacagttca gagaaagcaa aagctattag gtgttcctca tctacaaact   167460
tctctgtatt ttggattacc gatttctcca tgatacatta tccattccct gccctgtgcc   167520
cgcttcaact acctagaatg aatgaatgcc cttcttgatg tccatctgac taagggccta   167580
tactgactct ttaaaaatca attcactctc catcttctaa aagagcatct ccttatcttc   167640
accctcccca ttctggggtt aggcacctgt ccctgtccta gatttctatt gcatcctata   167700
atctgagaac acttatacaa tattatatta acttattagt ttgtctaatt ctcatggtag   167760
actttgagat acttaaagac agattccatt agtataaaaa aaccctaatt tttataataa   167820
actaaagaat gatggcaaga ccatttctct taccaaacac ataaatcagt tacattaagt   167880
gaatatttct aaattttatt gttagcacag taaatgagtg ataagaacctt actttcaagt   167940 gcaataaatg atatttaaat ttttttaaaaa cacaatactt taaaaaagtg agacactcac   168000
tgcttgcaaa agaagttagt tcaatatgta tttctacaat aacttgataa aattttatttt   168060 aaaaatgctt tcaaagtaaa gttactttgt ctgtattatc ttctctattt ctttcttcac   168120
atggtctaga tttaagtgat acagcattat ccactccatt ttccgatgtt ttagaaaaac   168180 caggttttte catagaactt gtcatttgca gtggtggttt aattcttcct ctttgtggtg   168240
ttgctaaaaa agaggacaaa agactgctgt ttttgtagga ttttaaaaaa ctgtatgttg   168300
ttattactgt ggtactttt agctgatgaa gggtaaaaaa aggaggttct aggatgggtc    168360
tgaggtttct agctcaaatg agttaagtgg acatggatgt tatttaccaa ggtaagaaat    168420
ggagaaaaac tgccagggag agttgaaaga tgaatttatt ttggacctgc caggtttgag   168480
gagttcgtca acattagat aatttccctg taggcaacta gattttggga gcagaaggtc    168540
attattaaat tgtcataaag attaaataag atgtgtttat agcagctaat agtatcaaat   168600
tactttaaat ttttttattta tcttactatg tacaggcacg gtctcaatat ttcacaatat   168660
ttgtattgaa tgaataactt ctatttaatt ctttaaacaa ttcgatgaag tagacacttt   168720
agttccattt catagaaagg ataaactggt tctaaactta gctagaggat aatctgtacc   168780
agggacacac ctggagtggg caaacaagcc taagaaggcc gactaattta acgttttgtc   168840
```

```
cactatgttg tgctgattcc cacttaaact ataataaatc actaatgctt gatattaata  168900
ttttgaataa tgtttatgtg tcaatatcca ttaaacctct cttagaagac atttgtggtt  168960
catatttttat caattttag atcctcaatt tatcctctag gtaaattatg tccagaatat  169020
ttctgagttt taaaaatgcc tgctttaaat aacaatacta gttagaagtc ttttaagact  169080
ataaagctta catgtgttga ttaaaagtat tggactcctc acagtgtatc tctctgcacc  169140
aggaacaatc attgatgctt cagacatttt tcttttgcta ggagtaatta tcttaaacca  169200
tgaggaaaag ccacagtaaa catatatttt cttttgaaat taaacatcct actactttat  169260
tcctaacatt ttacattaac tacacataaa agatatataa atagcatgat atccagaaat  169320
ctgtgtttta ggctgactag aagataaatc tgtgttttat cctaatgttt ggttctgaat  169380
agatagccaa aacagttaag gagtgttgtt tcaaagaata tttacagaat agccagatta  169440
gaaatacagt acctttaaag attagctgaa aatatttat tgattatcta gttaatagta  169500
aatggctcac aatttactat tctatttcat aaggatgatg tctgcaacac ctatttacat  169560
aaacatttga gaaagctctt ataatgttaa acattcttca aaactttcac acattaaaaa  169620
gctgtattaa tattttgtga agactaaatc gcctttggag taaaaagccg ttataagaat  169680
tcagagactc aacggcacac aaactagtgt tcccaaaacg attcgcattt tctaacttta  169740
gcctagaatg actgataaga gcaacagaaa tagataagca gagccagaga ctgttggggc  169800
cagaagttcc agagggtgac acagaaagga gtacatgatg acgaactgta aagaggcaga  169860
agtgagctgt ttttaaaaaa gcaactgccc ttgagaaaga gaaacaatac tgatggagtt  169920
ttgcacaggt atgtttatga ggcatggagg aagaggtggg aaaggataga agaaaagtga  169980
attctaagat taaccagaaa ataagctact gaaccagcag agtcttctta caggagttac  170040
agttcctagt ggtacataat gaatgtgatc caaaagttac ctattcatat aaatgcttca  170100
gttaatcctc atgaaaacac agtgggtatt taacaatagt gcttaacatc ttttccagat  170160
tttgtgttac gattcaaaag gtttaaggtg ggtggtgtct aagaattaaa taaggactca  170220
agttatgatt ctgatataaa gacacaaaac catggctttt ataatctaat catctgaggg  170280
aattataaaa cgacactttt aactttagga aggacacaga ccaaagggaa aaatagtaac  170340
acaatgaatg gaagagctta tgacagttat agttgtctac aggtgagaga tgagtaaaag  170400
ctaaaataat taggaagagc tccattaaga aaatgaaaat gaggagtttt ttgggggcac  170460
agtgcattag ggattcggct ttgtcactgc aatggctagg gtcgctgctg tggcacaggt  170520
ttgatccctg gcctgggaaa tttccatacg ctgcagatgt ggcagaaaaa aaaagaata  170580
tgaaaatgaa tgaagattta caaatggaag tacactttag ataagttaaa agaaaaggca  170640
caaatacaaa taccgtgaat gaaggcacag agacaagaat gagcatgaca taaagagag  170700
acagtaaagc agctgaccat acttaagtgc agggtatttt gacagagtaa aattaaatca  170760
cgggagattt ccaaactaag tcaaaattta gattcaatgg gataaaccca gaatcacaa  170820
ggctgagtgg aggacactgg tgttaagaaa aatcagtggt acaccacacc gggcagctta  170880
cagaatgaag caatagtatc aaaaacacta ttaggaggtt accatgcaac acaggtgtgc  170940
cagaatgagt agtggcagag ggagtaagga ggaaagggtg taagaggtac caggaacaat  171000
cactagcacc ttggttctag ttgtgagggg agaagaggct gggattgaga acataatcag  171060
aaaaattaac agtaacattc tcgaagtatg gaggcagatg caaatttgag gcaaaagggg  171120
ctttaggaaa gggcatgaag agacatacaa aaggaaatat tgaaagagta agtagagatg  171180
```

```
tagctataga agtttgaagt gaggtctggt atattttaag agcttaaatt atccacagga    171240
ggaaagctcc ctaaggagga agcacagaga tgtccagagg attgggtatc aagcttttag    171300
agcaaatcta catttagaag gtggcgagag aaagcatctc tgatgtagca acaggtaaga    171360
agagaattaa aatgctgata tagaagacaa aggataggac attaaaagag aactgtcagc    171420
aatgtcaagt gtcacagtaa gatgcggaga agactgctaa gaaatggctc tatcaagagt    171480
tcccgtcgtg gctcggtggt taatgaatct gactaggaac catgaggctg agggttcgat    171540
ccctggcctt gctcagtggg ttaaggatcc ggcgttgccg tgagctgtgg tgtaggttgc    171600
agatgcggct tggatccagc gttgctgtgg ctctggtgta ggccggcggc tacagcgccg    171660
attggacccc tagcctggga atctctatgt gcctcgggag tggcccaaga aatggcaaaa    171720
agccaaaaaa aaaaaaaaaa aaaaaaaaaa aaagaaatg cttctatcag atgtggcctg     171780
gaggaggagt tcccgtggtg gctcagcagt tatcgaaccc aactagtatc catgaagatg    171840
tgcgttcgac ccctggcccc actcagtggg ttgaggatcc agtattgctg tgacctgtgg    171900
tgtaggtcgc agatgcggct cagatctggt gtggctgtgg ctgtggcgaa ggccggtagc    171960
tacaactctg attggacccc tagcctggga acctccatat gctgcaggtg cagccctaaa    172020
aaaaccaaaa aaaaaaaaaa gaaaaaatgt ggcctggagg agatactcca tggaacaggc    172080
agaggaggaa aaagaaccta atactttgct ttcgttcctc atgcagatca acgcaacatt    172140
acgttatcaa tttgtattct acaaaaagtg gtggttactg tcctttccta tacatctcta    172200
atttgaaatt tacacgtgtg cagtacacct tgccttaaac ccttaaccct tatacataaa    172260
cacaatttgc tgaaacactc tattttgtta gcgtttgtaa aaggcagagg gaatatcatg    172320
aaatgttatg gacaaattct agattttgt aattatatat atcaatgatt tgacctatgt      172380
tgttttataa atgactattc tgacaccata tatacctcgg gctgaccatg ttttctgtcc    172440
cctttattac tgtttttgat atgttttgga ggtttaacaa attcctcttg agggttagct    172500
ttttctttca aagtagaaag ttcttcaact ggtgaaattt gactttctgg gactagaatc    172560
tgttggaaaa gaaggaaaaa gtgcttaaaa ctgcaaacca tagaaagttt ccaaaaatca    172620
ctgaatgtct taaaaaagca ctcattcatc tcacactcat aaaggtttat aattcttta     172680 tctatgcact gttacaaaag tgacccaaca aaaagcactc acttttcaa atataattag     172740 acataaaata ggcctcggca ttagtgggag aacacatatt tctaattttt taagctaaca    172800
aaactggtat taattaataa tgatctacct tctgcactga aatgaattat tattaacaac    172860
ctgtttaaaa agtcacacac atcttattga ggcaccattt caagacaatt tagatttag    172920 acattcacct tcccagatgg actttattac tatgctatcg ttatttaggg ttaaacttag    172980
cccagcgata aacatcaagt aagtcagaca catacctggg atccacttgc atcgaaaagt    173040
atatgcacag atgttttggc aactgaaata ccttgttttc gggaaaattc ctaaaattaa    173100
attaagggga tgtcattctc ctcccagttc ttcccatttt aatgcaatta tttcctgtat    173160
ctgcttcctt ccaaaactgc ccaatgttac caaagcatta ttatttatgt ctataaagac    173220
ttctctcaga acacatcaat gactccccag taaccacagt cttagcctgc cgttctgcat    173280
tttcctaagt gttcctcaca agcatattac ctgctattct tcaccacaaa ttttttaact    173340
gctacagacg aacatgtcct caacctatcc atgagttgaa acctagttcc caagaatggc    173400
attaggaagg gaggcctttg ggggttgctt agatcgtaag ggcagagtcc ttgggattgg    173460
tgcctttata aaagagaccc cagaaaactc gctcacccat tgaaccattt aaggacacag    173520
tgaaaaaatg gccatcaagg aagtaggaaa tgggccctca ccagacattg aatctgctgg    173580
```

```
catcctgatc tgattcccaa cctccagaac tctgagaaat aaatatttgt tgtttaaggc   173640
acccagtcta tagtatttt tgtttagtagc ctgaacaaac taagacatgc accattcaag   173700
cttgtcaaca gaacgtctcc ccaaacataa catgaactgc actttaattc ccagttaata   173760
tctgattcat aatgtctttc acaatcctga aaagcatctt atctaaattt cattcataac   173820
tttaaggcca tttcaaggcc catttccaca gcctttcttt catatctgac tcttaatgag   173880
cattctcttt cttcaacttc tatacttcat attccatatg ccacttaatt acttttctg    173940
aggcatattc cttaatttgc acaatgttta atatcttgaa aacaaggctt tgtctcatct   174000
cacttttaa acacatggta gaaattcatt aaatgtttg agtgtctgcc cctaattttg     174060
ccatctgaga ttctttctaa taggcatctc aaagggcatg gctaacaatg tgatggccat   174120
tccacaatac aaatttaaag gactaaaaat ctacatgtta ctttaagaac tgtagggaga   174180
aaaaaaaaa tcagtgaaac ttacagctcc aagtaactga aaggttcctg aattatgaaa    174240
aaaaaatgt ttattaagaa gagtttaact taccctgtat ttatttgcac caaatatttt    174300
ttgtgtcaca ttagtgatct ctaatgatgc atcaaaatac aaaagcaatt ctttcccttt   174360
tcgtttacta attttactg tatctttcag aattatagtc aggagcttct tcgagtctct    174420
cactgcatac aaagaaacca cactgattag tttatattca tttctatgac atcactctat   174480
aggtatacta taaataagta aagtatgcag cataccaatt aaagtgacct gaaataaaat   174540
taacttgtag aatttaacag tatttaaatc aatcaatttc ggtactactt aagtaaacaa   174600
gtcagtttat ttttcaaagt ctcagtttcc tgatctctaa attataaggt agtacaataa   174660
ctaatgatct aaagccctga atacattcta gacgataata ggtttttaat aaatattctt   174720
tgaacgcatc tcagaaaact attaatttaa aagaggcaaa gagaaaacaa ctttaattct   174780
gtaagtaact atttctagac acaagcacct attcaaacat ttctattaaa tccacagtgg   174840
ttacagaagt attgagagta aacaaccttt gataaaaact tgagtgccag gaaattgtga   174900
gctaggaagg atacagtgct aatcctcaat aaaatcacca gcccagtgaa aactgtggaa   174960
ttctcattgt ggctcagtgg taccaaacct gactagaata catgaggact tgggttcgat   175020
ccctggttct gctcagtggg ttaaaggatc cagcgttgcc atgagctgtg gtgtaggtca   175080
cagacatggc ctggatctgg catttctgtg gctctgattc ggcccctagt ctaggaaatt   175140
ccatatgctg tgggtatggc cctaaaataa ataaatgcaa tatttgcttc actgcttaaa   175200
tgaccctcat attagagttc agaattatca ccttgctgaa tgttttgtat ctatttgtac   175260
aaactattct ccacatgtat aatgactatc tatgtaagaa tttattgata cttgttatat   175320
tttattgctg aatttgttga aattttgat atttgctttg actgcctaga ctatatcatg   175380
gtttgctttt tagttggaat attactgaga tgccagatct atttgctgc ttgctataaa    175440
attcaagtat ttataggagt tcctgtcatg gctcagcggg gcaagaacct gactagtatc   175500
cataaggatg caggtttgat ccatggcctc actcagtgag ttaagaatct gacattgcca   175560
tgagctgatg tgtgggttgc agatacagct cagatcccat gctgctgtgg ctgtggtgta   175620
ggccagaggc ttagctccaa atccaccct cgcctgggaa cttctatata ctacaggtgg    175680
ggtccttaag aaaaaagag aaaaaaattc aagtatttag atgtcaacat atatggattt   175740
tatatgttac ctagacattt ctgtaggatt ccagtatact atatttatat gaatataata   175800
acatgctttc ttctgcaaag ccattcaaaa agaacttaaa aattgtgtgt gtggagttcc   175860
cgttgtggct cagtggttaa cgaatctgac taggaaccat gaggttgtgg gttcaatccc   175920
```

```
tggccttgct cagtgggttg aggatccagt gttgccgtga gctgtggtgt aggttgcaga    175980
cgtggctcgg atcctgcact gctgtggctc tggtataggc cagcagctac agctccaatt    176040
cgacccctag cctggggacc tccatacgcc gcgagagcag cccaagaaaa tggcaaaaag    176100
acaaaaaaaa aaaaaaattg tgtgtgcagc ctttatttta tacattacta taaacgaaca    176160
taaaaaagtc tcaccaggga gttcccgtcg tggcacagcg gaaacaaatc tgactaggaa    176220
ccatgaggct gcgggttcaa tccctggcct cgctcagtgg gttaaggatc cagtgttgcc    176280
ataagctgtg gtataggtcg cagatgtggc tcagatctgg tgttgctgtg gctgtggtgt    176340
aggctggtgg ctgtagctta gattagaccc ctagcctggg aacctccata tgcgacaggt    176400
gtggccctaa aatgcaaaaa cagaaaacaa acaaaaaagt ctaaccacac tctagcatgc    176460
tgctgcctcc catttccata atctgcaact gtagacattc tttttcacta gaaatactgc    176520
ttgatctcca gactctacac tttttttttt ttttaacttc catgagtttt ggtcacataa    176580
aaattcagat ctcacatgct ccacacagac tagaacactc ctttattaca aagggtacaa    176640
atgaatggtc agatggagag aggagagtgc aaagtctgga agggtcctga acacaggaga    176700
ccctgtccct atggagtctg gagtgcacta ccaagggtta gtataagaac tcaagtgttt    176760
ggagttccca ttgtggctca gtggttaacg aatccaacta ggaaccatgg gattgcaggt    176820
tcgatccctg gccttgctca gtgggttggg gatctggcgt tgccgtgagc tgtggtgtgg    176880
gttgcagatg tggctcagat cctgcattgc tgtggctctg gcataggcca gtggctacag    176940
ctctgacttg atccctagct ggggacttcc atatgctgca ggagcagccc aagaaatggc    177000
aaaaagacaa aaacaaacaa acaaacaaac aaatcccaac aactgaggtg tgtgtactga    177060
tgttaataca aagagtcaa ctattatctt gacatctgaa atttcagtgg aaattttgga    177120
ggagtgcaag gtaaaacaga atgtagaaca ggaatgaata acagaagtaa agagttaata    177180
aaaactatta tctcaaaaat gactatgaat ggaaaaagaa ataaccaca ggagaggacc    177240
ctatgttaaa tgaaatcata ctgtatgatt ccacttgaaa tagtcaattt catagaagaa    177300
aagctagaat ggtagttacc agaggctgag tagaaggggg caaggggcac tgcttaatga    177360
gcatagagtt tcaaattctc aagatgacaa aagttctatt tcacaataat gcgaatatat    177420
atttaacact attgaactat atacttaaaa atggttaaga tggtaaattt tatatgatttt    177480
ttaccgcaat aaaaataaga gaaactgagt aaggatgtat atggaaactt catgtactat    177540
tttatcaagt ttttataatc aaaaactatt ctaaaattaa taatttagct ttaaaaaaag    177600
acccaaatca aattcccaga gatgaaaaat ataatgcctg agataatcat tgcataggat    177660
aggattggaa gcagattagg ccctacagaa gaaaatatta attagcagta aaacacagca    177720
atataaaact attcaaatga aaagagagtg gaaataaaag tatagggtgt agggtggaga    177780
acccagagaa tcagtgagtt gtgggagaac ttcacatgtg taatcagagc ctccagaggg    177840
gaggagaaaa aaagagcaga aaaaaatctc aagaacaatg gataaaaact ttcgaagtgg    177900
agtacctgcc atggtgtagt gggttaagag tctacagagg gtacagagct gcaggtttga    177960
tccctggccc aatacagtag gttaaagaat ccagcactgc ctagctgcgg ctcagattca    178020
atccctggcc ccaggaactt tcatatactg ctggtgcagt cataaaaaaa ataaacaaac    178080
aaacaaaaaa acctgtagaa gcaagcagtt caacgaaccc caagaacaaa caacatgaag    178140
aaaattatac taaaagcacc ataatcatac taatgagcag aaaaatttta aaagcagccg    178200
gggaaaaaag actttaata aaaaggagca aatgtgaaaa cgacagactt ctcatcagaa    178260
ataacgcaaa caaagagaca atagagtaaa atctttaaac tgaaagaaaa agaataggca    178320
```

```
atctagaatt ctatatgtat caaaaacact tttcaaaaat aaagacaagc taacaatttt 178380
atgacatgaa aaaggtgcaa gtgcaagaac tcattaccag aatatttgca ttaaaagaaa 178440
tattggagaa gtaactcagg cagaagaaaa atagtaccag atgaaaatct gggtctatat 178500
aaatgaagcc acaacactgg aaatggtaaa tataaaatac ttaaaaaatc tctttaaaag 178560
ctaactggct gcataaagaa aaatattatt acagcatatt atgaagtctt tgacacatgc 178620
agagacaaaa gtaattttta gtactattga cagcaatgcc acaaaggtca ggaaaccaaa 178680
gtggaatata ttattattac tattaggttc ttacactatt cataaagagg tataatatta 178740
tttgtacaca ctattgaatt aaatatgtat aaaataaacc ctaaatcaac cactaaaaaa 178800
gtgagaataa agccaacaaa agaaatgcaa tgaaaccact gaaaatgaac taatacaaaa 178860
gaagaaaaag atgggaattc ccattgtggc tcagtgagtt aaggacctga cattgtcttt 178920
gtgaggatgt gggtttgaac cctggcctca ttcagtaggt taaggatctg gtgttgcctc 178980
aagctgtggt ataggtggca gatgtcactg cgatctggtg ttgtaggcct cagctgcagt 179040
tccagttcta ccccctagctt gggaacttgc atatgctaca ggtgtagctg ttaaaaaaaa 179100
aaaaaaaaga gggagttccc atcatggcgc agtggttaac gaacccaact aggaaccatg 179160
aggttgcggg ttcggtccct gcccttgctc agtgggttaa cgatccagcg ttgccgtgag 179220
ctgtggtgta ggttgcagac acggctcgga tcccgcgttg ctgtggctct ggcgtaggcc 179280
ggtggctaca gctctgattc gaccccctagc ctgggaacct ccatatgccg caggagcggc 179340
ccaagaaata gcaacaacaa caacaaaaaa aagacaaaag acaaaaaaaa aaaaagaga 179400 aaagaaaaa aaatggcaga tggaacagca ggtagaaaaa aacaaaaacc agatgataaa 179460
tttaatgtag attaatagtc acaataaaaa ccacaattac aaggccaaga ctgtcaaatt 179520
atatttaaaa aacaacaccc agtatctgat gactataaga aatctgcttt aaatatacag 179580
acacaaatga cttaaaaaca atgaaaagtt ttgtcatgct ataattaatc aacagaaatc 179640
ctgaaagagt atgtaaatac tacataaagt atattacaga gcaaagaata ttaccatagg 179700
aaaaacagag tcatttcata aagataaagg ggtcaattta tgaagaaaat accactaaag 179760
gtttatacga ctaataatag aaattcaaaa cgtctgaagt aaaaaatgat aaaactgaaa 179820
agaataggaa aaaatcacaa ttacagtggt gacttaatac ccctctctca ataactgata 179880
gaacaagtag gtaaacaatc tgggaagata tatgactcta acaacactcc tgacccaacc 179940
ctcaacccaa cagcagaata cacattcctt tcaagtgcac acaaaccaa ttacctagac 180000 aaactatatt ctgggtcata agataagcat catatatgta aaaggattct caaatcatac 180060
aacatactct ctgataacaa taaaattaag ttagaaatta gtaacaggaa gatatccctg 180120
aaatcccaag catgtagaaa ttaaataaaa tacttttaaa taaatctgtg tgtcaaggaa 180180
gaaatcaaaa gagaaattta agaatcaagt taatgaaaat ggaaacacaa cacactgtaa 180240
tttgtaggat gctgctaagg gagagtactt agggggagaa tttaaagcac taaaaggcta 180300
cattagacaa ggaaaaaaaa ggagttccca tcgtggctca gcagaaatga atacaaccac 180360
catccatgag gatgcagttt caatccctgg cttgtgcagt gggttaagga tctgggggttg 180420 ccatgagctg tggtgtaggt agcagatgcg gctcggatct ggagtttctg tggctgtagg 180480
ccggcagcca caactccaat tcgaccccta gcctaggaac ttccatatgc catgagtgtg 180540
gccttaaaaa gacggggtgg gggggtctca gatcaatgac ttcagcttcc aacctgaaat 180600
gctagaaatg ggaaagcaaa ttaaaactaa agtaagctga agaaaagaaa taacattaag 180660
```

```
aatacagatc aattaaattg aaaataagaa aacaaaaata gagaacaatc agtgaaacca    180720
aaggctggtt cttttgaaaat atcaataaat ttggtatacc tctcatcaaa ctgactagga    180780
aaagtagcta agacaggagg ccaacactac agaatctaca gacagtaaaa agataataag    180840
gggccattat aaaccacttt attccaataa atttgacaac atggatgaaa tggatagatt    180900
tcttgaaaga caaagattac caaagtttac tcaaggaaaa aaaataggta acctgaaaaa    180960
caatttatct attaataaac tgaatttgta gttaagagcc ttcagcaaag aaaagtaaaa    181020
gtctgagccc acattgcttc atttggtaaa tactaccaag cacttacaga agatacaata    181080
ccaactttac acacactctt agagaaaaat taaagactat ggattacttg ccaattaatt    181140
ctataaggct aagaattcct tgactctgaa acttgaagaa aaaaaaaaaa gacatacatt    181200
ataagaaaac aaaagagctt ctagaacatg aaataccaag ttgcctaact atatttcaca    181260
aatcatttcc aatgatatat tgttgcgaga catgtttcta cagtattttc ttagcctctt    181320
tgcttctatt ttctatgctg aaaattccat cttgttctgc tttactttat cccatattcc    181380
tgcttgaaaa acagtggcag tgctggtata tgacttaagc ttaaaatcaa agaagatgta    181440
aagaaatgga aagatattcc atgttcctgg attgggaaaa tcagtattgt aaaaatggcc    181500
atactaccca aagcaatcta cagattcaat gcaatcccta tcaaattacc catgacattt    181560
ttcacagaac tagaacaaac aatccaaaca tttatatgga acaataaaag acccagaatc    181620
gccaaagcaa tcctgagaaa caaaaaccaa gcaggaggca taactctccc agacttcagg    181680
aaatactaca aagccacagt catcaagaca gtgtgggact ggtatcaaaa cagacagaca    181740
gaccaatgga acagaataga gaatccagaa ataaaccctg cacctatgg tcaattaatc    181800 tttgacaagg gaggcaagaa cataaagtgg gaaaagaaaa gtctattcag caagcattgc    181860
tgggaaacct ggatagctgc atgcaaagca atgaaactag aacacaccct cacaccatgc    181920
acaaaaataa actccaaatg gctgaaagac ttaaatatac cacaggacac catcaaactc    181980
ctagaagaaa acataggcaa aacactctct gacatcaaca tcatgaatat tttctcaggt    182040
cagtctccca aagcaataga aattcgagca aaaataaacc catgggacct catcaaactg    182100
aaaagctttt gcacagcaaa ggaaacccaa agaaaacaa aagacaact ttcagaatgg    182160 gagaaaatag tttcaaatga tgcaaccaac aagggcttaa tctctagaat atataaacaa    182220
cttatacaac ccaacagcaa aaaagccaat cagtcaatgg aaaaatgggc aaaagacctc    182280
aatagacatt tctccaaaga agatatacag atggccagca aacacatgaa aaaatgctca    182340
ccattgctga ttataagaga aatgcaaatc aaaactacca tgagatacca cctcacacca    182400
gtcagaatgg ccatcattaa taaatccaca aataacaagt gctggagggg gtgtggagaa    182460
aagggaaccc tcctgcactg tcggtgggaa tgtaaactgg tacagccact atggggaaca    182520
gtttggagat accttagaaa tctatacata gaacttccat atgacccgc aatcccactc    182580 ttgggcatat atccggacaa aactctactt aaaagagaca cgtacacccg catgttcatt    182640
gcagcactat tcacaatagc caggacatgg aaacaaccca atgtccatt gacagatgat    182700 tggattcgga agatgtggta tatatacaca atggaatact actcagccat aaaaaagaat    182760
gacataatgc catttgcagc aacatggatg gaactagaa aatctcatac tgagtgaaat    182820
gagccagaaa gacaaagaca aataccatat gatatcactt ataactggaa tctaatatcc    182880
agcacaaatg aacatctcct cagaaaagaa aatcatggac ttggagaaga gacttgtggc    182940
tgcctgatgg gagggggagg gagtgggagg gatcaggagc ttgggcttat cagacacaac    183000
ttagaataga tttacaagga gatcctgctg aatagcattg agaactttgt ctagatactc    183060
```

```
atgttgcaac agaagaaagg ctgggggaaa aatgtaattg taatgtatac atgtaaggat   183120
aacctgaccc ccttgctgta cagtaggaaa attaaaaaaa aaaaaaaaga acaaagacct   183180
gaaggcataa gttatccatg tggtcaggct gaatgaggac ttaatgcgtt ggtctagaca   183240
tgctggacct gtgcagacag gcaagccatt tgcacagcat ggtatgtcct ctaaagaatg   183300
agaggaagat gagcctcgtg gccccaaggg gtttatgagg ggtctttagg aggatatgca   183360
ttagcaagga gaaccaggt gcaaacctaa gcatgctgtc tgcagaagca cagtggtgat    183420
tctctaggtg ctatgcatag atagctgaca cccagcttcc tcaatgctca tgattgttaa   183480
atgcctaaag ggcagaataa aagcttaacc agctaccaga tatgtgactt ttaaaatgat   183540
agaagaacta tattctgtac ctacaacccc cgcctcactt gacataatcc tagagagcag   183600
tatggtctct tgaggcgggg ctcttggtcc ctgaaacctt gagtccccc atttccacaa    183660
ttaagataaa tgtctctgtg tcttgtttta tgttaacttt ttccttaagt ttcacagcac   183720
ctgttcttca gccctcacct gctgagctgg tctcgcaatg tataaaagat taatctatca   183780
caaccaagtg gtgtttatcc caggaaagca aagttgatta acatctgaaa atcaatgtat   183840
ttctattaag aaactaaata aggaaaaata tatatcatta ttaatagatg cagaaaaagc   183900
cttttcccaa acccagcact gttaatgatc aaggaaggct ctcatccgca aattacaaat   183960
aaaagagaat ttcctcaatc tgatagaggg catatatgaa aaactgttat cataaatatt   184020
tcatgttgga aaaaacaact gctttcctcc ctaacatcgg ataccaggca aagatgtcgg   184080
ctctcatgac ttctattcaa cactgtactg aaggttcagg gcagtacaag caggtaagtt   184140
gggcaagaat gaccacaaga cttgttggca aggacgtgga acaaccagaa ctcttataca   184200
ctggtggtaa aaatgtaaaa tggtaaaacc attttggaca acagtttgga agttctgaa    184260
ataggtaaca tatagctaag ctatggcaca gtcactatac tccttagtat ttatctaaga   184320
gaaacaaaaa cagatatcca catagataat aacataaata ttcgcagcaa catttttaa    184380
tacctaaaaa ctgagaacat tccatatacc catcaactgg tgaataagta aattcaagta   184440
tattcataca gtggaacacc acccagcaat gaaaaggaat aaaccattga tatatataat   184500
actgctgagt cttaaaaaaa aaaacaaaac tacctattag tttctagct agataaatac    184560
agtactgaaa gaaaatagtc aataattcct actgtatttt ttcaattata taaattctaa   184620
aaaatataaa ctaattcata gtagagaaaa tattagtgat tgcctgggga tggggtagga   184680
gatggataga ttaaaaggaa cctcaacatt tggaggcgat gtatttttat tacttgattg   184740
caatgaagac tgcatgtgtg tttacacacg tgaagaccca cccactccct caatctgatg   184800
aaatatatct tcgaaagacc tttatccaac atcatgctta acagtcaagt atcactgttc   184860
ttccctaagc aaagatcatg agaactagga acaatgacc actttgacca tttctaatca    184920
gtactaaact ggaggttcta gccatcgtac taaggcaaac ggaggaagga aggaataaag   184980
ggagaaaaga ctagcaggag ggagggaggg aggaaagaaa caaagacgaa gaaggaagtt   185040
agttaaggaa gggcataagg atcagaaagt agcaagtaaa accaagctct actcgcagat   185100
accatgacga tccctagacc accctcagga atctacactg caagtactag aaccaaacag   185160
agattttggc aaggtcatag gaaacaagcg aagtacttca aattcaactg tattttata    185220
taccagtaaa aaatatttgg aaaatgaaat caagtcaatt ctatttacaa acatttaagg   185280
caagattgaa gacttaggaa gaagttcatc aaaggatgta tacgacttct acactggaaa   185340
ctacaaaaca ttgttgacag aaattaaaga cttaaataaa tggaaaaata tataccatgt   185400
```

```
tcatgaactc aaatactatt gttatgttat ttctccctgt atcaaaccac aaaccctgtc  185460
acaattctag ctggtaatgt gtagcaattg ataaaccaat tctaaaattt aagtggaaat  185520
tcaaaaggtc tagaatttcc aaaactgtct tgaaaaacac ccacaatgtc agaagactta  185580
cactagctga cttttgagact cactatgaat ctatggtaat aaactagcat agggaatggc  185640
aaatggatca atggaatgga gtataggaac aagacctgaa cctgaatcag tcattcgatt  185700
ttcaacaaag gaaccagaaa tccagtggga aaggaaaac cttttttgtca aatagtcctg  185760 gaataactgt atattcatat gaaaaaatga acctaaactt ctgtgccata ccataaccaa  185820
gtattaattt gagatagata aaaatcctaa aaaaaaaaac caggagaaca tctttgtgac  185880
ttggtagtta ggcaaaaata tgttaggaca cacgaagcaa taaccacgaa agaaaataga  185940
tcatataaac ttcaagttta aaacttctg ctcattaaag acactactgg cagagttcct  186000
gttttggcac agaggtaatg aatctgacta gtatccatga agatatgggt ttgatccctg  186060
gccttgatca ctgggtctag gatctggcga tgctgtgagc tgtggtgtag gtcgtagatt  186120
tggctcagat cccacgttgc tgtgggtgtg gggtaggccg gcagctgtag ctccgattta  186180
acctctagct tggtaacttc cataatgcca tgggtgtggc cctaaaaagc aaaaaaaaaa  186240 aaaaaaaaa aaaaaaagac acccttggga aaatgaatat gtaagacaga tacagattgg  186300
gagaaaatac tcaaagaaca catatatgct aaaggattag tacccagcgt atgtaagaag  186360
tcaaaagtca ataaaaagat agtccaatta aaaaacggcc aaaatatttg aggaaatacc  186420
tcacagggaa gatacatgaa tagccattaa gtacatgaaa aagttctcaa catcactggt  186480
tattaggaaa atgcaaataa aacctattat gataccatta tatgcccact gaaataatta  186540
aaatatgtct tcatatctga atttgtgttg gtaccagttc tccaagttat atgacttctt  186600
ccaactagtg ttacacaact ccagttatag gagtggagaa agaataaatg tttggaccta  186660
atcaaacaaa tacgatacaa gggcaagagc cttgaacgca ctgacacatt gatcatggtt  186720
ttagattaga tagagaagga aataaataca agtattgcg gggtaaggga atttgatgat  186780
attggactat caaatttatg aatgcaaaca tgcgaaaatg tgattttgct tttattagac  186840
tatgtggttt tccacacagt atgcaactta tactccatat aataagaatc aagaagcaaa  186900
ttataggaaa aaagtttaat accttctatg ctgtatattt gcacttttc ctcaggcaca  186960 gtgactgctt cccactgatg atccttaaat ttaaaaatag attttggtaa aaataatttt  187020
ttttcctgct ttaaatctcc tttaaacatc atatacaaac agtaaaggta gttttttttt  187080
tttttttttt tttactaagt ataactaagt aacacatttc ttgctacatc aattgattac  187140
atattatact tgtcacattt aatatttgtt aattcttaaa ggtaaatgac agtactgatt  187200
acttttttga attataactc tttttttttc ttttttgggg ccacacctgt ggcatatcaa  187260
agttcccagg ctagggtca atcggagct actgctgctg gcctaagcca caggcacagc  187320
aacaccagat ccgagtcacg tctgcaacct acaccatagg tcatagcaac accagatcct  187380
taacccactg agcaaggcca gggatcaaac ccgagtcctc atggatccca gtcgggttct  187440
ttaaccattg agccaggaag gaaattctaa attcctattc ttgatcaaaa aagaatgat  187500 tatccattaa tatttactag agtatactcc tttaaaaaaa ttaccaaatc ctagagttcc  187560
ctttgtggca cagcagaaac aaacccctact agtatcaatg aggacttggg tttgatccct  187620
ggcctcactc aggggtcagg gatccagcaa tgccatgagc tgtggtgaag gtcacagagg  187680
aagcttggat cccatgttgc tgtggctggt agctatagct ccaattcaac ccctagcctg  187740
ggaacttcca tatgccatgg gtgtggccct aaaaagaaaa aaaaattacc aaatcttgtc  187800
```

```
atttgtcctc tgcaatgttt tgtgaaacca cagtcatcct ccaatttcca tgcattaatc  187860
accaccgggg cctgtgagtg ggctctgtgt tatgttctta gatacaaaca ttgaatgcat  187920
atcaataata acctaaaatg ttttcccctc ccgagtattt tccttgaaca tctgtataaa  187980
tgaataaaat aatatgaatt cacctaaaaa actcatagta acaattagaa ccattcttaa  188040
aagatgggat cctaaaacct tccaggaatc ttatgaggaa aatagattca aatctttagc  188100
tatttaagga acaccatcc tacagaaatt ccgctaaatc ctccacctct tccctgtact  188160
ctgagggcag cctccagcta aggtgctaac tctcccagac ctcaaagcct cagggtcagg  188220
aggaaagggt tggtatcctc ttctccccc agtgctttga gcagtttctt atttctctgc  188280
tgtaaaacct tgctcctta tggcacacat gagctggcat acataccacg aacttcgaag  188340
agactcttct tcacatatgg agacacctgg tttaaagcct tcctttttta aaaaaagtc  188400
tacattacat aaattttcaa acatgctttt aaaaatagaa atcatagtat ggcgaattca  188460
aactatgccc ttactcctat taccaacagg gtaatagttc caacagttac caacaggagt  188520
tcttgctgtg gcgcaatggg actggtggca tcttgggagc tcccttggga gctctgggat  188580
gcaggttcta ttcccagccc aggcacagtg ggggaaggat cctgcattac cttagctgcg  188640
gcttaggtca caagtgcagc tcagatctga tccctggcct gggaactcca tgtgccacag  188700
ggcacagaaa aaaccaaacc aaaccaaacc aaaccaacaa cccccaaaac cagttaccaa  188760
tatattgtgc ccacttgttt cgtcttcacc ccctactctc cctccattac actctcttcc  188820
tcttgacctc aattttttct tcaatctctc accccagcca tcaatttaaa acccctccc   188880
ttgaatccat acctcgcttt agctccttct atgttcttcc ccttaatttg tctttacttt  188940
ctctacaaat agttcaactt tcaagactg cctaattcca atacttagtg aaactgctct  189000
ttcacagatc accagtttta acatttgttt tgacagtaat gatcatttcc tcccctaaaa  189060
cacagtttta tgattatcca gtaacattta ttactggata aatataactc ttccttttgcc 189120
ttttataagt tgatagcttt ttaatatgtt ctttttttagc cggttcgtca agtgcccttc  189180
aggctagagt cccttctacc tatcctgtat aaatttgtgt tcttctcagt tctcttatct  189240
agacactcct taagtcccat gcttttattt atcatctaaa tatggagggc ttctaaatct  189300
ccacctatgg ctcaggtgtc tactctgaac ttcacaccaa tatatccaac tgcctacgag  189360
aggtcttcag ctgaatatcc tacaagcacc tccaaatcaa aacactcaag gctgaactca  189420
tctttctcat acagaaatta tcatcctgtg acagcatctc catccaacca gttaccaact  189480
tttattaatc cttcttcttt ttattataaa taaataccat gtctacttaa ttcttcctct  189540
caagttttc tggaatccat ccatttccat cctttctcaa tgtcactttc taagactatg  189600
ccaccacaat ttctctcacc tggattacta caaaagtctc ctaactgcct ctggtcttgt  189660
ccctttaaa ccttttctct ccaccagggg aatctttcac acagatgtga tcctcagtgc  189720
ctagcgaatt atctggcaca cagtaagctc ttactaaata tttgttgaac tgatgttatg  189780
tcctatctat aacccttctt tggctccaca ctgccttatt tcttgccaat ctcccttgaa  189840
ttctatgcac taaccatatt acgtatcctt cagttctttg agtattctat ctactcatta  189900
ttaaaatata tgagcccttg agtgagaaaa agacaagtcc ccaatttaat aaatcttatg  189960
tcctatgagg ggaaaatggg caaaaaaaat cctagataaa ctaaaggatt taaatagca   190020
ataactacta gaaggaaat aaaacaggac aatgtgatat gatatggctg gaaggctact   190080
ttatactgag ttaccacaga atacctctat aaggaggtaa tatttatgct gaaatctaaa  190140
```

```
tgggaaggaa ctaagatgca aagatctgga ggtccatagg cagaagaacc agcaaacaga    190200
aagacctgaa ataagcatga tctagaatgt ggctagaaca tagtaaacat agagaacact    190260
ctgagcgtat gagagaaaca accagggcca ggtcataaaa gccatcacac accgtgttaa    190320
agagacaacg gaaggatctt aggcagtcac aatattggag catagcatct aggggagcaa    190380
gagagtacag ggagaatgta ctgctgctcc agaaatccag gggagagagg agtctaacta    190440
taactgtggg aagaagagtc tctcagcacc tctagaccag tgtctggaac acagaaggca    190500
cttaatactt aaaaatgcat tttattctat cgctgtcacg tataatacta taattatttt    190560
ctggtctgaa tattccatta gaccaagcaa gtgaagtcag aaaccacatc aatcctattc    190620
tatcctcttc tcccaaaata aaatccagtt cctaaagaaa atccagttaa caatactcct    190680
acaaaccctg cagagattaa cacactaatg aaaaccatca gtaaccctga gtagtggtgc    190740
tagtttttgg aatccaattt tcagtaagca ttctaagaag gcacgttaaa ataaaaagaa    190800
aggaatgtgg aaatcctaaa aggcatttgg ctcatgtttg tctacagagt ttacctggaa    190860
caaaaagcag gattttagaa gagacagaca aaaaaaaaaa aaaaaacaaa aaaaacaaaa    190920
aaaaaagcgt aaaaagcctc tttatattat cagcagccac aattaggtta gtaaatgcag    190980
atcaattcct gctcagatct tgtcaaagtg actacaagta tgccaatgta gcaaatatta    191040
agtgccagct atttggaaac aatgattcaa gaattttcct cagattaaaa agaggtcagt    191100
agaagacata ccacttggtt ggaaggttta acacagcaa  agacatagca cagaaagaaa    191160
agatctaaaa ttcacttcta gaggcagatc agatggcaga ggagtaagac atcttgctca    191220
cctctcaaaa cacatcaaga aaacacatct acatgtaaaa cgactcgcac agaacatcta    191280
ctgaatgctg gcagaagaac ttaaaccttc aagaagggca agaaactctt gacataactg    191340
ggtagaacaa aaggaaaaaa gagagagcga aaaaaggaat cagacaggac tagcactcct    191400
gaaagggagc tgtgaaagag aaaaggaacc cacatcctgg gaagccacct aaccgaccag    191460
gaggatcagc ttagacagag ggacctcaaa gtcaccgaga aaagcagagc agctggacta    191520
aggaggtcaa agtagagtga gagccacaga gatcatctga accaccagcc cggacaccac    191580
agcctgagac actcgggtgg gggctgggca ctgagactca ggctccgggg tcagtccggg    191640
gaagaggact aggctggctg tgtggggaca gcctgagggg ctaaggagtg gtgcactaca    191700
ggcagaggag cagtgtgcta caggcttggg agtggaacgc cacaggggag ggaacccagg    191760
agaagggctg ggcctgcagg agaagcaagg ctccattgtt gaggagggtg agaggaggag    191820
gggcggagcg tcagaggagt ctccttgggc ctgagcatgt gcccgcatgc tctcagaggg    191880
cagggccgcc gtggtgcagg ctacggggg  caagaagcca cttgctcagg ctacaggaga    191940
ctgggcgcat cttgtccagg ctgtgggtgg ccaggcacct cttgtgtggg ctgagggtag    192000
cgctgggcta agtgcaatgt ggtgcctctt gtgtgatcta caggaggcat ggacaaatgg    192060
cggtggtctt ctcagaggcc agagggaggt gtggcctgcc accactgggg ccagcaagt     192120 tggctccgct tgcagtccag tcatcacagg ggttggcaaa aaagaaaaaa aaaaagagg     192180 gcactgcaac cacgcaccac acattgttgc tctcaggccc atgggaacac accagccctg    192240
cagctgccac tgccaaacac tctggtggt  gtgcagatgc ttgatcactg ttccttccca    192300
agaccctaca actaggagca gttggtgcag cacctcctgc atggcctacg tgggacgagg    192360
tgcttcttgc atggtctaca ggtggcgggg gcaagccacc acagttatca ctgattctag    192420
aggttggcat gctacagcag gggtccgtga acaggcacca cttgaggctc caatcacctc    192480
agaggaaggc tttgcaaatg aacactacct gttgtggctc tcattctcct gggaattcac    192540
```

```
acatcctgct gctgccactg ccaaatgctc tgggcaccct gtcaatctgc ataaggctca  192600
ttaccacttc ccagggccct gcaactagga gtagccagtg gcaccttcct gcaggtcctt  192660
gctgctgtta agagcccagc aaccaggcac tgactataag ccctacccat ggccgctttc  192720
tccctggaaa cacactcagc accctgggaa taacagcctg ctcacaccaa agaaaaagac  192780
agcaaatatc caaactccca caccaaaaat aaatagtaac cccccacaaa atacaaaggg  192840
gtgctctcgc acagaagtag cccccaacac tatagtttcg cttccctaaa cccacagaaa  192900
aagaaaaact taagcaagat gtagaagctc agaaaccatt cccagttaaa ggaacaggac  192960
aattcacctg aagtagcaaa aaatgaaacg gacttctgca gtctgaaaga cattgagtcc  193020
aaaagggaga cagtgaaaat actgaaggaa ttaaggctga atatcaacga actaaaagca  193080
gagataaaca gtaatgcaga ttcctttaga aagaactag aaaataaaag gaggaacata  193140
aaaaattaga aaattcattt gcggagacac aaactgagct aaaggcacta aagagcagaa  193200
tgaataatgc agaggaacaa attagtgact tggaagatag aataatggaa atcatccaat  193260
caggacagca gacaacaaac caaatgaaaa aacacaaaag caatataagg gatttatggg  193320
aaaatataaa gtgggccaat ctacacataa tagaaattcc agaaggagaa gaaaagaaa  193380 aggggattga aaatatattt gaagaaatta tggctgaaaa ctttccaaat ctaaaggaaa  193440
ctgatatcaa gacacaggaa gcacagaggg ccccaaacaa gttgaaccca aacaagccca  193500
caccaagaca cattataata aaaacggcaa aagttaaaga ctaaagagg attctaaagg  193560 cagcaaaaga aaaactaagc gttaactata agggaacccc cacagtgcta tcagctgatt  193620
tctctgattt ctctatagaa acactacatg tcagaaggga gtgacaagat atatttaaag  193680
ttctgaaagg aaaaattttg cagcctagaa tactctatcc agcaagaata tcatttaaaa  193740
tagaaataaa caatttctcc aacaaacaaa agctaaaaga gtacagcaat actaaatgca  193800
ttctaaaaga aatactgaaa gagcttctct aaataaaaaa aagaattaag aagaaatagg  193860
atggaggaaa ccacaattgg aaagcaatca cttaaataag ccatcataca aatctaaaca  193920
tgaagatgtt taaaaaaaga aaaagacttc aaaatcatag aatgtgggga aggaaagtaa  193980
gaaaaaaaga cttcaaaatc atagaatatg gggaaggaaa gtaagaaaat acattcttt  194040 tttttttttt taataatgtg tttaatccta catgactatc aagctaaagc aagcagatac  194100
aggaaaagat taacatactt aaaaaacagg gcaaccacaa atcaaaacca aacactatat  194160
tcaaaaaaac taaaagaaaa agtactcaag cataaaataa atggaaacca tacaaccaaa  194220 aaagaatgg aagaaaagag aaatatagac tcaactggaa aacaaggttt aaaatggcaa  194280
caaatacata tcaataatta ccttatatgt caatgactga atgctccaat caaaggacat  194340
agtgtggcag attggataaa aaagcaaaaa cctataatct gctgtctaca agagactctt  194400
cttagggcaa acgacacata tagactgaaa gtgaggggt gggaaaagat atttcacgcc  194460
aatggacaag acaggaaagc aggagttgca atacccatat cagacaaaac agactttcaa  194520
atgagggcca taagaaaaga caaggagga cactatttaa tggtaaaagg atccattcaa  194580
gaagagaata ttacaatcat caatacatat gcccttaata tagttgcacc cagcacactta  194640 caacaaatac taacagacat aaaaggagaa attgatggga atacaatcat agtaggagac  194700
tttaacaccc cactcacatc aatggacaga tcctctcgac agaaaatcaa taaggcaaaa  194760
gagatcctaa atgacacaat agaaaaatta gacttattcg acattttcag gacattacat  194820
ccaaaaaaac cagaatatac attcttctca agtgcacatg gaacattcta aaggatggat  194880
```

```
cacatattgg ggcacaaagc taaccttaac aaatttaaga gtatagaaat tatttcaagt   194940
atcttctctg accacaatgg catgaaagta gaaatcaacc acaagcaaag aaatgagaca   195000
aaattaacta catggagact aaacaacatg ctactaaaaa accaatgggt caatgaggaa   195060
atcaagaagg aaattaaaaa ataccttgag tcaaatagta atgaagacac aaccattcaa   195120
aatctatggg atgccacaaa agcagtgctc agagggaaat tcatagcaat gaagggcttc   195180
ctcaaaaaga agaaaaatct caacaactta acctatcacc taaatgaatt acaaaaagag   195240
gaacaaatga aacctaaagt cagcagaagg aaggaaatca taaaaatcag aaaggaaatc   195300
aataaaatag agattcaaaa aacaatagaa aaaaaaatta atgaaaccaa gagctgattc   195360
tttgaaaagg taaacaaaat tgacaaacca ctggccagaa taaccaagaa gaggagagaa   195420
aaaaatccat ataaataaga aatgaaaaag gataaatcac aacagataca gcatacacac   195480
aaaaaaaggt aagagaatac tctcaacaac tgtatgccaa ccaatttgac aacctggaag   195540
aaatggacaa ctttgtagag gcatacagcc cgccaaaact gaatcaagaa gaaatcaatt   195600
gaatagactg atccttagaa atgaaacagg gggagttccc gtcgtggcgc agtggttaac   195660
gaatccgact aggaaccatg aggttgcggg ttcggtccct gcccttgctc agtgggttaa   195720
caattcggcg ttgccgtgag ctgtggtgta gattgcagat gcggctcgga tcccgcgttg   195780
ctgtggctct ggcgtaggcc ggtggctaca gctctgattc aaccoctagc ctgggaacct   195840 ccatatgccg cgggagcggc ccaagaaata gcaacaacaa caacaaaaga caaaagatta   195900
aaaaaaaaaa aaaaagaaag agaaataaaa cagaatatgt aataaaaaca ttccctataa   195960
acaaaagtca ggaccagatg gcttcacagg cgaattctgc caaacataca aagaacttat   196020
aacccatctt tcttgaattt ttctgaaagg ttgaaggagg aggagcactc ccaaggactc   196080
tctgaagcca ccatcaccct aataccaaaa ccagacaaag atactcccca aaaagaagat   196140
gatatgccaa tatctctgat gaatatagac tcaaaaattc tcaacaaaat tttagccaac   196200
tgaatccaac aacatagaag aaagatcaca caccacgacc aagtgggatt cagcccaggt   196260
tcacaaggac ggttcaacgt acgcaaatca atcaatgtca tacaccacat taacaaaaga   196320
aaagtcaaaa accacatgat catctcagta gatgcagaaa aagcatccga ccaagcccaa   196380
catccattca tgatcaaaac ttttaccaaa gtgggtatag agggcacata ccttaatata   196440
acagaagctg tttatgacaa acccagagca aatatactac tcaatggaga aaagctgaaa   196500
gcctacccac gaaaatctgg aactagacaa ggatgcccac ctcaccactt ttattcaaca   196560
tgtattgaaa gtcctagcca cagcaatcaa caaacaaaag aaacaaaagg tatccaaatt   196620
ggaagagaag aggtaaaagt gtcactgtgt gcagatgaca tgatactata cataggaaac   196680
cctaaggacg ccacacaaaa actactcaaa ctgatcaaca aattcagcca agtagcagga   196740
tataagatta acattcagaa atcagtcaca tttctgtata ctaacaatga aataccagag   196800
aaggaaaaca aaaatataat gccttttaaa attcacccc ccaaaattaa atacctagga   196860
ataaacctga caggaaggtg aaagacttac atgctgagaa ctataaaaga ggatgcaaag   196920
aaatggaaag atattccatg ctcctgagtt ggaaaaatta atattgtaaa atggccata   196980 ctacccaagg caatctacag attcagtgca atccctatca aattacccat gacatttttc   197040
acagaactag aacaaacagt ccgaaaattt atatggaacc acaaaagatc cagaattgcc   197100
acagcaatct caagaacaaa accaagcag gaggcatcac tctcccagac ttcaggcaat   197160
attacaaagc cacagtcatc aagacagtgt ggtactggta ccaaaacaga catacagacc   197220
aatggaacag aacagagaac ccagaaataa acccagacac ctatggtcaa ttaatcttcg   197280
```

```
acaaaggagg caagaatata aaatggctaa aagacagtct tttcagcaaa tggtgctggg   197340
agaactggac agtcacatgt aagtcagtga aactggaaca caccctaaca ccatgcacac   197400
acaaaaaaaa aactaaactc aaaatggctt aaagacttaa atgtaagacg agacaccatc   197460
aaactcccag aagagaacat aagcaaaaca tcctctgata tcaaccttaa caaatgtttt   197520
ctcaggtcag tctcccaaag caacagaaat aaaagcgaaa acaaaaacca atggggccta   197580
atcaaactga caagcttttg cacagcaaag gaaaccataa aaaaacaaaa aaaaacaaga   197640
caacttacag aatgggagaa aatatagttt caaaggatgc aactgacaag ggcttaatct   197700
ctaaaatata caaacagttt atacaactca acagcaaaaa agccaacaat ccaattgaaa   197760
aatgggcaaa agacctgaac agacatttct ctgaagagga tatacagatg ccaacgggc    197820 acgtgaaaaa atgctcaaca tcactgatta tttgagaaat gcaaatcaaa actacatcga   197880
gataccacct cacactagtc agaatggccg tcattaacaa gtcaacaaat aacacatgct   197940
ggagagggcg tggagaaaag agaaccctcc tgcacgttgg tgggaatgta aattggtaca   198000
accactatgg agaacagtat ggaggtacct cggaaagcta aatatagaac taccacatga   198060
cccagcaatc ccactcttgg gcatatgtct ggacaaaact tcccttgaac aagatacata   198120 taccectatg ttcattgcag cgctattcac aacagccaag acatggaaac aacctaaatg   198180
tccatcgaca gactaagaag atgtatatat acacaatgga tgactactca gccatagaaa   198240
gaacaaaata atgccatttg cagcaatatg gatggaacta gatactttca tactgagtga   198300
agtaagtcag aaaaagacaa acaccgtatg acttcatttg tatctggaat ctaatgtatg   198360
gcacaaatta acctttccac agaaaagaaa atcatggact tggagaacag actatggttg   198420
cccatagggg gggggaggga ctaggaggga ctgggaattt gggcttaata gatgcaaact   198480
cttgcctttg gaatggatag gcaatgggat cctgctgcat agcaagggga actatgtctg   198540
gtcacttgtg atggagcatg ataatgtgag aaaaaaaaac atatacatgt atttgcgact   198600
gggtcacctt gctgtgcatt agaaaactga agaacactg aatgtcagct ataagggaa    198660 aaataaaaat catcatgtat gaaaaataa aattcactc tcaatactac cataataatc    198720
aatccttcac tattcttaaa tagaagattc tacaaatgag taagtccatt tgtcattatg   198780
tgtcaatgtt acatctttt tttttttttt taggtttgca cctggggtgt atggaaatcc     198840
caggctaggg agctgcaggt gctggccttc atcacagcca ctgtaactcc atatccaagc   198900
cacatctgca acctacacca caggttgcag caacacttcc ttaacccact gagcaagacc   198960
agggattgaa cacccatgct catggatact ggtcgggctc ttaacccact gagccacaac   199020
tggaactcct gttgatgtta tttttaactg agtgcctctg tatttgaata actattaact   199080
tttccagatt caattcattt tgttcatgtg aatgttaaat tttatcatta acatgtaatt   199140
tacttctgaa aaacttatat taaaaaacta gcattaggaa ttcctgttat ggctcagcag   199200
taatgaaccc aactagtacc tgtaaggatg caggtttgat ccctggcctc actcagtggg   199260
ttaaggatcc ggcgttgcca tgagctgtgg tataggttgc agatgtggct tggaaatggc   199320
attcctatgg ctgcggtgta ggccagcagc tacagctcca attcgacccc tagcctggga   199380
acttccatat gctgcagatg aggccctaaa atgaaaaaaa caaacaaaaa acctagcatt   199440
aattttagca ttttttctgt tacaataaaa catcagaaat aattttcatt tctaattagc   199500
ttgataggtt accatgctaa tcaaaactac tggaggtaac agtgataact attaaaacag   199560
caagaaaata aatatacaaa gaaatccaca ttcttttttt tcttttttct tttagggct    199620
```

```
gcacctgtga aacatggaag ttaccaggct agaggatgaa acagctgcag ctgccagcct    199680
ttgccacagc cacagcaaat ctgagctgca tctacaacct acgccatagc ttgcggcaat    199740
gctggatcct taacccagtg aaggaggcca gggaaagaat tgacatcctc atgaagacta    199800
gttgggttct taacctgctg agtcacaaca ggagttccca gaaatcccata ttcctaaatt    199860 gaatgacaat actgtgcata tgcgtgtgtg tgtgtgtgta gacacacaca tataaaatgg    199920
tacagaggaa ataaagctta catcattgtc tccagcgatg tagaaagaca gagtctggct    199980
cccaagatta aaatctatcc aaaagtcctc aagttttttca tctgacggta tttgcagcta    200040
ataaaataaa catataaaac tagtacacta cgctttcaaa agtgacaaaa gaaaattacg    200100
agcatgttat agttgaattt caggaaaaag aaaagaacat agctagaagg taaggggaga    200160
taaaaagcag acatgtacag catttaaatc aattcagaaa caagggaaag aaatgctgct    200220
taatacttca cacaggagaa agctagcttc aagaaatcac aactgttcca agtgcaaata    200280
aagtttaaag tattttcatg tttgaatatc ttcatcaaca ataaacaata atgggcttga    200340
ttaagaaaaa aataaaaaaa tttcaagtag agcttttata tttcatttat ccttggctac    200400
aaacatgcca tttcataaaa tgtcacttca gataaagaat aatgcattgg ctatatctgt    200460
gatgtaatta tgataacatt aataatgctc ttgtcaattt gtgacctgaa atcactcgat    200520
ccctgaatca aagttcatct attaaaattt attaaattga aaacttacct catatttatc    200580
aagaaacgct gataaacaag gaaatgtaaa gaccctgaaa taaagagcag cttgagttaa    200640
agaaaaaatt aacaagcctt cacagcataa tcttgatgag ccatacaaat cacacctagg    200700
atcaaaagga aattgggcag tagtgacaac ttaaaataaa ttgtatttcc ttcttcatca    200760
ctttttaaag attttaatgg aaatttcttt ctgagagaaa acatattact ttgaggatac    200820
tactcgacct accactttga ctaaagttaa actgtaccaa attacttttc atgctattga    200880
ctatgtgcag agattcctaa tttagtttat actagtaata taatggaagt tcccaaagga    200940
ttagatggga gaaggagaat agaagtgcta ataaaaatgg ctgaattcac ggaatacttt    201000
cttggtcaga tgctgttata agtacatagc atgtaaccat ctcattgaat ctttacaaca    201060
aacatataaa ggtagatatt attagtattc ttatcctata gctaaggaaa ctgaggcaag    201120
gaagcttaaa taacttgtcc aacattaaaa tagtaagagg ggaacctatt atccaaatct    201180
aaccagaatg actcttgcac ttaacctatc ttttgtttcc ttagtaggga aaacaaatgt    201240
gaactcattc atccaatgtg tcctgagcat ctataaggtg ccaggcactg cactaaaaat    201300
actcagttct tctgtcattg aaagaagtaa taaaaattta cattacctat ccttccatga    201360
ccattcctga ggttaaataa cctcagaaag aacatcctta gagtatgtta attataaaag    201420
ataatttata tctgctatat agttttactc cagtatgtga acaaaggagg tagctcaagt    201480
gatatttata cctagatttt taaaaattcc ttaaacatta aatttacaat ttagtacatg    201540
cagttctaaa atatagtaaa ccaattttag acaaagttat taactgatat tgactgaata    201600
aagttttcct ctaaaaagtg caaagaaaaa aaaaaggagt tcccatcgtg gagcagcaga    201660
aactaatctg catccgacta ggaaccatga ggttgcaggt tcaatccctg cctcgctca     201720 gtaggttaag gatctggtgt tgccatgagg tgtggtgtac gtcgcagaca tggctcagat    201780
ctggcgttgc tgtagctgtg gctgtggtgt aggctggcag ctgtagctcc aattcaaccc    201840
ccagcatggg aacctccata tgttgcgagt gcagcccaaa aaagcaaaaa taaaaaaatt    201900
aaaaaaaaaa aaaaaacac taaaaagtac aaagtcaaat aagaccagtg gaggattatt    201960
tcagcctagc ggtgtgtgct ctctcttgag ctctgtttaa tcattaaatg gttgtatttt    202020
```

```
gcattgttta ccttctcttg tctccaagta tgccatttac aaggttgaga aacatcctgc 202080
aatcctaatt ttaaaaaaga gagagttttt aaaaacacag caattataaa gaactattgt 202140
taacttgcta ttctgatact acttactgtt tcaaattcag agtctttaat tcctttaaat 202200
gcattagcaa caaaatccat tgaaaaccac tgacatgcta gttcttgcct ctgtttttct 202260
gtggtcattc tgcataaagc ttctacgata cccacttgta agtcataatc tttaaaaaaa 202320
attgttaatg tactattaaa attatgaaaa ttaagacttt acagaggtca ctatacttta 202380
taaagtgtta gaacaaccaa gagaaataag gaacatgttg taatttactc atcttttgcc 202440
attttcttca tattgactag aaatatctta tcattataga aatgaataca gaccaaataa 202500
caaaaacaaa tttactaaca gcagacagaa ctaaaaaaaa aattttttaag gaaatttttaa 202560 aaaacgccca aatatgcaaa gattgtgtca ctttattatt aagagttgtg aacgcagaat 202620
aattcacaca aaagtctata aatcacaggt aatctttgtt ttccttacag ttattctaaa 202680
gcactttaaa ccagtggttt attctatacg taaatcacta catcaaattt tttgtctttt 202740
cagggttgca cccatggcat atggaagttc tcatgctagg gtcgaatcag agctgcagct 202800
accagcctat gccacagcca caacaatgtg ggatccgagc cttgtctgcg acctacacca 202860
tagctcacca catcactgga tccttaaccc actgagcaag accagggatt gaaccctcgt 202920
cctcagggat actagtcagg ttcattactg ctgatccacg atgggaactc ctacatcaaa 202980
attttctaat atgtaactct gaactggaga ttggctcatg ccatctgcct ctacatggat 203040
taaatcatga gctactgcag ctgctgacat gctgcacccc ctgagcggag ctcaaggtgg 203100
agaccagtta tgaggcactc tgtgctctgg gaaaagtgaa agaatggatc ttgaaacaga 203160 tattttttata agatttttatg agcccaatac ttgcatctcc tcatatccag aaaaactcca 203220
aaatccttca tgacaactga tgtctgtgtc tagtaataac cttaggacca gcgacaaaat 203280
tctataagat gtgtgcatgg ttttatgcac ttccccttc accttcatca tatatatact 203340
gatattcccc ctttcgtctt tggggcagta tctcagagct gtctgaaata ctgctgccag 203400
ggctattctt tctaaaaaca gaaagatgtc acagtcatct gtgaatgtag ccactcgcaa 203460
gggtgagcta gtgagccctg agggaattca ggaaagaaac aaagaatact gacccccaatt 203520 gctgaagtgc catatcaaag ggtgattcca ctaagcccag acctttgctt cttcccctg 203580 aattccttaa cttgagataa tctggttctg taaatctttt gtttctacta ctcgcttgtt 203640
gctgaaaaag ctcctataaa tcctagctac cccctcacct cctcagagca gttttttcag 203700
ggctacctga gatgctgtct ccctgactta aatcctaatt ttgccccaag taaagcttaa 203760
ctctcagctt tcaggttgtg cattttttta aattgacata acttaggaaa gacaatttga 203820
gttctttaaa gaaaaacata gctttacaat tcaaatatat gagtcccaag aatatcaaac 203880
cttctaattt catataatac agttaagaca tttctgggca aagggaattc aaatctatta 203940
ggaaactgag ttatgattca tatatctacc attaggcaca aattatattt gacaactcct 204000
actataacac ttattatttt tagtccctca gatatttatc ctttaattac ttattagagc 204060
aattaaaact tgcttgattg tacatggaca gcttatacgt accctatttt cacattcaa 204120 tgttaacatt attttgattg agatactata ttctaataat aaatttgaaa taatttcaaa 204180
tatgaacatt ttgaaaaaac atacctccag catctaaaat cctttctccc atactactcc 204240
tgtgaatcaa aacaacagat tatatactag gactactatc aattaaatat aaagctcata 204300
tgttgactag tatcaatacg actttggcag aaaacatatt cataaattat attagaaatc 204360
```

```
tacaatagtt tattattttt aattattaat ggatgtcatg gttgccttat ttgccttata 204420
aaacattatt atattcttga cctgaaccac taatttaccc ataaagcaca aattattaca 204480
tgagaatcaa catttcttgg ttaaagagta ttttcctggc atcttgaggc atcttgtcaa 204540
gcatagcatt cattttcttt agagtctaga aagaaaaaa agttaatccg ttaactttat 204600
atattcaatg aaacattaag tacttagaga tatattctag gtacataaac ttagaagcct 204660 atttttttt aatcacagtt aatcacagca tgttatacaa ggaataaagg gtggaggaaa 204720
gtatgtatgt ataaaatagt gaatacaaga aaatataaaa cacagaatat caaaaacaaa 204780
atataccatg attcctgtac ctaaagcagt tatactctta gcagcatgac atgtgtttat 204840
tactactcta ttataggagt taaggaagca aatgatagta ccccattgat atctgttctt 204900
gtggtcacac acatgtacat acacatagac actaatacaa gttattttta gcatttaaat 204960
acttaagaac tccaaatatg tagacagtat agtttatatt ttcatatgag ctataggtat 205020
acacaaactc acatgattat aaatttccaa cacacacata taatatactc atgtcaggca 205080
atgaattgtt aggacaatca aaacagacca tattaaaatt aatttaatgc caagataaca 205140
taattattca atttgataaa ttgctaccaa actttcttca ttttctcttt aggttttaaa 205200
agaaaatcta aaaaaatgac tttacctcct gctgaacaca aatattcact cttgagtcaa 205260
taaccagggc acaaattcgg ggtatgaaac tttccactac ttgcctttta cctgaataaa 205320
agtgttaagt tattggcaaa tgtgtacttt aaactctttt aaatgacaat cttttctcat 205380
atgagttaat ggaaaggaca tactagttca gttcagaaga aggcccactg actggcctgg 205440
caccaggaca catgaaattc agttctggtt ctgccactaa ctagctatgt aactgaaaaa 205500
tcaccattca acagatgtga ctaatcttaa ctctggcaaa ggaataaccc cagatccagc 205560
tgcttctttt aggcacataa agcagtatta ctttttggga taaacagata tagttcaaaa 205620
cttctatttt gaggttttca caaaaactgg cctcggtaat ttacagtcat actttcaaaa 205680
ctccataatg gccattaaca ccctttatct tataaagatc taaatatcct cacctatgtc 205740
taaatgtgac cctgtcctct caaaagacaa ggttttatta acattaacta tattcagaga 205800
aatctgccac atgctaattt catgatgcaa atttttaaaa taattttaaa taatggcaat 205860
actgcaacag aaaatgtaca gttttataag gtaactaact acattaaaag aaaaaaaatc 205920
actgaattac gtgaaaagat aaaatgattt acttaaaaaa agttaatca cttcataatc 205980 atgggtgctt taggactgtt ttctccccta aaaacttaag aattgagact agattgttag 206040
gtaattgcaa agaaacctat gaaaaggtag cattaactac tactgaaata aatagcaatt 206100
gatcttttaa aatgttttgg ctttgaaggc agcaaatagc tgtttcttta tttataagca 206160
attcaccagg ctcaattacc aatcatagat aattcttcct caaccaacac agagataaaa 206220
taacttgaac caactgtctg gcactaggca atgccaagca caagtgaaat tatgagttat 206280
aacatgttct gtattctcct tgtactactg agaattttgt ttcatgagac caaggacaaa 206340
ctatggccca cagaccaaat ctgacccact gccccttttc ctatggctgt attcatcagc 206400
aggtattctg tggaaatacc tatcatgatt tagtgagcca gtagtctcag gtgaagttca 206460
ttcattctga taaatgagc caccatcaac caccactgaa aggctctggt aattagcttg 206520
ggctgcagag ttggtaaggt ttcttaatga attcaacctc aaactccaag gcaaaatagt 206580
atttacatga gaaacttata cttcagtaaa gttacttcaa tgaaactatg gtcatctgaa 206640
tcacaagtaa tgtgcagctg ctttatacat tttccaggct atcaaaagct aagacaggaa 206700
gtgacatctc cattcccaac acaaatttat aggggatata ttttttccaa gctccaacca 206760
```

```
cagacccagc agcatttta gatgctgatg taagtgcaaa ggaaatttcc ttatttcaaa  206820
gttcatttaa ctgtgcaact gaagagcttc cacctaacct tcaactgaaa gtgattaaaa  206880
gtccttaaaa gtcattaaaa gtccttaaaa gtcatctcat ggcaatgaca ctctaaatgg  206940
caaatattaa gaacaaaagt ttgaaatatt tccataaatg acttccaagt gatgaatatg  207000
ctcaattaaa aatcatgttc atgaactgat accagtattc ggcattatct gcataaaaag  207060 acattttct  aatgcaataa atacaaaacc tcattacaga taagcatgaa caaataaaca  207120
tttgcaatta attttttaa cagcaaacac taactctgaa ccttaactaa gaattaatga  207180
acccgactag catccatgag gatgcaggtt caatccctgg cctgctcagt gggttaagga  207240
tctggcatta ctgtaagctg tggtgtaggt cacagactca gctcggattc tgcgttgctg  207300
tggttctggc ataggctggc ggtacagctc tgattcgacc tctagcctgg gaacctccat  207360
gtgctgccag tgcagcccta aaagacaaaa taaataaata aataaaaatt aaaaaagaga  207420
gactgagatt cttattaata gacctgtatc acaaaaacac tgtactagat tattgctata  207480
ttttgagttg cattaataaa acatttgtgg acatttgttt tctttccagt ttaataagta  207540
cttacataat accctcattt tctttcttgg cccacaaagt ctaaaatatt taccacctga  207600 cccttacag  aaaagatctg ttgatccatg aattaggtaa tgaactccta atacgacaat  207660
acaatgagaa ttgcaaaatt taccaaaac  tctaacagca aattattgtt ccaacgaaa   207720 tagaatgttc atgataccTT catcatcaat gtcatgtatg acctgaaaag aaagtgaata  207780
atatttaatt gaaaacttac tctcttatac ttaaatcatt acaaatagta ttaaagtaac  207840
atgtaacttt tgaacttaac catgtgatta cttaattaat caggataaaa tcactagcca  207900
atctgttagt gattttttta ggctcagggc atcgagaaca caaattgttt ttaaataaac  207960
acatgctttg taacattggt gaatcaacgt gactgttacc atcaaaagat caaaaaagtc  208020
ttctatcata tttataacag cttcatcttt tgaacttcct tgactcagaa taatctcctt  208080 ggattttca  aaccaggcaa ccatgtaaaa aaaagaaatg tatacattag ttactttgaa  208140
ttcagtttta caatttaag  aatgtattca cacaaacagt aaacctaata gagaaatatc  208200
gaaataaaat tccagcattg catcaaagta aatttatgct cttaaacatc ttcacggttt  208260 ttgcttttg  ataattcact atatgtcccc ccccccttt ttttttttgg tcttttgcc   208320 tcttctaggg ccgcttccca tggcatatgg aggttcccag gctaggggtc taatcggagc  208380
tgtagccgct ggcctacacc acagccacag caacccggga tccgagccgc gtctgcaacc  208440
tacaccacag ctcacggcaa tgctggatcg ttaacccact gagcaagggc agggatcgaa  208500
cccgcaacct catggttcct agtcggattc gtttaccact gagccacgac gggaactcct  208560
atatgtttcc attttaaaga tgcaaatgga tgaagttaat tcatttccaa agtagatgat  208620
c                                                                 208621
```

<210> SEQ ID NO 16
<211> LENGTH: 2889
<212> TYPE: DNA
<213> ORGANISM: Xenopus tropicalis

<400> SEQUENCE: 16

```
gtgaagccgt gacaagctga caggctctgg aagcggatat caccatcatg catcccaaac    60
aggagtctaa gctggaagca atattgacc  acgggttgag gaccaaagga cacgaccttc   120 gcccctgaa  atcatttctt ctgactgaat cctgtgccgg cacatccatt aaatgcagca   180
```

-continued

```
aattccttct tggaaaactt gacaaactga tatgcatgga gcttgatcag agagaagtaa      240
agaacgcatt gctggttctt aatgtaatac ttaaatttgc cagctgtatg acactgaata      300
atgaggaatg gctgactgct tccataaaac agggacttgt acagaagatg attatttggc      360
ttgaaaaatc aacatatttt ttggcttata gtgaaaaaca gaaaaatgaa actgttctca      420
actttgcaga gatttttttt gatattgtta tgctcgttca tgaccacagc agtgagggaa      480
aaatgcagat actggagcat tcctcgtca gagcatgttc cttagtatcc aacgctgcaa       540
caaatatctt cgttaaacaa gaggtagtgc gtaggctgaa tttaatgctg aacactatgc      600
ctctggttgc cagaaagaaa atcctttcta cagaagagat gacttctgcc atggcatcta      660
tggctaaaag aatattagat gctggcgatt ttgatttgca agtggcgatc acagaagctt      720
tgtgccggat gacatcagaa gcgcaaagag aactcaccag tcagtggttt cccatggaat      780
ttatcgctga agcattcaaa agaataaagg attctgagtt tgaaactgac tgcaggaaat      840
tccttaacct gatcaatgga attttgggcg gcaaaaaaag cgttgttacc ttgccttgtc      900
tgtctgcata tcttgacaac cacaagttcc agatgccatg tgatgaaaag ctggaagaat      960
tctggattga ttttaatacc ggtacccaaa gcatttcctt ctacatttct gcaggtgccg     1020
cagaggagca tcagtgggac acagtatgcg tgaaagacag tgatgtgatt gtgtacagca     1080
ttgcagaagt agacaataac aagttactga cagtggatct gaaagcaccg attgccgccg     1140
gtcagtatga agggaagcag atacggatat attttagttg tcctttggat atcttgtctg     1200
ctgctcagag ggtgtttgct gcacaaaaga ataaggactt tattaaaaaa caaaccgcgt     1260
cagatgcaga acaacagtc cgtgttatat ttgaagaatg tcgatctcag atccttctgt      1320
ctgaaagcca agggtccaat tcttctgtga agcctgtggc tgaaccagat gtcaaagatt     1380
ttgctgggaa aaaccaacct ccctctgcag cttcaagcct caagcaaact acttgtaacc     1440
acgagcataa cactaacagc ttaatgccta caactcctgt taaagttaaa atgtcagaat     1500
cttcaatggt tgggtctgga ctgaagataa ctaacatagc cacaaacaac cctgcatcta     1560
ggagaattag gacaaaacct cctttagaaa tggtaaggcc tgctgaaagg aacactgtgc     1620
caccaaataa atcccgaggt gggtcccctt gcagcgacag aactcctcaa ctgccaaagc     1680
ataaatccag tactgatgct gcatgtacat ccaatatgt aaacaaagct cctaaagatg      1740
aattaaatga gattgtgcca gacacacaat attgtgccac aaaggattca tctttattgc     1800
ctggtctcac taagagatct gtaaatcaac atgaaaggaa caggaagcag gaaaacagtg     1860
gcggttttgg aaataaaata agtgtatcgt ctgtatgtat tgctaatcag ggaaagatca     1920
gcagccacct tgtcaagcag cattctaatg aaatatccac aactcccaca aaagaaatgt     1980
ctgctagatc atcagaatca agcattcaga acactgcga gaaacacttg aaagagaaac      2040
ctaaagaact gatccaggct acagatttgt tagttgagaa tatcagaaga agtacgcca      2100 ggctgacaga ggaggataaa agagaagaga atcgttttga gaggaaaaat gtggataaac     2160 atccctgca tacaaacaag gataaaaata gaacaagagg cttcaatcag cacagcccta     2220 aagattttc aacgacgaca aaaaagccat ggaaggatgt ttatgatttc cagtttagcg      2280
caacagataa tccaacgatc aatcttgagg tatcagcacc tactgtgtcg gagaggatga     2340
gcagcaaagc gctggccatt ggcaagaaat caaccaaaaa caaacagaag ggaaagacag     2400
gcacagagat aaagactaaa gctcaccaaa ggcatctgtt cagtgatact gaaagtgaga     2460 gaggggggtga tgatactaaa tccaatttaa gctggttgca agaacaacac agcaaaacga     2520
aacctcccat tgcaacctat agaaggcaaa aagcacagaa gcaacaagaa caaaccatgc     2580
```

-continued

| | |
|---|---|
| catacaagat gaggcacata acaacaaata attcaccaga gcccaaaaca ggcaagaaat | 2640 |
| catataatag gagtggcggc aataagcata ataagctcaa gcgtccttgc agaacagctg | 2700 |
| ccaaaagcac caactataaa gatctctcca actcagagtc agatgctgag gtgcctttt | 2760 |
| cacccccgaa aagagaggag cctgtaagac gcagatgttt gaaataaaaa aaaaaaaaa | 2820 |
| aaaaaaaaaa aaaaaaaaa aaaaaaaaa aaaaagaaa aaaaaaaaa aaaaaaaaa | 2880 |
| aaaaaaaaa | 2889 |

<210> SEQ ID NO 17
<211> LENGTH: 5559
<212> TYPE: DNA
<213> ORGANISM: Pan troglodytes

<400> SEQUENCE: 17

| | |
|---|---|
| gaggcgcaga gttgcgacgc tcggcagcat agggggcggc tccaccgaca ctacgcggac | 60 |
| gcctccttcc gcagatacac agtcatcatc ttactagttc tctgtgttgc tcgctaacca | 120 |
| gtcccccagt tcagtagact ggggcccaaa gcctgcttac ttgacaggtg tttattttgt | 180 |
| cttgcttttt tttttttaa atgaagtcaa atgccaata agaccagatc tccagcagtt | 240 |
| ggaaaaatgc attgatgatg ctttaagaaa aaatgatttc aaacctttga aaacacttt | 300 |
| gcaaattgat atttgtgaag atgtgaagat taaatgcagc aaacagtttt tccacaaggt | 360 |
| ggacaacctt atatgcaggg aacttaataa agaggatatc cacaatgttt cagccatttt | 420 |
| ggtttctgtt ggaagatgtg gcaaaaatat cagtgtattg gggcaagctg gacttctaac | 480 |
| gatgataaaa caaggactaa tacaaaagat ggttgcctgg tttgaaaaat ccaaggacat | 540 |
| tattcagagt caaggaaatt caaaagatga agctgttcta aatatgatag aagacttagt | 600 |
| tgatcttctg ctggtcatac atgatgtcag tgatgaaggt aaaaaacaag tagtggaaag | 660 |
| tttcgtacct cgcatttgtt ccctggttat tgactcaaga gtgaatattt gtattcagca | 720 |
| agagataata aaaagaatga atgctatgct tgacaaaatg cctcaagatg cccggaaaat | 780 |
| actctctaac caagaaatgt taattctcat gagtagtatg ggagaaagga ttttagatgc | 840 |
| tggagattat gacttacagg taggcattgt agaagctttg tgtagaatga ccacagaaaa | 900 |
| acaaagacaa gaactggcac atcagtggtt ttcaatggat tttattgcta aggcatttaa | 960 |
| aagaattaag gactctgaat tgaaacaga ttgcaggata tttctcaacc ttgtaaatgg | 1020 |
| catgcttgga gacaaaagaa gggtctttac atttccttgt ttatcagcat ttcttgataa | 1080 |
| atatgagctg caaataccat cagatgaaaa acttgaggaa ttttggattg attttaatct | 1140 |
| tgggagtcag actctctcat tctacattgc tggagataat gatgatcatc aatgggaagc | 1200 |
| agttactgtg ccagaggaaa aagtacaaat atacagcatt gaagtgagag aatcaaagaa | 1260 |
| gctactgaca ataattctga aaaatacagt aaaaattagc aaaagagaag ggaaagaatt | 1320 |
| gcttttgtat tttgatgcat cactagaaat cactaatgta actcaaaaaa tttttggtgc | 1380 |
| aaataaacat agggaatcta tcagaaaaca aggtatttca gttgccaaaa cgtcgctgca | 1440 |
| tatactttt gatgcaagtg gatcacagat tctagtgcca gaaagtcaaa tctcaccagt | 1500 |
| cggagaagag ctcgttagtt taaggaaaa atcaaagtcc ccaaaggaat ttgctaaacc | 1560 |
| ttcaaaatat atcaaaaaca gtgacaaagg gaatagaaat aatagtcagc ttgagaaaat | 1620 |
| tactcctagc aaaagaaaaa tgtctgaagc atcaatgatt gttctggtg cagatagata | 1680 |
| cactatgaga agtccagtac ttttcagcaa cacatcaata ccaccacgaa gaagaagaat | 1740 |

```
taaaccacca ctgcaaatga tgagttctgc agagaaacct agtgtttctc aaacatcaga    1800
aaatagagtg gataatgctg catcactgaa atctagatca tcagaagaaa gacatagaag    1860
agataataca gacaaacata tcaaaactgc taagtgtgta gaaaacacag aaaataagaa    1920
tgttgaattc ccaaaccaaa attttagtga actccaggat gttataccag attcacagcc    1980
agtggaaaaa agagatcatg ctatattacc tggtgtttta gacaacatct gtggaaataa    2040
aatacacagc aaatgggcat gttggacacc tgtaacaaac attgaactat gtaataacca    2100
aagagcaagt acttcatcag gagacacatt gaatcaagat attgttataa ataaaaaact    2160
tactaaacaa aaatcatcct cttcaatatc tgatcataat tctgaaggaa caggaaaagt    2220
gaaatataag aaagaacaaa ccgaccatat caaaatagat aaagcagaag tagaagtttg    2280
caagaaacac aatcagcaac aaaatcatcc taaatattca gggcagaaaa atactgaaaa    2340
tgccaagcag agtgattggc ctgttgaatc tgaaactact tttaaatcgg ttctcctaaa    2400
taagacaatt gaagaatcgc tgatatataa gaagaaatac atattgtcaa agatgtgaa    2460 tactgctact tgcgataaaa atccatctgc tagcaaaaat gtgcaaagtc atagaaaagc    2520
agagaaagaa ttgacttctg agcttgattc ctgggatttg aaacaaaaaa aaatgagaga    2580
aaagtcaaaa gggaaagaat ttaccgatgt agcagaatcc ttgataagcc aaatcaataa    2640
aagatacaaa acaaaagatg acatcaagtc tacaagaaaa ttaaaggagt ctttgattaa    2700
cagtgatttt tcaaacaaac ctgttgtaca actcagtaag gaaaaagttc agaaaaaag    2760 ctacagaaaa ctgaagacta cctttgttaa tgttacttct gaatgcccag tgaatgatgt    2820 ttacaattttt aatttgaatg gagctgatga ccctatcata aaacttggaa tccaagagtt    2880
tcaagctaca gctaagaag cttgtgcgga taggtcaatt agattggtag gtccaaggaa    2940
tcatgatgaa cttaaatctt ctgtcaaaac aaaagataaa aaaattataa caaatcatca    3000
aaagaaaaat ctgtttagtg atactgaaac agagtacaga tgtgatgaca gcaagactga    3060
tattagctgg ctaagagaac caaaatcaaa accacagcta atagactata gcagaaataa    3120
aaatgtgagg aatcataaaa gtggaaaatc aagatcatcc ttggaaaagg gacagccaag    3180
ctctaaaatg acacccagta aaatatcat gaaaaagacg gacaagacaa ttccggaagg    3240
aagaatcaga cttccacgaa aagcaaccaa aacaaaaaaa aattataaag atctctcaaa    3300
ttcagaatca gagtgtgaac aagaattttc acattcattt aaagagaaca taccagtaaa    3360
ggaggagaat atccattcca gaatgaaaac ggtaaagcta ccaaagaaac aacagaaagt    3420
cttctgtgct gaaacagaaa aggaactatc aaaacaatgc aaaaactcat ctctactaaa    3480
agatgctata cgagataatt gccttgactt atctcccaga tctttatctg gcagtccatc    3540
atctatagaa gtaacgagat gtatagaaa aataacagaa aaggatttta ctcaggatta    3600
tgactgcata acaaaatcta tatcaccttta tccaaaaact tcatcacttg aatccttaaa    3660
tagtaacagt ggagttggag gtacaataaa gtcacccaaa acaatgaga aaacttcct    3720 gtgtgcaagt gaaagttgtt caccaattcc acgaccactg ttttttgccca gacatactcc    3780 aactaagagt aatactattg taaatagaaa aaaaaaagt tctctggtac ttacacaaga    3840
aacacaaaac tgtaacagct attcagatgt aagcagttat agttcagaag aacggtttat    3900
ggaaattgaa tctccacata tcaatgaaaa ttatatacaa agcaaaagag aggaaagtca    3960
tttagcatct tcattatcca agtctagtga aggaagagag aaaacgtggt tgatatgcc    4020 ctgtgatgct actcatgtat caggccccac ccaacatctt agtcgcaaaa gaatatatat    4080
agaagataat ctaagtaatt ccaatgaagt agaaatggaa gagaaaggag aaaggagagc    4140
```

```
aaacttgctt cccaaaaaac tgtgtaaaat tgaagatgca gatcatcata tccacaaaat    4200
gtctgaaagt gtatcttcat tatcaacaaa tgacttttct attccttggg agacctggcg    4260
aaatgaattt gcaggtatag agatgactta tgagacttac gagaggctca attcagaatt    4320
taagagaagg aataatatcc gacataaaat gttgagttat tttactacgc agtcttggaa    4380
aacagctcag caacatctga gaacaataaa tcatcaaagt caggactcta ggattaaaaa    4440
acttgataaa ttccaattca ttatcataga ggagctggag aattttgaaa aagattcaca    4500
gtctttaaaa gatttggaaa aggaatttgt ggacttttgg gaaagatat ttcagatgtt     4560 cagtgcatat caaaaatttt tacttcttag gcttcatctt ttgaaaactt cattggctaa    4620
aagtgtcttc tgtaatactg ataatgaaga aactgttttt acatccgaga tgtgtttgat    4680
gaaagaagat atgaaagtgc tgcaagacag gcttcttaag gacatgctag aagaggagct    4740
tcttaatgta cgcagagaac tgatgtcagt attcatgtct catgaaagaa atgctaatgt    4800
gtgaaatcta gttttatca ccatacttta tctaattatt attctctgtg tataactgag     4860
gaaataagaa tagtcctaca aagagaaaaa tatacatgtc accgaagcaa gtgtacccgtt   4920 tataggaacc ctcaaattaa aaaaaaatgt cttttaatgg atgagaggga accactataa    4980
catgagtcca agcccagaag acttctgtct atacaatatt ttttttact tttggagata     5040 gaagctttaa gaaactttt tgagttaatt atactcataa aatgagtttc tttaataaat     5100
taaattttat tgtgtaaaat gtattattac ataaaatgtg tttttgaatc aatgcagttt    5160
ggggatgaat ataattaaaa tatgtttaat aacttagaat tcaactaata aaaatttagc    5220
cacacttaca aggggagga agtccctagt ttaaaatgta taactgagtg gtagatcagt     5280
actttcagca cactgttgga aacatttatt cagatatggc tctaatgtat taggaagcac    5340
taaatggcct aaaaaagcta ctacattgcc taaatatgtt aattcaatat agaagtccta    5400
tttcataagc aggctgtttg acaaatactt ttaatctagt agtcattgta atatcttgct    5460
agattaattt ataaaatga gtatacattt gatttgcttt taatgaagtt gaaataaatg     5520
cttatgtcac ttgaataaat ataaatcatt atattccta                           5559
```

<210> SEQ ID NO 18
<211> LENGTH: 1225
<212> TYPE: PRT
<213> ORGANISM: Homo sapiens

<400> SEQUENCE: 18

```
Met Ser Ser Pro Leu Gln Arg Ala Val Gly Asp Thr Lys Arg Ala Leu
1               5                   10                  15

Ser Ala Ser Ser Ser Ser Ala Ser Leu Pro Phe Asp Asp Arg Asp
            20                  25                  30

Ser Asn His Thr Ser Glu Gly Asn Gly Asp Ser Leu Leu Ala Asp Glu
        35                  40                  45

Asp Thr Asp Phe Glu Asp Ser Leu Asn Arg Asn Val Lys Lys Arg Ala
    50                  55                  60

Ala Lys Arg Pro Pro Lys Thr Thr Pro Val Ala Lys His Pro Lys Lys
65                  70                  75                  80

Gly Ser Arg Val Val His Arg His Ser Arg Lys Gln Ser Glu Pro Pro
                85                  90                  95

Ala Asn Asp Leu Phe Asn Ala Val Lys Ala Ala Lys Ser Asp Met Gln
            100                 105                 110

Ser Leu Val Asp Glu Trp Leu Asp Ser Tyr Lys Gln Asp Gln Asp Ala
```

```
            115                 120                 125
Gly Phe Leu Glu Leu Val Asn Phe Phe Ile Gln Ser Cys Gly Cys Lys
130                 135                 140

Gly Ile Val Thr Pro Glu Met Phe Lys Lys Met Ser Asn Ser Glu Ile
145                 150                 155                 160

Ile Gln His Leu Thr Glu Gln Phe Asn Glu Asp Ser Gly Asp Tyr Pro
                165                 170                 175

Leu Ile Ala Pro Gly Pro Ser Trp Lys Lys Phe Gln Gly Ser Phe Cys
                180                 185                 190

Glu Phe Val Arg Thr Leu Val Cys Gln Cys Gln Tyr Ser Leu Leu Tyr
                195                 200                 205

Asp Gly Phe Pro Met Asp Asp Leu Ile Ser Leu Thr Gly Leu Ser
210                 215                 220

Asp Ser Gln Val Arg Ala Phe Arg His Thr Ser Thr Leu Ala Ala Met
225                 230                 235                 240

Lys Leu Met Thr Ser Leu Val Lys Val Ala Leu Gln Leu Ser Val His
                245                 250                 255

Gln Asp Asn Asn Gln Arg Gln Tyr Glu Ala Glu Arg Asn Lys Gly Pro
                260                 265                 270

Gly Gln Arg Ala Pro Glu Arg Leu Glu Ser Leu Leu Glu Lys Arg Lys
                275                 280                 285

Glu Leu Gln Glu His Gln Glu Glu Ile Glu Gly Met Met Asn Ala Leu
                290                 295                 300

Phe Arg Gly Val Phe Val His Arg Tyr Arg Asp Val Leu Pro Glu Ile
305                 310                 315                 320

Arg Ala Ile Cys Ile Glu Ile Gly Cys Trp Met Gln Ser Tyr Ser
                325                 330                 335

Thr Ser Phe Leu Thr Asp Ser Tyr Leu Lys Tyr Ile Gly Trp Thr Leu
                340                 345                 350

His Asp Lys His Arg Glu Val Arg Val Lys Cys Val Lys Ala Leu Lys
                355                 360                 365

Gly Leu Tyr Gly Asn Arg Asp Leu Thr Ala Arg Leu Glu Leu Phe Thr
                370                 375                 380

Ser Arg Phe Lys Asp Arg Met Val Ser Met Ile Met Asp Arg Glu Tyr
385                 390                 395                 400

Ser Val Ala Val Glu Ala Val Arg Leu Leu Ile Leu Ile Leu Lys Asn
                405                 410                 415

Met Glu Gly Leu Leu Thr Asp Ala Asp Cys Glu Ser Val Tyr Pro Val
                420                 425                 430

Val Tyr Pro Ser Asn Arg Gly Leu Ala Ser Ala Ala Gly Glu Phe Leu
                435                 440                 445

Tyr Trp Lys Leu Phe Tyr Pro Glu Cys Glu Ile Arg Thr Met Gly Gly
                450                 455                 460

Arg Glu Gln Arg Gln Ser Pro Gly Ala Gln Arg Thr Phe Phe Gln Leu
465                 470                 475                 480

Leu Leu Ser Phe Phe Val Glu Ser Glu Leu His Asp His Ala Ala Tyr
                485                 490                 495

Leu Val Asp Ser Leu Trp Asp Cys Ala Gly Ala Arg Leu Lys Asp Trp
                500                 505                 510

Glu Gly Leu Thr Ser Leu Leu Leu Glu Lys Asp Gln Asn Leu Gly Asp
                515                 520                 525

Val Gln Glu Ser Thr Leu Ile Glu Ile Leu Val Ser Ser Ala Arg Gln
530                 535                 540
```

```
Ala Ser Glu Gly His Pro Val Gly Arg Val Thr Gly Arg Lys Gly
545                 550                 555                 560

Leu Thr Ser Lys Glu Arg Lys Thr Gln Ala Asp Asp Arg Val Lys Leu
            565                 570                 575

Thr Glu His Leu Ile Pro Leu Leu Pro Gln Leu Leu Ala Lys Phe Ser
                580                 585                 590

Ala Asp Ala Glu Lys Val Thr Pro Leu Leu Gln Leu Leu Ser Cys Phe
            595                 600                 605

Asp Leu His Ile Tyr Cys Thr Gly Arg Leu Glu Lys His Leu Glu Leu
            610                 615                 620

Phe Leu Gln Gln Leu Gln Glu Val Val Lys His Ala Glu Pro Ala
625                 630                 635                 640

Val Leu Glu Ala Gly Ala His Ala Leu Tyr Leu Leu Cys Asn Pro Glu
                645                 650                 655

Phe Thr Phe Phe Ser Arg Ala Asp Phe Ala Arg Ser Gln Leu Val Asp
                660                 665                 670

Leu Leu Thr Asp Arg Phe Gln Gln Glu Leu Glu Glu Leu Leu Gln Ser
            675                 680                 685

Ser Phe Leu Asp Glu Asp Glu Val Tyr Asn Leu Ala Ala Thr Leu Lys
690                 695                 700

Arg Leu Ser Ala Phe Tyr Asn Thr His Asp Leu Thr Arg Trp Glu Leu
705                 710                 715                 720

Tyr Glu Pro Cys Cys Gln Leu Leu Gln Lys Ala Val Asp Thr Gly Glu
                725                 730                 735

Val Pro His Gln Val Ile Leu Pro Ala Leu Thr Leu Val Tyr Phe Ser
                740                 745                 750

Ile Leu Trp Thr Leu Thr His Ile Ser Lys Ser Asp Ala Ser Gln Lys
                755                 760                 765

Gln Leu Ser Ser Leu Arg Asp Arg Met Val Ala Phe Cys Glu Leu Cys
            770                 775                 780

Gln Ser Cys Leu Ser Asp Val Asp Thr Glu Ile Gln Glu Gln Ala Phe
785                 790                 795                 800

Val Leu Leu Ser Asp Leu Leu Ile Phe Ser Pro Gln Met Ile Val
                805                 810                 815

Gly Gly Arg Asp Phe Leu Arg Pro Leu Val Phe Phe Pro Glu Ala Thr
                820                 825                 830

Leu Gln Ser Glu Leu Ala Ser Phe Leu Met Asp His Val Phe Ile Gln
            835                 840                 845

Pro Gly Asp Leu Gly Ser Gly Asp Ser Gln Glu Asp His Leu Gln Ile
    850                 855                 860

Glu Arg Leu His Gln Arg Arg Leu Leu Ala Gly Phe Cys Lys Leu
865                 870                 875                 880

Leu Leu Tyr Gly Val Leu Glu Met Asp Ala Ala Ser Asp Val Phe Lys
                885                 890                 895

His Tyr Asn Lys Phe Tyr Asn Asp Tyr Gly Asp Ile Ile Lys Glu Thr
            900                 905                 910

Leu Thr Arg Ala Arg Gln Ile Asp Arg Ser His Cys Ser Arg Ile Leu
            915                 920                 925

Leu Leu Ser Leu Lys Gln Leu Tyr Thr Glu Leu Leu Gln Glu His Gly
            930                 935                 940

Pro Gln Gly Leu Asn Glu Leu Pro Ala Phe Ile Glu Met Arg Asp Leu
945                 950                 955                 960
```

Ala Arg Arg Phe Ala Leu Ser Phe Gly Pro Gln Gln Leu Gln Asn Arg
                965                 970                 975

Asp Leu Val Val Met Leu His Lys Glu Gly Ile Gln Phe Ser Leu Ser
            980                 985                 990

Glu Leu Pro Pro Ala Gly Ser Ser Asn Gln Pro Pro Asn Leu Ala Phe
        995                 1000                1005

Leu Glu Leu Leu Ser Glu Phe Ser Pro Arg Leu Phe His Gln Asp
    1010                1015                1020

Lys Gln Leu Leu Leu Ser Tyr Leu Glu Lys Cys Leu Gln His Val
    1025                1030                1035

Ser Gln Ala Pro Gly His Pro Trp Gly Pro Val Thr Thr Tyr Cys
    1040                1045                1050

His Ser Leu Ser Pro Val Glu Asn Thr Ala Glu Thr Ser Pro Gln
    1055                1060                1065

Val Leu Pro Ser Ser Lys Arg Lys Arg Val Glu Gly Pro Ala Lys
    1070                1075                1080

Pro Asn Arg Glu Asp Val Ser Ser Gln Glu Glu Ser Leu Gln
    1085                1090                1095

Leu Asn Ser Ile Pro Pro Thr Pro Thr Leu Thr Ser Thr Ala Val
    1100                1105                1110

Lys Ser Arg Gln Pro Leu Trp Gly Leu Lys Glu Met Glu Glu Glu
    1115                1120                1125

Asp Gly Ser Glu Leu Asp Phe Ala Gln Gly Gln Pro Val Ala Gly
    1130                1135                1140

Thr Glu Arg Ser Arg Phe Leu Gly Pro Gln Tyr Phe Gln Thr Pro
    1145                1150                1155

His Asn Pro Ser Gly Pro Gly Leu Gly Asn Gln Leu Met Arg Leu
    1160                1165                1170

Ser Leu Met Glu Glu Asp Glu Glu Glu Leu Glu Ile Gln Asp
    1175                1180                1185

Glu Ser Asn Glu Glu Arg Gln Asp Thr Asp Met Gln Ala Ser Ser
    1190                1195                1200

Tyr Ser Ser Thr Ser Glu Arg Gly Leu Asp Leu Leu Asp Ser Thr
    1205                1210                1215

Glu Leu Asp Ile Glu Asp Phe
    1220                1225

<210> SEQ ID NO 19
<211> LENGTH: 1240
<212> TYPE: PRT
<213> ORGANISM: Mus musculus

<400> SEQUENCE: 19

Met Pro Thr Leu Trp Ser Pro Thr Gln His His Gly Ser Ser Ser
1               5                   10                  15

Gly Ser Glu Ser Ser Pro Leu Gln Lys Ser Val Arg Arg Ala Gln Met
                20                  25                  30

Ala Leu Ser Pro Cys Ser Ser Ile Leu Pro Cys Asp Asp Arg Asp
            35                  40                  45

Ser Gln Gly Thr Ala Glu Trp Asp Ser Pro Ser Thr Asn Glu Asp Ser
    50                  55                  60

Asp Phe Glu Asp Ser Leu Arg Arg Asn Val Lys Lys Arg Ala Ala Lys
65                  70                  75                  80

Gln Pro Pro Lys Ala Val Pro Ala Ala Lys His Arg Lys Lys Gln Ser
                85                  90                  95

```
Arg Ile Val Ser Ser Gly Asn Gly Lys Asn Glu Ser Val Pro Ser Thr
            100                 105                 110

Asn Tyr Leu Phe Asp Ala Val Lys Ala Ala Arg Ser Cys Met Gln Ser
            115                 120                 125

Leu Val Asp Glu Trp Leu Asp Asn Tyr Lys Gln Asp Glu Asn Ala Gly
        130                 135                 140

Phe Leu Glu Leu Ile Asn Phe Phe Ile Arg Ala Cys Gly Cys Lys Ser
145                 150                 155                 160

Thr Val Thr Pro Glu Met Phe Lys Thr Met Ser Asn Ser Glu Ile Ile
                165                 170                 175

Gln His Leu Thr Glu Glu Phe Asn Glu Asp Ser Gly Asp Tyr Pro Leu
            180                 185                 190

Thr Ala Pro Gly Pro Ser Trp Lys Lys Phe Gln Gly Ser Phe Cys Glu
        195                 200                 205

Phe Val Lys Thr Leu Val Tyr Gln Cys Gln Tyr Ser Leu Leu Tyr Asp
    210                 215                 220

Gly Phe Pro Met Asp Asp Leu Ile Ser Leu Leu Ile Gly Leu Ser Asp
225                 230                 235                 240

Ser Gln Val Arg Ala Phe Arg His Thr Ser Thr Leu Ala Ala Met Lys
                245                 250                 255

Leu Met Thr Ser Leu Val Lys Val Ala Leu Gln Leu Ser Leu His Lys
            260                 265                 270

Asp Asn Asn Gln Arg Gln Tyr Glu Ala Glu Arg Asn Lys Gly Pro Glu
        275                 280                 285

Gln Arg Ala Pro Glu Arg Leu Glu Ser Leu Leu Glu Lys Arg Lys Glu
    290                 295                 300

Phe Gln Glu Asn Gln Glu Asp Ile Glu Gly Met Met Asn Ala Ile Phe
305                 310                 315                 320

Arg Gly Val Phe Val His Arg Tyr Arg Asp Ile Leu Pro Glu Ile Arg
                325                 330                 335

Ala Ile Cys Ile Glu Glu Ile Gly Tyr Trp Met Gln Ser Tyr Ser Thr
            340                 345                 350

Ser Phe Leu Asn Asp Ser Tyr Leu Lys Tyr Ile Gly Trp Thr Leu His
        355                 360                 365

Asp Lys His Lys Glu Val Arg Leu Lys Cys Val Lys Ala Leu Ala Gly
    370                 375                 380

Leu Tyr Ser Asn Gln Glu Leu Ser Leu Arg Met Glu Leu Phe Thr Asn
385                 390                 395                 400

Arg Phe Lys Asp Arg Met Val Ser Met Val Met Asp Arg Glu Cys Glu
                405                 410                 415

Val Ala Val Glu Ala Ile Arg Leu Leu Thr Leu Ile Leu Lys Asn Met
            420                 425                 430

Glu Gly Val Leu Thr Ser Ala Asp Cys Glu Lys Ile Tyr Ser Ile Val
        435                 440                 445

Tyr Ile Ser Asn Arg Ala Met Ala Ser Ser Ala Gly Glu Phe Val Tyr
    450                 455                 460

Trp Lys Ile Phe His Pro Glu Cys Gly Ala Lys Ala Val Ser Asp Arg
465                 470                 475                 480

Glu Arg Arg Arg Ser Pro Gln Ala Gln Lys Thr Phe Ile Tyr Leu Leu
                485                 490                 495

Leu Ala Phe Phe Met Glu Ser Glu His His Asn His Ala Ala Tyr Leu
            500                 505                 510
```

```
Val Asp Ser Leu Trp Asp Cys Ala Gly Ser Tyr Leu Lys Asp Trp Glu
            515                 520                 525

Ser Leu Thr Asn Leu Leu Leu Gln Lys Asp Gln Asn Leu Gly Asp Met
        530                 535                 540

Gln Glu Arg Met Leu Ile Glu Ile Leu Val Ser Ser Ala Arg Gln Ala
545                 550                 555                 560

Ala Glu Gly His Pro Pro Val Gly Arg Ile Thr Gly Lys Lys Ser Leu
                565                 570                 575

Thr Ala Lys Glu Arg Lys Leu Gln Ala Tyr Asp Lys Met Lys Leu Ala
            580                 585                 590

Glu His Leu Ile Pro Leu Pro Gln Leu Leu Ala Lys Phe Ser Ala
        595                 600                 605

Asp Ala Glu Asn Val Ala Pro Leu Leu Gln Leu Leu Ser Tyr Phe Asp
            610                 615                 620

Leu Ser Ile Tyr Cys Thr Gln Arg Leu Glu Lys His Leu Glu Leu Leu
625                 630                 635                 640

Leu Gln Gln Leu Gln Glu Val Val Lys His Val Glu Pro Glu Val
                645                 650                 655

Leu Glu Ala Ala Ala His Ala Leu Tyr Leu Leu Cys Lys Pro Glu Phe
            660                 665                 670

Thr Phe Phe Ser Arg Val Asp Phe Ala Arg Ser Gln Leu Val Asp Phe
        675                 680                 685

Leu Thr Asp Arg Phe Gln Gln Glu Leu Asp Asp Leu Met Gln Ser Ser
            690                 695                 700

Phe Leu Asp Glu Asp Glu Val Tyr Ser Leu Thr Ala Thr Leu Lys Arg
705                 710                 715                 720

Leu Ser Ala Phe Tyr Asn Ala His Asp Leu Thr Arg Trp Glu Ile Ser
                725                 730                 735

Glu Pro Cys Ser Arg Leu Leu Arg Lys Ala Val Asp Thr Gly Glu Val
            740                 745                 750

Pro His Gln Val Ile Leu Pro Ala Leu Thr Leu Val Tyr Phe Ser Ile
        755                 760                 765

Leu Trp Thr Val Thr His Ile Ser Glu Ser Thr Ser His Lys Gln Leu
770                 775                 780

Met Ser Leu Lys Lys Arg Met Val Ala Phe Cys Glu Leu Cys Gln Ser
785                 790                 795                 800

Cys Leu Ser Asp Val Asp Pro Glu Ile Gln Glu Ala Phe Val Leu
                805                 810                 815

Leu Ser Asp Leu Leu Ile Phe Ser Pro Gln Met Ile Val Gly Gly
            820                 825                 830

Arg Asp Phe Leu Arg Pro Leu Val Phe Phe Pro Glu Ala Thr Leu Gln
            835                 840                 845

Ser Glu Leu Ala Ser Phe Leu Met Asp His Val Phe Leu Gln Pro Gly
        850                 855                 860

Glu Leu Gly Asn Gly Gln Ser Gln Glu Asp His Val Gln Ile Glu Leu
865                 870                 875                 880

Leu His Gln Arg Arg Leu Leu Ala Gly Phe Cys Lys Leu Leu Leu
                885                 890                 895

Tyr Gly Val Leu Glu Leu Asp Ala Ala Ser Asp Val Phe Lys His Tyr
            900                 905                 910

Asn Lys Phe Tyr Glu Asp Tyr Gly Asp Ile Ile Lys Glu Thr Leu Thr
        915                 920                 925

Arg Ala Arg Gln Ile Asp Arg Cys Gln Cys Ser Arg Ile Leu Leu Leu
```

930             935             940
Ser Leu Lys Gln Leu Tyr Thr Glu Leu Ile Gln Glu Gln Gly Pro Gln
945                 950             955                 960

Gly Leu Thr Glu Leu Pro Ala Phe Ile Glu Met Arg Asp Leu Ala Arg
                965             970             975

Arg Phe Ala Leu Ser Phe Gly Pro Gln Gln Leu His Asn Arg Asp Leu
            980             985             990

Val Val Met Leu His Lys Glu Gly Ile Lys Phe Ser Leu Ser Glu Leu
        995             1000            1005

Pro Pro Ala Gly Ser Ser His Glu Pro Pro Asn Leu Ala Phe Leu
    1010            1015            1020

Glu Leu Leu Ser Glu Phe Ser Pro Arg Leu Phe His Gln Asp Lys
    1025            1030            1035

Arg Leu Leu Leu Ser Tyr Leu Glu Lys Cys Leu Gln Arg Val Ser
    1040            1045            1050

Lys Ala Pro Asn His Pro Trp Gly Pro Val Thr Thr Tyr Cys His
    1055            1060            1065

Ser Leu His Pro Leu Glu Ile Thr Ala Glu Ala Ser Pro Arg Gly
    1070            1075            1080

Pro Pro His Ser Lys Lys Arg Cys Val Glu Gly Pro Cys Arg Pro
    1085            1090            1095

Gln Glu Glu Ser Ser Ser Gln Glu Glu Ser Leu Gln Leu Asn
    1100            1105            1110

Ser Gly Pro Thr Thr Pro Leu Thr Ser Thr Ala Val Lys Arg
    1115            1120            1125

Lys Gln Ser Leu Arg Thr Val Gly Lys Lys Gln Lys Gly Arg Pro
    1130            1135            1140

Gly Pro Gly Pro Gly Pro Gly Pro Glu Leu Ile Cys Ser Gln Gln
    1145            1150            1155

Leu Leu Gly Thr Gln Arg Leu Lys Met Ser Ser Ala Pro Cys Phe
    1160            1165            1170

Gln Ile Arg Cys Asp Pro Ser Gly Ser Gly Leu Gly Lys Gln Leu
    1175            1180            1185

Thr Arg Leu Ser Leu Met Glu Glu Asp Glu Glu Glu Glu Leu Arg
    1190            1195            1200

Leu Leu Asp Glu Glu Trp Gln Arg Gly Asp Lys Met Leu His Ser
    1205            1210            1215

Pro Ser Ser Pro Ser Glu His Gly Leu Asp Leu Leu Asp Thr Thr
    1220            1225            1230

Glu Leu Asn Met Glu Asp Phe
    1235            1240

<210> SEQ ID NO 20
<211> LENGTH: 1256
<212> TYPE: PRT
<213> ORGANISM: Rattus norvegicus

<400> SEQUENCE: 20

Met Pro Thr Leu Trp Ser Pro Ser Thr Gln His His Gly Ser Ser Ser
1               5                   10                  15

Gly Ser Met Ser Ser Pro Leu Arg Lys Ser Val Arg Cys Ala Gln Met
            20                  25                  30

Ala Leu Ser Pro Cys Ser Ser Asn Ile Gln Pro Cys Asp Asp Arg Asp
        35                  40                  45

```
Ser Gln Gly Thr Ala Glu Trp Asp Ser Ser Thr Ser Glu Asp Ser
    50                  55                  60
Asp Phe Glu Asp Ser Leu Arg Arg Asn Val Arg Lys Arg Ala Ala Lys
65                  70                  75                  80
Arg Pro Pro Lys Ala Ile Pro Val Ala Lys His Pro Lys Lys Gln Ser
                85                  90                  95
His Ile Val Pro Gly Gly Asn Asp Lys Asn Lys Ser Val Pro Pro Thr
            100                 105                 110
Ser Asp Leu Phe Asp Ala Val Lys Ala Ala Arg Ser Cys Ala Gln Ser
            115                 120                 125
Leu Val Asp Glu Trp Leu Glu Asn Tyr Lys Gln Asp Glu Asn Ala Gly
        130                 135                 140
Phe Leu Glu Leu Val Asn Phe Phe Ile Arg Ala Cys Gly Cys Lys Ser
145                 150                 155                 160
Thr Val Thr Pro Glu Met Phe Lys Thr Met Ser Asn Ser Glu Ile Ile
                165                 170                 175
Gln His Leu Thr Glu Glu Phe Asn Glu Asp Ser Gly Asp Tyr Pro Leu
            180                 185                 190
Thr Ala Pro Gly Pro Ser Trp Lys Lys Phe Gln Gly Ser Phe Cys Glu
            195                 200                 205
Phe Val Lys Thr Leu Val Cys Gln Cys Gln Tyr Ser Leu Leu Phe Asp
210                 215                 220
Gly Phe Pro Met Asp Asp Leu Ile Ser Leu Leu Ile Gly Leu Ser Asp
225                 230                 235                 240
Ser Gln Val Arg Ala Phe Arg His Thr Ser Thr Leu Ala Ala Met Lys
                245                 250                 255
Leu Met Thr Ser Leu Val Lys Val Ala Leu Gln Leu Ser Leu His Lys
            260                 265                 270
Asp Asn Asn Gln Arg Gln Tyr Glu Ala Glu Arg Asn Lys Gly Pro Glu
        275                 280                 285
Gln Arg Ala Pro Glu Arg Leu Gly Ser Leu Leu Glu Lys Arg Lys Glu
290                 295                 300
Phe Gln Glu Asn Gln Glu Glu Ile Glu Gly Met Met Asn Ala Ile Phe
305                 310                 315                 320
Arg Gly Val Phe Val His Arg Tyr Arg Asp Ile Leu Pro Glu Ile Arg
                325                 330                 335
Ala Val Cys Ile Glu Glu Ile Gly Cys Trp Met Gln Ser Tyr Ser Thr
            340                 345                 350
Ser Phe Leu Asn Asp Ser Tyr Leu Lys Tyr Ile Gly Trp Thr Leu His
        355                 360                 365
Asp Lys His Lys Glu Val Arg Leu Lys Cys Val Lys Ala Leu Ala Gly
    370                 375                 380
Leu Tyr Ser Asn Gln Glu Leu Ser Ser Arg Met Glu Leu Phe Thr Asn
385                 390                 395                 400
Arg Phe Lys Asp Arg Met Val Ser Met Val Met Asp Arg Glu Ser Glu
                405                 410                 415
Val Ala Val Glu Ala Ile Arg Leu Leu Thr Leu Ile Leu Lys Asn Met
            420                 425                 430
Glu Gly Val Leu Thr Ser Ala Asp Cys Glu Lys Ile Tyr Ser Ile Val
        435                 440                 445
Tyr Ile Ser Asn Arg Ala Met Ala Ser Ser Ala Gly Glu Phe Val Tyr
    450                 455                 460
Trp Lys Ile Phe His Pro Glu Cys Gly Ala Lys Ala Val Ser Gly Arg
```

```
                465                 470                 475                 480
         Glu Arg Arg Arg Ser Pro Gln Ala Gln Arg Thr Phe Ile Tyr Leu Leu
                             485                 490                 495

Leu Ala Phe Phe Met Glu Ser Glu His His Asp His Ala Ala Tyr Leu
                         500                 505                 510

Val Asp Ser Leu Trp Asp Cys Ala Gly Ser Tyr Leu Lys Asp Trp Glu
                         515                 520                 525

Ser Leu Thr Ser Leu Leu Leu Gln Lys Asp Gln Asn Leu Gly Asp Met
                         530                 535                 540

Gln Glu Arg Met Leu Ile Glu Ile Leu Val Ser Ser Ala Arg Gln Ala
         545                 550                 555                 560

Ala Glu Gly His Pro Pro Val Gly Arg Ile Thr Gly Lys Lys Ser Leu
                             565                 570                 575

Thr Ala Lys Glu Arg Lys Leu Gln Ala Tyr Asp Lys Val Lys Leu Ala
                         580                 585                 590

Glu His Leu Ile Pro Leu Leu Pro Gln Leu Leu Ala Lys Phe Ser Ala
                         595                 600                 605

Asp Ala Glu Asn Val Ala Pro Leu Leu Arg Leu Leu Ser Tyr Phe Asp
         610                 615                 620

Leu Asn Ile Tyr Cys Thr Gln Arg Leu Glu Lys His Leu Glu Leu Leu
         625                 630                 635                 640

Leu Gln Gln Leu Gln Glu Val Val Val Lys His Val Glu Pro Glu Val
                             645                 650                 655

Leu Glu Ala Ala Ala His Ala Leu Tyr Leu Leu Cys Lys Pro Glu Phe
                         660                 665                 670

Thr Phe Phe Ser Arg Val Asp Phe Ala Arg Ser Gln Leu Val Asp Leu
                         675                 680                 685

Leu Thr Asp Arg Phe Gln Gln Glu Leu Asp Asp Leu Met Gln Ser Ser
                         690                 695                 700

Phe Leu Asp Glu Asp Glu Val Tyr Ser Leu Thr Ala Thr Leu Lys Arg
         705                 710                 715                 720

Leu Ser Ala Phe Tyr Asn Ala His Asp Leu Thr Arg Trp Glu Ile Ser
                             725                 730                 735

Glu Pro Cys Ser Arg Leu Leu Arg Lys Ala Val Asp Thr Gly Glu Val
                         740                 745                 750

Pro His Gln Val Ile Leu Pro Ala Leu Thr Leu Val Tyr Phe Ser Ile
                         755                 760                 765

Leu Trp Thr Val Thr His Ile Ser Glu Ser Thr Ser Gln Lys Gln Leu
                         770                 775                 780

Met Ser Leu Lys Lys Arg Met Val Ala Phe Cys Glu Leu Cys Gln Ser
         785                 790                 795                 800

Cys Leu Ser Asp Val Asp Pro Glu Ile Gln Glu Gln Ala Phe Val Leu
                             805                 810                 815

Leu Ser Asp Leu Leu Ile Phe Ser Pro Gln Met Val Val Gly Gly
                         820                 825                 830

Arg Asp Phe Leu Arg Pro Leu Val Phe Pro Glu Ala Thr Leu Gln
                         835                 840                 845

Ser Glu Leu Ala Ser Phe Leu Met Asp His Val Phe Leu Gln Pro Gly
                         850                 855                 860

Glu Leu Gly Asn Gly Gln Ser Gln Glu Asp His Val Gln Ile Glu Leu
         865                 870                 875                 880

Leu His Gln Arg Arg Arg Leu Leu Ala Gly Phe Cys Lys Leu Leu Leu
                             885                 890                 895
```

```
Tyr Gly Val Leu Glu Leu Asp Ala Ala Ser Asp Val Phe Lys His Tyr
            900                 905                 910

Asn Lys Phe Tyr Glu Asp Tyr Gly Asp Ile Ile Lys Glu Thr Leu Thr
        915                 920                 925

Arg Ala Arg Gln Ile Asp Arg Cys Gln Cys Ser Arg Ile Leu Leu Leu
    930                 935                 940

Ser Leu Lys Gln Leu Tyr Thr Glu Leu Ile Gln Glu Gln Gly Pro Gln
945                 950                 955                 960

Asp Leu Thr Glu Leu Pro Ala Phe Ile Glu Met Arg Asp Leu Ala Arg
                965                 970                 975

Arg Phe Ala Leu Ser Phe Gly Pro Gln Gln Leu His Asn Arg Asp Leu
            980                 985                 990

Val Val Met Leu His Lys Glu Gly Ile Lys Phe Ser Leu Ser Glu Leu
        995                1000                1005

Pro Pro Ala Gly Ser Ser Arg Glu Pro Pro Asn Ile Ala Phe Leu
   1010                1015                1020

Glu Leu Leu Ser Glu Phe Ser Pro Arg Leu Phe His Gln Asp Lys
   1025                1030                1035

Gln Leu Leu Leu Ser Tyr Leu Glu Lys Cys Leu Gln Arg Val Ser
   1040                1045                1050

Met Ala Pro Ser His Pro Trp Gly Pro Val Thr Thr Tyr Cys His
   1055                1060                1065

Ser Leu His Leu Val Glu Asn Thr Ala Glu Ala Ser Ser Gln Gly
   1070                1075                1080

Pro Pro His Ser Lys Lys Arg Cys Ile Glu Val Pro Arg Arg Leu
   1085                1090                1095

Gln Glu Glu Glu Ser Ser Ser Gln Gly Glu Ser Leu Gln Leu Asn
   1100                1105                1110

Ser Gly Pro Thr Thr Pro Thr Leu Thr Ser Thr Ala Val Lys Arg
   1115                1120                1125

Arg Gln Ser Pro Arg Thr Val Gly Lys Arg Gln Lys Gly Gly Pro
   1130                1135                1140

Gly Pro Gly Pro Gly Pro Gly Pro Gly Pro Gly Pro Gly Pro Gly
   1145                1150                1155

Pro Gly Pro Gly Pro Gly Pro Gly Pro Glu Leu Ile Cys Ser Gln
   1160                1165                1170

Gln Leu Ser Gly Thr Gln Arg Leu Lys Met Ser Ser Ala Pro Cys
   1175                1180                1185

Phe Gln Ile Arg Cys Asp Pro Ser Gly Ser Gly Leu Gly Lys Gln
   1190                1195                1200

Met Thr Arg Leu Ser Leu Met Glu Glu Asp Glu Glu Glu Leu
   1205                1210                1215

Arg Leu Leu Asp Glu Glu Trp Gln Cys Gly Asp Lys Leu Leu His
   1220                1225                1230

Ser Pro Ser Ser Pro Ser Glu His Gly Leu Asp Leu Leu Asp Thr
   1235                1240                1245

Thr Glu Leu Asn Met Glu Asp Phe
   1250                1255

<210> SEQ ID NO 21
<211> LENGTH: 1226
<212> TYPE: PRT
<213> ORGANISM: Pan troglodytes
```

-continued

```
<400> SEQUENCE: 21

Met Ser Ser Pro Leu Gln Arg Ala Met Gly Asp Thr Lys Arg Ala Leu
1               5                  10                  15

Ser Ala Ser Ser Ser Ser Ala Ser Leu Pro Phe Asp Asp Arg Asp
            20                  25                  30

Ser Asn His Thr Ser Glu Gly Asn Gly Asp Ser Leu Leu Ala Asp Glu
            35                  40                  45

Asp Thr Asp Phe Glu Asp Ser Leu Asn Arg Asn Val Lys Lys Arg Ala
        50                  55                  60

Ala Lys Arg Pro Pro Lys Thr Thr Pro Val Ala Lys His Pro Lys Lys
65                  70                  75                  80

Gly Ser Arg Val Val His Arg Tyr Ser Arg Lys Gln Ser Glu Pro Pro
                85                  90                  95

Ala Asn Asp Leu Phe Asn Ala Val Lys Ala Lys Ser Asp Met Gln
            100                 105                 110

Ser Leu Val Asp Glu Trp Leu Asp Ser Tyr Lys Gln Asp Gln Asp Ala
            115                 120                 125

Gly Phe Leu Glu Leu Val Asn Phe Phe Ile Gln Ser Cys Gly Cys Lys
130                 135                 140

Gly Ile Val Thr Pro Glu Met Phe Lys Lys Met Ser Asn Ser Glu Ile
145                 150                 155                 160

Ile Gln His Leu Thr Glu Gln Phe Asn Glu Asp Ser Gly Asp Tyr Pro
                165                 170                 175

Leu Ile Ala Pro Gly Pro Ser Trp Lys Lys Phe Gln Gly Ser Phe Cys
            180                 185                 190

Glu Phe Val Arg Thr Leu Val Cys Gln Cys Gln Tyr Ser Leu Leu Tyr
            195                 200                 205

Asp Gly Phe Pro Met Asp Asn Leu Ile Ser Leu Thr Gly Leu Ser
210                 215                 220

Asp Ser Gln Val Arg Ala Phe Arg His Thr Ser Thr Leu Ala Ala Met
225                 230                 235                 240

Lys Leu Met Thr Ser Leu Val Lys Val Ala Leu Gln Leu Ser Val His
                245                 250                 255

Gln Asp Asn Asn Gln Arg Gln Tyr Glu Ala Glu Arg Asn Lys Gly Pro
            260                 265                 270

Gly Gln Arg Ala Pro Glu Arg Leu Glu Ser Leu Leu Glu Lys Arg Lys
        275                 280                 285

Glu Leu Gln Glu His Gln Glu Glu Ile Glu Gly Met Met Asn Ala Leu
290                 295                 300

Phe Arg Gly Val Phe Val His Arg Tyr Arg Asp Val Leu Pro Glu Ile
305                 310                 315                 320

Arg Ala Ile Cys Ile Glu Glu Ile Gly Cys Trp Met Gln Ser Tyr Ser
                325                 330                 335

Thr Ser Phe Leu Thr Asp Ser Tyr Leu Lys Tyr Ile Gly Trp Thr Leu
            340                 345                 350

His Asp Lys His Arg Glu Val Arg Leu Lys Cys Val Lys Ala Leu Lys
        355                 360                 365

Gly Leu Tyr Gly Asn Arg Asp Leu Thr Thr Arg Leu Glu Leu Phe Thr
370                 375                 380

Ser Arg Phe Lys Asp Arg Met Val Ser Met Val Met Asp Arg Glu Tyr
385                 390                 395                 400

Asp Val Ala Val Glu Ala Val Arg Leu Leu Ile Leu Ile Leu Lys Asn
                405                 410                 415
```

```
Met Glu Gly Val Leu Thr Asp Ala Asp Cys Glu Ser Val Tyr Pro Val
            420                 425                 430

Val Tyr Ala Ser His Arg Gly Leu Ala Ser Ala Ala Gly Glu Phe Leu
            435                 440                 445

Tyr Trp Lys Leu Phe Tyr Pro Glu Cys Glu Ile Arg Met Met Gly Gly
450                 455                 460

Arg Glu Gln Arg Gln Ser Pro Gly Ala Gln Arg Thr Phe Phe Gln Leu
465                 470                 475                 480

Leu Leu Ser Phe Phe Val Glu Ser Glu Leu His Asp His Ala Ala Tyr
                485                 490                 495

Leu Val Asp Ser Leu Trp Asp Cys Ala Gly Ala Arg Leu Lys Asp Trp
            500                 505                 510

Glu Gly Leu Thr Ser Leu Leu Leu Glu Lys Asp Gln Asn Leu Gly Asp
            515                 520                 525

Val Gln Glu Ser Thr Leu Ile Glu Ile Leu Val Ser Ser Ala Arg Gln
            530                 535                 540

Ala Ser Glu Gly His Pro Pro Val Gly Arg Val Thr Gly Arg Lys Gly
545                 550                 555                 560

Leu Thr Ser Lys Glu Arg Lys Thr Gln Ala Asp Asp Arg Val Lys Leu
                565                 570                 575

Thr Glu His Leu Ile Pro Leu Leu Pro Gln Leu Leu Ala Lys Phe Ser
            580                 585                 590

Ala Asp Ala Glu Lys Val Thr Pro Leu Leu Gln Leu Leu Ser Cys Phe
            595                 600                 605

Asp Leu His Ile Tyr Cys Thr Gly Arg Leu Glu Lys His Leu Glu Leu
            610                 615                 620

Phe Leu Gln Gln Leu Gln Glu Val Val Lys His Ala Glu Pro Ala
625                 630                 635                 640

Val Leu Glu Ala Gly Ala His Ala Leu Tyr Leu Leu Cys Asn Pro Glu
                645                 650                 655

Phe Thr Phe Phe Ser Arg Ala Asp Phe Ala Arg Ser Gln Leu Val Asp
            660                 665                 670

Leu Leu Thr Asp Arg Phe Gln Gln Glu Leu Glu Glu Leu Leu Gln Ser
            675                 680                 685

Ser Phe Leu Asp Glu Asp Glu Val Tyr Asn Leu Ala Ala Thr Leu Lys
            690                 695                 700

Arg Leu Ser Ala Phe Tyr Asn Ala His Asp Leu Thr Arg Trp Glu Leu
705                 710                 715                 720

Tyr Glu Pro Cys Cys Gln Leu Leu Gln Lys Ala Val Asp Thr Gly Glu
                725                 730                 735

Val Pro His Gln Val Ile Leu Pro Ala Leu Thr Leu Val Tyr Phe Ser
            740                 745                 750

Ile Leu Trp Thr Leu Thr His Ile Ser Lys Ser Asp Ala Ser Gln Lys
            755                 760                 765

Gln Leu Ser Ser Leu Arg Asp Arg Met Val Ala Phe Cys Glu Leu Cys
            770                 775                 780

Gln Ser Cys Leu Ser Asp Val Asp Thr Glu Ile Gln Glu Gln Ala Phe
785                 790                 795                 800

Val Leu Leu Ser Asp Leu Leu Ile Phe Ser Pro Gln Met Ile Val
                805                 810                 815

Gly Gly Arg Asp Phe Leu Arg Pro Leu Val Phe Phe Pro Glu Ala Thr
            820                 825                 830
```

```
Leu Gln Ser Glu Leu Ala Ser Phe Leu Met Asp His Val Phe Ile Gln
        835                 840                 845

Pro Gly Asp Leu Gly Ser Gly Asp Ser Gln Glu Asp His Leu Gln Ile
850                 855                 860

Glu Arg Leu His Gln Arg Arg Leu Leu Ala Gly Phe Cys Lys Leu
865             870                 875                 880

Leu Leu Tyr Gly Val Leu Glu Met Asp Ala Ala Ser Asp Val Phe Lys
                885                 890                 895

His Tyr Asn Lys Phe Tyr Asn Asp Tyr Gly Asp Ile Ile Lys Glu Thr
            900                 905                 910

Leu Thr Arg Ala Arg Gln Ile Asp Arg Ser His Cys Ser Arg Ile Leu
        915                 920                 925

Leu Leu Ser Leu Lys Gln Leu Tyr Thr Glu Leu Leu Gln Glu His Gly
    930                 935                 940

Pro Gln Gly Leu Asn Glu Leu Pro Ala Phe Ile Glu Met Arg Asp Leu
945                 950                 955                 960

Ala Arg Arg Phe Ala Leu Ser Phe Gly Pro Gln Gln Leu Gln Asn Arg
                965                 970                 975

Asp Leu Val Val Met Leu His Lys Glu Gly Ile Lys Phe Ser Leu Ser
            980                 985                 990

Glu Leu Pro Pro Ala Gly Ser Ser Asn Gln Pro Pro Asn Leu Ala Phe
        995                 1000                1005

Leu Glu Leu Leu Ser Glu Phe Ser Pro Arg Leu Phe His Gln Asp
    1010                1015                1020

Lys Gln Leu Leu Leu Ser Tyr Leu Glu Lys Cys Leu Gln His Val
    1025                1030                1035

Ser Gln Ala Pro Gly Arg Pro Trp Gly Pro Val Thr Thr Tyr Cys
    1040                1045                1050

His Ser Leu Ser Pro Val Glu Asn Thr Ala Glu Thr Ser Pro Gln
    1055                1060                1065

Val Leu Pro Ser Ser Lys Arg Arg Arg Val Glu Gly Pro Ala Lys
    1070                1075                1080

Pro Asn Arg Glu Asp Val Ser Ser Gln Glu Glu Ser Leu Gln
    1085                1090                1095

Leu Asn Ser Ile Pro Pro Thr Pro Thr Leu Thr Ser Thr Ala Val
    1100                1105                1110

Lys Ser Arg Gln Pro Leu Trp Gly Leu Lys Glu Met Glu Glu Glu
    1115                1120                1125

Asp Gly Ser Glu Leu Asp Phe Ala Gln Gly Ser Gln Pro Val Ala
    1130                1135                1140

Gly Thr Glu Arg Ser Arg Phe Leu Gly Pro Gln Tyr Phe Gln Thr
    1145                1150                1155

Pro His Asn Pro Ser Gly Pro Gly Leu Gly Asn Gln Leu Met Arg
    1160                1165                1170

Leu Ser Leu Met Glu Glu Asp Glu Glu Glu Glu Leu Glu Ile Gln
    1175                1180                1185

Asp Glu Ser Asn Glu Glu Arg Gln Asp Thr Asp Met Gln Ala Ser
    1190                1195                1200

Ser Tyr Cys Ser Thr Ser Glu Arg Gly Leu Asp Leu Leu Asp Ser
    1205                1210                1215

Thr Glu Leu Asp Ile Glu Asp Phe
    1220                1225
```

<210> SEQ ID NO 22
<211> LENGTH: 432
<212> TYPE: PRT
<213> ORGANISM: Ornithorhynchus anatinus

<400> SEQUENCE: 22

Met Ala Arg Arg Trp Gly Val Ala Cys Val Ser Lys Arg Val Gly Asp
1               5                   10                  15

Glu Asn Glu Ala Gln Arg Ala Gly Glu Val Asp Lys Asn Glu Gly Ile
            20                  25                  30

Glu Leu Gly Gly Ser Gly Arg Arg Leu Glu Arg Leu Asp Phe Trp Val
        35                  40                  45

Val Phe Cys Leu Ser Thr Pro Gly Pro Ala Leu Gly Ser Glu Leu
    50                  55                  60

Val His Ser Pro Leu Ala Val Arg Glu Pro Val Arg Ser Pro Ser Ser
65                  70                  75                  80

Pro Pro Thr Arg Leu Ala Leu Leu Ala Gly Gly Ser Arg Asn Gly Pro
                85                  90                  95

Val Leu Pro Ile Phe Phe Thr Ile Leu Pro Pro Ser Gly Thr Val
            100                 105                 110

Thr Leu Glu Met Phe Lys Thr Leu Gln Asn Ser Glu Ile Ile Gln Gln
        115                 120                 125

Met Thr Glu Lys Phe Asn Glu Asp Ser Val Glu Tyr Pro Leu Ser Ala
130                 135                 140

Ser Gly Pro Thr Trp Lys Lys Phe Arg Gly Ser Phe Cys Glu Phe Val
145                 150                 155                 160

Ser Ser Leu Val His Gln Cys Arg Tyr Ser Phe Leu Tyr Asp Glu Phe
                165                 170                 175

Leu Met Asp Thr Leu Ile Ser Leu Leu Thr Gly Leu Ser Asp Ser Gln
            180                 185                 190

Val Arg Ala Phe Arg His Thr Ser Thr Leu Arg Arg Pro Ala Ser Phe
        195                 200                 205

Leu Gln Pro Arg Arg Asp Gly Gly Pro Ala Lys Thr Pro Pro Cys Cys
    210                 215                 220

Asp Ile Pro Pro Pro Phe Pro Asn Leu Leu Gln His Arg Pro Pro Leu
225                 230                 235                 240

Leu Ala Phe Pro Gln Ala Lys Pro Ala Gly Pro Ala Gly Pro Ala Arg
                245                 250                 255

Val Pro Gly Asp Gly Ala Ser Arg Leu Pro Val Ile Cys His Ala Lys
            260                 265                 270

Asp Thr Ser Gly Pro Phe Pro Phe Val Gln Val Ser Gly Arg Asp Pro
        275                 280                 285

Val Ala His Pro Pro Ala Lys Ala Glu Arg Glu Glu Lys Gly Leu Pro
    290                 295                 300

Pro Ser Ala Ile Pro Val Arg Ser Gln Gly Ala Glu Gly Leu Leu Ala
305                 310                 315                 320

Arg Ile His Ala Gly Gly Asp Arg Gly Gly Gly Arg Thr Gly Leu
                325                 330                 335

Pro Val Pro Cys Gln Thr Phe Pro Ala Cys His Arg Asn Gly Asp Leu
            340                 345                 350

Thr Gly Gly Tyr Arg Leu Gly Arg Ser Ala Ser Thr Ser Gly Val Arg
        355                 360                 365

Gln Ala Ala Leu His Thr Pro Arg Pro Cys Ser Gln Ala Arg Glu Ser
    370                 375                 380

Pro Ser Gln Val Arg Lys Ala Asp Gly Ser Leu Thr Gly Leu Leu Gly
385                 390                 395                 400

Leu Gly Leu Arg Glu Gly Gly Pro Glu Glu Pro Val Leu Glu Thr Arg
            405                 410                 415

Ala Gly Gly Gly Ala Ser Glu Gly Arg Glu Gly Trp Arg Pro Gly Arg
            420                 425                 430

<210> SEQ ID NO 23
<211> LENGTH: 1140
<212> TYPE: DNA
<213> ORGANISM: Homo sapiens

<400> SEQUENCE: 23

| | | | | | |
|---|---|---|---|---|---|
| gcacaccgga | ctgcgttttt | tttccgaacg | cccgcagcag | ggtcagaagg | gaggtggtcg | 60 |
| ccctccgtcg | tggtctggcg | tgtattccga | gcgttggtgt | ctggcggttt | ccgagcgttg | 120 |
| gtgtctggcg | gtttccgacc | gttggtgtct | ggcggtttcc | gaccgttggt | gtctggcacg | 180 |
| cgccaccctc | tcttgctttg | gttgcgccat | gccgatgtac | cagacaagaa | gacaagaaaa | 240 |
| tgatttgagg | acagcttcaa | tcgcggtgtg | aagaagaaag | cagcaaaacg | accactgaaa | 300 |
| acaacgccgg | tggcaaaata | tccaaagaaa | gggtcccaag | cggtacatcg | tcatagccgg | 360 |
| aaacagtcag | agccaccagc | caatgatatt | ttcaatgctg | cgaaagctgc | caaaagtgac | 420 |
| atgcagggat | gtccttcctg | agatccgtgc | tatctgcatt | gaggaaattg | ggtgttggat | 480 |
| gcaaagctac | agcacgtctt | tcctcaccga | cagctattta | aaatatattg | gttggactct | 540 |
| gcatgataag | caccgagaag | tccgcgtgaa | gtgcgtgaag | gctctgaaag | ggctgtacgg | 600 |
| taaccgggac | ctgaccgcac | gcctggagct | cttcactggc | cgcttcaagg | actggatggt | 660 |
| ttccatgatc | gtggacagag | agtacagtgt | ggcagtggag | gccgtcagat | tactgatact | 720 |
| tatccttaag | aacatggaag | gggtgctgat | ggacgtggac | tgtgagagcg | tctacccat | 780 |
| tgtgtaggcc | tctaattgag | gcctggcctc | tgctgtgggt | gaatttctgt | actggaaact | 840 |
| tttctaccct | gagtgcgaga | taagaacgat | gggtggaaga | gagcaacgcc | agagcccagg | 900 |
| cgcccagagg | actttcttcc | agcttctgct | gtccttcttt | gtggagagca | aggtgacata | 960 |
| cacagagaga | actctggctg | ttgtgcatag | gacctacaag | tgggctgggg | ttggtggctc | 1020 |
| acgcctgtaa | gcccagcact | ttgggaggct | gaggtgggag | gatcctttga | gcccaggagt | 1080 |
| ttgagaccag | cttgggcaac | atagtgagac | cctgtctcta | ccaaaaaaaa | aaaaaaaaaa | 1140 |

<210> SEQ ID NO 24
<211> LENGTH: 4246
<212> TYPE: DNA
<213> ORGANISM: Mus musculus

<400> SEQUENCE: 24

| | | | | | |
|---|---|---|---|---|---|
| ccgcgttttt | ttctaaggct | taaccgcccg | ccaccagagg | aagaagagca | gctgcggcgg | 60 |
| gcgtctcgcg | accgaggtgg | gatgtccact | gagacctgaa | aggacctctg | aggtggtgac | 120 |
| ctttcttcag | ccgtgttcat | ctaaagctgg | attaacatgc | ctactctgtg | gtcaccttct | 180 |
| acccagcacc | atggctcttc | ctcaggcagt | gagtcttccc | cacttcaaaa | gtctgtgaga | 240 |
| cgtgcacaga | tggccttgtc | tccttgttcc | tcctccatcc | tacccctgtga | tgacagagac | 300 |
| tcacagggaa | ctgcagagtg | ggatagtccc | tcaactaacg | aagacagcga | ctttgaagac | 360 |
| agcttaagac | gaaatgtgaa | gaagagagca | gcaaagcaac | cacccaaagc | tgttccagca | 420 |
| gcaaaacatc | ggaagaagca | gtcccgaata | gtatctagtg | ggaatggcaa | gaatgaatca | 480 |

```
gtgccatcaa ccaattacct tttttgatgct gtgaaagctg ctagaagttg catgcagtct    540
ttggtggatg agtggctaga taactacaag caagatgaaa atgcaggatt cttggagctc    600
attaattttt tcatccgagc ctgtggatgt aaaagcactg tgactcctga gatgttcaag    660
acaatgtcca attcagagat catccaacac ctaacgaaag agtttaatga ggactcgggg    720
gactatcccc tgacagctcc aggtccctcc tggaagaagt tccagggaag cttctgtgag    780
tttgtgaaga cattggtcta tcagtgccag tacagtctcc tctatgatgg cttttcctatg   840 gatgacctta tctccctgct cattggcctc tcagattccc aggtccgagc ctttcgtcat    900
actagtaccc tggctgccat gaagctaatg acttctctgg taaaagttgc actccagttg    960
agtctgcaca aagacaacaa tcaacgtcag tatgaggctg aacgaaacaa ggggccagag   1020
cagagagcac cggaacgact ggagagtctg ctggagaaac gaaaagagtt ccaagagaat   1080
caagaggaca tagaggggat gatgaatgcc atcttcagag gtgtctttgt ccatcggtac   1140
agggacatcc ttcctgagat ccgcgctatc tgcattgagg agattgggta ttggatgcaa   1200
agctacagca cctcctttct taatgacagc tacctaaaat acatcggctg gaccctgcat   1260
gataagcaca aggaagttcg cctgaagtgt gtgaaggctc tggcagggct gtacagcaac   1320
caggagctga gcttacggat ggagctcttt acaaatcgct tcaaggaccg gatggtttcc   1380
atggtcatgg acagagagtg tgaagtagca gtggaggcca tcagattgct gacccttatt   1440
ctgaagaaca tggagggagt gctgactagt gcagactgtg agaaaattta ctccattgta   1500
tacatttcta atcgtgctat ggcctcttct gcagggaat ttgtgtattg aagatcttc     1560 catcctgaat gtggggcaaa agcagtgagt gatagagagc gacgccggag tccacaagcc   1620
cagaagactt tcatttatct tttactggcc ttctttatgg agagtgagca tcacaaccat   1680
gctgcttact tagtagacag cttgtgggac tgtgcgggt cttacctgaa ggactggag    1740 agtctgacaa acctgttgct gcagaaagac cagaatctgg gtgatatgca agagagaatg   1800
ctgatagaaa tccttgtgtc tagtgcccgg caagctgcag agggtcaccc tccagtgggg   1860
cgcatcactg gaaagaagag tctgacggcc aaagaacgca agcttcaagc ctatgataag   1920
atgaagctgg ctgagcacct catccccctc ttgccccagc tccttgccaa gttctcagca   1980
gatgcagaga atgttgctcc cttgctccag ctgctcagtt actttgacct cagcatatat   2040
tgcactcagc gcttggaaaa gcacttggag ctgcttctgc aacaactcca ggaggtggtg   2100
gtgaagcatg tagagcctga ggtgcttgag gcagcagccc atgccctcta tctgctctgc   2160
aaaccagagt tcaccttctt cagcagagtg gactttgcca gaagccaatt agtagatttt   2220
ctgactgata gattccagca ggagcttgat gacctaatgc agtcatcctt cctagatgag   2280
gatgaggtat acagcctgac agccaccctg aagcgtctct ctgccttttta caatgctcat   2340 gacctgaccc gatgggagat ctctgaacca tgttctcgac tcctccggaa ggctgtagac   2400
acaggagaag ttcctcacca ggtgattttg ccagccttga ctctggtata ttttttccatt   2460 ctctggacag taacccacat ttcagagtct acttctcata agcagctgat gagtctgaag   2520
aaaagaatgg tagccttctg tgagctttgc caaagctgcc tctcagacgt ggacccagag   2580
atccaggagc aggcttttgt cttattaagt gacctgcttc tcatcttcag ccctcagatg   2640
attgtagggg gacgggattt ccttaggcct cttgtctttt ttccggaagc tactctccag   2700
tcggaactag ccagcttcct catgaccat gtctttctcc agcctggaga actgggcaac    2760
ggtcagtcac aggaggatca cgtccagata gaacttctgc accagaggcg ccgcctgctt   2820
gcaggatttt gtaagctgct gctttatggg gtattggagc tggatgcagc ctcagacgtt   2880
```

| | |
|---|---|
| ttcaaacact acaacaagtt ctatgaagac tatggtgaca ttatcaagga aacattaact | 2940 |
| cgagcaagac aaattgacag atgtcagtgc tctcggatcc tgctcctgag cctaaagcag | 3000 |
| ctctacacag aactgataca ggagcagggc ccccagggcc tgacagaact gccagccttc | 3060 |
| attgagatga gagacttggc tcggaggttt gccttgagct ttggacccca gcagctccat | 3120 |
| aaccgagatc ttgtggtcat gctgcacaag gaaggcatca agttctcatt gtctgagctt | 3180 |
| cctcctgctg gttcttctca tgagccccca aatcttgcat tcctggagct tctttcagag | 3240 |
| ttctcccctc gcctcttcca tcaggacaag cggctactac tatcctacct ggaaaagtgt | 3300 |
| ctgcagcgtg tctccaaggc acctaaccat ccctggggtc cagtcaccac ctactgccac | 3360 |
| tcccttcacc ctctagagat cacagcagag gccagccctc gtggaccccc ccactccaag | 3420 |
| aagaggtgtg ttgaaggccc tgcaggcct caggaagaag agtcctcatc ccaggaagaa | 3480 |
| agccttcagc tgaacagtgg ccccacaacc cctaccctca cctccaccgc agtgaagagg | 3540 |
| aagcagtctc tgaggacagt gggcaagaag caaaaaggta gaccaggacc aggaccagga | 3600 |
| ccaggaccag agctgatctg cagtcagcaa ctcttaggca cccagaggtt gaagatgtcg | 3660 |
| agtgcaccat gtttccagat tcgatgtgat ccttcaggct ctggcttggg caagcagctg | 3720 |
| acccgactca gccttatgga agaagatgag gaagaagagc taagacttct ggatgaagaa | 3780 |
| tggcaacgtg gagacaagat gcttcatagc ccttcttctc ccagtgagca tgggttggac | 3840 |
| ctattagata caacagagct gaacatggag gatttctgat gggactttag gcctctcccc | 3900 |
| ttctccactt accactgcaa gtccttgagt gagcagaagg aaggagtaaa atgaagcatt | 3960 |
| ctttgggtcc tagccaagta ctttaaagga aaagagaaat ggccttattt ttcaaatctc | 4020 |
| tatttctttc tgaagtgggt gctatatata gatgctatga gccttgtcat ccttaatgcg | 4080 |
| ccatcgcttt atgcttttgc ctgtttgcag tgataggagt tgggtaggga gggctttacg | 4140 |
| tcagcactga agtttagtaa aacttctatt tgatattttg tccccaaaca ctgccaaact | 4200 |
| ttcaataaac atgttcagct atctcataaa aaaaaaaaa aaaaaa | 4246 |

<210> SEQ ID NO 25
<211> LENGTH: 4181
<212> TYPE: DNA
<213> ORGANISM: Rattus norvegicus

<400> SEQUENCE: 25

| | |
|---|---|
| aactgtgttc atctagaggt cattcttcca agctcaaaca ctggattaac atgcctactc | 60 |
| tgtggtcacc ctccacccag caccatggct cttcctcagg cagtatgtcc tcccctcttc | 120 |
| gaaagtctgt gagatgtgca cagatggcct tgtctccttg ttcttccaac atccaaccct | 180 |
| gtgatgacag agactcccag ggaactgcag aatgggatag ttcctcaact agtgaagaca | 240 |
| gtgactttga agatagctta agaagaaatg tgaggaagag agcagcaaaa cgaccaccca | 300 |
| aagctatccc agtggcaaaa catccgaaga agcagtccca catagtacct ggtgggaatg | 360 |
| acaagaacaa gtcagtgccg ccaaccagtg accttttga tgctgtgaaa gctgctagaa | 420 |
| gttgtgcgca gtctttggta gatgagtggc tagaaaacta caagcaagat gaaaatgcag | 480 |
| gattcttgga acttgttaat ttttcatcc gagcctgtgg atgtaaaagc actgtcacac | 540 |
| ccgagatgtt caagacaatg tccaactcag agatcatcca gcacctaaca gaagagttta | 600 |
| atgaggactc aggtgactat cccctgcag ctccaggtcc atcctggaag aagttccagg | 660 |
| gaagcttctg tgagtttgtg aagacactag tctgtcagtg ccagtacagc ctcctctttg | 720 |

```
acggctttcc aatggatgac cttatctccc tgctcattgg cctctcagat tcccaggtcc      780
gagcctttcg tcatactagt actttggctg ccatgaagct aatgacttct ctggtaaaag      840
ttgcactcca gttgagtctg cacaaagaca acaatcaacg tcagtatgag cagaacgaa       900 acaaggggcc agagcagagg gcaccagagc ggctcgagag tctgctggag aaacgaaaag      960
agttccaaga gaatcaagag gagatagagg ggatgatgaa tgccatcttc agggGtgtct     1020
ttgttcatcg gtacagggac atccttcctg agatccgtgc tgtctgcatc gaggagatcg     1080
ggtgttggat gcaaagctac agcacctcct ttcttaatga cagctaccta aaatatattg     1140
gctggaccct gcatgacaag cacaaggaag tccgcctaaa gtgtgtgaag gctctggcag     1200
ggctgtacag caaccaggag ctgagttcac ggatggagct ctttactaat cgcttcaagg     1260
accggatggt ttccatggtc atggacagag agagtgaagt agcagtggag gccatcagat     1320
tgctgaccct tattctgaag aacatggagg gagtactgac tagtgcagat tgtgagaaaa     1380
tttactccat tgtatacatt tctaatcgtg ccatggcctc ttctgcaggg gaatttgtgt     1440
actggaagat tttccatcct gaatgtgggg caaaagcagt gagtggcagg gagcgacgcc     1500
ggagtccaca agcccagagg actttcattt acctttattt ggccttcttt atggagagtg     1560
agcatcacga ccatgctgct tacctagttg acagcttgtg ggactgtgca gggtcttacc     1620
tgaaggactg ggagagtctg acaagtctgt tgctgcagaa agaccagaat ctgggtgata     1680
tgcaagagag aatgttgata gaaatcctgg tgtccagtgc ccggcaagct gcagagggtc     1740
acccaccagt ggggcgcatc actggaaaga gagtctgac cgccaaagaa cgcaagcttc      1800
aagcttatga taaggtgaag ctggctgagc acctcatccc cctcttgccc cagctccttg     1860
ccaagttctc agcagatgca gagaacgttg ctcccttgct ccggctgctc agttactttg     1920
acctcaacat ttattgcact cagcgcttgg agaagcactt ggagctgctt ctgcaacaac     1980
tccaggaggt ggtggtgaag cacgtagagc ctgaggtgct tgaggctgca gcacatgccc     2040
tctatttgct ctgcaagcca gagttcacct tcttcagcag agtggacttc gccagaagcc     2100
aattagtaga tctgctgact gatagattcc agcaggagct tgacgaccta atgcagtcat     2160
ccttcctaga tgaggatgag gtatacagtc tgacagccac tctgaagcgt ctctctgcct     2220
tttacaatgc tcatgacctg actcgctggg agatctctga accatgttct cgactcctcc     2280
ggaaggctgt agacacagga gaagttcctc accaggtgat tttgccagcc ttgactctgg     2340
tatatttttc cattctctgg acagtgaccc acatttcaga gtctacttcc caaaagcagc     2400
tgatgagtct gaagaaaaga atggtagcct tctgtgaact ttgccaaagc tgcctctcag     2460
acgtggaccc agagatccag gagcaggctt ttgttttatt aagtgacctg cttctcatct     2520 tcagcccca gatggttgta gggggccggg atttccttag gcctcttgtc ttttttccgg      2580
aagctactct ccagtcggaa ctagccagct tcctcatgga ccatgtcttt ctccagcctg     2640
gagaattggg caacggtcaa tcacaggagg atcacgtcca aatagagctt ctgcaccaga     2700
ggcgccgcct gcttgcagga ttttgtaagc tgttgcttta gggggtattg gaactggatg     2760
cggcctcaga tgttttcaaa cactacaaca agttctatga agattatggt gacattatca     2820
aggaaacatt aactcgggcg agacaaattg accgatgtca gtgctctcgg atcctgctcc     2880
tgagcctaaa gcagctctac acagaactga tacaggagca ggggccccag gacctgacag     2940
aactgccagc cttcattgag atgagagacc tggcccggag gtttgccttg agctttggac     3000
cccagcagct ccataacaga gatcttgtgg tcatgctgca caaggaaggc atcaagttct     3060
cattgtctga gcttcctcct gctggctctt ctcgagagcc cccaaatatt gcattcctgg     3120
```

```
agcttctttc agagttctcc ccccgcctct tccatcagga caaacagcta ctactatcat    3180
acctggaaaa gtgtctgcag cgtgtctcca tggcacctag ccatccctgg ggtccagtca    3240
ccacctactg ccactccctc catctagtag agaacacagc agaggccagc tctcaggggc    3300
ccccccactc caagaagagg tgtattgaag ttccccgcag gcttcaggaa gaagagtctt    3360
catcccaggg agaaagcctt cagctgaaca gtggccccac aacacctaca ctcacctcca    3420
cagcagtgaa gagaaggcag tctccgagga cagtaggcaa gaggcaaaaa ggtggaccag    3480
gaccaggacc aggaccagga ccaggaccag gaccaggacc aggaccagga ccaggaccag    3540
gaccaggacc agagctgatc tgcagtcagc agctctcagg cacccagagg ttgaaaatgt    3600
cgagtgcacc gtgtttccag attcgatgtg atccttctgg ctctggcttg ggcaagcaga    3660
tgacccgact cagccttatg gaagaagatg aggaagaaga gctgagactt ctggatgaag    3720
aatggcaatg tggagacaag ctacttcata gcccttcttc tcccagtgag catgggctgg    3780
acctattaga tacaacagag ctgaacatgg aggatttctg atgggactta ggcttctccc    3840
cttctccact taccacactg caaggccatg agtgagcaaa cgaaggagta aaatgaagca    3900
ttctttgggt cccagccaag tactttaagg gaatagagaa atggccttat tcaaacctcc    3960
atttcttttct gaagtgggtg ctgtatatag atgctatgag ccctgtgatc cttaattcac    4020
cctagcttta tgcttttgcc tgtttgaagt ggtgggagtt gggtagggag ctttacctca    4080
gtattgaagt ttaataaacc ttctgtttga tatctcttcc ccaaacactg ccaagctctc    4140
aataaacatg ttcacatcag ctaaaaaaaa aaaaaaaaa a                         4181
```

<210> SEQ ID NO 26
<211> LENGTH: 4220
<212> TYPE: DNA
<213> ORGANISM: Pan troglodytes

<400> SEQUENCE: 26

```
tcttgtacgt tcccgcgctt ttttggaatc tttcgccccc ggaagggcag cggcgggcgc     60
ctgtgtggaa ggtggggtgg ccagagagac ccgaggggacc tgagctggat cgccataccct   120
accctgtggt cctcatcttc ctgtcctcat agctcctcct ctccaagcat gtcttccccg    180
ttgcaaagag ctatgggaga taccaagagg gccttgtctg catcttctag ttcctctgcc    240
agtctaccct ttgatgacag ggactcaaac catacctcag aggggaatgg cgactctttg    300
ttagctgatg aagacactga ctttgaagac agcttgaatc gcaatgtgaa gaagagagca    360
gcaaaacgac caccgaaaac aacaccggtg gcaaaacatc aaagaaagg gtcccgagtg    420
gtacatcgtt atagccggaa acagtcagag ccaccagcca atgatctttt caatgctgtg    480
aaagccgcca aaagtgacat gcagtctttg gtagatgagt ggctggatag ctacaagcaa    540
gaccaggatg caggatttct ggagcttgtt aacttttttca tccaatcttg cggatgtaaa    600
ggcattgtga cccccgagat gttcaagaag atgtccaact cagagatcat ccagcaccta    660
acagagcagt ttaatgagga ctcgggggac tacccctctca tagctccagg tccatcctgg    720
aagaagttcc agggcagctt ctgtgaattt gtgaggacat ggtctgtca gtgccagtac    780
agcctcctct atgatggctt ccctatggac aacctcatct ccctgctcac tggcctctca    840
gactcacaag tccgcgcctt ccgtcacact agcaccctgg ctgctatgaa actgatgacc    900
tccctggtaa aagttgccct ccaactgagt gtgcaccaag ataacaatca gcgtcagtat    960
gaggctgaaa gaaacaaggg gccagggcag agggcacctg agcggctgga gagcctgttg   1020
```

```
gagaaacgca aagagctcca agagcatcaa gaggagattg aggggatgat gaatgccctc    1080
ttcaggggtg tctttgttca tcggtacagg gatgtccttc ctgagatccg tgctatctgc    1140
attgaggaaa ttgggtgttg gatgcaaagc tacagcacgt ctttcctcac cgacagctat    1200
ttaaaatata ttggttggac tctgcatgat aagcaccgag aagtccgcct gaagtgtgtg    1260
aaggccctga aagggctgta cggtaaccgg gacctgacca cacgcctgga gctcttcacc    1320
agccgcttca aggaccggat ggtttccatg gtcatggaca gagagtatga tgtggcagtg    1380
gaggctgtca gattactgat acttatcctt aagaacatgg aaggggtgct gacggacgcg    1440
gactgtgaga gcgtctaccc cgttgtgtat gcctctcatc gaggcctggc ctctgccgca    1500
ggcgaatttc tgtactggaa actcttctac cctgagtgcg agataagaat gatgggtgga    1560
agagagcaac gccagagccc aggcgcccag aggactttct tccagcttct gctgtccttc    1620
tttgtggaga gcgagctcca tgaccacgct gcttacttag tagacagtct gtgggactgt    1680 gcagggctc ggctgaagga ctgggagggt ctgacaagcc tgctgctgga aaggaccag    1740 aacctgggtg atgtgcagga gagcacactg atagaaatcc ttgtgtccag tgcccggcaa    1800
gcttcagagg ggcacccgcc tgtgggccgg gtcactggga ggaagggctt aacctctaag    1860
gagcgcaaga cccaagccga tgacagggtg aagttgactg agcacctcat cccccctgctg    1920 ccccagctcc tggccaagtt ctcagctgat gcagagaagg tcactcccct gctccagctt    1980
ctcagctgct ttgacctcca catctactgc actgggcgct tggagaagca cctggagctg    2040
ttcctgcagc aactccagga ggtggtggtg aagcatgcag agccagcggt gcttgaggct    2100
ggggcgcatg ccctctacct gctctgtaat cccgaattca ctttcttcag ccgggcggac    2160
tttgcccgca gccagctagt agatttgctg actgaccgct tccagcagga gcttgaagag    2220
ctgttacagt cgtccttcct agatgaggat gaggtatata atctggcagc cactctgaaa    2280
cgcctctctg ccttctacaa cgctcatgac ctgactcgct gggagctcta tgagccatgt    2340
tgccaactcc tgcagaaggc tgtggacaca ggagaggttc ctcaccaggt tatcctgcca    2400
gccttgactc ttgtctattt ttccattctc tggacactaa cccacatttc taaatcagat    2460
gcttcccaga gcagctgtc gagtttgagg acagaatgg tggccttctg tgaactctgc    2520
cagagttgcc tctcagatgt ggatactgag atccaggagc aggcttttgt cttattaagt    2580
gatctacttc tcatctttag ccctcagatg attgttgggg gccgtgattt ccttaggcca    2640
cttgtctttt ttcctgaagc tactctccag tctgagctag ccagcttcct catggaccac    2700
gtcttcatcc agccgggaga cctgggcagt ggtgattccc aggaggatca tttacagata    2760
gagcggctac accagcggcg ccgcctccta gccgggttct gcaagctgtt gctttatggg    2820
gtgctggaga tggatgcagc ctcagatgtt ttcaaacact acaacaagtt ctacaatgac    2880
tatggtgaca ttatcaagga aacattaact agagcaaggc agattgaccg aagtcattgt    2940
tcccgaatcc tgctgctgag cctcaagcag ctgtacacag aactgctgca ggagcatggg    3000
ccccagggcc tgaatgagct tcctgccttc atcgagatga gggacctggc ccggaggttt    3060
gccttgagtt ttggaccccca gcagctgcag aaccgtgacc tcgtggtcat gctacacaag    3120
gaaggcatca agttctcctt gtctgagctt cctccagctg ctcctccaa tcagcctcca    3180 aatctggcat tcctggagct cctttcagag ttttcccccc gactcttcca tcaggacaag    3240
cagcttttac tgtcctatct agaaaagtgc ctgcagcatg tctcccaggc acctggccgt    3300
ccctggggcc cagtcaccac ctactgccac tccctcagcc ctgtggagaa cacagcagag    3360
accagccctc aggtcctccc cagctccaag aggaggcgcg ttgaagggcc tgccaagcct    3420
```

```
aacagagagg acgtctcctc gtcccaggaa gaaagtctgc agctgaacag catcccgccc    3480
acgcccaccc tcacctccac agctgtgaag agcaggcagc ccctgtgggg gttgaaagag    3540
atggaggaag aagatggctc agagttggat tttgcccagg gcagtcagcc cgttgcaggc    3600
accgagaggt caaggttctt gggtccacaa tatttccaga ctccacacaa cccttcaggt    3660
cctggcctgg gcaaccagct gatgcgactc agccttatgg aagaggacga ggaagaagag    3720
ttagaaatcc aggatgagtc aaatgaagaa cggcaggata cagacatgca agcaagtagc    3780
tactgttcca ccagtgagcg cgggctggac ctcttagatt ctacagagct ggatattgag    3840
gatttctgac aggactctgg gcccctcccc agctccactc cctacctcaa gaatgtgacc    3900
atttggaaaa ggcagagaaa aggagcaaaa tgaagcattc ccccaggctt cagccctggg    3960
ctctgagggg aaagagttgg gcattgtttt tctaacctaa cctttccctc tggggtagag    4020
aagccgagag accctgtcct ccctaatgca ctgtggccca gtccccttgc cttttcctg     4080 ttctgtttgg agtggagaag ggcagcacct ctgtgtttaa tggaaatagc ccatggtttt    4140
ctggattttt ggaacatctt tctcagccta ttttgtgtcc taatgattcg ctcaataaac    4200
atgtttgaat ccacacgttc                                                4220

<210> SEQ ID NO 27
<211> LENGTH: 1299
<212> TYPE: DNA
<213> ORGANISM: Ornithorhynchus anatinus

<400> SEQUENCE: 27
atggcgcggc ggtggggggt ggcgtgtgtg agcaagaggg tgggagatga gaacgaagca      60
cagcgagccg gtgaggtcga caagaatgaa ggtatcgagc tcgggggtag tgggagaaga     120
ctggaaagac tagattttg ggtcgtcttc tgcctctcaa ccccaccggg ccccgctctg      180
ggttccgaac tcgtgcactc tccgctcgct gtcagggagc cggtccgttc cccatcctcc     240
cccccaaccc gactcgccct cttggccggc ggaagccgta acggcccgt cctcccaatt      300 ttttttacca tccttcctcc cccatcaggc acggtgaccc tggagatgtt caagaccctg     360
cagaactcag agatcatcca acagatgacg gagaagttta cgaggactc ggtggaaatac     420 cccttgtcag cctccggccc gacctggaag aaattccggg ggagtttctg tgagttcgtc    480
agctcgctgg tgcatcagtg ccgctacagc ttcctctacg acgaattcct catggatacc    540
ctcatctccc tgctcacggg cctctccgac tcccaggtcc gcgccttccg ccacaccagc    600
accctgcgtc gccccgcctc tttcctccag ccccgcaggg acggggtcc cgccaagacc     660 ccgccgtgct gcgacatccc gccgcccttc ccaacctcc tccagcaccg gccgccgctc     720
ctcgccttcc cgcaggccaa gccggccggt cccgccggcc ccgccagggt ccccggggac    780
ggggcgtccc gcctgcccgt catctgccac gccaaggata cttccggccc tttcccct tc    840 gtccaagtgt ctgggcggga tccggttgcc cacccgccgg ccaaagcgga gcgggaggag    900
aaggggctcc cgccctcggc catccccgtg aggagccagg gggccgaggg cctgctggcc    960
cgaatccacg ccggaggaga ccgaggcggc ggggccggga cggggctccc cgtgccctgc   1020
cagaccttcc ccgcctgcca ccgcaacgga gacttgacgg ggggctaccg ccttgggcgc   1080
tcagcctcca cctccggggt ccgccaggca gcccctccaca ccccgcgccc ctgcagccag   1140
```

-continued

```
gcccgggagt cgcccagcca ggtgaggaag gcggacggat ccctgacggg cctcctcggg    1200
ctcggcctca gggagggcgg cccggaggag ccggtcttgg agacgagggc aggaggagga    1260
gcttctgagg gccgggaggg atggcggccc ggacggtga                           1299
```